US012251395B2

(12) United States Patent
Mueller et al.

(10) Patent No.: US 12,251,395 B2
(45) Date of Patent: Mar. 18, 2025

(54) RNAS FOR COMPLEMENT INHIBITION

(71) Applicant: Apellis Pharmaceuticals, Inc., Waltham, MA (US)

(72) Inventors: Christian Mueller, Concord, MA (US); Lukas Scheibler, Telluride, CO (US)

(73) Assignee: Apellis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 17/942,698

(22) Filed: Sep. 12, 2022

(65) Prior Publication Data

US 2023/0302038 A1 Sep. 28, 2023

Related U.S. Application Data

(62) Division of application No. 16/853,732, filed on Apr. 20, 2020, now Pat. No. 11,510,939.

(60) Provisional application No. 62/836,412, filed on Apr. 19, 2019.

(51) Int. Cl.
| | | |
|---|---|---|
| C07H 21/02 | (2006.01) | |
| A61K 31/713 | (2006.01) | |
| A61P 43/00 | (2006.01) | |
| C07K 16/18 | (2006.01) | |
| C12N 15/113 | (2010.01) | |
| C12N 15/86 | (2006.01) | |

(52) U.S. Cl.
CPC ............ *A61K 31/713* (2013.01); *A61P 43/00* (2018.01); *C07K 16/18* (2013.01); *C12N 15/113* (2013.01); *C12N 15/86* (2013.01); *C12N 2310/14* (2013.01); *C12N 2310/141* (2013.01)

(58) Field of Classification Search
CPC .................. C12N 15/113; C12N 2310/141
See application file for complete search history.

(56) References Cited

U.S. PATENT DOCUMENTS

| | | |
|---|---|---|
| 7,427,605 B2 | 9/2008 | Davis et al. |
| 7,582,746 B2 | 9/2009 | Khvorova et al. |
| 7,888,323 B2 | 2/2011 | Lambris et al. |
| 8,158,601 B2 | 4/2012 | Chen et al. |
| 8,729,041 B2 | 5/2014 | Mendell et al. |
| 9,012,498 B2 | 4/2015 | Manoharan et al. |
| 9,062,021 B2 | 6/2015 | Budzik et al. |
| 9,402,816 B2 | 8/2016 | Colletti et al. |
| 9,415,109 B2 | 8/2016 | Kumar et al. |
| 10,480,011 B2 | 11/2019 | Gao et al. |
| 11,338,013 B2 | 5/2022 | Francois |
| 11,510,939 B1 | 11/2022 | Mueller et al. |
| 2007/0178068 A1 | 8/2007 | Reich et al. |
| 2009/0093425 A1 | 4/2009 | Dowdy et al. |
| 2011/0190221 A1 | 8/2011 | Francois et al. |
| 2011/0294869 A1 | 12/2011 | Petersen |
| 2012/0142763 A1 | 6/2012 | Dowdy et al. |
| 2012/0157509 A1 | 6/2012 | Hadwiger et al. |
| 2012/0178694 A1 | 7/2012 | Lambris et al. |
| 2013/0245091 A1 | 9/2013 | Rozema et al. |
| 2014/0323407 A1 | 10/2014 | Francois et al. |
| 2015/0197746 A1 | 7/2015 | Rajeev et al. |
| 2015/0238516 A1 | 8/2015 | Dowdy et al. |
| 2015/0247143 A1 | 9/2015 | Fitzgerald et al. |
| 2016/0194359 A1 | 7/2016 | Francois et al. |
| 2016/0215022 A1 | 7/2016 | Francois et al. |
| 2016/0298124 A1 | 10/2016 | Borodovsky et al. |
| 2020/0282012 A1 | 9/2020 | Francois |
| 2023/0009757 A1 | 1/2023 | Francois |
| 2023/0095695 A1 | 3/2023 | Hoßbach et al. |

FOREIGN PATENT DOCUMENTS

| | | |
|---|---|---|
| CN | 105051057 A | 11/2015 |
| CN | 105814205 A | 7/2016 |
| JP | 2016-505527 A | 2/2016 |
| RU | 2474586 C2 | 2/2013 |
| WO | WO-03/066805 A2 | 8/2003 |
| WO | WO-2007/089375 A2 | 8/2007 |
| WO | WO-2008/097525 A2 | 8/2008 |
| WO | WO-2012/083046 A2 | 6/2012 |
| WO | WO-2013/036778 A2 | 3/2013 |
| WO | WO-2014/078731 A2 | 5/2014 |
| WO | WO-2014/078734 A2 | 5/2014 |
| WO | WO-2014/152391 A1 | 9/2014 |
| WO | WO-2015/089368 A2 | 6/2015 |
| WO | WO-2017/021385 A1 | 2/2017 |
| WO | WO-2017/055423 A1 | 4/2017 |
| WO | WO-2017/084987 A1 | 5/2017 |
| WO | WO-2017/178656 A1 | 10/2017 |
| WO | WO-2018/075373 A1 | 4/2018 |
| WO | WO-2018/215391 A1 | 11/2018 |
| WO | WO-2019/089922 A1 | 5/2019 |
| WO | WO-2019/145543 A1 | 8/2019 |
| WO | WO-2020/104669 A1 | 5/2020 |
| WO | WO-2021/037941 A1 | 3/2021 |
| WO | WO-2021/081026 A1 | 4/2021 |
| WO | WO-2021/163654 A1 | 8/2021 |
| WO | WO-2021/178607 A1 | 9/2021 |

(Continued)

OTHER PUBLICATIONS

Kanasty, R. et al., Delivery materials for siRNA therapeutics, Nature Materials, 12(11):967-977 (2013).

Bao, L. et al., Administration of a Soluble Recombinant Complement C3 Inhibitor Protects Against Renal Disease in MRL/lpr Mice, J Am Soc Nephrol, 14:670-679 (2003).

Broun et al., Catalytic Plasticity of Fatty Acid Modification Enzymes Underlying Chemical Diversity of Plant Lipids, Science, 282:1315-1317 (1998), abstract.

Cho, M. et al., Autocrine Effect of Tumor-Derived Complement, Cell Rep., 6(6):1085-1095 (2014).

(Continued)

*Primary Examiner* — Amy Rose Hudson
(74) *Attorney, Agent, or Firm* — Choate, Hall & Stewart LLP; Brenda Herschbach Jarrell; Rolando Medina

(57) ABSTRACT

RNAs, such as miRNA and siRNA, and their use in treating complement-mediated disorders, are described.

7 Claims, 16 Drawing Sheets

Specification includes a Sequence Listing.

(56) References Cited

FOREIGN PATENT DOCUMENTS

| WO | WO-2021/163654 A8 | 10/2021 |
| WO | WO-2022/251484 A1 | 12/2022 |
| WO | WO-2022/251484 A9 | 10/2023 |

OTHER PUBLICATIONS

Elliot, K. J. et al., ADAM17 silencing by adenovirus encoding miRNA-embedded siRNA revealed essential signal transduction by angiotensin II in vascular smooth muscle cells, Journal of Molecular and Cellular Cardiology, 62:1-7 (2013).

Grossi, Federico, APL-1, a Complement C3 Inhibitor for the Potential Treatment of Paroxysmal Nocturnal Hemoglobinuria (PNH): Phase I Data from Two Completed Studies in Healthy Volunteers, retrieved from Internet on Apr. 17, 2020, high resolution poster.

Han, X. et al., MicroRNA-130b Ameliorates Murine Lupus Nephritis Through Targeting the Type I Interferon Pathway on Renal Masangial Cells, Arthritis and Rheumatology, 68(9):2232-2243 (2016).

International Search Report for PCT/US2017/56708 (Combination Therapy for C3 Inhibition, filed Oct. 16, 2017), issued by ISA/US, 4 pages (Jan. 18, 2018).

International Search Report for PCT/US21/18071 (RNAS for Complement Inhibition, filed Feb. 13, 2021), received by ISA/US, 4 pages (Jun. 8, 2021).

Karaki S. et al. Antisense Oligonucleotides, A Novel Developing Targeting Therapy, Antisense Therapy (2019).

Lapidot, M. et al., Genome-wide natural antisense transcription: coupling its regulation to its different regulatory mechanisms, EMBO Rep., 7(12):1216-1222 (2006).

Liu, X. et al., miR-130b promotes bladder cancer cell proliferation, migration and invasion by targeting VGLL4, Oncology Reports, 39:2324-2332 (2018).

Ozcan, G. et al., Preclinical and clinical development of siRNA-based therapeutics, Advanced Drug Delivery Reviews, 87:108-119 (2015).

Seffernick J. L. et al., Melamine Deaminase and Atrazine Chlorohydrolase: 98 Percent Identical but Functionally Different, Journal of Bacteriology, 183(8):2405-2410 (2001).

Vega, Carolina, APL-2 and complement inhibition; a potential treatment of PNH and other complement-mediated diseases, retrieved from https://apellis.com/presentations/07c97663e2ad43e581dd4fdea522be63.pdf<https://protect-us.mimecast.com/s/wAPqC4xWk2CI38NkHOwFCB?domain=apellis.com>, 39 pages (Sep. 27, 2016).

Witkowski, A. et al., Conversion of a β-Ketoacyl Synthase to a Malonyl Decarboxylase by Replacement of the Active-Site Cysteine with Glutamine, Biochemistry, 38:11643-11650 (1999).

Written Opinion for PCT/US2017/56708 (Combination Therapy for C3 Inhibition, filed Oct. 16, 2017), issued by ISA/US, 8 pages (Jan. 18, 2018).

Written Opinion for PCT/US21/18071 (RNAS for Complement Inhibition, filed Feb. 13, 2021), 4 pages (Jun. 8, 2021).

Zheng, X. et al., Preventing renal ischemia-reperfusion injury using small interfering RNA by targeting complement 3 gene, Am J Transplant, 6(9):2099-108 (2006).

Cheng, et al., Developement of optimized AAV3 serotype vectors: mechanism of high-efficiency transduction of human liver cancer cells, Gene. Ther., 19:375-384 (2012).

Devalet, et al., Pathophsiology, diagnosis, and treatment of paraoxysmal nocturnal hemoglobinuria: a review, Eur. J. Haematol., 95:190-198 (2015).

Lam, et al., siRNA versus as therapeutics for gene silencing, Molec. Ther. Nuc. Ac., 4:e252 (2015).

De Jong, S. et al., Implications of genetic variation in the complement system in age-related macular degeneration, Progress in Retinal and Eye Research, 84:100952, 31 pages (2021).

Hammond, S. et al., Delivery of oligonucleotide-based therapeutics: challenges and opportunities, EMBO Molecular Medicine, 13:e13243, 23 pages (2021).

Hu, B. et al., Therapeutic siRNA: state of the art, Sig. Transduct. Target Ther., 5(101), 25 pages (2020).

International Search Report for PCT/US22/31115, 5 pages (Sep. 23, 2022).

Natoli, R. et al., Retinal Macrophages Synthesize C3 and Activate Complement in AMD and in Models of Focal Retinal Degeneration, Invest Ophthalmol Vis Sci., 58:2977-2990 (2017).

Rutar, M. et al., Synthesis and Propagation of Complement C3 by Microglia/Monocytes in the Aging Retina, PLOS One, 9(4):e93343, 10 pages (2014).

Schick, T. et al., Local complement activation in aqueous humor in patients with age-related macular degeneration, Eye, 31:810-813 (2017).

Springer, A. and Dowdy, S., GalNAc-siRNA Conjugates: Leading the Way for Delivery of RNAi Therapeutics, Nucleic Acid Therapeutics, 28(3): 109-118 (2018).

Written Opinion for PCT/US22/31115, 4 pages (Sep. 23, 2022).

Summary of transduction efficiencies
of different AAV serotypes in
HepG2 and human hepatocytes

|  | HepG2 | Human Hepatocytes |
|---|---|---|
| AAV3B | ++++ | ++ |
| AAVrh10-A2 | ++ | +++ |
| AAV6 | + | n.d |
| AAV8 | n.d | + |

RNAS FOR COMPLEMENT INHIBITION

CROSS REFERENCE TO RELATED APPLICATIONS

The present application is a divisional of U.S. application Ser. No. 16/853,732, filed Apr. 20, 2020, which claims priority to U.S. Provisional Patent Application No. 62/836,412, filed Apr. 19, 2019, the entire contents of all of which are hereby incorporated by reference in their entirety.

SEQUENCE LISTING

The present specification makes reference to a Sequence Listing (submitted electronically as a .xml file named "2008575-0647_ST26.xml"). The .xml file was generated on Apr. 27, 2023 and is 173,201 bytes in size. The entire contents of the Sequence Listing are herein incorporated by reference.

BACKGROUND

Complement is a system consisting of more than 30 plasma and cell-bound proteins that plays a significant role in both innate and adaptive immunity. The proteins of the complement system act in a series of enzymatic cascades through a variety of protein interactions and cleavage events. Complement activation occurs via three main pathways: the antibody-dependent classical pathway, the alternative pathway, and the mannose-binding lectin (MBL) pathway. Inappropriate or excessive complement activation is an underlying cause or contributing factor to a number of serious diseases and conditions, and considerable effort has been devoted over the past several decades to exploring various complement inhibitors as therapeutic agents.

SUMMARY

In one aspect, the disclosure features an miRNA or siRNA comprising a nucleotide sequence at least 90% (e.g., at least 91%, 92%, 93%, 94%, 95%, 96%, 97%, 98%, 99%, or 100%) identical to any one of SEQ ID NOs: 76-85, or a portion thereof.

In another aspect, the disclosure features a nucleic acid encoding an miRNA or siRNA comprising a nucleotide sequence at least 90% (e.g., at least 91%, 92%, 93%, 94%, 95%, 96%, 97%, 98%, 99%, or 100%) identical to any one of SEQ ID NOs: 76-85, or a portion thereof. In some embodiments, the nucleic acid comprises any one of SEQ ID NOs: 86-115.

In another aspect, the disclosure features a nucleotide sequence encoding an miRNA, wherein the nucleotide sequence is at least 90% (e.g., at least 91%, 92%, 93%, 94%, 95%, 96%, 97%, 98%, 99%, or 100%) identical to any one of SEQ ID NOs: 86-115, or a portion thereof. In some embodiments, the miRNA comprises a sequence at least 90% (e.g., at least 91%, 92%, 93%, 94%, 95%, 96%, 97%, 98%, 99%, or 100%) identical to any one of SEQ ID NOs:76-85.

In another aspect, the disclosure features an expression vector comprising a nucleotide sequence encoding an miRNA, wherein the nucleotide sequence is at least 90% (e.g., at least 91%, 92%, 93%, 94%, 95%, 96%, 97%, 98%, 99%, or 100%) identical to any one of SEQ ID NOs: 86-115, or a portion thereof. In some embodiments, the miRNA comprises a sequence at least 90% (e.g., at least 91%, 92%, 93%, 94%, 95%, 96%, 97%, 98%, 99%, or 100%) identical to any one of SEQ ID NOs:76-85. In some embodiments, the expression vector is a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector. In some embodiments, the AAV vector is an AAV3B vector.

In some embodiments, the nucleotide sequence is operably linked to a promoter. In some embodiments, the promoter is a liver-specific promoter, e.g., an α-antitrypsin, apolipoprotein C-I, apolipoprotein C-IV, apolipoprotein H, transthyretin, albumin, aldolase B, CYP2E1, fibrinogen alpha chain, transferrin, haptoglobin related protein, or thyroxin binding globulin (TBG) promoter.

In some embodiments, the expression vector further comprises a nucleotide sequence encoding a C3 inhibitor (e.g., an aptamer, an anti-C3 antibody, an anti-C3b antibody, a mammalian complement regulatory protein, or mini factor H).

In another aspect, the disclosure features a host cell comprising an expression vector comprising a nucleotide sequence encoding an miRNA, wherein the nucleotide sequence is at least 90% (e.g., at least 91%, 92%, 93%, 94%, 95%, 96%, 97%, 98%, 99%, or 100%) identical to any one of SEQ ID NOs: 86-115, or a portion thereof. In some embodiments, the miRNA comprises a sequence at least 90% (e.g., at least 91%, 92%, 93%, 94%, 95%, 96%, 97%, 98%, 99%, or 100%) identical to any one of SEQ ID NOs:76-85. In some embodiments, the expression vector is a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV 11 vector. In some embodiments, the AAV vector is an AAV3B vector.

In some embodiments, the nucleotide sequence is operably linked to a promoter. In some embodiments, the promoter is a liver-specific promoter, e.g., an α-antitrypsin, apolipoprotein C-I, apolipoprotein C-IV, apolipoprotein H, transthyretin, albumin, aldolase B, CYP2E1, fibrinogen alpha chain, transferrin, haptoglobin related protein, or thyroxin binding globulin (TBG) promoter.

In some embodiments, the expression vector further comprises a nucleotide sequence encoding a C3 inhibitor (e.g., an aptamer, an anti-C3 antibody, an anti-C3b antibody, a mammalian complement regulatory protein, or mini factor H).

In another aspect, the disclosure features a method of treating a subject having or at risk of a complement-mediated disorder, the method comprising administering to the subject a composition comprising an effective amount of an miRNA or siRNA comprising a nucleotide sequence at least 90% identical (e.g., at least 91%, 92%, 93%, 94%, 95%, 96%, 97%, 98%, 99%, or 100%) to any one of SEQ ID NOs: 76-85, or a portion thereof. In some embodiments, the method comprises administering to the subject a composition comprising a nucleic acid encoding the miRNA or siRNA. In some embodiments, the nucleic acid comprises any one of SEQ ID NOs: 86-115, or a portion thereof.

In some embodiments, after the administration of the composition, a level of C3 transcript or C3 protein in the subject or in a biological sample from the subject is reduced relative to a level before the administration of the composition. In some embodiments, the level of C3 transcript or C3 protein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%, relative to a level before the administration.

In some embodiments, the composition is administered intravenously to the subject. In some embodiments, the composition is administered to a hepatocyte of the subject. In some embodiments, the composition is administered to the hepatocyte ex vivo. In some embodiments, the composition is administered to the hepatocyte in vivo.

In some embodiments, the method further comprises administering to the subject a second agent, e.g., an anti-C3 antibody or a compstatin analog. In some embodiments, the compstatin analog comprises a clearance reducing moiety (CRM) and at least one compstatin analog moiety. In some embodiments, the compstatin analog comprises a CRM having at least two compstatin analog moieties attached thereto. In some embodiments, the CRM comprises a PEG. In some embodiments, the CRM has an average molecular weight of between about 10 kD and about 50 kD, e.g., between about 35 kD and about 45 kD, e.g., about 40 kD. In some embodiments, the compstatin analog comprises a linear polymer having a compstatin analog moiety attached to each end. In some embodiments, each compstatin analog moiety comprises a cyclic peptide that comprises the amino acid sequence of one of SEQ ID NOs: 3-36, 37, 69, 70, 71, and 72. In some embodiments, the compstatin analog comprises one or more clearance-reducing moieties attached to one or more compstatin analog moieties, wherein: each compstatin analog moiety comprises a cyclic peptide having an amino acid sequence as set forth in any of SEQ ID NOs:3-36, extended by one or more terminal amino acids at the N-terminus, C-terminus, or both, wherein one or more of the amino acids has a side chain comprising a primary or secondary amine and is separated from the cyclic peptide by a rigid or flexible spacer optionally comprising an oligo (ethylene glycol) moiety; and each clearance-reducing moiety optionally comprises a polyethylene glycol (PEG), wherein each clearance-reducing moiety is covalently attached via a linking moiety to one or more compstatin analog moieties, and wherein the linking moiety comprises an unsaturated alkyl moiety, a moiety comprising a nonaromatic cyclic ring system, an aromatic moiety, an ether moiety, an amide moiety, an ester moiety, a carbonyl moiety, an imine moiety, a thioether moiety, and/or an amino acid residue. In some embodiments, each compstatin analog moiety comprises a cyclic peptide extended by one or more amino acids at the N-terminus, C-terminus, or both, wherein the one or more amino acids is separated from the cyclic portion of the peptide by a rigid or flexible spacer that comprises 8-amino-3,6-dioxaoctanoic acid (AEEAc) or 11-amino-3,6,9-trioxaundecanoic acid. In some embodiments, the compstatin analog comprises CA28-2TS-BF.

In some embodiments, the subject has a defect in complement regulation, optionally wherein the defect comprises abnormally low expression of one or more complement regulatory proteins by at least some of the subject's cells.

In some embodiments, the complement-mediated disorder is a chronic disorder. In some embodiments, the complement-mediated disorder involves complement-mediated damage to red blood cells, optionally wherein the disorder is paroxysmal nocturnal hemoglobinuria or atypical hemolytic uremic syndrome. In some embodiments, the complement-mediated disorder is an autoimmune disease, optionally wherein the disorder is multiple sclerosis. In some embodiments, the complement-mediated disorder involves the kidney, optionally wherein the disorder is membranoproliferative glomerulonephritis, lupus nephritis, IgA nephropathy (IgAN), primary membranous nephropathy (primary MN), C3 glomerulopathy (C3G), or acute kidney injury. In some embodiments, the complement-mediated disorder involves the central or peripheral nervous system or neuromuscular junction, optionally wherein the disorder is neuromyelitis optica, Guillain-Barré syndrome, multifocal motor neuropathy, or myasthenia gravis. In some embodiments, the complement-mediated disorder involves the respiratory system, optionally wherein the disorder is characterized by pulmonary fibrosis. In some embodiments, the complement-mediated disorder involves the vascular system, optionally wherein the disorder is characterized by vasculitis.

In another aspect, the disclosure features a method of treating a subject having or at risk of a complement-mediated disorder, the method comprising administering to the subject an effective amount a composition comprising a nucleotide sequence encoding an miRNA, wherein the nucleotide sequence is at least 90% (e.g., at least 91%, 92%, 93%, 94%, 95%, 96%, 97%, 98%, 99%, or 100%) identical to any one of SEQ ID NOs: 86-115, or a portion thereof. In some embodiments, the miRNA comprises a sequence at least 90% identical (e.g., at least 91%, 92%, 93%, 94%, 95%, 96%, 97%, 98%, 99%, or 100%) to any one of SEQ ID NOs:76-85.

In some embodiments, the composition comprises an expression vector comprising the nucleotide sequence. In some embodiments, the expression vector is a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector. In some embodiments, the AAV vector is an AAV3B vector.

In some embodiments, the nucleotide sequence is operably linked to a promoter. In some embodiments, the promoter is a liver-specific promoter, e.g., an α-antitrypsin, apolipoprotein C-I, apolipoprotein C-IV, apolipoprotein H, transthyretin, albumin, aldolase B, CYP2E1, fibrinogen alpha chain, transferrin, haptoglobin related protein, or thyroxin binding globulin (TBG) promoter.

In some embodiments, the expression vector further comprises a nucleotide sequence encoding a C3 inhibitor (e.g., an aptamer, an anti-C3 antibody, an anti-C3b antibody, a mammalian complement regulatory protein, or mini factor H).

In some embodiments, after the administration of the composition, a level of C3 transcript or C3 protein in the subject or in a biological sample from the subject is reduced relative to a level before the administration of the composition. In some embodiments, the level of C3 transcript or C3 protein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%, relative to a level before the administration.

In some embodiments, the composition is administered intravenously to the subject. In some embodiments, the composition is administered to a hepatocyte of the subject. In some embodiments, the composition is administered to the hepatocyte ex vivo. In some embodiments, the composition is administered to the hepatocyte in vivo.

In some embodiments, the method further comprises administering to the subject a second agent, e.g., an anti-C3 antibody or a compstatin analog. In some embodiments, the compstatin analog comprises a clearance reducing moiety (CRM) and at least one compstatin analog moiety. In some embodiments, the compstatin analog comprises a CRM having at least two compstatin analog moieties attached thereto. In some embodiments, the CRM comprises a PEG.

In some embodiments, the CRM has an average molecular weight of between about 10 kD and about 50 kD, e.g., between about 35 kD and about 45 kD, e.g., about 40 kD. In some embodiments, the compstatin analog comprises a linear polymer having a compstatin analog moiety attached to each end. In some embodiments, each compstatin analog moiety comprises a cyclic peptide that comprises the amino acid sequence of one of SEQ ID NOs: 3-36, 37, 69, 70, 71, and 72. In some embodiments, the compstatin analog comprises one or more clearance-reducing moieties attached to one or more compstatin analog moieties, wherein: each compstatin analog moiety comprises a cyclic peptide having an amino acid sequence as set forth in any of SEQ ID NOs:3-36, extended by one or more terminal amino acids at the N-terminus, C-terminus, or both, wherein one or more of the amino acids has a side chain comprising a primary or secondary amine and is separated from the cyclic peptide by a rigid or flexible spacer optionally comprising an oligo (ethylene glycol) moiety; and each clearance-reducing moiety optionally comprises a polyethylene glycol (PEG), wherein each clearance-reducing moiety is covalently attached via a linking moiety to one or more compstatin analog moieties, and wherein the linking moiety comprises an unsaturated alkyl moiety, a moiety comprising a nonaromatic cyclic ring system, an aromatic moiety, an ether moiety, an amide moiety, an ester moiety, a carbonyl moiety, an imine moiety, a thioether moiety, and/or an amino acid residue. In some embodiments, each compstatin analog moiety comprises a cyclic peptide extended by one or more amino acids at the N-terminus, C-terminus, or both, wherein the one or more amino acids is separated from the cyclic portion of the peptide by a rigid or flexible spacer that comprises 8-amino-3,6-dioxaoctanoic acid (AEEAc) or 11-amino-3,6,9-trioxaundecanoic acid. In some embodiments, the compstatin analog comprises CA28-2TS-BF.

In some embodiments, the subject has a defect in complement regulation, optionally wherein the defect comprises abnormally low expression of one or more complement regulatory proteins by at least some of the subject's cells.

In some embodiments, the complement-mediated disorder is a chronic disorder. In some embodiments, the complement-mediated disorder involves complement-mediated damage to red blood cells, optionally wherein the disorder is paroxysmal nocturnal hemoglobinuria or atypical hemolytic uremic syndrome. In some embodiments, the complement-mediated disorder is an autoimmune disease, optionally wherein the disorder is multiple sclerosis. In some embodiments, the complement-mediated disorder involves the kidney, optionally wherein the disorder is membranoproliferative glomerulonephritis, lupus nephritis, IgA nephropathy (IgAN), primary membranous nephropathy (primary MN), C3 glomerulopathy (C3G), or acute kidney injury. In some embodiments, the complement-mediated disorder involves the central or peripheral nervous system or neuromuscular junction, optionally wherein the disorder is neuromyelitis optica, Guillain-Barré syndrome, multifocal motor neuropathy, or myasthenia gravis. In some embodiments, the complement-mediated disorder involves the respiratory system, optionally wherein the disorder is characterized by pulmonary fibrosis. In some embodiments, the complement-mediated disorder involves the vascular system, optionally wherein the disorder is characterized by vasculitis.

In another aspect, the disclosure features an miRNA or siRNA comprising a nucleotide sequence that targets nucleotides 617-637, 753-773, 1740-1760, 2811-2831, 2835-2855, 3541-3561, 3849-3869, 4125-4145, 4309-4329, and/or 4394-4414 of SEQ ID NO:75, or a portion thereof. In some embodiments, the miRNA or siRNA comprises a nucleotide sequence at least 90% (e.g., at least 91%, 92%, 93%, 94%, 95%, 96%, 97%, 98%, 99%, or 100%) identical to any one of SEQ ID NOs: 76-85, or a portion thereof.

In another aspect, the disclosure features a composition comprising an miRNA or siRNA comprising a nucleotide sequence that targets nucleotides 617-637, 753-773, 1740-1760, 2811-2831, 2835-2855, 3541-3561, 3849-3869, 4125-4145, 4309-4329, and/or 4394-4414 of SEQ ID NO:75, or a portion thereof and a carrier and/or excipient. In some embodiments, the miRNA or siRNA comprises a nucleotide sequence at least 90% (e.g., at least 91%, 92%, 93%, 94%, 95%, 96%, 97%, 98%, 99%, or 100%) identical to any one of SEQ ID NOs: 76-85, or a portion thereof.

In another aspect, the disclosure features an expression vector comprising one or more nucleotide sequences encoding one or more miRNA or siRNA comprising a nucleotide sequence that targets nucleotides 617-637, 753-773, 1740-1760, 2811-2831, 2835-2855, 3541-3561, 3849-3869, 4125-4145, 4309-4329, and/or 4394-4414 of SEQ ID NO:75, or a portion thereof. In some embodiments, the miRNA or siRNA comprises a nucleotide sequence at least 90% (e.g., at least 91%, 92%, 93%, 94%, 95%, 96%, 97%, 98%, 99%, or 100%) identical to any one of SEQ ID NOs: 76-85, or a portion thereof.

In some embodiments, the expression vector further comprises a nucleotide sequence encoding a C3 inhibitor (e.g., an aptamer, an anti-C3 antibody, an anti-C3b antibody, a mammalian complement regulatory protein, or mini factor H).

BRIEF DESCRIPTION OF THE DRAWING

FIG. 5 summarizes the transduction efficiencies of different rAAV serotypes in HepG2 and human hepatocytes.

FIG. 7 is a schematic of the experimental design to deliver and validate rAAV3B-miRNA in HepG2 cells, where shmirC3_753 corresponds to SEQ ID NO:77, and MOI of 100,000 corresponds to an MOI of 100K (i.e. 100,000).

DEFINITIONS

Figure 1:
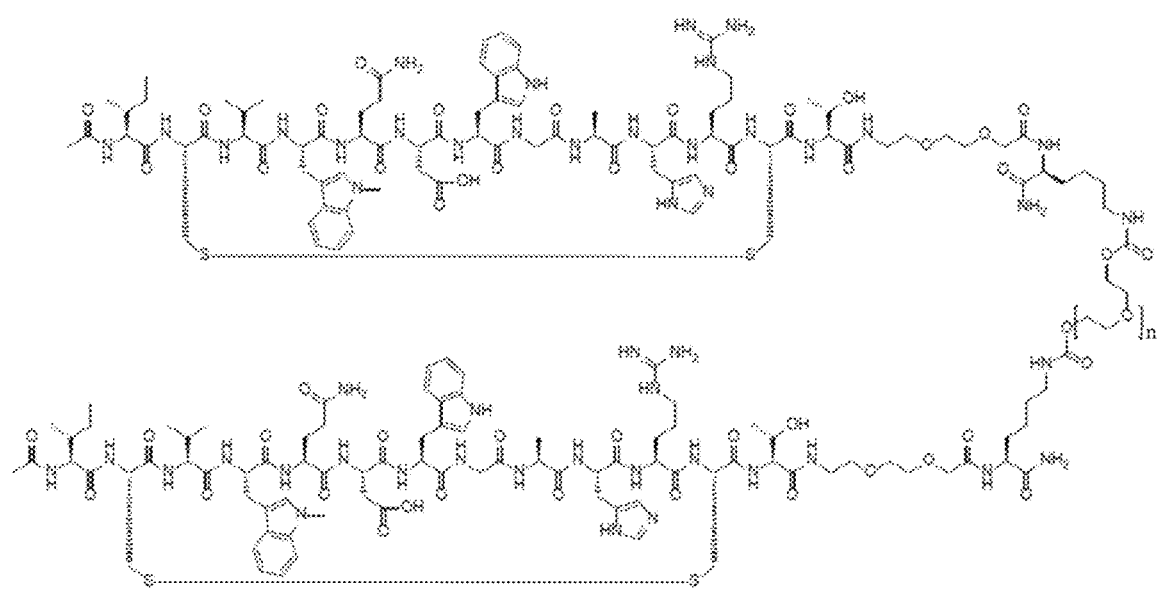
FIG. 1 shows the structure of CA28-2TS-BF, assuming n of about 800 to about 1100 and a PEG of about 40 kD.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Antibody: As used herein, the term "antibody" refers to an immunoglobulin or a derivative thereof containing an an immunoglobulin domain capable of binding to an antigen. The antibody can be of any species, e.g., human, rodent, rabbit, goat, chicken, etc. The antibody may be a member of any immunoglobulin class, including any of the human classes: IgG, IgM, IgA, IgD, and IgE, or subclasses thereof such as IgG1, IgG2, etc. In various embodiments of the invention the antibody is a fragment such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. The antibody can be monovalent, bivalent or multivalent. The antibody may be a chimeric or "humanized" antibody in which, for example, a variable domain of rodent origin is fused to a constant domain of human origin, thus retaining the specificity of the rodent antibody. The domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Methods for producing antibodies that specifically bind to virtually any molecule of interest are known in the art. For example, monoclonal or polyclonal antibodies can be purified from blood or ascites fluid of an animal that produces the antibody (e.g., following natural exposure to or immunization with the molecule or an antigenic fragment thereof), can be produced using recombinant techniques in cell culture or transgenic organisms, or can be made at least in part by chemical synthesis.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Complement component: As used herein, the terms "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin, with factor H being a negative regulator of the pathway. Components of the lectin pathway include, e.g., MBL2, MASP-1, and MASP-2. Complement components also include cell-bound receptors for soluble complement components. Such receptors include, e.g., C5a receptor (C5aR), C3a receptor (C3aR), Complement Receptor 1 (CR1), Complement Receptor 2 (CR2), Complement Receptor 3 (CR3), etc. It will be appreciated that the term "complement component" is not intended to include those molecules and molecular structures that serve as "triggers" for complement activation, e.g., antigen-antibody complexes, foreign structures found on microbial or artificial surfaces, etc.

Complementary DNA: As used herein, a "complementary DNA" or "cDNA" includes recombinant polynucleotides synthesized by reverse transcription of mRNA and from which intervening sequences (introns) have been removed.

Concurrent administration: As used herein, the term "Concurrent administration" with respect to two or more agents, e.g., therapeutic agents, is administration performed using doses and time intervals such that the administered agents are present together within the body, e.g., at one or more sites of action in the body, over a time interval in non-negligible quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks, etc.). Accordingly, the agents may, but need not be, administered together as part of a single composition. In addition, the agents may, but need not be, administered essentially simultaneously (e.g., within less than 5 minutes, or within less than 1 minute apart) or within a short time of one another (e.g., less than 1 hour, less than 30 minutes, less than 10 minutes, approximately 5 minutes apart). According to various embodiments of the disclosure, agents administered within such time intervals may be considered to be administered at substantially the same time. In certain embodiments of the disclosure, concurrently administered agents are present at effective concentrations within the body (e.g., in the blood and/or at a site of local complement activation) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The non-negligible concentration of an agent may be, for example, less than approximately 5% of the concentration that would be required to elicit a particular biological response, e.g., a desired biological response.

Host cell: As used herein, the term "host cell" refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO Kl, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

Linked: As used herein, the term "linked", when used with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

Local administration: As used herein, the term "local administration" or "local delivery", in reference to delivery of a composition or agent, refers to delivery that does not rely upon transport of the composition or agent to its intended target tissue or site via the vascular system. The composition or agent may be delivered directly to its intended target tissue or site, or in the vicinity thereof, e.g., in close proximity to the intended target tissue or site. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site. It will be understood that once having been locally delivered a fraction of a therapeutic agent (typically only a minor fraction of the administered dose) may enter the vascular system and be transported to another location, including back to its intended target tissue or site.

Local complement activation: As used herein, the term "local complement activation" refers to complement activation that occurs outside the vascular system.

MicroRNA (miRNA): As used herein, the term "microRNA" or "miRNA" refers to a small non-coding RNA molecule that can function in transcriptional and/or post-transcriptional regulation of target gene expression. The terms encompass a mature miRNA sequence or a precursor miRNA sequence, including a primary transcript (pri-miRNA) and a stem-loop precursor (pre-miRNA). The biogenesis of a naturally occurring miRNA initiates in the nucleus by RNA polymerase II transcription, generating a primary transcript (pri-miRNA). The primary transcript is cleaved by Drosha ribonuclease III enzyme to produce an approximately 70 nt stem-loop precursor miRNA (pre-miRNA). The pre-miRNA is then actively exported to the cytoplasm where it is cleaved by Dicer ribonuclease to form the mature miRNA, which includes an "antisense strand" or "guide strand" (that includes a region that is substantially complementary to a target sequence) and a "sense strand" or "passenger strand" (that includes a region that is substantially complementary to a region of the antisense strand). Those of ordinary skill in the art will appreciate that a guide strand may be perfectly complementary to a target region of a target RNA or may have less than perfect complementarity to a target region of a target RNA. The guide strand of this miRNA is incorporated into an RNA-induced silencing complex (RISC) that recognizes target mRNAs through base pairing with the miRNA, and commonly results in translational inhibition or destabilization of the target mRNA. As is understood in the field, for naturally occurring miRNAs, target mRNA recognition occurs through imperfect base pairing with the mRNA. In some embodiments, an miRNA is synthetic or engineered, and target mRNA recognition occurs through perfect base pairing with the mRNA. Typically, the target mRNA contains a sequence complementary to a "seed" sequence of the miRNA, which usually corresponds to nucleotides 2-8 of the miRNA. Information concerning miRNAs and associated pri-miRNA and pre-miRNA sequences is available in miRNA databases such as miRBase (Griffiths-Jones et al. 2008 Nucl Acids Res 36, (Database Issue: D154-D158) and the NCBI human genome database.

Operably linked: As used herein, the term "operably linked" refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Recombinant: As used herein, the term "recombinant" is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

RNA interference: As used herein, the term "RNA interference" or "RNAi" refers generally to a process in which a double-stranded RNA molecule or a short hairpin RNA molecule reduces or inhibits expression of a nucleic acid sequence with which the double-stranded or short hairpin RNA molecule shares substantial or total homology. Without wishing to be bound by any theory, it is believed that, in nature, the RNAi pathway is initiated by a Type III endonuclease known as Dicer, which cleaves long double-stranded RNA (dsRNA) into double-stranded fragments typically of 21-23 base pairs with 2-base 3' overhangs (although variations in length and overhangs are also contemplated), referred to as "short interfering RNAs" ("siRNAs"). Such siRNAs comprise two single-stranded RNAs (ssRNAs), with an "antisense strand" or "guide strand" that includes a region that is substantially complementary to a target sequence, and a "sense strand" or "passenger strand" that includes a region that is substantially complementary to a region of the antisense strand. Those of ordinary skill in the art will appreciate that a guide strand may be perfectly complementary to a target region of a target RNA or may have less than perfect complementarity to a target region of a target RNA.

Sequential administration: As used herein, the term "Sequential administration" of two or more agents refers to administration of two or more agents to a subject such that the agents are not present together in the subject's body, or at a relevant site of activity in the body, at greater than non-negligible concentrations. Administration of the agents may, but need not, alternate. Each agent may be administered multiple times.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Systemic: As used herein, the term "systemic" in reference to complement components, refers to complement proteins that are synthesized by liver hepatocytes and enter the bloodstream, or are synthesized by circulating macrophages or monocytes and secreted into the bloodstream.

Systemic complement activation: As used herein, the term "systemic complement activation" is complement activation that occurs in the blood, plasma, or serum and/or involves activation of systemic complement proteins at many locations throughout the body, affecting many body tissues, systems, or organs.

Systemic administration: As used herein, the term "systemic administration" and like terms are used herein consistently with their usage in the art to refer to administration of an agent such that the agent becomes widely distributed in the body in significant amounts and has a biological effect, e.g., its desired effect, in the blood and/or reaches its desired site of action via the vascular system. Typical systemic routes of administration include administration by (i) introducing the agent directly into the vascular system or (ii) subcutaneous, oral, pulmonary, or intramuscular administration wherein the agent is absorbed, enters the vascular system, and is carried to one or more desired site(s) of action via the blood.

Target gene: A "target gene", as used herein, refers to a gene whose expression is to be modulated, e.g., inhibited. As used herein, the term "target RNA" refers to an RNA to be degraded or translationally repressed or otherwise inhibited using one or more miRNAs. A target RNA may also be referred to as a target sequence or target transcript. The RNA may be a primary RNA transcript transcribed from the target gene (e.g., a pre-mRNA) or a processed transcript, e.g., mRNA encoding a polypeptide. As used herein, the term "target portion" or "target region" refers to a contiguous portion of the nucleotide sequence of a target RNA. In some embodiments, a target portion an mRNA is at least long enough to serve as a substrate for RNA interference (RNAi)-mediated cleavage within that portion in the presence of a suitable miRNA or siRNA. A target portion may be from about 8-36 nucleotides in length, e.g., about 10-20 or about 15-30 nucleotides in length. A target portion length may have specific value or subrange within the afore-mentioned ranges. For example, in certain embodiments a target portion may be between about 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or signs of the disease, disorder, and/or condition. In some embodiments, a therapeutically effective amount is administered in a single dose; in some embodiments, multiple unit doses are required to deliver a therapeutically effective amount.

Treating: As used herein, the term "treating" refers to providing treatment, i.e, providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur for at least a period of time in at least some individuals. Treating can include administering an agent to the subject following the development of one or more symptoms or manifestations indicative of a complement-mediated condition, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of the disclosure can be administered to a subject who has developed a complement-mediated disorder or is at increased risk of developing such a disorder relative to a member of the general population. A composition of the disclosure can be administered prophylactically, i.e., before development of any symptom or manifestation of the condition. Typically in this case the subject will be at risk of developing the condition.

Nucleic acid: The term "nucleic acid" includes any nucleotides, analogs thereof, and polymers thereof. The term "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotide linkages"). The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. In some embodiments, the prefix poly- refers to a nucleic acid containing 2 to about 10,000, 2 to about 50,000, or 2 to about 100,000 nucleotide monomer units. In some embodiments, the prefix oligo- refers to a nucleic acid containing 2 to about 200 nucleotide monomer units.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

I. Complement System

To facilitate understanding of the disclosure, and without intending to limit the invention in any way, this section provides an overview of complement and its pathways of activation. Further details are found, e.g., in Kuby Immunology, 6th ed., 2006; Paul, W. E., Fundamental Immunology, Lippincott Williams & Wilkins; 6th ed., 2008; and Walport M J., Complement. First of two parts. N Engl J Med., 344(14):1058-66, 2001.

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils. It will be understood that the names "C2a" and "C2b" used initially were subsequently reversed in the scientific literature.

The alternative pathway is initiated by and amplified at, e.g., microbial surfaces and various complex polysaccharides. In this pathway, hydrolysis of C3 to $C3(H_2O)$, which occurs spontaneously at a low level, leads to binding of factor B, which is cleaved by factor D, generating a fluid phase C3 convertase that activates complement by cleaving C3 into C3a and C3b. C3b binds to targets such as cell surfaces and forms a complex with factor B, which is later cleaved by factor D, resulting in a C3 convertase. Surface-bound C3 convertases cleave and activate additional C3 molecules, resulting in rapid C3b deposition in close proximity to the site of activation and leading to formation of additional C3 convertase, which in turn generates additional C3b. This process results in a cycle of C3 cleavage and C3 convertase formation that significantly amplifies the response. Cleavage of C3 and binding of another molecule of C3b to the C3 convertase gives rise to a C5 convertase. C3 and C5 convertases of this pathway are regulated by cellular molecules CR1, DAF, MCP, CD59, and fH. The mode of action of these proteins involves either decay accelerating activity (i.e., ability to dissociate convertases), ability to serve as cofactors in the degradation of C3b or C4b by factor I, or both. Normally the presence of complement regulatory proteins on cell surfaces prevents significant complement activation from occurring thereon.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above.

Complement activity is regulated by various mammalian proteins referred to as complement control proteins (CCPs) or regulators of complement activation (RCA) proteins (U.S. Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4 bp). CD59 is a membrane-bound complement regulatory protein unrelated structurally to the CCPs. Complement regulatory proteins normally serve to limit complement activation that might otherwise occur on cells and tissues of the mammalian, e.g., human host. Thus, "self" cells are normally protected from the deleterious effects that would otherwise ensue were complement activation to proceed on these cells. Deficiencies or defects in complement regulatory protein(s) are involved in the pathogenesis of a variety of complement-mediated disorders, e.g., as discussed herein.

II. MicroRNAs

The disclosure includes compositions and methods related to one or more nucleotide sequences that are, comprise, or encode, microRNAs. MicroRNAs (miRNAs) are a highly conserved class of small RNA molecules that are transcribed from DNA in the genomes of plants and animals, but are not translated into protein. Naturally occurring miRNAs are first transcribed as long hairpin-containing primary transcripts (pri-miRNAs). The primary transcript is cleaved by Drosha ribonuclease III enzyme to produce an approximately 70 nt stem-loop precursor miRNA (pre-miRNA), which includes an "antisense strand" or "guide strand" (that includes a region that is substantially complementary to a target sequence) and a "sense strand" or "passenger strand" (that includes a region that is substantially complementary to a region of the antisense strand). The pre-miRNA is then actively exported to the cytoplasm where it is cleaved by Dicer ribonuclease to form the mature miRNA. Processed microRNAs are incorporated into the RNA-induced silencing complex (RISC) to form mature gene-silencing complexes, which induce target mRNA degradation and/or translation repression. The number of miRNA sequences identified to date is large and growing, illustrative examples of which can be found, for example, in: "miRBase: microRIVA sequences, targets and gene nomenclature" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111.

In some embodiments, miRNAs can be synthesized and locally or systemically administered to a subject, e.g., for therapeutic purposes. miRNAs can be designed and/or synthesized as mature molecules or precursors (e.g., pri- or pre-miRNAs). In some embodiments, a pre-miRNA includes a guide strand and a passenger strand that are the same length (e.g., about 15, 16, 17, 18, 19, 20, 21, 22, 23, 24, or 25 nucleotides). In some embodiments, a pre-miRNA includes a guide strand and a passenger strand that are different lengths (e.g., one strand is about 19 nucleotides, and the other is about 21 nucleotides). In some embodiments, an miRNA can target the coding region, the 5' untranslated region, and/or 3' untranslated region, of endogenous mRNA. In some embodiments, an miRNA comprises a guide strand comprising a nucleotide sequence having sufficient sequence complementary with an endogenous mRNA of a subject to hybridize with and inhibit expression of the endogenous mRNA.

In some embodiments, an miRNA comprises a nucleic acid strand that is complementary to a target portion of a C3 transcript, e.g., C3 mRNA (e.g., complementary to a nucleotide sequence that is at least 90%, 91%, 92%, 93%, 94%, 95%, 96%, 97%, 98%, 99%, or 100% identical to a portion of SEQ ID NO:75). The target portion may be 15-30 nucleotides long, e.g., 15, 16, 17, 18, 19, 20, 21, 22, 23, 24, 25, 26, 27, 28, 29, or 30 nucleotides long, although shorter and longer target portions are also contemplated. Human C3 is of particular interest herein. In some embodiments, the miRNA comprises a nucleic acid strand that comprises a region that is perfectly complementary to at least 6, 7, 8, 9, 10, 11, 12, 13 14, 15, 16, 17, 18, 19, 20, 21, 22, 23, 24, 25, 26, 27, 28, 29, or 30 consecutive nucleotides of SEQ ID NO:75 (e.g., within nucleotides 617-637, 753-773, 1740-1760, 2811-2831, 2835-2855, 3541-3561, 3849-3869, 4125-4145, 4309-4329, and/or 4394-4414 of SEQ ID NO:75). The amino acid and nucleotide sequences of human C3 are known in the art and can be found in publicly available databases, for example, the National Center for Biotechnology Information (NCBI) Reference Sequence (RefSeq) database, where they are listed under RefSeq accession numbers NP_000055 (accession.version number NP_000055.2) and NM_000064 (accession.version number NM_000064.4), respectively (where "amino acid sequence" refers to the sequence of the C3 polypeptide and "nucleotide sequence" in this context refers to the C3 mRNA sequence as represented in genomic DNA, it being understood that the actual mRNA nucleotide sequence contains U rather than T). One of ordinary skill in the art will appreciate that the afore-mentioned sequences are for the complement C3 pre-proprotein, which includes a signal sequence that is cleaved off and is therefore not present in the mature protein. The human C3 gene has been assigned NCBI Gene ID: 718, and the genomic C3 sequence has RefSeq accession number NG_009557 (accession.version number NG_009557.1). The nucleotide sequence of human C3 mRNA is presented below (from RefSeq accession number NM_000064.3 with T replaced by U; AUG initiation codon underlined starting at position 94).

(SEQ ID NO: 75)
AGAUAAAAAGCCAGCUCCAGCAGGCGCUGCUCACUCCUCCCCAUCCUCU

CCCUCUGUCCCUCUGUCCCUCUGACCCUGCACUGUCCCAGCACC<u>AUG</u>GG

ACCCACCUCAGGUCCCAGCCUGCUGCUCCUGCUACUAACCCACCUCCCC

CUGGCUCUGGGGAGUCCCAUGUACUCUAUCAUCACCCCCAACAUCUUGC

GGCUGGAGAGCGAGGAGACCAUGGUGCUGGAGGCCCACGACGCGCAAGG

GGAUGUUCCAGUCACUGUUACUGUCCACGACUUCCCAGGCAAAAAACUA

GUGCUGUCCAGUGAGAAGACUGUGCUGACCCCUGCCACCAACCACAUGG

GCAACGUCACCUUCACGAUCCCAGCCAACAGGGAGUUCAAGUCAGAAAA

GGGGCGCAACAAGUUCGUGACCGUGCAGGCCACCUUCGGGACCCAAGUG

GUGGAGAAGGUGGUGCUGGUCAGCCUGCAGAGCGGGUACCUCUUCAUCC

AGACAGACAAGACCAUCUACACCCCUGGCUCCACAGUUCUCUAUCGGAU

CUUCACCGUCAACCACAAGCUGCUACCCGUGGGCCGGACGGUCAUGGUC

AACAUUGAGAACCCGGAAGGCAUCCCGGUCAAGCAGGACUCCUUGUCUU

CUCAGAACCAGCUUGGCGUCUUGCCCUUGUCUUGGGACAUUCCGGAACU

CGUCAACAUGGGCCAGUGGAAGAUCCGAGCCUACUAUGAAAACUCACCA

CAGCAGGUCUUCUCCACUGAGUUUGAGGUGAAGGAGUACGUGCUGCCCA

GUUUCGAGGUCAUAGUGGAGCCUACAGAGAAAUUCUACUACAUCUAUAA

CGAGAAGGGCCUGGAGGUCACCAUCACCGCCAGGUUCCUCUACGGGAAG

AAAGUGGAGGGAACUGCCUUUGUCAUCUUCGGGAUCCAGGAUGGCGAAC
AGAGGAUUUCCCUGCCUGAAUCCCUCAAGCGCAUUCCGAUUGAGGAUGG
CUCGGGGAGGUUGUGCUGAGCCGGAAGGUACUGCUGGACGGGGUGCAG
AACCCCCGAGCAGAAGACCUGGUGGGGAAGUCUUUGUACGUGUCUGCCA
CCGUCAUCUUGCACUCAGGCAGUGACAUGGUGCAGGCAGAGCGCAGCGG
GAUCCCCAUCGUGACCUCUCCCUACCAGAUCCACUUCACCAAGACACCC
AAGUACUUCAAACCAGGAAUGCCCUUUGACCUCAUGGUGUUCGUGACGA
ACCCUGAUGGCUCUCCAGCCUACCGAGUCCCCGUGGCAGUCCAGGGCGA
GGACACUGUGCAGUCUCUAACCCAGGGAGAUGGCGUGGCCAAACUCAGC
AUCAACACACACCCCAGCCAGAAGCCCUUGAGCAUCACGGUGCGCACGA
AGAAGCAGGAGCUCUCGGAGGCAGAGCAGGCUACCAGGACCAUGCAGGC
UCUGCCCUACAGCACCGUGGGCAACUCCAACAAUUACCUGCAUCUCUCA
GUGCUACGUACAGAGCUCAGACCCGGGGAGACCCUCAACGUCAACUUCC
UCCUGCGAAUGGACCGCGCCCACGAGGCCAAGAUCCGCUACUACACCUA
CCUGAUCAUGAACAAGGGCAGGCUGUUGAAGGCGGGACGCCAGGUGCGA
GAGCCCGGCCAGGACCUGGUGGUGCUGCCCCUGUCCAUCACCACCGACU
UCAUCCCUUCCUUCCGCCUGGUGGCGUACUACACGCUGAUCGGUGCCAG
CGGCCAGAGGGAGGUGGUGGCCGACUCCGUGUGGGUGGACGUCAAGGAC
UCCUGCGUGGGCUCGCUGGUGGUAAAAAGCGGCCAGUCAGAAGACCGGC
AGCCUGUACCUGGGCAGCAGAUGACCCUGAAGAUAGAGGGUGACCACGG
GGCCCGGGUGGUACUGGUGGCCGUGGACAAGGGCGUGUUCGUGCUGAAU
AAGAAGAACAAACUGACGCAGAGUAAGAUCUGGGACGUGGUGGAGAAGG
CAGACAUCGGCUGCACCCCGGGCAGUGGGAAGGAUUACGCCGGUGUCUU
CUCCGACGCAGGGCUGACCUUCACGAGCAGCAGUGGCCAGCAGACCGCC
CAGAGGGCAGAACUUCAGUGCCCGCAGCCAGCCGCCCGCCGACGCCGUU
CCGUGCAGCUCACGGAGAAGCGAAUGGACAAAGUCGGCAAGUACCCCAA
GGAGCUGCGCAAGUGCUGCGAGGACGGCAUGCGGGAGAACCCCAUGAGG
UUCUCGUGCCAGCGCCGGACCCGUUUCAUCUCCCUGGGCGAGGCGUGCA
AGAAGGUCUUCCUGGACUGCUGCAACUACAUCACAGAGCUGCGGCGGCA
GCACGCGCGGGCCAGCCACCUGGGCCUGGCCAGGAGUAACCUGGAUGAG
GACAUCAUUGCAGAAGAGAACAUCGUUUCCCGAAGUGAGUUCCCAGAGA
GCUGGCUGUGGAACGUUGAGGACUUGAAAGAGCCACCGAAAAAUGGAAU
CUCUACGAAGCUCAUGAAUAUAUUUUUGAAAGACUCCAUCACCACGUGG
GAGAUUCUGGCUGUGAGCAUGUCGGACAAGAAAGGGAUCUGUGUGGCAG
ACCCCUUCGAGGUCACAGUAAUGCAGGACUUCUUCAUCGACCUGCGGCU
ACCCUACUCUGUUGUUCGAAACGAGCAGGUGGAAAUCCGAGCCGUUCUC
UACAAUUACCGGCAGAACCAAGAGCUCAAGGUGAGGGUGGAACUACUCC
ACAAUCCAGCCUUCUGCAGCCUGGCCACCACCAAGAGGCGUCACCAGCA
GACCGUAACCAUCCCCCCCAAGUCCUCGUUGUCCGUUCCAUAUGUCAUC
GUGCCGCUAAAGACCGGCCUGCAGGAAGUGGAAGUCAAGGCUGCUGUCU
ACCAUCAUUUCAUCAGUGACGGUGUCAGGAAGUCCCUGAAGGUCGUGCC

GGAAGGAAUCAGAAUGAACAAAACUGUGGCUGUUCGCACCCUGGAUCCA
GAACGCCUGGGCCGUGAAGGAGUGCAGAAAGAGGACAUCCCACCUGCAG
ACCUCAGUGACCAAGUCCCGGACACCGAGUCUGAGACCAGAAUUCUCCU
GCAAGGGACCCCAGUGGCCAGAUGACAGAGGAUGCCGUCGACGCGGAA
CGGCUGAAGCACCUCAUUGUGACCCCCUCGGGCUGCGGGGAACAGAACA
UGAUCGGCAUGACGCCCACGGUCAUCGCUGUGCAUUACCUGGAUGAAAC
GGAGCAGUGGGAGAAGUUCGGCCUAGAGAAGCGGCAGGGGGCCUUGGAG
CUCAUCAAGAAGGGGUACACCCAGCAGCUGGCCUUCAGACAACCCAGCU
CUGCCUUUGCGGCCUUCGUGAAACGGGCACCCAGCACCUGGCUGACCGC
CUACGUGGUCAAGGUCUUCUCUCUGGCUGUCAACCUCAUCGCCAUCGAC
UCCCAAGUCCUCUGCGGGGCUGUUAAAUGGCUGAUCCUGGAGAAGCAGA
AGCCCGACGGGGUCUUCCAGGAGGAUGCGCCCGUGAUACACCAAGAAAU
GAUUGGUGGAUUACGGAACAACAACGAGAAAGACAUGGCCCUCACGGCC
UUUGUUCUCAUCUCGCUGCAGGAGGCUAAAGAUAUUUGCGAGGAGCAGG
UCAACAGCCUGCCAGGCAGCAUCACUAAAGCAGGAGACUUCCUUGAAGC
CAACUACAUGAACCUACAGAGAUCCUACACUGUGGCCAUUGCUGGCUAU
GCUCUGGCCCAGAUGGGCAGGCUGAAGGGGCCUCUUCUUAACAAAUUUC
UGACCACAGCCAAAGAUAAGAACCGCUGGGAGGACCCUGGUAAGCAGCU
CUACAACGUGGAGGCCACAUCCUAUGCCCUCUUGGCCCUACUGCAGCUA
AAAGACUUUGACUUUGUGCCUCCCGUCGUGCGUUGGCUCAAUGAACAGA
GAUACUACGGUGGUGGCUAUGGCUCUACCCAGGCCACCUUCAUGGUGUU
CCAAGCCUUGGCUCAAUACCAAAAGGACGCCCCUGACCACCAGGAACUG
AACCUUGAUGUGUCCUCCAACUGCCCAGCCGCAGCUCCAAGAUCACCC
ACCGUAUCCACUGGGAAUCUGCCAGCCUCCUGCGAUCAGAAGAGACCAA
GGAAAAUGAGGGUUUCACAGUCACAGCUGAAGGAAAAGGCCAAGGCACC
UUGUCGGUGGUGACAAUGUACCAUGCUAAGGCCAAAGAUCAACUCACCU
GUAAUAAAUUCGACCUCAAGGUCACCAUAAAACCAGCACCGGAAACAGA
AAAGAGGCCUCAGGAUGCCAAGAACACUAUGAUCCUUGAGAUCUGUACC
AGGUACCGGGGAGACCAGGAUGCCACUAUGUCUAUAUUGGACAUAUCCA
UGAUGACUGGCUUUGCUCCAGACACAGAUGACCUGAAGCAGCUGGCCAA
UGGUGUUGACAGAUACAUCUCCAAGUAUGAGCUGGACAAAGCCUUCUCC
GAUAGGAACACCCUCAUCAUCUACCUGGACAAGGUCUCACACUCUGAGG
AUGACUGCUAGCUUUCAAAGUUCACCAAUACUUUAAUGUAGAGCUUAU
CCAGCCUGGAGCAGUCAAGGUCUACGCCUAUUACAACCUGGAGGAAAGC
UGUACCGGUUCUACCAUCCGGAAAAGGAGGAUGGAAAGCUGAACAAGC
UCUGCCGUGAUGAACUGUGCCGCUGUGCUGAGGAGAAUUGCUUCAUACA
AAAGUCGGAUGACAAGGUCACCCUGGAAGAACGGCUGGACAAGGCCUGU
GAGCCAGGAGUGGACUAUGUGUACAAGACCCGACUGGUCAAGGUUCAGC
UGUCCAAUGACUUUGACGAGUACAUCAUGGCCAUUGAGCAGACCAUCAA
GUCAGGCUCGGAUGAGGUGCAGGUUGGACAGCAGCGCACGUUCAUCAGC

-continued

CCCAUCAAGUGCAGAGAAGCCCUGAAGCUGGAGGAGAAGAAACACUACC

UCAUGUGGGGUCUCUCCUCCGAUUUCUGGGGAGAGAAGCCCAACCUCAG

CUACAUCAUCGGGAAGGACACUUGGGUGGAGCACUGGCCCGAGGAGGAC

GAAUGCCAAGACGAAGAGAACCAGAAACAAUGCCAGGACCUCGGCGCCU

UCACCGAGAGCAUGGUUGUCUUUGGGUGCCCCAACUGACCACACCCCA

UUCCCCCACUCCAGAUAAAGCUUCAGUUAUAUCUC

In some embodiments an miRNA is capable of inhibiting expression of C3 of one or more non-human species, e.g., a non-human primate C3, e.g., *Macaca fascicularis* C3, in addition to human C3. The *Macaca fascicularis* C3 gene has been assigned NCBI Gene ID: 102131458 and the predicted amino acid and nucleotide sequence of *Macaca fascicularis* C3 are listed under NCBI RefSeq accession numbers XP_005587776.1 and XM_005587719.2, respectively. In some embodiments, an miRNA is complementary to a target portion that is identical in the human and *Macaca fascicularis* C3 transcripts. In some embodiments, an miRNA is complementary to a target portion of a human C3 transcript that differs by 1, 2, or 3 nucleotides from a sequence in a *Macaca fascicularis* C3 transcript. It will be appreciated that an miRNA that inhibits expression of human C3 may also inhibit expression of non-primate C3, e.g., rat or mouse C3, particularly if conserved regions of C3 transcript are targeted.

In some embodiments, an miRNA comprises a mature guide strand having a nucleotide sequence that is at least 90%, 91%, 92%, 93%, 94%, 95%, 96%, 97%, 98%, 99%, or 100% identical to any one of SEQ ID NOs:76-85 (or a portion thereof) listed in Table 1. In some embodiments, the portion is 15, 16, 17, 18, 19, or 20 nucleotides long. In some embodiments, an miRNA comprises a mature guide strand having a nucleotide sequence that is 100% identical to nucleotides 2-8 of any one of SEQ ID NOs: 76-85.

TABLE 1

| Sequence Number | miR Sequence |
|---|---|
| SEQ ID NO: 76 | 5'-AAGACAAGGAGUCCUGCUUGA-3' |
| SEQ ID NO: 77 | 5'-UACUCCUUCACCUCAAACUCA-3' |
| SEQ ID NO: 78 | 5'-UUGACGUCCACCCACACGGAG-3' |
| SEQ ID NO: 79 | 5'-UUGACUUCCACUUCCUGCAGG-3' |
| SEQ ID NO: 80 | 5'-AUGAAAUGAUGGUAGACAGCA-3' |
| SEQ ID NO: 81 | 5'-AUCUUUAGCCUCCUGCAGCGA-3' |
| SEQ ID NO: 82 | 5'-UGUUCAUUGAGCCAACGCACG-3' |
| SEQ ID NO: 83 | 5'-UUAGCAUGGUACAUUGUCACC-3' |
| SEQ ID NO: 84 | 5'-AGCAAAGCCAGUCAUCAUGGA-3' |
| SEQ ID NO: 85 | 5'-UAUCGGAGAAGGCUUUGUCCA-3' |

III. siRNAs

RNA interference (RNAi) is a process of sequence-specific post-transcriptional gene silencing by which, e.g., double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing can be mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). RNAi can involve the use of, e.g., siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296: 550-553; Paul et al., Nature Biotechnol. 2002; 20:505-508).

The disclosure includes siRNA molecules targeting C3 transcript, e.g., C3 mRNA (SEQ ID NO:75). In some embodiments, an siRNA molecule targets nucleotides 617-637, 753-773, 1740-1760, 2811-2831, 2835-2855, 3541-3561, 3849-3869, 4125-4145, 4309-4329, and/or 4394-4414 of SEQ ID NO:75, or a portion thereof. In some embodiments, an siRNA molecule comprises (i) a nucleotide sequence that is at least 90%, 91%, 92%, 93%, 94%, 95%, 96%, 97%, 98%, 99%, or 100% identical to any one of SEQ ID NOs:76-85 (or a portion thereof) and/or (ii) a nucleotide sequence that is complementary to a nucleotide sequence that is at least 90%, 91%, 92%, 93%, 94%, 95%, 96%, 97%, 98%, 99%, or 100% identical to any one of SEQ ID NOs:76-85 (or a portion thereof).

In some embodiments, siRNAs of the disclosure are double stranded nucleic acid duplexes (of, e.g., 15, 16, 17, 18, 19, 20, 21, 22, 23, 24, 25, 26, or 27 base pairs) comprising annealed complementary single stranded nucleic acid molecules. In some embodiments, the siRNAs are short dsRNAs comprising annealed complementary single strand RNAs. In some embodiments, the siRNAs comprise an annealed RNA:DNA duplex, wherein the sense strand of the duplex is a DNA molecule and the antisense strand of the duplex is a RNA molecule.

In some embodiments, duplexed siRNAs comprise a 2 or 3 nucleotide 3' overhang on each strand of the duplex. In some embodiments, siRNAs comprise 5'-phosphate and 3'-hydroxyl groups.

Modifications

In some embodiments, an inhibitory RNA (e.g., siRNA) of the disclosure includes one or more natural nucleobase and/or one or more modified nucleobases derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Exemplary modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313.

Modified nucleobases also include expanded-size nucleobases in which one or more aryl rings, such as phenyl rings, have been added. Nucleic base replacements described in the Glen Research catalog (www.glenresearch.com); Krueger A T et al, Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for siRNA molecules described herein. Modified nucleobases also encompass structures that are not considered nucleobases but are other moieties such as, but not limited to, corrin- or porphyrin-derived rings. Porphyrin-derived base replacements have been described in Morales-Rojas, H and Kool, ET, Org. Lett., 2002, 4, 4377-4380.

In some embodiments, modified nucleobases are of any one of the following structures, optionally substituted:

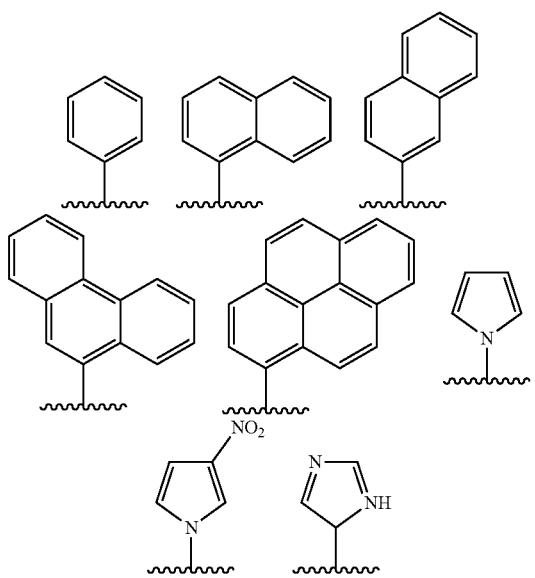

In some embodiments, a modified nucleobase is fluorescent. Exemplary such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

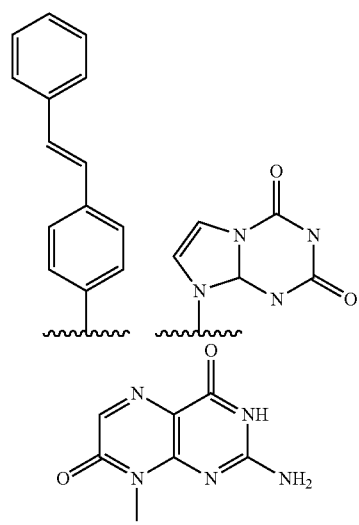

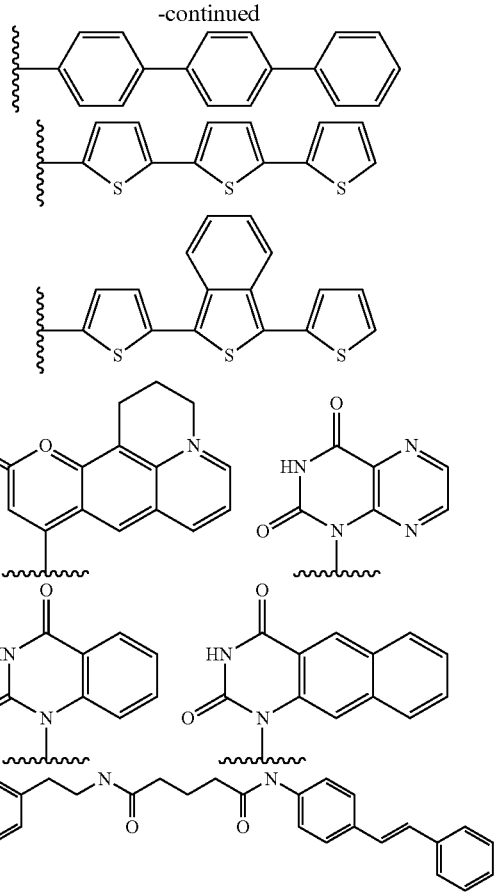

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, an siRNA described herein includes nucleosides that incorporate modified nucleobases and/or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in U.S. Publ. No. 20070287831. In some embodiments, a nucleobase or modified nucleobase is 5-bromouracil, 5-iodouracil, or 2,6-diaminopurine. In some embodiments, a nucleobase or modified nucleobase is modified by substitution with a fluorescent moiety.

Methods of preparing modified nucleobases are described in, e.g., U.S. Pat. Nos. 3,687,808; 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088.

In some embodiments, an siRNA described herein includes one or more modified nucleotides wherein a phosphate group or linkage phosphorus in the nucleotides are linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context.

Other modified sugars can also be incorporated within an siRNA molecule. In some embodiments, a modified sugar contains one or more substituents at the 2' position including one of the following: —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. Examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —OCH$_2$CH$_2$OMe.

Modified sugars also include locked nucleic acids (LNAs). In some embodiments, the locked nucleic acid has the structure indicated below. A locked nucleic acid of the structure below is indicated, wherein Ba represents a nucleobase or modified nucleobase as described herein, and wherein $R^{2S}$ is —OCH$_2$C4'-

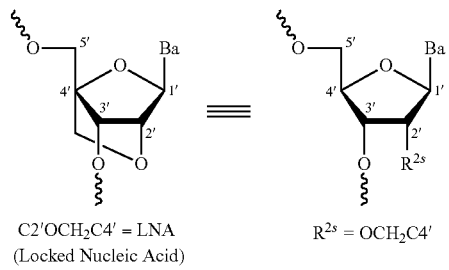

C2'OCH$_2$C4' = LNA
(Locked Nucleic Acid)

$R^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xeno-nucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar (see, e.g., U.S. Pat. Nos. 4,981,957; 5,118,800; 5,319,080; and 5,359,044). Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

Non-limiting examples of modified sugars include glycerol, which form glycerol nucleic acid (GNA) analogues. One example of a GNA analogue is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603. Another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413. Additional non-limiting examples of modified sugars include hexopyranosyl (6' to 4'), pentopyranosyl (4' to 2'), pentopyranosyl (4' to 3'), or tetrofuranosyl (3' to 2') sugars.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in Chemical Synthesis: Gnosis to Prognosis, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310); PCT Publication No. WO2012/030683.

According to certain embodiments various nucleotide modifications or nucleotide modification patterns may be used selectively in either the sense or antisense strand of an inhibitory RNA (e.g., siRNA) described herein. For example, in some embodiments one may utilize unmodified ribonucleotides in the antisense strand (at least within the duplex portion thereof) while employing modified nucleotides and/or modified or unmodified deoxyribonucleotides at some or all positions in the sense strand. In some embodiments, particular patterns of modifications are employed throughout part or all of either or both strands of an siRNA. Nucleotide modifications may occur in any of a variety of patterns. For example, an alternating pattern may be used. For example, the antisense, sense strand, or both, may have 2'-O-methyl or 2'-fluoro modifications on every other nucleotide. In some embodiments, an inhibitory RNA (e.g, siRNA) comprises a sense and/or antisense strand with at least one unmodified nucleotide.

In some embodiments, a sense and/or antisense strand comprises one or more motifs of three identical modifications on three consecutive nucleotides. For example, in some embodiments a double-stranded siRNA comprises one or more motifs of three identical modifications on three consecutive nucleotides in a sense strand, antisense strand, or both. In some embodiments such a motif may occur at or near the cleavage site in either or both strands. Examples of such motifs are described in US Pat. App. Pubs. 20150197746, 20150247143, and 20160298124.

In some embodiments, an inhibitory RNA (e.g., siRNA) is a bluntmer of 19 nucleotides in length, wherein the sense strand contains at least one motif of three 2'-F modifications on three consecutive nucleotides at positions 7, 8, 9 from the 5'end, and where the antisense strand contains at least one motif of three 2'-O-methyl modifications on three consecutive nucleotides at positions 11, 12, 13 from the 5'end. In some embodiments, an inhibitory RNA (e.g., siRNA) is a double ended bluntmer of 20 nucleotides in length, wherein the sense strand contains at least one motif of three 2'-F modifications on three consecutive nucleotides at positions 8, 9, 10 from the 5'end, and where the antisense strand contains at least one motif of three 2'-O-methyl modifications on three consecutive nucleotides at positions 11, 12, 13 from the 5'end. In some embodiments an inhibitory RNA (e.g., siRNA) is a double ended bluntmer of 21 nucleotides in length, wherein the sense strand contains at least one motif of three 2'-F modifications on three consecutive nucleotides at positions 9, 10, 11 from the 5'end, and where the antisense strand contains at least one motif of three 2'-O-methyl modifications on three consecutive nucleotides at positions 11, 12, 13 from the 5'end.

In some embodiments, an inhibitory RNA (e.g., siRNA) comprises a 19 nucleotide sense strand and a 21 nucleotide antisense strand, wherein the sense strand contains at least one motif of three 2'-F modifications on three consecutive nucleotides at positions 7, 8, 9 from the 5'end; the antisense strand contains at least one motif of three 2'-O-methyl modifications on three consecutive nucleotides at positions 11, 12, 13 from the 5'end, wherein one end of the inhibitory RNA (e.g., siRNA) is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In some embodiments, the inhibitory RNA (e.g., siRNA) additionally has two phosphorothioate internucleotide linkages between the terminal three nucleotides at both the 5'-end of the sense strand and at the 5'-end of the antisense strand. In some embodiments, every nucleotide in the sense strand and the antisense strand of an inhibitory RNA (e.g., siRNA), including the nucleotides that are part of the motifs are modified nucleotides. In some embodiments each residue is independently modified with a 2'-O-methyl or 3'-fluoro, e.g., in an alternating motif.

In some embodiments, an inhibitory RNA (e.g., siRNA) comprises a 19 nucleotide sense strand and a 21 nucleotide antisense strand, wherein (i) the sense strand contains 2'-F modifications at positions 3, 7, 8, 9, 12, and 17 from the 5'end; (ii) the sense strand contains 2'-O-methyl modifications at positions 1, 2, 4, 5, 6, 10, 11, 13, 14, 15, 16, 18, and 19 from the 5'end; (iii) the antisense strand contains 2'-F modifications at positions 2 and 14 from the 5'end; and (iv) the antisense strand contains 2'-O-methyl modifications at positions 1, 3, 4, 5, 6, 7, 8, 9, 10, 11, 12, 13, 15, 16, 17, 18, 19, 20, and 21 from the 5'end; wherein one end of the inhibitory RNA (e.g., siRNA) is blunt, while the other end comprises a 2 nucleotide overhang at the 3'-end of the antisense strand. In some embodiments, the inhibitory RNA (e.g., siRNA) includes an antisense strand comprising two phosphorothioate internucleotide linkages between the terminal three nucleotides at the 3' end, wherein two of the three nucleotides are the overhang nucleotides, and the third nucleotide is a paired nucleotide next to the overhang nucleotide. In some embodiments, the an inhibitory RNA (e.g., siRNA) additionally has two phosphorothioate internucleotide linkages between the terminal three nucleotides at both the 5'-end of the sense strand and at the 5'-end of the antisense strand.

In some embodiments, every nucleotide in the sense strand and antisense strand of an inhibitory RNA (e.g., siRNA), including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers;

modification or replacement of a naturally occurring base; and replacement or modification of the ribose-phosphate backbone.

In some embodiments at least 50%, 60%, 70%, 80%, 90%, or more, e.g., 100% of the residues of the sense strand and antisense strand is independently modified with LNA, CRN, cET, UNA, HNA (1,5-anhydrohexitol nucleic acid), CeNA (cyclohexenyl nucleic acid—a DNA mimic in which the deoxyribose is replaced by a six-membered cyclohexene ring), 2'-methoxyethyl, 2'-O-methyl, 2'-O-allyl, 2'-C-allyl, 2'-deoxy, 2'-hydroxyl, or 2'-fluoro. The strands can contain more than one modification. In some embodiments at least 50%, 60%, 70%, 80%, 90%, or more, e.g., 100% of the residues of the sense strand and antisense strand is independently modified with 2'-O-methyl or 2'-fluoro. In some embodiments at least two different modifications are present on the sense strand and antisense strand. Those two modifications may be the 2'-O-methyl or 2'-fluoro modifications, or others.

In some embodiments, the sense and/or antisense strand comprises modifications of an alternating pattern. The term "alternating motif" as used herein refers to a motif having one or more modifications, each modification occurring on alternating groups of one or more nucleotides of one strand. For example, an alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAAB-BAABB . . . ," "AABAABAABAAB . . . ," "AAABAAA-BAAAB . . . ". "AAABBBAAABBB . . . ," or "ABCAB-CABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In some embodiments, an inhibitory RNA (e.g., siRNA) comprises the modification pattern for the alternating motif on the sense strand that is shifted relative to the modification pattern for the alternating motif on the antisense strand. The shift may be such that the modified group of nucleotides of the sense strand corresponds to a differently modified group of nucleotides of the antisense strand and vice versa. For example, when paired with the antisense strand in the dsRNA duplex, the alternating motif in the sense strand may start with "ABABAB" from 5'-3' of the strand and the alternating motif in the antisense strand may start with "BAB ABA" from 5'-3 of the strand, within the duplex portion. As another example, the alternating motif in the sense strand may start with "AABBAABB" from 5'-3' of the strand and the alternating motif in the antisense strand may start with "BBAABBAA" from 5'-3' of the strand, within the duplex portion, so that there is a complete or partial shift of the modification patterns between the sense strand and the antisense strand.

In some embodiments, an inhibitory RNA (e.g., siRNA) comprises the pattern of the alternating motif of 2'-O-methyl modification and 2'-F modification on the sense strand has a shift relative to the pattern of the alternating motif of 2'-O-methyl modification and 2'-F modification on the antisense strand, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

In some embodiments, one or more motifs of three identical modifications can be introduced on three consecutive nucleotides of the sense strand and/or antisense strand to interrupt the initial modification pattern present in the sense strand and/or antisense strand. In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . NaYYYNb . . . ," where "Y" represents the modification of the motif of three identical modifications on three consecutive nucleotide, and "Na" and "Nb" represent a modification to the nucleotide next to the motif "YYY" that is different than the modification of Y, and where Na and Nb can be the same or different modifications.

An inhibitory RNA (e.g., siRNA) may further comprise at least one phosphorothioate or methylphosphonate internucleotide linkage. In some embodiments, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In some embodiments, an inhibitory RNA (e.g., siRNA) comprises 6-8 phosphorothioate internucleotide linkages. In some embodiments, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In certain embodiments an inhibitory RNA (e.g., siRNA) may have any of the configurations and/or modification patterns described from p. 59 (line 20) to p. 65 (line 15) of WO/2015/089368, or corresponding paragraphs [0469]-[0537] of US Pat. App. Pub. No. 20160298124 or in the claims of either or both of said publications. For example, in some embodiments an inhibitory RNA (e.g., siRNA) comprises a sense strand and an antisense strand, wherein said sense strand is complementary to said antisense strand, wherein said antisense strand comprises a region complementary to part of an mRNA encoding C3 (e.g., a target region described herein), wherein each strand is about 14 to about 30 nucleotides in length, wherein said agent is represented by formula (III):

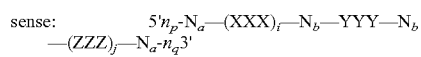

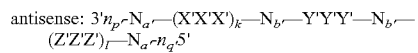

wherein: i, j, k, and l are each independently 0 or 1; p, p', q, and q' are each independently 0-6; each $N_a$ and $N_a'$ independently represents an oligonucleotide sequence comprising 0-25 nucleotides which are either modified or unmodified or combinations thereof, each sequence comprising at least two differently modified nucleotides; each $N_b$ and $N_b'$ independently represents an oligonucleotide sequence comprising 0-10 nucleotides which are either modified or unmodified or combinations thereof; each $n_p$, $n_p'$, $n_q$, and $n_q'$, each of which may or may not be present, independently represents an overhang nucleotide; XXX, YYY, ZZZ, X'X'X', Y'Y'Y', and Z'Z'Z' each independently represent one motif of three identical modifications on three consecutive nucleotides; modifications on $N_b$ differ from the modification on Y and modifications on $N_b'$ differ from the modification on Y'; and wherein the sense strand is conjugated to at least one ligand. In some embodiments i is 0; j is 0; i is 1; j is 1; both i and j are 0; or both i and j are 1. In some embodiments XXX is complementary to X'X'X', YYY is complementary to Y'Y'Y', and ZZZ is complementary to Z'Z'Z'. It should be understood that each X may comprise a different base, so long as each X comprises the same modification. For example, XXX could represent AGC where each nucleotide comprises a 2-F modification. Similarly, each X', each Y, each Y', each Z, and each Z may be different.

In some embodiments formula (III) is represented by formula (IIIa):

sense: 5'$n_p$-$N_a$—YYY—$N_a$-$n_q$3' antisense: 3'$n_p$-$N_a$—Y'Y'Y'—$N_a$-$n_q$5' or wherein formula (III) is represented by formula (IIIb):

sense: 5'$n_p$-$N_a$—YYY—$N_b$—ZZZ—$N_a$-$n_q$3' antisense:3'$n_p$-$N_a$—Y'Y'Y'—$N_b$—Z'Z'Z'—$N_a$-$n_q$5' wherein each $N_b$ and $N_b'$ independently represents an oligonucleotide sequence comprising 1-5 modified nucleotides; or wherein formula (III) is represented by formula (IIIc):

sense: 5'$n_p$-$N_a$—XXX—$N_b$—YYY—$N_a$-$n_q$3' antisense: 3'$n_p$-$N_a$—X'X'X'—$N_b$—Y'Y'Y'—$N_a$-$n_q$5' wherein each $N_b$ and $N_b'$ independently represents an oligonucleotide sequence comprising 1-5 modified nucleotides; or wherein formula (III) is represented by formula (IIId):

sense: 5'$n_p$-$N_a$—XXX—$N_b$—YYY—$N_b$—ZZZ—$N_a$-$n_q$3' antisense: 3'$n_p$-$N_a$—X'X'X'—$N_b$—Y'Y'Y'—$N_b$—Z'Z'Z'—$N_a$-$n_q$5 wherein each $N_b$ and $N_b'$ independently represents an oligonucleotide sequence comprising 1-5 modified nucleotides and each $N_a$ and $N_a'$ independently represents an oligonucleotide sequence comprising 2-10 modified nucleotides.

In some embodiments, the modifications on the nucleotides are selected from the group consisting of LNA, CRN, cET, UNA, HNA, CeNA, 2'-methoxyethyl, 2'-O-methyl, 2'-O-alkyl, 2'-O-allyl, 2'-C-allyl, 2'-fluoro, 2'-deoxy, 2'-hydroxyl, and combinations thereof.

In some embodiments, the modifications on the nucleotides are 2'-O-methyl or 2'-fluoro modifications. In some embodiments the ligand is one or more GalNAc derivatives attached through a bivalent or trivalent branched linker. In some embodiments the ligand is depicted in Formula XA, XB, or XC, or another GalNAc structure shown below.

In some embodiments the ligand is attached to the 3' end of the sense strand. In some embodiments the attachment is as depicted in Formula XD shown below.

In some embodiments, an inhibitory RNA (e.g., siRNA) further comprises at least one phosphorothioate or methylphosphonate internucleotide linkage.

In some embodiments p'>0; or p'=2.

In some embodiments q'=0, p=0, q=0, and p' overhang nucleotides are complementary to C3 mRNA. In some embodiments q'=0, p=0, q=0, and p' overhang nucleotides are non-complementary to C3 mRNA.

In some embodiments at least one $n_p'$ is linked to a neighboring nucleotide via a phosphorothioate linkage In some embodiments the ligand targets the nucleic acid molecule to hepatocytes. For example, in some embodiments the ligand binds to hepatocyte-specific asialoglycoprotein receptor (ASGPR), e.g., the ligand comprises a galactose derivative, e.g., GalNAc.

In some embodiments an inhibitory RNA (e.g., siRNA) is conjugated to or otherwise physically associated with one or more moieties that modulate, e.g., enhance, the activity, stability, cellular distribution, and/or cellular uptake of the inhibitory RNA (e.g., siRNA) and/or alter one or more physical properties of the inhibitory RNA (e.g., siRNA), such as charge or solubility. In some embodiments, a moiety may comprise an antibody or ligand. A ligand may be a carbohydrate, lectin, protein, glycoprotein, lipid, cholesterol, steroid, bile acid, nucleic acid hormone, growth factor, or receptor. In some embodiments a biologically inactive variant of a naturally occurring hormone, growth factor, or other ligand may be used. In some embodiments, the moiety comprises a targeting moiety that targets the inhibitory RNA (e.g., siRNA) to a specified cell type, e.g., a hepatocyte. In some embodiments a targeting moiety binds to hepatocyte-specific asialoglycoprotein receptor (ASGPR).

In some embodiments a moiety is attached to an inhibitory RNA (e.g., siRNA) via a reversible linkage. A "reversible linkage" is a linkage that comprises a reversible bond. A "reversible bond" (also referred to as a labile bond or cleavable bond) is a covalent bond other than a covalent bond to a hydrogen atom that is capable of being selectively broken or cleaved more rapidly than other bonds in a molecule under selected conditions, the bond is capable of being selectively broken or cleaved under conditions that substantially will not break or cleave other covalent bonds in the same molecule. Cleavage or lability of a bond may be described in terms of the half-life ($t_{1/2}$) of bond cleavage (the time required for half of the bonds to cleave). Unless otherwise indicated, a reversible bond of interest herein is a "physiologically reversible bond", by which is meant that the bond is cleavable under conditions normally encountered or analogous to those encountered within a mammalian body. A physiologically reversible linkage is a linkage that comprises at least one physiologically reversible bond. In some embodiments, a physiologically reversible bond is reversible under mammalian intracellular conditions, which include chemical conditions such as pH, temperature, oxidative or reductive conditions or agents, and salt concentration found in or analogous to those found in mammalian cells. Mammalian intracellular conditions also include the presence of enzymatic activity normally present in a mammalian cell, such as from proteolytic or hydrolytic enzymes. Enzymatically labile bonds are cleaved by enzymes in the body, e.g., intracellular enzymes. pH labile bonds are cleaved at a pH less than or equal to 7.0. Examples of reversible bonds and linkages and their use to conjugate moieties to an inhibitory RNA (e.g., siRNA) are described in, e.g., US Pat. App. Pub. Nos. 20130281685 and 20150273081.

In some embodiments, a moiety comprises a protein transduction domain (PTD). Protein transduction domains are polypeptides or portions thereof that facilitate uptake of heterologous molecules attached to the domain (such heterologous molecules may be referred to as "cargo"). A protein transduction domain that is a peptide may be referred to as a cell penetrating peptide (CPP)). A number of protein transduction domains/peptides are known in the art. PTDs include a variety of naturally occurring or synthetic arginine-rich peptides. An arginine-rich peptide is a peptide that contains at least 30% arginine residues, e.g., at least 40%, 50%, 60%, or more. Examples of PTDs include TAT (at least amino acids 49-56), Antennopedia homeodomain, HSV VP22, and polyarginine. Such peptides may be a cationic, hydrophobic, or amphipathic peptide and may include non-standard amino acids and/or various modifications or variations such as use of circularly permuted, inverso, retro, retro-inverso, or peptidomimetic versions. The attachment of a PTD and a cargo may be covalent or noncovalent.

Exemplary PTDs that may be used are described in U.S. Pat. App. Pub. Nos. 20090093026, 20090093425, 20120142763, 20150238516, and 20160215022. A PTD may comprise two or more PTDs (e.g., between 2 and 10 PTDs), which may be the same or different. PTDs may be directly linked to one another or may be separated by a linking portion that may comprise one or more amino acids and/or one or more non-amino acid moieties, such as an alkyl chain or oligoethylene glycol moiety.

In some embodiments, an inhibitory RNA (e.g., siRNA) comprises or is physically associated with an anionic charge neutralizing moiety. An anionic charge neutralizing moiety refers to a molecule or chemical group that can reduce the overall net anionic charge of a nucleic acid with which it is physically associated. One or more anionic charge neutralizing molecules or groups can be associated with a nucleic acid wherein each independently contributes to a reduction of the anionic charge and or increase in cationic charge. By charge neutralized is meant that the anionic charge of the nucleic acid is reduced, neutralized or more cationic than the same nucleic acid in the absence of an anionic charge neutralizing molecule or group. Phosphodiester and/or phosphothioate protecting groups are examples of anionic charge neutralizing groups. In some embodiments, an inhibitory RNA (e.g., siRNA) comprises a protecting group at one or more positions that reduces the net anionic charge of a backbone that contains negatively charged groups (e.g., a phosphodiester or phosphorothioate backbone). In some embodiments, the negatively charged phosphodiester backbone is neutralized by synthesis with bioreversible phosphotriester protecting groups that are converted into charged phosphodiester bonds inside cells by the action of cytoplasmic thioesterases, resulting in an agent that is biologically active for inhibiting expression, e.g., an inhibitory RNA (e.g., siRNA) that can mediate RNAi. Such agents, which are sometimes referred to as short interfering ribonucleic neutrals (siRNNs) can therefore serve as siRNA prodrugs. It should be understood that the backbone need not be completely neutralized (i.e., uncharged). In some embodiments, between 5% and 100% of the phosphate groups are protected, e.g., 25%-50% or 50% to 75% or 75% to 100%. In certain embodiments at least 5, 6, 7, 8, 9, or 10 of the phosphate groups on one or both strands are protected. Examples of useful phosphodiester and/or phosphothioate protecting groups, methods of making them, and their use in nucleic acids (e.g., to generate RNAi agent prodrugs) are described in US Pat. App. Pub. Nos. 20110294869, 20090093425, 20120142763, and 20150238516. In various embodiments a siRNA may comprise any of the modifications described herein. For example, in some embodiments it may contain 2' sugar modifications (e.g., 2'-F, 2'-O-Me). Furthermore, a siRNN may have any of the configurations or modification patterns described herein.

In some embodiments a moiety attached to an inhibitory RNA (e.g., siRNA) comprises a carbohydrate. Representative carbohydrates include mono-, di-, tri- and oligosaccharides containing from about 4, 5, 6, 7, 8, or 9 monosaccharide units. In certain embodiments the carbohydrate comprises galactose or a galactose derivative such as galactosamine, N-formyl-galactosamine, N-acetylgalactosamine, N-propionyl-galactosamine, N-n-butanoyl-galactosamine, and N-iso-butanoylgalactos-amine. In certain embodiments of particular interest the galactose derivative comprises N-acetylgalactosamine (GalNAc). In certain embodiments, the moiety comprises multiple instances of the galactose or galactose derivative, e.g., multiple N-acetylgalactosamine moieties, e.g., 3 GalNAc moieties. As used herein, the term "galactose derivative" includes both galactose and derivatives of galactose having affinity for the asialoglycoprotein receptor equal to or greater than that of galactose. The term "galactose cluster" refers to a structure comprising at least 2 galactose derivatives that are physically associated with each other, typically by being covalently attached to another moiety. In some embodiments, a galactose cluster has 2-10 (e.g., 6), or 2-4 (e.g., 3) terminal galactose derivatives. A terminal galactose derivative may be attached to another moiety through the C-1 carbon of the galactose derivative. In some embodiments two or more, e.g., three, galactose derivatives are attached to a moiety that serves as a branch point and that can be attached to an inhibitory RNA (e.g., siRNA). In some embodiments, a galactose derivative is linked to the moiety that serves as a branch point via a linker or spacer. In some embodiments, the moiety that serves as a branch point may be attached to an inhibitory RNA (e.g., siRNA) via a linker or spacer. For example, in some embodiments, a galactose derivative is attached to a branch point via a linker or spacer that comprises an amide, carbonyl, alkyl, oligoethylene glycol moiety, or combination thereof. In some embodiments the linkers or spacers attached to each galactose derivative are the same. In some embodiments, a galactose cluster has three terminal galactosamines or galactosamine derivatives (e.g., GalNAc) each having affinity for the asialoglycoprotein receptor. A structure in which 3 terminal GalNAc moieties are attached (e.g., through the C-1 carbons of the saccharides) to a moiety that serves as branch point may be referred to as tri-antennary N-acetylgalactosamine (GalNAc$_3$). In some embodiments, one or more monomeric units comprising a galactose derivative may be incorporated site-specifically into an inhibitory RNA (e.g., siRNA). Such galactose derivative-containing monomeric units may comprise a galactose derivative, e.g., GalNAc, attached to a nucleoside or to a non-nucleoside moiety. In some embodiments, at least 3 nucleoside-GalNAc monomers or at least 3 non-nucleoside-GalNAc monomers are incorporated site-specifically into an inhibitory RNA (e.g., siRNA). In some embodiments, such incorporation may occur during solid-phase synthesis using phosphoramidite chemistry or via postsynthetic conjugation. In some embodiments, the galactose derivative-containing monomeric units are joined via phosphodiester bonds to each other and/or to nucleosides of the inhibitory RNA (e.g., siRNA) that do not have a galactose derivative attached. In some embodiments 2, 3, or more galactose derivative-containing monomeric units are arranged consecutively, i.e., without any intervening units that lack a galactose derivative. In some embodiments a carbohydrate, e.g., a galactose cluster, e.g., tri-antennary N-acetylgalactosamine or two or more GalNAc-containing monomeric units, is present at the end of a strand, e.g., at the 3' end of the sense strand or at the 5' end of an antisense strand. Exemplary carbohydrates (e.g., galactose clusters), galactose derivative-containing monomeric units, carbohydrate-modified INAAs, and methods of manufacture and use thereof are described in US Pat. App. Pub. Nos. 20090203135, 20090239814, 20110207799, 20120157509, 20150247143, US Pub. '124; Nair, J K, et al., J. Am. Chem. Soc. 136, 16958-16961 (2014); Matsuda, S., et al., ACS Chem. Biol. 10, 1181-1187 (2015); Rajeev, K., et al., ChemBioChem 16, 903-908 (2015); Migawa, M T., et al., Bioorg Med Chem Lett. 26(9):2194-7 (2016); Prakash, T P, et al., J Med Chem. 59(6):2718-33 (2016). Exemplary galactose clusters are depicted below.

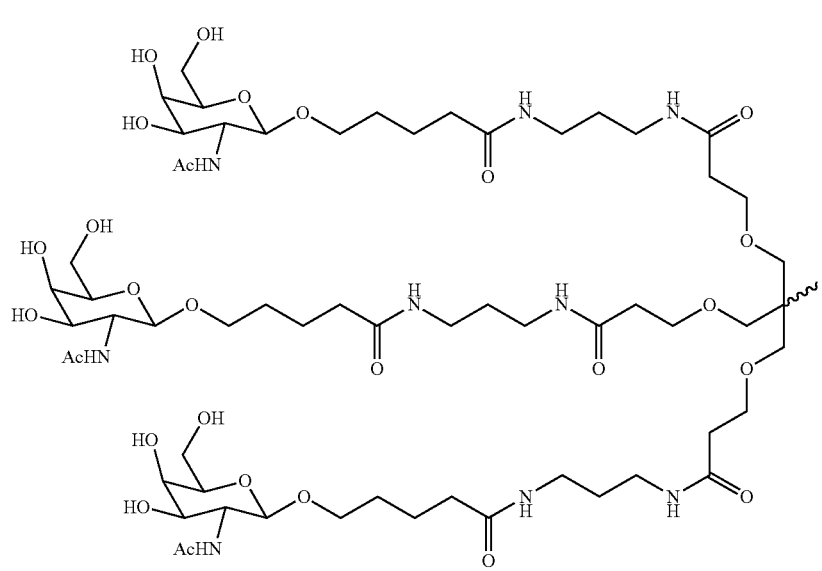

Formula XA

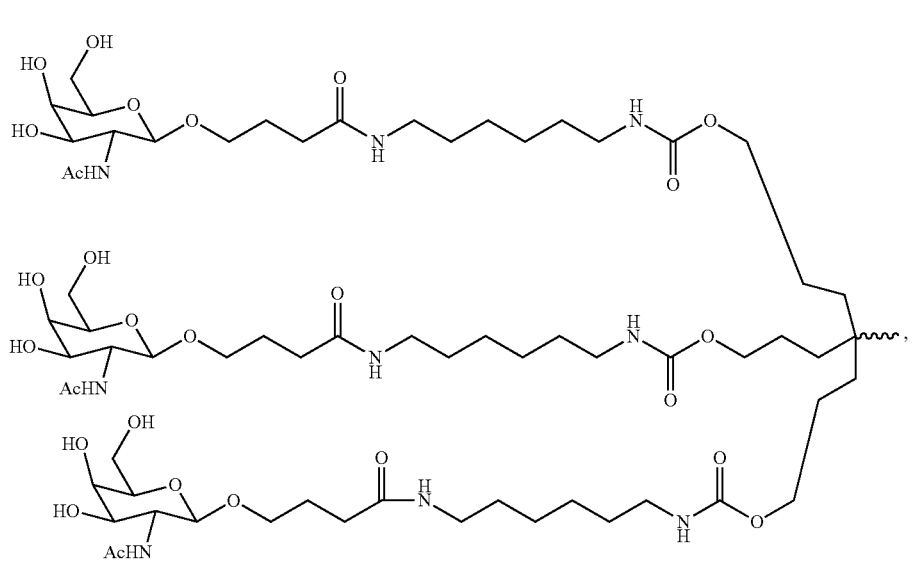

Formula XB

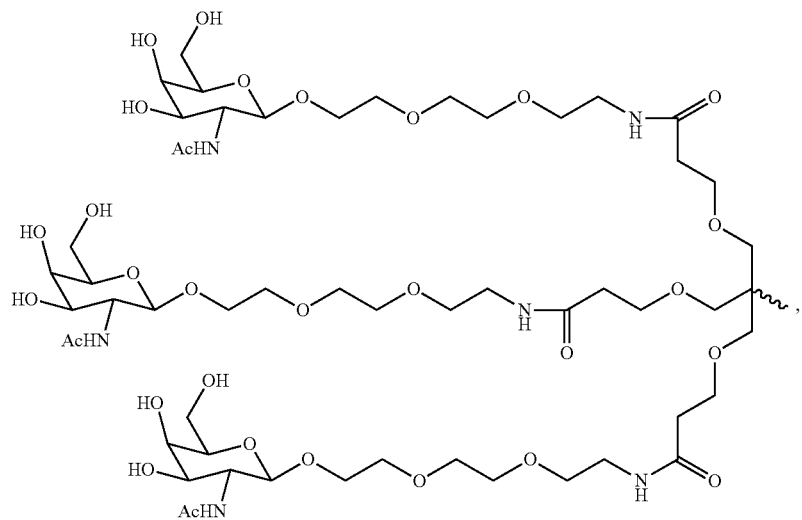
Formula XC
Additional GalNAc structures are depicted below (and can be synthesized as described in Sharma et al., Bioconjug. Chem. 29:2478-2488 (2018)):
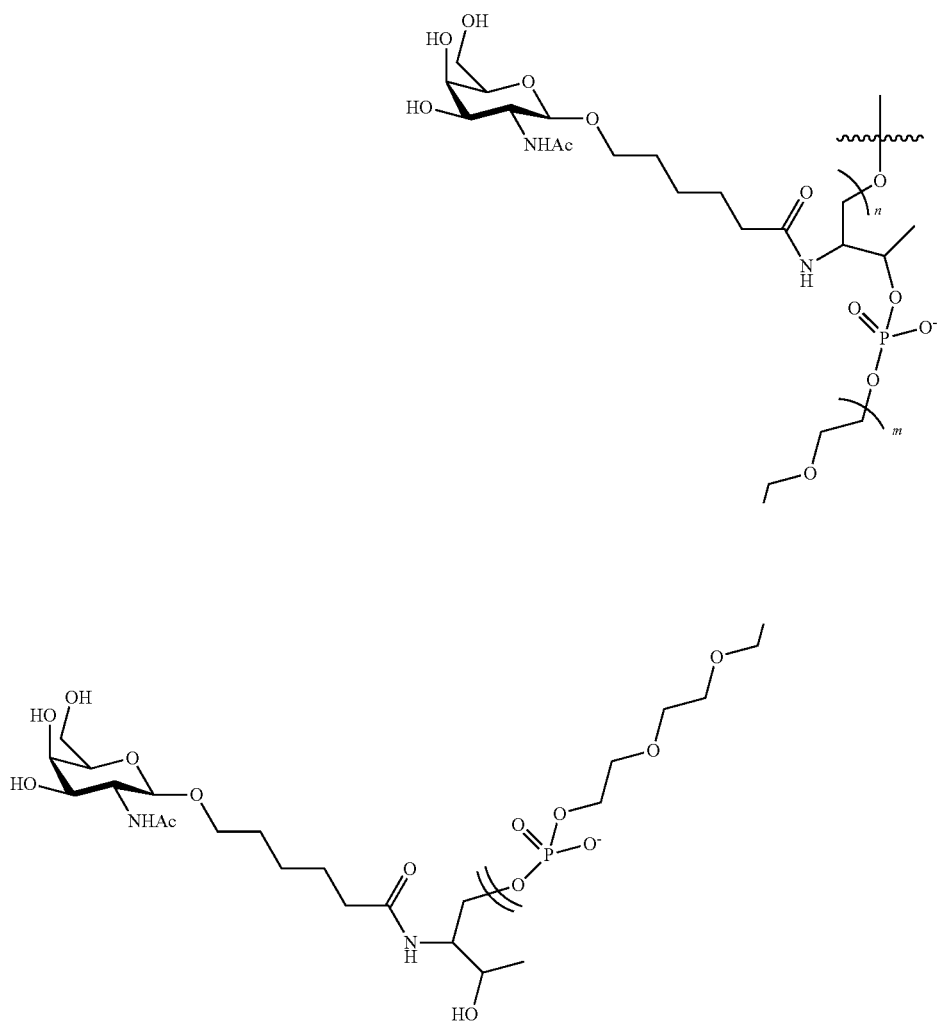

In some embodiments, m=0 and n=2. In some embodiments, m=1 and n=1. In some embodiments, m=1 and n=2. In some embodiments, m=1 and n=3.
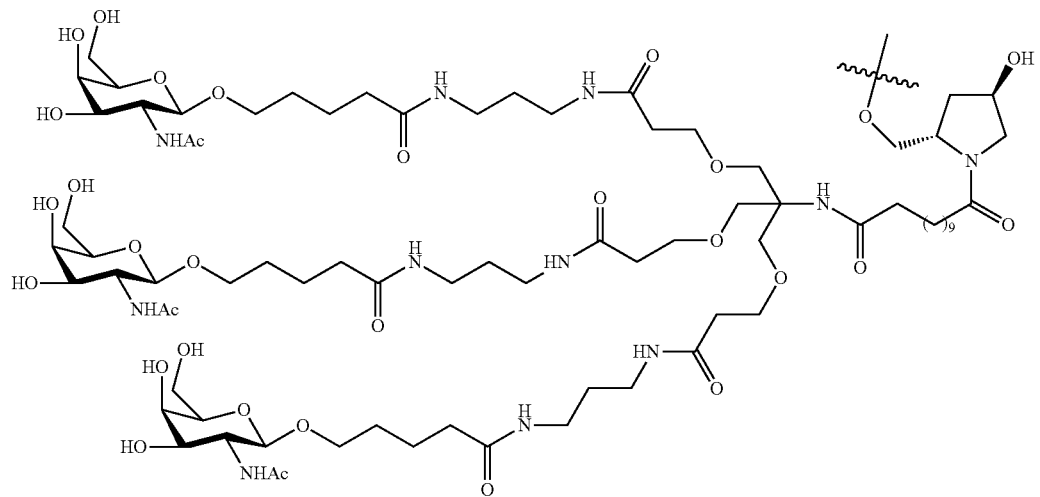
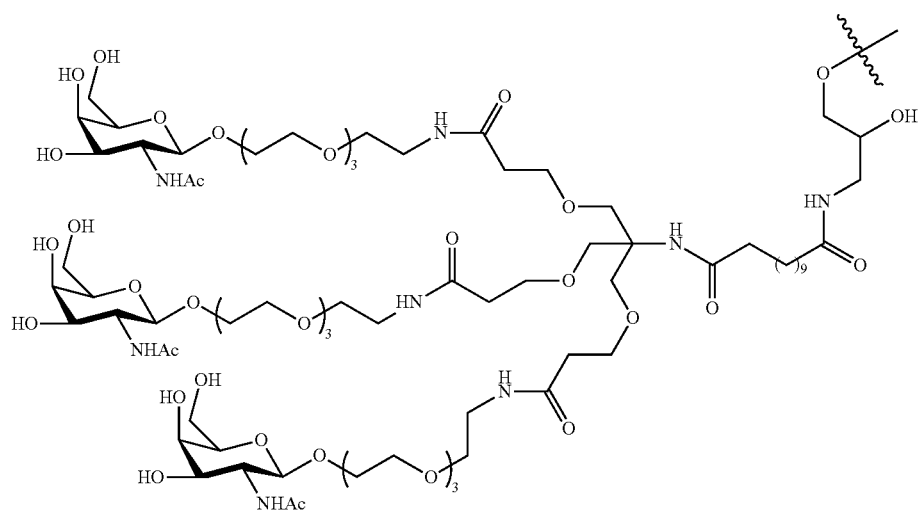

One of ordinary skill in the art appreciates that the structure of the linking moieties that connect each GalNAc to the branch point may vary.

In some embodiments an inhibitory RNA (e.g., siRNA) is conjugated to a ligand as depicted below.

In general, a moiety may be attached at a terminus or internal subunit of an inhibitory RNA (e.g., siRNA). In some embodiments a moiety is attached to a modified subunit of the inhibitory RNA (e.g., siRNA). Those of ordinary skill in the art are aware of suitable methods to manufacture nucleic

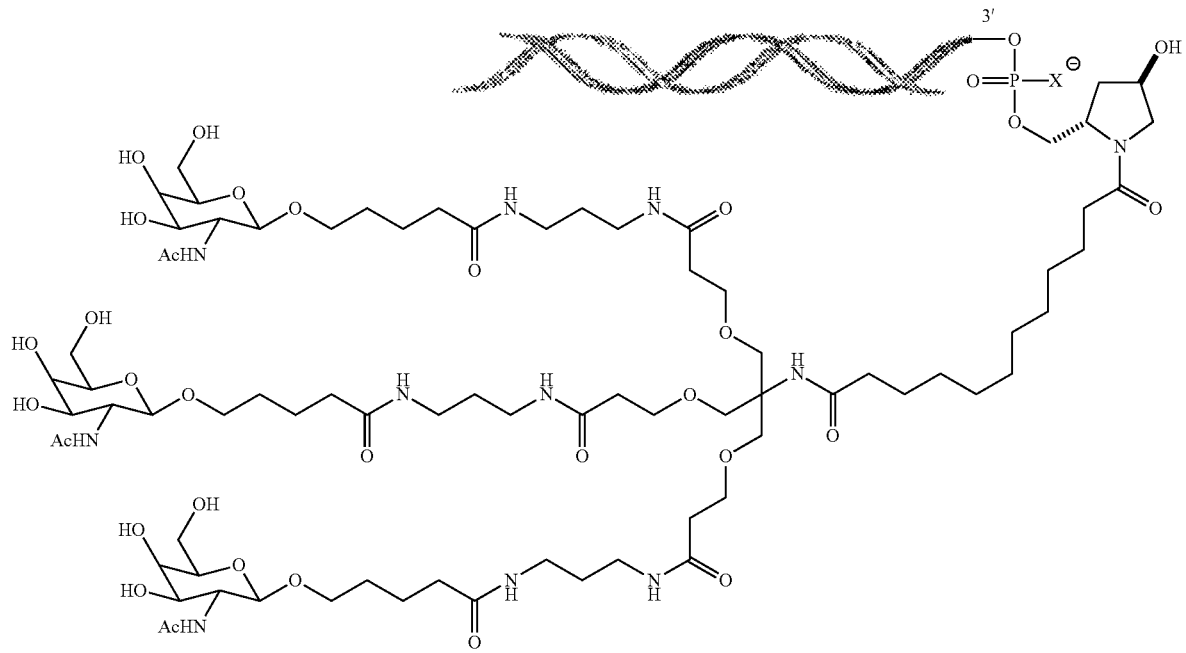

and, wherein X is O or S. In most embodiments, X is O. One of ordinary skill in the art will appreciate that the structure of the linking moiety that connects the galactose cluster to the phosphate group may vary.

In certain embodiments the moiety comprises a lipophilic moiety. In some embodiments the lipophilic moiety comprises a tocopherol, e.g., alpha-tocopherol. In some embodiments the lipophilic moiety comprises cholesterol. In some embodiments the lipophilic compound comprises an alkyl or heteroalkyl group. In some embodiments the lipophilic compound comprises palmitoyl, hexadec-8-enoyl, oleyl, (9E,12E)-octadeca-9,12-dienoyl, dioctanoyl, or C16-C20 acyl. In some embodiments the lipophilic moiety comprises at least 16 carbon atoms. In some embodiments the lipophilic moiety comprises —(CH)$_n$—NH—(C=O)—(CH)$_m$μ-CH$_3$. In some embodiments n and m are each independently between 1 and 20. In some embodiments n+m is at least 10, 12, 14, or 16. In some embodiments the lipophilic moiety is as shown below and/or is attached to a sugar moiety as shown below.

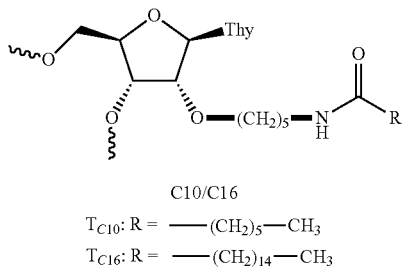

C10/C16

$T_{C10}$: R = —(CH$_2$)$_5$—CH$_3$ $T_{C16}$: R = —(CH$_2$)$_{14}$—CH$_3$ acids having moieties conjugated thereto. A nucleic acid strand comprising a modified nucleotide comprising a reactive functional group may be reacted with a moiety comprising a second reactive functional group, wherein the first and second reactive functional groups are capable of reacting with one another under conditions compatible with maintaining the structure of the nucleic acid strand. In some embodiments a moiety may be attached to a sense strand or an antisense strand prior to hybridization of the strand with the complementary antisense or sense strand, respectively. In some embodiments strands may be hybridized to form a duplex prior to incorporation of the moiety. In general, various methods of conjugation described herein may be used. See, e.g., Hermanson, G., Bioconjugate Techniques, 2nd ed., Academic Press, San Diego, 2008.

In some embodiments, an inhibitory RNA (e.g., siRNA) is a chimeric siRNA. "Chimeric" siRNAs as used herein, are siRNAs that contain two or more chemically distinct regions, each made up of at least one monomer unit, wherein the regions confer distinct properties on the compound. In some embodiments at least one region is modified so as to confer upon the siRNA increased resistance to nuclease degradation, increased cellular uptake, and/or increased binding affinity for the target nucleic acid and at least one additional region of the siRNA can serve as a substrate for enzymes (e.g., RNase H) capable of cleaving RNA:DNA or RNA:RNA hybrids. In some embodiments at least one region of the siRNA can serve as a substrate for enzymes (e.g., RNase H) capable of cleaving RNA:DNA or RNA:RNA hybrids and at least one region can inhibit translation by steric blocking.

In some embodiments, an inhibitory RNA (e.g., siRNA) described herein can be introduced to a target cell as an annealed duplex siRNA. In some embodiments, an inhibitory RNA (e.g., siRNA) described herein is introduced to a target cell as single stranded sense and antisense nucleic acid sequences that, once within the target cell, anneal to form an inhibitory RNA (e.g., siRNA) duplex. Alternatively, the sense and antisense strands of the inhibitory RNA (e.g., siRNA) can be encoded by an expression vector (such as an expression vector described herein) that is introduced to the target cell. Upon expression within the target cell, the transcribed sense and antisense strands can anneal to reconstitute the inhibitory RNA (e.g., siRNA).

An inhibitory RNA (e.g., siRNA) described herein can be synthesized by standard methods known in the art, e.g., by use of an automated synthesizer. RNAs produced by such methodologies tend to be highly pure and to anneal efficiently to form inhibitory RNA (e.g., siRNA) duplexes. Following chemical synthesis, single stranded RNA molecules can be deprotected, annealed to form siRNAs, and purified (e.g., by gel electrophoresis or HPLC). Alternatively, standard procedures can be used for in vitro transcription of RNA from DNA templates, e.g., carrying one or more RNA polymerase promoter sequences (e.g., T7 or SP6 RNA polymerase promoter sequences). Protocols for preparation of siRNAs using T7 RNA polymerase are known in the art (see, e.g., Donze and Picard, Nucleic Acids Res. 2002; 30:e46; and Yu et al., Proc. Natl. Acad. Sci. USA 2002; 99:6047-6052). The sense and antisense transcripts can be synthesized in two independent reactions and annealed later, or they can be synthesized simultaneously in a single reaction.

An inhibitory RNA (e.g., siRNA) can also be formed within a cell by transcription of RNA from an expression construct introduced into the cell (see, e.g., Yu et al., Proc. Natl. Acad. Sci. USA 2002; 99:6047-6052). An expression construct for in vivo production of inhibitory RNA (e.g., siRNA) molecules can include one or more siRNA encoding sequences operably linked to elements necessary for the proper transcription of the siRNA encoding sequence(s), including, e.g., promoter elements and transcription termination signals. Preferred promoters for use in such expression constructs include the polymerase-III HI-RNA promoter (see, e.g., Brummelkamp et al., Science 2002; 296:550-553) and the U6 polymerase-III promoter (see, e.g., Sui et al., Proc. Natl. Acad. Sci. USA 2002; Paul et al., Nature Biotechnol. 2002; 20:505-508; and Yu et al., Proc. Natl. Acad. Sci. USA 2002; 99:6047-6052). An siRNA expression construct can further comprise one or more vector sequences that facilitate the cloning of the expression construct. Standard vectors that can be used include, e.g., pSilencer 2.0-U6 vector (Ambion Inc., Austin, Tex.).

In some embodiments, an siRNA molecule of the disclosure includes one or more natural nucleobase and/or one or more modified nucleobases derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Exemplary modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313.

Modified nucleobases also include expanded-size nucleobases in which one or more aryl rings, such as phenyl rings, have been added. Nucleic base replacements described in the Glen Research catalog (www.glenresearch.com); Krueger A T et al, Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for siRNA molecules described herein. Modified nucleobases also encompass structures that are not considered nucleobases but are other moieties such as, but not limited to, corrin- or porphyrin-derived rings. Porphyrin-derived base replacements have been described in Morales-Rojas, H and Kool, ET, Org. Lett., 2002, 4, 4377-4380.

In some embodiments, modified nucleobases are of any one of the following structures, optionally substituted:

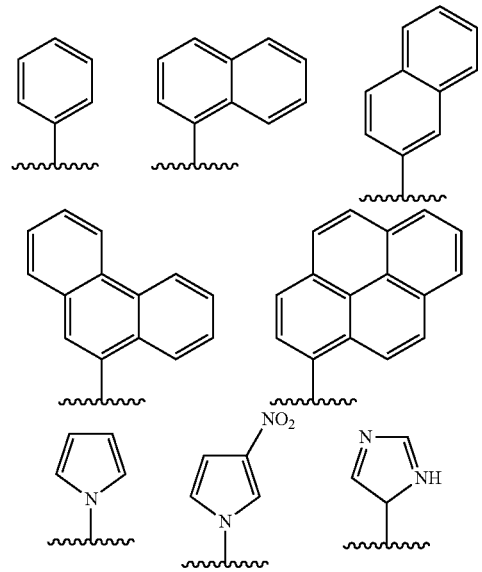

In some embodiments, a modified nucleobase is fluorescent. Exemplary such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

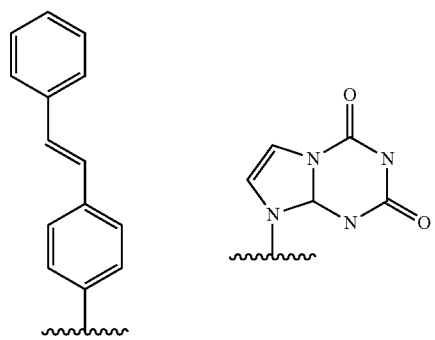

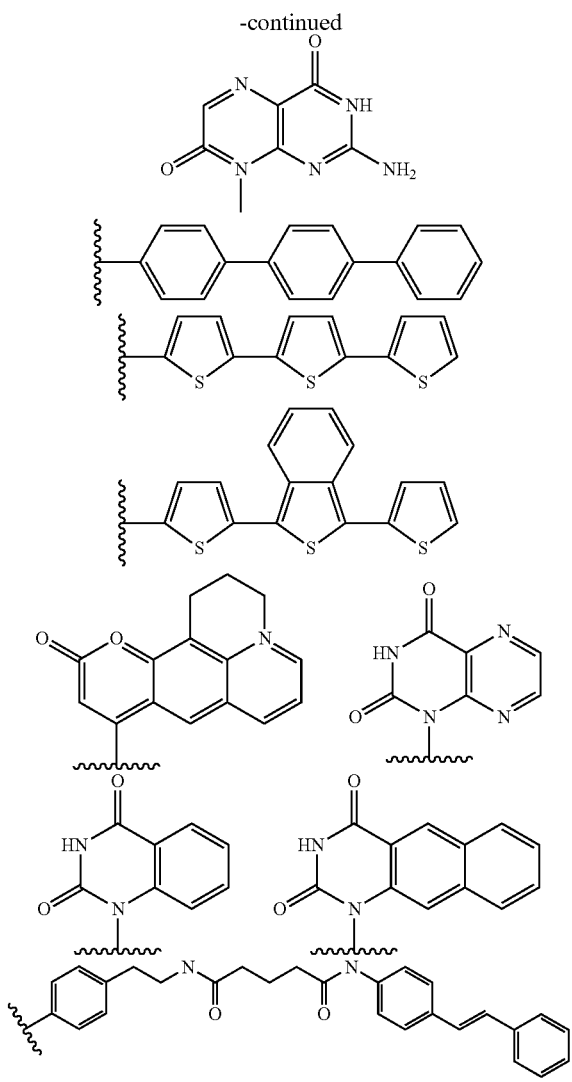

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, siRNA molecules described herein include nucleosides that incorporate modified nucleobases and/or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; M-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-N-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in U.S. Publ. No. 20070287831. In some embodiments, a nucleobase or modified nucleobase is 5-bromouracil, 5-iodouracil, or 2,6-diaminopurine. In some embodiments, a nucleobase or modified nucleobase is modified by substitution with a fluorescent moiety.

Methods of preparing modified nucleobases are described in, e.g., U.S. Pat. Nos. 3,687,808; 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088.

In some embodiments, an siRNA molecule described herein includes one or more modified nucleotides wherein a phosphate group or linkage phosphorus in the nucleotides are linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context.

Other modified sugars can also be incorporated within an siRNA molecule. In some embodiments, a modified sugar contains one or more substituents at the 2' position including one of the following: —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C10 alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. Examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —OCH$_2$CH$_2$OMe.

Modified sugars also include locked nucleic acids (LNAs). In some embodiments, the locked nucleic acid has the structure indicated below. A locked nucleic acid of the structure below is indicated, wherein Ba represents a nucleobase or modified nucleobase as described herein, and wherein R$^{2s}$ is —OCH$_2$C4'-

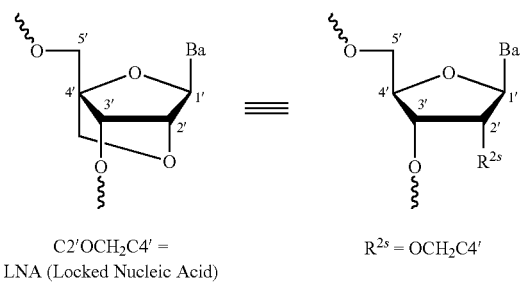

C2'OCH$_2$C4' = LNA (Locked Nucleic Acid)

R$^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar (see, e.g., U.S. Pat. Nos. 4,981,957; 5,118, 800; 5,319,080; and 5,359,044). Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603. Another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413. Additional non-limiting examples of modified sugars include hexopyranosyl (6' to 4'), pentopyranosyl (4' to 2'), pentopyranosyl (4' to 3'), or tetrofuranosyl (3' to 2') sugars.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in Chemical Synthesis: Gnosis to Prognosis, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310); PCT Publication No. WO2012/030683.

In some embodiments, an siRNA described herein can be introduced to a target cell as an annealed duplex siRNA. In some embodiments, an siRNA described herein is introduced to a target cell as single stranded sense and antisense nucleic acid sequences that, once within the target cell, anneal to form an siRNA duplex. Alternatively, the sense and antisense strands of the siRNA can be encoded by an expression vector (such as an expression vector described herein) that is introduced to the target cell. Upon expression within the target cell, the transcribed sense and antisense strands can anneal to reconstitute the siRNA.

An siRNA molecule described herein can be synthesized by standard methods known in the art, e.g., by use of an automated synthesizer. RNAs produced by such methodologies tend to be highly pure and to anneal efficiently to form siRNA duplexes. Following chemical synthesis, single stranded RNA molecules can be deprotected, annealed to form siRNAs, and purified (e.g., by gel electrophoresis or HPLC). Alternatively, standard procedures can be used for in vitro transcription of RNA from DNA templates, e.g., carrying one or more RNA polymerase promoter sequences (e.g., T7 or SP6 RNA polymerase promoter sequences). Protocols for preparation of siRNAs using T7 RNA polymerase are known in the art (see, e.g., Donze and Picard, Nucleic Acids Res. 2002; 30:e46; and Yu et al., Proc. Natl. Acad. Sci. USA 2002; 99:6047-6052). The sense and antisense transcripts can be synthesized in two independent reactions and annealed later, or they can be synthesized simultaneously in a single reaction.

An siRNA molecule can also be formed within a cell by transcription of RNA from an expression construct introduced into the cell (see, e.g., Yu et al., Proc. Natl. Acad. Sci. USA 2002; 99:6047-6052). An expression construct for in vivo production of siRNA molecules can include one or more siRNA encoding sequences operably linked to elements necessary for the proper transcription of the siRNA encoding sequence(s), including, e.g., promoter elements and transcription termination signals. Preferred promoters for use in such expression constructs include the polymerase-III HI-RNA promoter (see, e.g., Brummelkamp et al., Science 2002; 296:550-553) and the U6 polymerase-III promoter (see, e.g., Sui et al., Proc. Natl. Acad. Sci. USA 2002; Paul et al., Nature Biotechnol. 2002; 20:505-508; and Yu et al., Proc. Natl. Acad. Sci. USA 2002; 99:6047-6052). An siRNA expression construct can further comprise one or more vector sequences that facilitate the cloning of the expression construct. Standard vectors that can be used include, e.g., pSilencer 2.0-U6 vector (Ambion Inc., Austin, Tex.).

IV. Expression Vectors

In some embodiments, an miRNA or siRNA described herein is delivered to a subject (e.g., to a cell of a subject, e.g., a liver cell of a subject) using an expression vector. Many forms of vectors can be used to deliver an miRNA or siRNA described herein. Non-limiting examples of expression vectors include viral vectors (e.g., vectors suitable for gene therapy), plasmid vectors, bacteriophage vectors, cosmids, phagemids, artificial chromosomes, and the like.

In some embodiments, a nucleotide sequence encoding an miRNA or siRNA described herein is integrated into a viral vector. Non-limiting examples of viral vectors include: retrovirus (e.g., Moloney murine leukemia virus (MMLV), Harvey murine sarcoma virus, murine mammary tumor virus, Rous sarcoma virus), adenovirus, adeno-associated virus, SV40-type virus, polyomavirus, Epstein-Barr virus, papilloma virus, herpes virus, vaccinia virus, and polio virus.

In vivo, many complement proteins, including C3, are synthesized primarily in the liver. As such, in some embodiments, hepatocytes are targeted for delivery of an miRNA or siRNA described herein. Several classes of viral vectors have been shown competent for liver-targeted delivery of a gene therapy construct, including retroviral vectors (see, e.g., Axelrod et al., PNAS 87:5173-5177 (1990); Kay et al., Hum. Gene Ther. 3:641-647 (1992); Van den Driessche et al., PNAS 96:10379-10384 (1999); Xu et al., ASAIO J. 49:407-416 (2003); and Xu et al., PNAS 102:6080-6085 (2005)), lentiviral vectors (see, e.g., McKay et al., Curr. Pharm. Des. 17:2528-2541 (2011); Brown et al., Blood 109:2797-2805 (2007); and Matrai et al., Hepatology 53:1696-1707 (2011)), adeno-associated viral (AAV) vectors (see, e.g., Herzog et al., Blood 91:4600-4607 (1998)), and adenoviral vectors (see, e.g., Brown et al., Blood 103:804-810 (2004) and Ehrhardt et al., Blood 99:3923-3930 (2002)).

Retroviruses are enveloped viruses that belong to the viral family Retroviridae. Once in a host's cell, the virus replicates by using a viral reverse transcriptase enzyme to transcribe its RNA into DNA. The retroviral DNA replicates as part of the host genome, and is referred to as a provirus. A selected nucleic acid can be inserted into a vector and packaged in retroviral particles using techniques known in the art. Protocols for the production of replication-deficient retroviruses are known in the art (see, e.g., Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991)). The recombinant virus can then be isolated and delivered to cells of the subject either in vivo or ex vivo. A number of retroviral systems are known in the art, for example See U.S. Pat. Nos. 5,994,136, 6,165,782, and 6,428,953. Retroviruses include the genus of Alpharetrovirus (e.g., avian leukosis virus), the genus of Betaretrovirus; (e.g., mouse mammary tumor virus) the genus of Deltaretrovirus (e.g., bovine leukemia virus and human T-lymphotropic virus), the genus of Epsilonretrovirus (e.g., Walleye dermal sarcoma virus), and the genus of Lentivirus.

In some embodiments, the retrovirus is a lentivirus of the Retroviridae family. Lentiviral vectors can transduce non-proliferating cells and show low immunogenicity. In some examples, the lentivirus is, but is not limited to, human immunodeficiency viruses (HIV-1 and HIV-2), simian immunodeficiency virus (S1V), feline immunodeficiency virus (FIV), equine infections anemia (EIA), and visna virus. Vectors derived from lentiviruses can achieve significant levels of nucleic acid transfer in vivo.

In some embodiments, the vector is an adenovirus vector. Adenoviruses are a large family of viruses containing double stranded DNA. They replicate within the nucleus of a host cell, using the host's cell machinery to synthesize viral RNA, DNA and proteins. Adenoviruses are known in the art to affect both replicating and non-replicating cells, to accommodate large transgenes, and to code for proteins without integrating into the host cell genome.

In some embodiments, the viral vector is an adeno-associated virus (AAV) vector. AAV systems are generally well known in the art (see, e.g., Kelleher and Vos, Biotechniques, 17(6):1110-17 (1994); Cotten et al., P.N.A.S. U.S.A., 89(13):6094-98 (1992); Curiel, Nat Immun, 13(2-3):141-64 (1994); Muzyczka, Curr Top Microbiol Immunol, 158:97-129 (1992); and Asokan A, et al., Mol. Ther., 20(4):699-708 (2012)). Methods for generating and using recombinant AAV (rAAV) vectors are described, for example, in U.S. Pat. Nos. 5,139,941 and 4,797,368.

Several AAV serotypes have been characterized, including AAV1, AAV2, AAV3 (e.g., AAV3B), AAV4, AAV5, AAV6, AAV7, AAV8, AAV9, AAV10, and AAV11, as well as variants thereof. Generally, any AAV serotype may be used to deliver an miRNA or siRNA described herein. However, the serotypes have different tropisms, e.g., they preferentially infect different tissues. In one embodiment, because complement proteins are produced in the liver, an AAV serotype is selected based on a liver tropism, found in at least serotypes AAV3 (e.g., AAV3B), AAV7, AAV8, and AAV9 (see, e.g., Shaoyong et al., Mol. Ther. 23:1867-1876 (2015)). In some embodiments, an AAV is a self-complementary AAV. In some embodiments, an AAV is a single-stranded AAV. In some embodiments, an AAV comprises a stuffer sequence (e.g., a random stuffer sequence).

The AAV sequences of a rAAV vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. In some embodiments, substantially the entire sequences encoding the ITRs are used in an rAAV vector, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of an rAAV vector of the present disclosure is a "cis-acting" plasmid containing the transgene (e.g., nucleic acid encoding an miRNA described herein), in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for an rAAV vector, the vector can also include conventional control elements operably linked to the transgene in a manner that permits its transcription, translation and/or expression in a cell transfected with the vector or infected with the virus produced by the disclosure. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters that are native, constitutive, inducible and/or tissue-specific, are known in the art and may be included in a vector described herein. In some embodiments, operably linked coding sequences yield a functional RNA (e.g., miRNA). In some embodiments, a vector, e.g., an rAAV vector, can comprise a flanking sequence on the 5' and/or 3' end of a transgene, e.g., from one or more known miRNAs, e.g., miR-30 or miR-155.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, a native promoter, or fragment thereof, for a transgene will be used. In a further embodiment, other native expression control elements, such as enhancer elements, polyadenylation sites or Kozak consensus sequences may also be used to mimic the native expression.

In some embodiments, regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken β-actin promoter, an H1 promoter, a pol VI promotor, a pol II promoter, or a pol III promoter.

In some embodiments, an rAAV is designed for expressing an miRNA or siRNA described herein in hepatocytes, and an rAAV includes one or more liver-specific regulatory elements, which substantially limit expression of the miRNA or siRNA to hepatic cells. Generally, liver-specific regulatory elements can be derived from any gene known to be exclusively expressed in the liver. WO 2009/130208 identifies several genes expressed in a liver-specific fashion, including serpin peptidase inhibitor, clade A member 1, also known as α-antitrypsin (SERPINA1; GeneID 5265), apolipoprotein C-I (APOC1; GeneID 341), apolipoprotein C-IV (APOC4; GeneID 346), apolipoprotein H (APOH; GeneID 350), transthyretin (TTR; GeneID 7276), albumin (ALB; GeneID 213), aldolase B (ALDOB; GeneID 229), cytochrome P450, family 2, subfamily E, polypeptide 1 (CYP2E1; GeneID 1571), fibrinogen alpha chain (FGA; GeneID 2243), transferrin (TF; GeneID 7018), and haptoglobin related protein (HPR; GeneID 3250). In some embodiments, a viral vector described herein includes a liver-specific regulatory element derived from the genomic loci of one or more of these proteins. In some embodiments, a promoter may be the liver-specific promoter thyroxin binding globulin (TBG). Alternatively, other liver-specific promoters may be used (see, e.g., The Liver Specific Gene Promoter Database, Cold Spring Harbor, http://rulai.cshl.edu/LSPD/, such as, e.g., alpha 1 anti-trypsin (A1AT); human albumin (Miyatake et al., J. Virol. 71:5124 32 (1997)); humA1b; hepatitis B virus core promoter (Sandig et al., Gene Ther. 3:1002 9 (1996)); or LSP1. Additional vectors and regulatory elements are described in, e.g., Baruteau et al., J. Inherit. Metab. Dis. 40:497-517 (2017)).

In some embodiments, a viral vector (e.g., an rAAV vector) comprises a DNA sequence encoding a miRNA or siRNA described herein. For example, a viral vector can comprise a DNA sequence that is at least 90%, 91%, 92%, 93%, 94%, 95%, 96%, 97%, 98%, 99%, or 100% identical to one or more of SEQ ID NOs:86-95 (or a portion thereof) listed in Table 2:

TABLE 2

| Sequence Number | DNA Sequence |
| --- | --- |
| SEQ ID NO: 86 | 5'-AAGACAAGGAGTCCTGCTTGA-3' |
| SEQ ID NO: 87 | 5'-TACTCCTTCACCTCAAACTCA-3' |
| SEQ ID NO: 88 | 5'-TTGACGTCCACCCACACGGAG-3' |
| SEQ ID NO: 89 | 5'-TTGACTTCCACTTCCTGCAGG-3' |
| SEQ ID NO: 90 | 5'-ATGAAATGATGGTAGACAGCA-3' |
| SEQ ID NO: 91 | 5'-ATCTTTAGCCTCCTGCAGCGA-3' |
| SEQ ID NO: 92 | 5'-TGTTCATTGAGCCAACGCACG-3' |
| SEQ ID NO: 93 | 5'-TTAGCATGGTACATTGTCACC-3' |
| SEQ ID NO: 94 | 5'-AGCAAAGCCAGTCATCATGGA-3' |
| SEQ ID NO: 95 | 5'-TATCGGAGAAGGCTTTGTCCA-3' |

In some embodiments, a viral vector (e.g., an rAAV vector) comprises a double stranded DNA sequence, wherein at least one strand is at least 90%, 91%, 92%, 93%, 94%, 95%, 96%, 97%, 98%, 99%, or 100% identical to one or more of SEQ ID NOs:96-115 (or a portion thereof) listed in Table 3:

TABLE 3

Bold nucleotides correspond to the encoded RNA guide strand sequence and the underlined nucleotides correspond to the encoded passenger strand sequence.

| DNA strand | Sequence # | Sequence |
|---|---|---|
| Top | 96 | 5'-TGCTGAAGACAAGGAGTCCTGCTTGAGTTTTGGCCACTGACTGACTCAAGCAGCTCCTTGTCTT-3' |
| Bottom | 97 | 5'-CCTGAAGACAAGGAGCTGCTTGAGTCAGTCAGTGGCCAAAACTCAAGCAGGACTCCTTGTCTTC-3' |
| Top | 98 | 5'-TGCTGTACTCCTTCACCTCAAACTCAGTTTTGGCCACTGACTGACTGAGTTTGGTGAAGGAGTA-3' |
| Bottom | 99 | 5'-CCTGTACTCCTTCACCAAACTCAGTCAGTCAGTGGCCAAAACTGAGTTTGAGGTGAAGGAGTAC-3' |
| Top | 100 | 5'-TGCTGTTGACGTCCACCCACACGGAGGTTTTGGCCACTGACTGACCTCCGTGTGTGGACGTCAA-3' |
| Bottom | 101 | 5'-CCTGTTGACGTCCACACACGGAGGTCAGTCAGTGGCCAAAACCTCCGTGTGGGTGGACGTCAAC-3' |
| Top | 102 | 5'-TGCTGTTGACTTCCACTTCCTGCAGGGTTTTGGCCACTGACTGACCCTGCAGGGTGGAAGTCAA-3' |
| Bottom | 103 | 5'-CCTGTTGACTTCCACCCTGCAGGGTCAGTCAGTGGCCAAAACCCTGCAGGAAGTGGAAGTCAAC-3' |
| Top | 104 | 5'-TGCTGATGAAATGATGGTAGACAGCAGTTTTGGCCACTGACTGACTGCTGTCTCATCATTTCAT-3' |
| Bottom | 105 | 5'-CCTGATGAAATGATGAGACAGCAGTCAGTCAGTGGCCAAAACTGCTGTCTACCATCATTTCATC-3' |
| Top | 106 | 5'-TGCTGATCTTTAGCCTCCTGCAGCGAGTTTTGGCCACTGACTGACTCGCTGCAAGGCTAAAGAT-3' |
| Bottom | 107 | 5'-CCTGATCTTTAGCCTTGCAGCGAGTCAGTCAGTGGCCAAAACTCGCTGCAGGAGGCTAAAGATC-3' |
| Top | 108 | 5'-TGCTGTGTTCATTGAGCCAACGCACGGTTTTGGCCACTGACTGACCGTGCGTTCTCAATGAACA-3' |
| Bottom | 109 | 5'-CCTGTGTTCATTGAGAACGCACGGTCAGTCAGTGGCCAAAACCGTGCGTTGGCTCAATGAACAC-3' |
| Top | 110 | 5'-TGCTGTTAGCATGGTACATTGTCACCGTTTTGGCCACTGACTGACGGTGACAATACCATGCTAA-3' |
| Bottom | 111 | 5'-CCTGTTAGCATGGTATTGTCACCGTCAGTCAGTGGCCAAAACGGTGACAATGTACCATGCTAAC-3' |
| Top | 112 | 5'-TGCTGAGCAAAGCCAGTCATCATGGAGTTTTGGCCACTGACTGACTCCATGATCTGGCTTTGCT-3' |
| Bottom | 113 | 5'-CCTGAGCAAAGCCAGATCATGGAGTCAGTCAGTGGCCAAAACTCCATGATGACTGGCTTTGCTC-3' |
| Top | 114 | 5'-TGCTGTATCGGAGAAGGCTTTGTCCAGTTTTGGCCACTGACTGACTGGACAAACTTCTCCGATA-3' |
| Bottom | 115 | 5'-CCTGTATCGGAGAAGTTTGTCCAGTCAGTCAGTGGCCAAAACTGGACAAAGCCTTCTCCGATAC-3' |

For example, in some embodiments, a viral vector comprises a double-stranded DNA sequence that comprises (i) a first strand comprising a first sequence that is at least 90%, 91%, 92%, 93%, 94%, 95%, 96%, 97%, 98%, 99%, or 100% identical to one or more of SEQ ID NOs:86-95 (or a portion thereof); and (ii) a second strand comprising a second sequence that is complementary to the first sequence. In some embodiments, a DNA strand encodes an RNA sequence and, upon transcription, produces a stem-loop precursor miRNA (pre-miRNA) comprising a mature miRNA described herein (e.g., comprising a nucleotide sequence that is at least 90%, 91%, 92%, 93%, 94%, 95%, 96%, 97%, 98%, 99%, or 100% identical to any one of SEQ ID NOs:76-85 (or a portion thereof, e.g., 15, 16, 17, 18, 19, or 20 nucleotides long)).

In some embodiments, a vector (e.g., a viral vector) comprises one or more nucleotide sequences that encode more than one (e.g., 2, 3, 4, 5, or more) miRNAs or siRNAs comprising a nucleic acid strand that is complementary to a target portion of a C3 transcript, e.g., C3 mRNA (SEQ ID NO:75). In some such embodiments, at least one miRNA or siRNA comprises a guide strand having a nucleotide sequence that is at least 90%, 91%, 92%, 93%, 94%, 95%, 96%, 97%, 98%, 99%, or 100% identical to any one of SEQ ID NOs:76-85 (or portion thereof). In some embodiments, a vector comprises two or more (e.g., 3, 4, 5, or more) copies of a nucleotide sequence encoding a single miRNA or siRNA described herein. In some embodiments, a vector comprises multiple nucleotide sequences, where each nucleotide sequence encodes a different miRNA or siRNA described herein. In some embodiments, a vector comprises multiple nucleotide sequences encoding at least 2 different miRNAs or siRNAs, wherein at least two of the nucleotide sequences are copies of the same miRNA or siRNA described herein.

In some embodiments, in addition to one or more sequences encoding one or more miRNAs or siRNAs described herein, a vector (e.g., a viral vector) comprises one or more additional nucleotide sequences encoding one or more C3 inhibitors, e.g., a C3 inhibitor described herein. For example, a C3 inhibitor can be a polypeptide inhibitor and/or a nucleic acid aptamer (see, e.g., U.S. Publ. No. 20030191084). Exemplary polypeptide inhibitors include a compstatin analog (e.g., a compstatin analog described herein that includes genetically encodable amino acids), an anti-C3 or anti-C3b antibody (e.g., scFv or single domain antibody, e.g., a nanobody), an enzyme that degrades C3 or C3b (see, e.g., U.S. Pat. No. 6,676,943), or a mammalian complement regulatory protein (e.g., CR1, DAF, MCP, CFH, CFI, C1 inhibitor (C1-INH), a soluble form of complement receptor 1 (sCR1), TP10 or TP20 (Avant Therapeutics), or portion thereof. Additional polypeptide inhibitors include mini-factor H (see, e.g., U.S. Publ. No. 20150110766), Efb protein or complement inhibitor (SCIN) protein from *Staphylococcus aureus*, or a variant or derivative or mimetic thereof (see, e.g., U.S. Publ. 20140371133).

In some embodiments, a polypeptide inhibitor is linked to a secretion signal sequence for secretion of the expressed polypeptide inhibitor from a host cell.

V. Production of Expression Vectors

Methods for obtaining expression vectors, e.g., rAAVs, are known in the art. Typically, the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and/or sufficient helper functions to permit packaging of the recombinant AAV vector into the AAV capsid proteins.

The components to be cultured in a host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell that has been engineered to contain one or more of the required components using methods known to those of skill in the art. In some embodiments, such a stable host cell contains the required component(s) under the control of an inducible promoter. In other embodiments, the required component(s) may be under the control of a constitutive promoter. In other embodiments, a selected stable host cell may contain selected component(s) under the control of a constitutive promoter and other selected component(s) under the control of one or more inducible promoters. For example, a stable host cell may be generated that is derived from 293 cells (which contain E1 helper functions under the control of a constitutive promoter), but that contain the rep and/or cap proteins under the control of inducible promoters. Other stable host cells may be generated by one of skill in the art using routine methods.

Recombinant AAV vector, rep sequences, cap sequences, and helper functions required for producing an rAAV of the disclosure may be delivered to a packaging host cell using any appropriate genetic element (e.g., vector). A selected genetic element may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y.). Similarly, methods of generating rAAV virions are well known and any suitable method can be used with the present disclosure (see, e.g., K. Fisher et al, J. Virol., 70:520-532 (1993) and U.S. Pat. No. 5,478,745).

In some embodiments, recombinant AAVs may be produced using a triple transfection method (e.g., as described in U.S. Pat. No. 6,001,650). In some embodiments, recombinant AAVs are produced by transfecting a host cell with a recombinant AAV vector (comprising a transgene) to be packaged into AAV particles, an AAV helper function vector, and an accessory function vector. An AAV helper function vector encodes "AAV helper function" sequences (i.e., rep and cap), which function in trans for productive AAV replication and encapsidation. In some embodiments, the AAV helper function vector supports efficient AAV vector production without generating any detectable wild-type AAV virions (i.e., AAV virions containing functional rep and cap genes). Non-limiting examples of vectors suitable for use with the present disclosure include pHLP19 (see, e.g., U.S. Pat. No. 6,001,650) and pRep6cap6 vector (see, e.g., U.S. Pat. No. 6,156,303). An accessory function vector encodes nucleotide sequences for non-AAV derived viral and/or cellular functions upon which AAV is dependent for replication (i.e., "accessory functions"). Accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any known helper viruses such as adenovirus, herpesvirus (other than herpes simplex virus type-1), and vaccinia virus.

In some embodiments, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art (see, e.g., Graham et al. (1973) Virology, 52:456; Sambrook et al. (1989) Molecular Cloning, a laboratory manual, Cold Spring Harbor Laboratories, New York, Davis et al. (1986) Basic Methods in Molecular Biology, Elsevier; and Chu et al. (1981) Gene 13:197). Such techniques can be used to introduce one or more exogenous nucleic acids, such as a nucleotide integration vector and other nucleic acid molecules, into suitable host cells.

In some embodiments, a host cell is a mammalian cell. A host cell may be used as a recipient of an AAV helper construct, an AAV minigene plasmid, an accessory function vector, and/or other transfer DNA associated with the production of recombinant AAVs. The term includes the progeny of an original cell that has been transfected. Thus, a "host cell" as used herein may refer to a cell that has been transfected with an exogenous DNA sequence. It is understood that the progeny of a single parental cell may not necessarily be completely identical in morphology or in genomic or total DNA complement as the original parent, due to natural, accidental, or deliberate mutation.

Additional methods for generating and isolating AAV viral vectors suitable for delivery to a subject are described in, e.g., U.S. Pat. Nos. 7,790,449; 7,282,199; WO 2003/042397; WO 2005/033321, WO 2006/110689; and U.S. Pat. No. 7,588,772. In one system, a producer cell line is transiently transfected with a construct that encodes the transgene flanked by ITRs and a construct(s) that encodes rep and cap. In another system, a packaging cell line that stably supplies rep and cap is transiently transfected with a construct encoding the transgene flanked by ITRs. In each of these systems, AAV virions are produced in response to infection with helper adenovirus or herpesvirus, and rAAVs are separated from contaminating virus. Other systems do not require infection with helper virus to recover the AAV— the helper functions (i.e., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of the cells with constructs that encode the helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect host cells by infection with baculovirus-based vectors. Such production systems are known in the art (see generally, e.g., Zhang et al., 2009, Human Gene Therapy 20:922-929). Methods of making and using these and other AAV production systems are also described in U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The foregoing methods for producing recombinant vectors are not meant to be limiting, and other suitable methods will be apparent to the skilled artisan.

VI. Compositions and Administration

Vectors described herein (e.g., vectors comprising a nucleotide sequence encoding an miRNA described herein) can be used to treat a complement-mediated disease or disorder, e.g., subjects suffering from or susceptible to a complement-mediated disease or disorder described herein. The route and/or mode of administration of a vector described herein can vary depending upon the desired results. One with skill in the art, i.e., a physician, is aware that dosage regimens can be adjusted to provide the desired response, e.g., a therapeutic response. Methods of administration include, but are not limited to, intradermal, intramuscular, intraperitoneal, intravenous, subcutaneous, intranasal, epidural, oral, sublingual, intracerebral, intrathecal, intravaginal, transdermal, rectal, by inhalation, or topical, particularly to the ears, nose, eyes, or skin. The mode of administration is left to the discretion of the practitioner.

Vectors described herein can be incorporated into pharmaceutical compositions. Such pharmaceutical compositions are useful for, among other things, administration and delivery to a subject in vivo or ex vivo. In some embodiments, pharmaceutical compositions also contain a pharmaceutically acceptable carrier or excipient. Such excipients include any pharmaceutical agent, e.g., a pharmaceutical agent that does not itself induce an immune response harmful to the individual receiving the composition, and which may be administered without undue toxicity. As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

Pharmaceutical compositions may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In some embodiments, a pharmaceutical composition may be a lyophilized powder.

Pharmaceutical compositions can include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration can comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran. Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility to allow for the preparation of highly concentrated solutions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. Such labeling can include amount, frequency, and method of administration.

Pharmaceutical compositions and delivery systems appropriate for the compositions, methods and uses of the disclosure are known in the art (see, e.g., Remington: The Science and Practice of Pharmacy. 21st Edition. Philadelphia, PA. Lippincott Williams & Wilkins, 2005).

The disclosure also provides methods for introducing vectors described herein into a cell or an animal. In some embodiments, such methods include contacting a subject (e.g., a cell or tissue of a subject) with, or administering to a subject (e.g., a subject such as a mammal), a vector (e.g., an rAAV vector) comprising a nucleotide sequence encoding a miRNA or siRNA described herein, such that the miRNA or siRNA is expressed in the subject (e.g., in a cell or tissue of a subject). In another embodiment, a method includes providing cells of an individual (patient or subject such as a mammal) with a vector (e.g., an rAAV vector) comprising a nucleotide sequence encoding a miRNA or siRNA described herein, such that the miRNA or siRNA is expressed in the individual.

Compositions of a vector (e.g., an rAAV vector) comprising a nucleotide sequence encoding a miRNA or siRNA described herein can be administered in a sufficient or effective amount to a subject in need thereof. Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of miRNA or siRNA expression required to achieve a therapeutic effect, the specific disease treated, any host immune response to the viral vector, a host immune response to the heterologous miRNA or siRNA, and the stability of the miRNA or siRNA expressed. One skilled in the art can determine a rAAV/vector genome dose range to treat a patient having a particular disease or disorder based on the aforementioned factors, as well as other factors. Generally, doses will range from at least $1 \times 10^8$, or more, for example, $1 \times 10^9$, $1 \times 10^{10}$, $1 \times 10^{11}$, $1 \times 10^{12}$, $1 \times 10^{13}$, $1 \times 10^{14}$, or more, vector genomes per kilogram (vg/kg) of the weight of the subject, to achieve a therapeutic effect.

An effective amount or a sufficient amount can (but need not) be provided in a single administration, may require multiple administrations, and, can (but need not) be, administered alone or in combination with another composition (e.g., another complement inhibitor described herein). For example, the amount may be proportionally increased as indicated by the need of the subject, type, status and severity of the disease treated or side effects (if any) of treatment. Amounts considered effective also include amounts that result in a reduction of the use of another treatment, therapeutic regimen or protocol, such as administration of another complement inhibitor described herein.

Accordingly, pharmaceutical compositions of the disclosure include compositions wherein the active ingredients are contained in an effective amount to achieve the intended therapeutic purpose. Determining a therapeutically effective dose is well within the capability of a skilled medical practitioner using the techniques and guidance provided in the disclosure. Therapeutic doses can depend on, among other factors, the age and general condition of the subject, the severity of the complement-mediated disease or disorder, and the strength of the control sequences regulating the expression levels of an miRNA or siRNA described herein. Thus, a therapeutically effective amount in humans will fall in a relatively broad range that may be determined by a medical practitioner based on the response of an individual patient to vector-based treatment. Pharmaceutical compositions may be delivered to a subject, so as to allow production of an miRNA or siRNA described herein in vivo by gene- and or cell-based therapies or by ex-vivo modification of the patient's or donor's cells.

Methods and uses of the disclosure include delivery and administration systemically, regionally or locally, or by any route, for example, by injection or infusion. Delivery of a pharmaceutical composition in vivo may generally be accomplished via injection using a conventional syringe, although other delivery methods such as convection-enhanced delivery can also be used (see, e.g., U.S. Pat. No. 5,720,720). For example, compositions may be delivered subcutaneously, epidermally, intradermally, intrathecally, intraorbitally, intramucosally, intraperitoneally, intravenously, intra-pleurally, intraarterially, orally, intrahepatically, via the portal vein, or intramuscularly. Other modes of administration include oral and pulmonary administration, suppositories, and transdermal applications. A clinician specializing in the treatment of patients with complement-mediated disorders may determine the optimal route for administration of vectors described herein.

In some embodiments, an miRNA or siRNA described herein (or a vector comprising a nucleotide sequence encoding an miRNA or siRNA described herein) may be administered to a subject once daily, weekly, every 2, 3, or 4 weeks, or even at longer intervals. In some embodiments, an siRNA or an miRNA described herein is administered to a subject once daily, once weekly, once every 2, 3, or 4 weeks, or once at longer intervals. In some embodiments, a vector comprising a nucleotide sequence encoding an miRNA or siRNA described herein is administered to a subject once, e.g., as a single injection or as a single infusion over time (e.g., over 5, 10, 15, 20, 30, 40, 50, 60, 90, 120 minutes, or longer). In some embodiments, a vector comprising a nucleotide sequence encoding an miRNA or siRNA described herein is administered to a subject twice, e.g., as two injections (e.g., 2, 4, 6, 8, 10, or 12 hours apart) or as two infusions (e.g., 2, 4, 6, 8, 10, or 12 hours apart). In some embodiments, an miRNA or siRNA described herein (or a vector comprising a nucleotide sequence encoding an miRNA or siRNA described herein) may be administered according to a dosing regimen that includes (i) a single administration or an initial administration that is once daily, weekly, every 2, 3, or 4 weeks, or even at longer intervals; followed by (ii) a period of no administration of, e.g., 1, 2, 3, 4, 5, 6, 8, or 10 months, or 1, 2, 3, 4, 5, 6, 7, 8, 9, or 10 years. In some embodiments a vector comprising a nucleotide sequence encoding an miRNA or siRNA described herein may be administered (i) one or more times during an initial time period (e.g., over 48 hours, 24 hours, 12 hours, 6 hours, 3 hours, 2 hours, 1 hour, 30 minutes, 15 minutes); followed by (ii) a period of no administration of, e.g., 1, 2, 3, 4, 5, 6, 7, 8, 9, or 10 years. In some embodiments, a subject is monitored before and/or following treatment for level of C3 expression and/or activity, e.g., as measured using an alternative pathway assay, a classical pathway assay, or both. Suitable assays are known in the art and include, e.g., a hemolysis assay. In some embodiments, a subject is treated, or is retreated, if a measured level of C3 expression and/or activity is more than 10%, 20%, 30%, 40%, 50%, 100%, 200%, or more, relative to measured level of C3 expression and/or activity in a control subject.

VII. Diseases, Disorders, and Conditions

In some embodiments, an miRNA or siRNA described herein (or a vector comprising a nucleotide sequence encoding an miRNA or siRNA described herein) is administered to a subject suffering from or at risk of complement-mediated damage to an organ, tissue, or cells. In some embodiments, an miRNA or siRNA described herein (or a vector comprising a nucleotide encoding an miRNA or siRNA described herein) is administered in combination with one or more additional complement inhibitors to a subject suffering from or at risk of complement-mediated damage to an organ, tissue, or cells. In some embodiments, an miRNA or siRNA described herein (or a vector comprising a nucleotide sequence encoding an miRNA or siRNA described herein) is contacted with an organ, tissue, or cells ex vivo. The organ, tissue, or cells can be introduced into a subject and can be protected from damage that would otherwise be caused by the recipient's complement system.

Certain uses of interest include: (1) protecting red blood cells (RBCs) from complement-mediated damage in individuals with disorders such as paroxysmal nocturnal hemoglobinuria or atypical hemolytic uremic syndrome or other disorders characterized by complement-mediated RBC lysis; (2) protecting transplanted organs, tissues, and cells from complement-mediated damage; (3) reducing ischemia/reperfusion (I/R) injury (e.g., in individuals suffering from trauma, vascular obstruction, myocardial infarction, or other situations in which I/R injury may occur); and (4) protecting various body structures (e.g., the retina) or membranes (e.g., synovial membrane) that may be exposed to complement components from complement mediated damage in any of a variety of different complement-mediated disorders. The beneficial effects of inhibiting complement activation at the surface of cells or other body structures are not limited to those resulting directly from protection of the cells or structures themselves against direct complement-mediated damage (e.g., preventing cell lysis). For example, inhibiting complement activation may reduce the generation of anaphylotoxins and resulting influx/activation of neutrophils and other pro-inflammatory events and/or reduce potentially damaging release of intracellular contents, thereby potentially having beneficial effects on remote organ systems or throughout the body.

A. Blood Cell Protection

In some embodiments, an miRNA or siRNA described herein (or a vector comprising a nucleotide sequence encoding an miRNA or siRNA described herein), alone or in combination with one or more additional compstatin inhibitors described herein, is used to protect blood cells against complement-mediated damage. The blood cells may be any cellular component of the blood, e.g., red blood cells (RBCs), white blood cells (WBCs), and/or platelets. A variety of disorders are associated with complement-mediated damage to blood cells. Such disorders can result, for example, from deficiencies or defects in one or more of an individual's cellular or soluble CRPs, e.g., due to (a) mutation(s) in the gene(s) encoding such proteins; (b) mutation(s) in genes required for production or proper function of one or more CRPs, and/or (c) presence of autoantibodies to one or more CRPs. Complement-mediated RBC lysis can result from the presence of autoantibodies against RBC antigens which may arise due to a diverse set of causes (often being idiopathic). Individuals having such mutation(s) in genes encoding CRPs and/or having antibodies against CRPs or against their own RBCs are at increased risk of disorders involving complement-mediated RBC damage. Individuals who have had one or more episodes characteristic of a disorder are at increased risk of a recurrence.

Paroxysmal nocturnal hemoglobinuria (PNH) is a relatively rare disorder comprising an acquired hemolytic anemia characterized by complement-mediated intravascular hemolysis, hemoglobinuria, bone marrow failure, and thrombophilia (propensity to develop blood clots). It affects an estimated 16 individuals per million worldwide, occurs in both sexes, and can arise at any age, frequently striking young adults (Bessler, M. & Hiken, J., Hematology Am Soc Hematol Educ Program, 104-110 (2008); Hillmen, P. Hematology Am Soc Hematol Educ Program, 116-123 (2008)). PNH is a chronic and debilitating disease punctuated by acute hemolytic episodes and results in significant morbidities and reduced life expectancy. In addition to anemia, many patients experience abdominal pain, dysphagia, erectile dysfunction, and pulmonary hypertension, and are at increased risk of renal failure and thromboembolic events.

PNH was first described as a distinct entity in the 1800s, but it was only in the 1950s, with discovery of the alternative pathway of complement activation, that the cause of hemolysis in PNH was firmly established (Parker C J. Paroxysmal nocturnal hemoglobinuria: an historical overview. Hematology Am Soc Hematol Educ Program. 93-103 (2008)). CD55 and CD59 are normally attached to the cell membrane via glycosyl phosphatidylinositol (GPI) anchors (glycolipid structures that anchor certain proteins to the plasma membrane). PNH arises as a consequence of non-malignant clonal expansion of hematopoietic stem cell(s) that have acquired a somatic mutation in the PIGA gene, which encodes a protein involved in synthesis of GPI anchors (Takeda J, et al. Deficiency of the GPI anchor caused by a somatic mutation of the PIG-A gene in paroxysmal nocturnal hemoglobinuria. Cell. 73:703-711 (1993)). Progeny of such stem cells are deficient in GPI-anchored proteins, including CD55 and CD59. This defect renders these cells susceptible to complement-mediated RBC lysis. Flow cytometric analysis using antibodies to GPI-anchored proteins is often used for diagnosis. It detects deficiency of GPI-anchored proteins at the cell surface and allows determination of the degree of deficiency and the proportion of affected cells (Brodsky R A. Advances in the diagnosis and therapy of paroxysmal nocturnal hemoglobinuria. Blood Rev. 22(2):65-74 (2008). PNH type III RBCs are completely deficient in GPI-linked proteins and are highly sensitive to complement whereas PNH type II RBCs have a partial deficiency and are less sensitive. FLAER is a fluorescently labeled inactive variant of proaerolysin (a bacterial toxin that binds GPI anchors) and is increasingly used together with flow cytometry for diagnosis of PNH. Lack of binding of FLAER to granulocytes is sufficient for diagnosis of PNH. In some embodiments, an miRNA or siRNA described herein (or a vector encoding an miRNA or siRNA described herein), alone or in combination with one or more additional complement inhibitors described herein, protects PNH RBCs, from deposition of C3b. In some embodiments an miRNA or siRNA described herein (or a vector encoding an miRNA or siRNA described herein), alone or in combination with one or more additional complement inhibitors described herein, inhibits intravascular and extravascular hemolysis in a subject suffering from PNH.

In some embodiments, an miRNA or siRNA described herein (or a vector comprising a nucleotide sequence encoding an miRNA or siRNA described herein), alone or in combination with one or more additional complement inhibitors described herein, is administered to a subject suffering from atypical hemolytic syndrome (aHUS). aHUS is a chronic disorder characterized by microangiopathic hemolytic anemia, thrombocytopenia, and acute renal failure and is caused by inappropriate complement activation, often due to mutations in genes encoding complement regulatory proteins (Warwicker, P., et al., Kidney Int 53, 836-844 (1998); Kavanagh, D. & Goodship, T. Pediatr Nephrol 25, 2431-2442 (2010). Mutations in the complement factor H (CFH) gene are the most common genetic abnormality in patients with aHUS, and 60-70% of these patients die or reach end stage renal failure within one year after disease onset (Kavanagh & Goodship, supra.) Mutations in factor I, factor B, C3, factor H-related proteins 1-5, and thrombomodulin have also been described. Other causes of aHUS include autoantibodies against complement regulatory proteins such as CFH. In some embodiments, an miRNA or siRNA described herein (or a vector comprising a nucleotide sequence encoding an miRNA or siRNA described herein), alone or in combination with one or more additional complement inhibitors described herein, is administered to a subject that has been identified as having a mutation in factor I, factor B, C3, factor H-related proteins 1-5, or thrombomodulin or has been identified as having antibodies against a complement regulatory protein, e.g., CFH.

Complement-mediated hemolysis occurs in a diverse group of other conditions including autoimmune hemolytic anemias that involve antibodies that bind to RBCs and lead to complement-mediated hemolysis. For example, such hemolysis can occur in primary chronic cold agglutinin disease and certain reactions to drugs and other foreign substances (Berentsen, S., et al., Hematology 12, 361-370 (2007); Rosse, W. F., Hillmen, P. & Schreiber, A. D. Hematology Am Soc Hematol Educ Program, 48-62 (2004)). In some embodiments, an miRNA or siRNA described herein (or a vector comprising a nucleotide sequence encoding an miRNA or siRNA described herein), alone or in combination with one or more additional complement inhibitors described herein, is administered to a subject suffering from or at risk of chronic cold agglutinin disease. In another embodiment, an miRNA or siRNA described herein (or a vector comprising a nucleotide sequence encoding an miRNA or siRNA described herein), alone or in combination with one or more additional complement inhibitors described herein, is used to treat a subject suffering from or at risk of the HELLP syndrome, which is defined by the existence of hemolysis, elevated liver enzymes, and low platelet count and is associated with mutations in complement regulatory protein(s) in at least some subjects (Fakhouri, F., et al., 112: 4542-4545 (2008)).

In some embodiments, an miRNA or siRNA described herein (or a vector comprising a nucleotide sequence encoding an miRNA or siRNA described herein), alone or in combination with one or more additional complement inhibitors described herein, is administered to a subject suffering from or at risk of warm autoimmune hemolytic anemia.

In other embodiments, an miRNA or siRNA described herein (or a vector comprising a nucleotide sequence encoding an miRNA or siRNA described herein), alone or in combination with one or more additional complement inhibitors described herein, is used to protect RBCs or other cellular components of blood to be transfused into a subject. Certain examples of such uses are discussed further in below.

B. Transplantation

Transplantation is a therapeutic approach of increasing importance, providing a means to replace organs and tissues that have been damaged through trauma, disease, or other conditions. Kidneys, liver, lungs, pancreas, and heart are among the organs that can be successfully transplanted. Tissues that are frequently transplanted include bones, cartilage, tendons, cornea, skin, heart valves, and blood vessels. Pancreatic islet or islet cell transplantation is a promising approach for treatment of diabetes, e.g., type I diabetes. For purposes of the invention, an organ, tissue, or cell (or population of cells) that is be transplanted, is being transplanted, or has been transplanted may be referred to as a "graft". For purposes hereof, a blood transfusion is considered a "graft".

Transplantation subjects the graft to a variety of damaging events and stimuli that can contribute to graft dysfunction and, potentially, failure. For example, ischemia-reperfusion (I/R) injury is a common and significant cause of morbidity and mortality in the case of many grafts (particularly solid organs) and can be a major determinant of likelihood of graft survival. Transplant rejection is one of the major risks associated with transplants between genetically different individuals and can lead to graft failure and a need to remove the graft from the recipient.

In some embodiments, an miRNA or siRNA described herein (or a vector comprising a nucleotide sequence encoding an miRNA or siRNA described herein), alone or in combination with one or more additional complement inhibitors described herein, is used to protect a graft from complement-mediated damage. For example, a cell-reactive compstatin analog reacts with cells of the graft, becomes covalently attached thereto, and inhibits complement activation. A cell-targeted compstatin analog binds to a target molecule in the graft (e.g., expressed by endothelial cells or other cells in the graft) and inhibits complement activation. A target molecule may be, e.g., is a molecule whose expression is induced or stimulated by a stimulus such as injury or inflammation, molecule that would be recognized as "non-self" by the recipient, a carbohydrate xenoantigen to which antibodies are commonly found in human beings such as a blood group antigen or a xenoantigen, e.g., a molecule comprising an alpha-gal epitope. In some embodiments, a reduction in complement activation can be demonstrated by a reduction in average C4d deposition in blood vessels of grafts that have been contacted with an miRNA or siRNA described herein (or a vector comprising a nucleotide sequence encoding an miRNA or siRNA described herein), alone or in combination with one or more additional complement inhibitors described herein, as compared with the average level of C4d deposition in grafts that have not been contacted with an miRNA or siRNA described herein (or a vector comprising a nucleotide sequence encoding an miRNA or siRNA described herein), alone or in combination with one or more additional complement inhibitors described herein (e.g., in subjects who are matched with respect to the grafts and other therapy that they receive).

A graft can be contacted with an miRNA or siRNA described herein (or a vector comprising a nucleotide sequence encoding an miRNA or siRNA described herein), alone or in combination with one or more additional complement inhibitors described herein, that inhibits C3 expression prior to, during, and/or after being transplanted, in various embodiments of the disclosure. For example, prior to transplantation a graft removed from a donor can be contacted with a liquid comprising a cell-reactive, long-acting, or targeted compstatin analog. For example, the graft can be bathed in and/or perfused with the solution. In another embodiment, an miRNA or siRNA described herein (or a vector comprising a nucleotide sequence encoding an miRNA or siRNA described herein), alone or in combination with one or more additional complement inhibitors described herein, is administered to a donor prior to removal of the graft. In some embodiments, an miRNA or siRNA described herein (or a vector comprising a nucleotide sequence encoding an miRNA or siRNA described herein), alone or in combination with one or more additional complement inhibitors described herein, is administered to a recipient during and/or after the introduction of the graft. In some embodiments, an miRNA or siRNA described herein (or a vector comprising a nucleotide sequence encoding an miRNA or siRNA described herein), alone or in combination with one or more additional complement inhibitors described herein, is delivered locally to the transplanted graft. In some embodiments a cell-reactive, long-acting, or targeted compstatin analog is administered systemically, e.g., intravenously or subcutaneously. In some embodiments, an miRNA or siRNA described herein (or a vector comprising a nucleotide sequence encoding an miRNA or siRNA described herein), alone or in combination with one or more additional complement inhibitors described herein, is administered to a recipient prior to the introduction of the graft. In some embodiments the subject receives one or more additional doses of the miRNA or siRNA, vector encoding the miRNA or siRNA, and/or one or more additional complement inhibitors after receiving the graft.

The disclosure provides a composition comprising: (a) an isolated graft; and (b) an miRNA or siRNA described herein (or a vector comprising a nucleotide sequence encoding an miRNA or siRNA described herein) that inhibits C3 expression. The disclosure also provides a composition comprising: (a) an isolated graft; (b) a cell-reactive, long-acting, or targeted compstatin analog and (c) an miRNA or siRNA described herein (or a vector comprising a nucleotide sequence encoding an miRNA or siRNA described herein) that inhibits C3 expression. In some embodiments the composition further comprises a liquid solution suitable for contacting (e.g., suitable for rinsing, washing, bathing, perfusing, maintaining, or storing) a graft (e.g., an organ) such as an isolated graft that has been removed from a donor and is awaiting transplantation to a recipient. In some embodiments the disclosure provides a composition comprising: (a) a liquid solution suitable for contacting a graft (e.g., an organ); and (b) an miRNA or siRNA described herein (or a vector comprising a nucleotide sequence encoding an miRNA or siRNA described herein) that inhibits C3 expression. In some embodiments the composition further comprises a cell-reactive, long-acting, or targeted compstatin analog. The liquid solution can be any liquid solution that is physiologically acceptable to the graft (e.g., appropriate osmotic composition, non-cytotoxic) and medically acceptable in view of the subsequent introduction of the graft into the recipient (e.g., preferably sterile or at least reasonably free from microorganisms or other contaminants) and compatible with the cell-reactive compstatin analog (i.e., will not destroy the reactivity of the compstatin analog) or compatible with the long-acting or targeted compstatin analog. In some embodiments, a solution is any solution known in the art for any such purposes. In some embodiments, a liquid solution is Marshall's or Hyperosmolar Citrate (Soltran®, Baxter Healthcare), University of Wisconsin (UW) solution (ViaSpan™, Bristol Myers Squibb), Histidine Tryptophan Ketoglutarate (HTK) solution (Custodial®, Kohler Medical Limited), EuroCollins (Fresenius), and Celsior® (Sangstat Medical), Polysol, IGL-1, or AQIX® RS-1. Of course other solutions, e.g., containing equivalent or similar ingredients in the same or different concentrations could be used within the scope of physiologically acceptable compositions. In some embodiments a solution does not contain ingredient(s) with which the cell-reactive compstatin analog would be expected to significantly react, and any solution may be modified or designed to lack such ingredients. In some embodiments, the cell-reactive compstatin analog is present in the graft-compatible solution at a concentration of, e.g., between 0.01 mg/ml and 100 mg/ml or may be added to the solution to achieve such concentration.

In some embodiments, a graft is or comprises a solid organ such as a kidney, liver, lung, pancreas, or heart. In some embodiments, a graft is or comprises bone, cartilage, fascia, tendon, ligament, cornea, sclera, pericardium, skin, heart valve, blood vessel, amniotic membrane, or dura mater. In some embodiments, a graft comprises multiple organs such as a heart-lung or pancreas-kidney graft. In some embodiments, a graft comprises less than a complete organ or tissue. For example, a graft may contain a portion of an organ or tissue, e.g., a liver valve, section of blood vessel, skin flap, or heart valve. In some embodiments, a graft comprises a preparation comprising isolated cells or tissue fragments that have been isolated from their tissue of origin but retain at least some tissue architecture, e.g., pancreatic islets. In some embodiments, a preparation comprises isolated cells that are not attached to each other via connective tissue, e.g., hematopoietic stem cells or progenitor cells derived from peripheral and/or cord blood, or whole blood or any cell-containing blood product such as red blood cells (RBCs) or platelets. In some embodiments a graft is obtained from a deceased donor (e.g., a "donation after brain death" (DBD) donor or "donation after cardiac death" donor). In some embodiments, depending on the particular type of graft, a graft is obtained from a living donor. For example, kidneys, liver sections, blood cells, are among the types of grafts that can often be obtained from a living donor without undue risk to the donor and consistent with sound medical practice.

In some embodiments, a graft is a xenograft (i.e., the donor and recipient are of different species). In some embodiments a graft is an autograft (i.e., a graft from one part of the body to another part of the body in the same individual). In some embodiments, a graft is an isograft (i.e., the donor and recipient are genetically identical). In most embodiments, the graft is an allograft (i.e., the donor and recipient are genetically non-identical members of the same species). In the case of an allograft, the donor and recipient may or may not be genetically related (e.g., family members). Typically, the donor and recipient have compatible blood groups (at least ABO compatibility and optionally Rh, Kell and/or other blood cell antigen compatibility). The recipient's blood may have been screened for alloantibodies to the graft and/or the recipient and donor since the presence of such antibodies can lead to hyperacute rejection (i.e., rejection beginning almost immediately, e.g., within several minutes after the graft comes into contact with the recipient's blood). A complement-dependent cytotoxicity (CDC) assay can be used to screen a subject's serum for anti-HLA antibodies. The serum is incubated with a panel of lymphocytes of known HLA phenotype. If the serum contains antibodies against HLA molecules on the target cells, cell death due to complement-mediated lysis occurs. Using a selected panel of target cells allows one to assign specificity to the detected antibody. Other techniques useful for determining the presence or absence anti-HLA antibodies and, optionally, determining their HLA specificity, include ELISA assays, flow cytometry assays, microbead array technology (e.g., Luminex technology). The methodology for performing these assays is well known, and a variety of kits for performing them are commercially available.

In some embodiments an miRNA or siRNA described herein (or a vector comprising a nucleotide sequence encoding an miRNA or siRNA described herein), alone or in combination with one or more additional complement inhibitors described herein, inhibits complement-mediated rejection. For example, in some embodiments, an miRNA or siRNA described herein (or a vector comprising a nucleotide sequence encoding an miRNA or siRNA described herein), alone or in combination with one or more additional complement inhibitors described herein, inhibits hyperacute rejection. Hyperacute rejection is caused at least in part by antibody-mediated activation of the recipient's complement system via the classical pathway and resulting MAC deposition on the graft. It typically results from the presence in the recipient of pre-existing antibodies that react with the graft. While it is desirable to attempt to avoid hyperacute rejection by appropriate matching prior to transplantation, it may not always possible to do so due, e.g., to time and/or resource constraints. Furthermore, some recipients (e.g., multiply transfused individuals, individuals who have previously received transplants, women who have had multiple pregnancies) may already have so many pre-formed antibodies, potentially including antibodies to antigens that are not typically tested for, that it can be difficult or perhaps almost impossible to obtain with confidence a compatible graft in a timely manner. Such individuals are at increased risk of hyperacute rejection.

In some embodiments, an miRNA or siRNA described herein (or a vector comprising a nucleotide sequence encoding an miRNA or siRNA described herein), alone or in combination with one or more additional complement inhibitors described herein, inhibits acute rejection or graft failure. As used herein, "acute rejection" refers to rejection occurring between at least 24 hours, typically at least several days to a week, after a transplant, up to 6 months after the transplant. Acute antibody-mediated rejection (AMR) often involves an acute rise in donor-specific alloantibody (DSA) in the first few weeks after transplantation. Without wishing to be bound by any theory, it is possible that pre-existing plasma cells and/or the conversion of memory B cells to new plasma cells play a role in the increased DSA production. Such antibodies can result in complement-mediated damage to the graft, which can be inhibited by contacting the graft with a cell-reactive compstatin analog. Without wishing to be bound by any theory, inhibiting complement activation at the graft may reduce leukocyte (e.g., neutrophil) infiltration, another contributor to acute graft failure.

In some embodiments, an miRNA or siRNA described herein (or a vector comprising a nucleotide sequence encoding an miRNA or siRNA described herein), alone or in combination with one or more additional complement inhibitors described herein, inhibits complement-mediated I/R injury to a graft. As discussed further below, I/R injury can occur upon reperfusion of tissue whose blood supply has been temporarily disrupted, as occurs in transplanted organs. Reducing I/R injury would reduce the likelihood of acute graft dysfunction or reduce its severity, and reduce the likelihood of acute graft failure.

In some embodiments, an miRNA or siRNA described herein (or a vector comprising a nucleotide sequence encoding an miRNA or siRNA described herein), alone or in combination with one or more additional complement inhibitors described herein, inhibits chronic rejection and/or chronic graft failure. As used herein, "chronic rejection or graft failure" refers to rejection or failure occurring at least 6 months post-transplant, e.g., between 6 months and 1, 2, 3, 4, 5 years, or more post-transplant, often after months to years of good graft function. It is caused by a chronic inflammatory and immune response against the graft. For purposes hereof, chronic rejection can include chronic allograft vasculopathy, a term used to refer to fibrosis of the internal blood vessels of the transplanted tissue. As immunosuppressive regimens have reduced the incidence of acute rejection, chronic rejection is becoming more prominent as a cause of graft dysfunction and failure. There is increasing evidence that B-cell production of alloantibody is an important element in the genesis of chronic rejection and graft failure (Kwun J. and Knechtle S J, Transplantation, 88(8): 955-61 (2009). Earlier damage to the graft may be a contributing factor leading to chronic processes such as fibrosis that can ultimately lead to chronic rejection. Thus, inhibiting such earlier damage using a cell-reactive compstatin analog may delay and/or reduce the likelihood or severity of chronic graft rejection.

In some embodiments, an miRNA or siRNA described herein (or a vector comprising a nucleotide sequence encoding an miRNA or siRNA described herein), alone or in combination with one or more additional complement inhibitors described herein, is administered to a graft recipient to inhibit graft rejection and/or graft failure.

C. Ischemia/Reperfusion Injury

Ischemia-reperfusion (I/R) injury is an important cause of tissue damage following trauma and in other conditions associated with temporary disruption of blood flow such as myocardial infarction, stroke, severe infection, vascular disease, aneurysm repair, cardiopulmonary bypass, and transplantation.

In the setting of trauma, systemic hypoxemia, hypotension, and local interruption of the blood supply resulting from contusions, compartment syndrome, and vascular injuries cause ischemia that damages metabolically active tissues. Restoration of the blood supply triggers an intense systemic inflammatory reaction that is often more harmful than the ischemia itself. Once the ischemic region is reperfused, factors that are produced and released locally enter the circulatory system and reach remote locations, sometimes causing significant damage to organs not affected by the original ischemic insult, such as the lungs and intestine, leading to single and multiple organ dysfunction. Complement activation occurs soon after reperfusion and is a key mediator of post-ischemic damage, both directly and through its chemoattractive and stimulatory effects on neutrophils. All three major complement pathways are activated and, acting cooperatively or independently, are involved in I/R related adverse events affecting numerous organ systems. In some embodiments of the disclosure, an miRNA or siRNA described herein (or a vector comprising a nucleotide sequence encoding an miRNA or siRNA described herein), alone or in combination with one or more additional complement inhibitors described herein, is administered to a subject who has recently (e.g., within the preceding 2, 4, 8, 12, 24, or 48 hours) experienced trauma, e.g., trauma that puts the subject at risk of I/R injury, e.g., due to systemic hypoxemia, hypotension, and/or local interruption of the blood supply. In some embodiments the cell-reactive compstatin analog may be administered intravascularly, optionally into a blood vessel that supplies an injured body part or directly to the body part. In some embodiments, the subject suffers from spinal cord injury, traumatic brain injury, burn, and/or hemorrhagic shock.

In some embodiments, an miRNA or siRNA described herein (or a vector comprising a nucleotide sequence encoding an miRNA or siRNA described herein), alone or in combination with one or more additional complement inhibitors described herein, is administered to a subject prior to, during, or after a surgical procedure, e.g., a surgical procedure that is expected to temporarily disrupt blood flow to a tissue, organ, or portion of the body. Examples of such procedures include cardiopulmonary bypass, angioplasty, heart valve repair/replacement, aneurysm repair, or other vascular surgeries. An miRNA or siRNA described herein (or a vector comprising a nucleotide sequence encoding an miRNA or siRNA described herein), alone or in combination with one or more additional complement inhibitors described herein, may be administered prior to, after, and/or during an overlapping time period with the surgical procedure.

In some embodiments, an miRNA or siRNA described herein (or a vector comprising a nucleotide sequence encoding an miRNA or siRNA described herein), alone or in combination with one or more additional complement inhibitors described herein, is administered to a subject who has suffered an MI, thromboembolic stroke, deep vein thrombosis, or pulmonary embolism. An miRNA or siRNA described herein (or a vector comprising a nucleotide sequence encoding an miRNA or siRNA described herein), alone or in combination with one or more additional complement inhibitors described herein, may be administered in combination with a thrombolytic agent such as tissue plasminogen activator (tPA) (e.g., alteplase (Activase), reteplase (Retavase), tenecteplase (TNKase)), anistreplase (Eminase), streptokinase (Kabikinase, Streptase), or urokinase (Abbokinase). An miRNA or siRNA described herein (or a vector comprising a nucleotide sequence encoding an miRNA or siRNA described herein), alone or in combination with one or more additional complement inhibitors described herein, may be administered prior to, after, and/or during an overlapping time period with the thrombolytic agent.

In some embodiments, an miRNA or siRNA described herein (or a vector comprising a nucleotide sequence encoding an miRNA or siRNA described herein), alone or in combination with one or more additional complement inhibitors described herein, is administered to a subject to treat I/R injury.

D. Other Complement-Mediated Disorders

In some embodiments, an miRNA or siRNA described herein (or a vector comprising a nucleotide sequence encoding an miRNA or siRNA described herein), alone or in combination with one or more additional complement inhibitors described herein, is introduced into the eye for treatment of an eye disorder such as age-related macular degeneration (AMD), diabetic retinopathy, glaucoma, or uveitis. For example, an miRNA or siRNA described herein (or a vector comprising a nucleotide sequence encoding an miRNA or siRNA described herein), alone or in combination with one or more additional complement inhibitors described herein, may be introduced into the vitreous cavity (e.g., by intravitreal injection) or introduced into the subretinal space (e.g., by subretinal injection), for treatment of a subject suffering from or at risk of AMD. In some embodiments the AMD is neovascular (wet) AMD. In some embodiments the AMD is dry AMD. As will be appreciated by those of ordinary skill in the art, dry AMD encompasses geographic atrophy (GA), intermediate AMD, and early AMD. In some embodiments, a subject with GA is treated in order to slow or halt progression of the disease. For example, in some embodiments, treatment of a subject with GA reduces the rate of retinal cell death. A reduction in the rate of retinal cell death may be evidenced by a reduction in the rate of GA lesion growth in patients treated with an miRNA or siRNA described herein (or a vector comprising a nucleotide sequence encoding an miRNA or siRNA described herein), alone or in combination with one or more additional complement inhibitors described herein, as compared with control (e.g., patients given a sham administration). In some embodiments, a subject has intermediate AMD. In some embodiments, a subject has early AMD. In some embodiments, a subject with intermediate or early AMD is treated in order to slow or halt progression of the disease. For example, in some embodiments, treatment of a subject with intermediate AMD may slow or prevent progression to an advanced form of AMD (neovascular AMD or GA). In some embodiments, treatment of a subject with early AMD may slow or prevent progression to intermediate AMD. In some embodiments an eye has both GA and neovascular AMD. In some embodiments an eye has GA but not wet AMD. In some embodiments an miRNA or siRNA described herein (or a vector comprising a nucleotide sequence encoding an miRNA or siRNA described herein), alone or in combination with one or more additional complement inhibitors described herein, is administered, e.g., by intravitreal injection or subretinal injection to treat glaucoma, uveitis (e.g., posterior uveitis), or diabetic retinopathy. In some embodiments an miRNA or siRNA described herein (or a vector comprising a nucleotide sequence encoding an miRNA or siRNA described herein), alone or in combination with one or more additional complement inhibitors described herein, is introduced into the anterior chamber, e.g., to treat anterior uveitis.

In some embodiments an miRNA or siRNA described herein (or a vector comprising a nucleotide sequence encoding an miRNA or siRNA described herein), alone or in combination with one or more additional complement inhibitors described herein, is used to treat a subject suffering from or at risk of an autoimmune disease, e.g., an autoimmune disease mediated at least in part by antibodies against one or more self antigens.

An miRNA or siRNA described herein (or a vector comprising a nucleotide sequence encoding an miRNA or siRNA described herein), alone or in combination with one or more additional complement inhibitors described herein may be introduced into the synovial cavity, e.g., in a subject suffering from arthritis (e.g., rheumatoid arthritis).

In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of an intracerebral hemorrhage.

In some embodiments an miRNA or siRNA described herein (or a vector comprising a nucleotide sequence encoding an miRNA or siRNA described herein), alone or in combination with one or more additional complement inhibitors described herein, is used to treat a subject suffering from or at risk of myasthenia gravis.

In some embodiments an miRNA or siRNA described herein (or a vector comprising a nucleotide sequence encoding an miRNA or siRNA described herein), alone or in combination with one or more additional complement inhibitors described herein, is used to treat a subject suffering from or at risk of neuromyelitis optica (NMO).

In some embodiments an miRNA or siRNA described herein (or a vector comprising a nucleotide sequence encoding an miRNA or siRNA described herein), alone or in combination with one or more additional complement inhibitors described herein, is used to treat a subject suffering from or at risk of a disorder affecting the kidney, e.g., the glomeruli of the kidney. In some embodiments the disorder is membranoproliferative glomerulonephritis (MPGN), e.g., MPGN type I, MPGN type II, or MPGN type III. In some embodiments the disorder is IgA nephropathy (IgAN). In some embodiments the disorder is primary membranous nephropathy. In some embodiments the disorder is C3 glomerulopathy. In some embodiments the disorder is characterized by glomerular deposits containing one or more complement activation products, e.g., C3b, in the kidney. In some embodiments treatment as described herein reduces the level of such deposits. In some embodiments a subject suffering from a complement-mediated kidney disorder suffers from proteinuria (an abnormally high level of protein in the urine) and/or an abnormally low glomerular filtration rate (GFR). In some embodiments treatment as described herein results in decreased proteinuria and/or an increased or stabilized GFR.

In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of a neurodegenerative disease. In some embodiments, an miRNA or siRNA described herein (or a vector comprising a nucleotide sequence encoding an miRNA or siRNA described herein), alone or in combination with one or more additional complement inhibitors described herein, is used to treat a subject suffering from neuropathic pain or at risk of developing neuropathic pain. In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of rhinosinusitis or nasal polyposis. In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of cancer. In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of sepsis. In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of adult respiratory distress syndrome.

In some embodiments, an miRNA or siRNA described herein (or a vector comprising a nucleotide sequence encoding an miRNA or siRNA described herein), alone or in combination with one or more additional complement inhibitors described herein, is used to treat a subject suffering from or at risk of anaphylaxis or infusion reaction. For example, in some embodiments, a subject may be treated prior to, during, or after receiving a drug or a vehicle that may cause anaphylaxis or infusion reaction. In some embodiments, a subject at risk of or suffering from anaphylaxis from a food (e.g., peanut, shellfish, or other food allergens), insect sting (e.g., bee, wasp), is treated with an miRNA or siRNA described herein (or a vector comprising a nucleotide sequence encoding an miRNA or siRNA described herein), alone or in combination with one or more additional complement inhibitors described herein.

An miRNA or siRNA described herein (or a vector comprising a nucleotide sequence encoding an miRNA or siRNA described herein), alone or in combination with one or more additional complement inhibitors described herein, may be administered locally or systemically, in various embodiments of the disclosure.

In some embodiments, an miRNA or siRNA described herein (or a vector comprising a nucleotide sequence encoding an miRNA or siRNA described herein), alone or in combination with one or more additional complement inhibitors described herein, is used to treat a respiratory disease, e.g., asthma or chronic obstructive pulmonary disease (COPD) or idiopathic pulmonary fibrosis. An miRNA or siRNA described herein (or a vector comprising a nucleotide sequence encoding an miRNA or siRNA described herein), alone or in combination with one or more additional complement inhibitors described herein, may, for example, be administered to the respiratory tract by inhalation, e.g., as a dry powder or via nebulization, or may be administered by injection, e.g., intravenously, intramuscularly, or subcutaneously, in various embodiments. In some embodiments, an miRNA or siRNA described herein (or a vector comprising a nucleotide sequence encoding an miRNA or siRNA described herein), alone or in combination with one or more additional complement inhibitors described herein, is used to treat severe asthma, e.g., asthma that is not sufficiently controlled by bronchodilators and/or inhaled corticosteroids.

In some aspects, methods of treating a complement-mediated disorder, e.g., a chronic complement-mediated disorder, are provided, the methods comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder. In some aspects, methods of treating a Th17-associated disorder are provided, the methods comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some aspects, a "chronic disorder" is a disorder that persists for at least 3 months and/or is accepted in the art as being a chronic disorder. In many embodiments, a chronic disorder persists for at least 6 months, e.g., at least 1 year, or more, e.g., indefinitely. One of ordinary skill in the art will appreciate that at least some manifestations of various chronic disorders may be intermittent and/or may wax and wane in severity over time. A chronic disorder may be progressive, e.g., having a tendency to become more severe or affect larger areas over time. A number of chronic complement-mediated disorders are discussed herein. A chronic complement-mediated disorder may be any chronic disorder in which complement activation (e.g., excessive or inappropriate complement activation) is involved, e.g., as a contributing and/or at least partially causative factor. For convenience, disorders are sometimes grouped by reference to an organ or system that is often particularly affected in subjects suffering from the disorder. It will be appreciated that a number of disorders can affect multiple organs or systems, and such classification(s) are in no way limiting. Furthermore, a number of manifestations (e.g., symptoms) may occur in subjects suffering from any of a number of different disorders. Non-limiting information regarding disorders of interest herein may be found, e.g., in standard textbooks of internal medicine such as Cecil Textbook of Medicine (e.g., 23rd edition), Harrison's Principles of Internal Medicine (e.g., 17th edition), and/or standard textbooks focusing on particular areas of medicine, particular body systems or organs, and/or particular disorders.

In some embodiments, a chronic complement-mediated disorder is a Th2-associated disorder. As used herein, a Th2-associated disorder is a disorder characterized by an excessive number and/or excessive or inappropriate activity of CD4+ helper T cells of the Th2 subtype ("Th2 cells") in the body or a portion thereof, e.g., in at least one tissue, organ, or structure. For example, there may be a predominance of Th2 cells relative to CD4+ helper T cells of the Th1 subtype ("Th1 cells") e.g., in at least one tissue, organ, or structure affected by a disorder. As known in the art, Th2 cells typically secrete characteristic cytokines such as interleukin-4 (IL-4), interleukin-5 (IL-5), and interleukin-13 (IL-13), while Th1 cells typically secrete interferon-γ (IFN-γ) and tumor necrosis factor β (TNF β). In some embodiments, a Th2-associated disorder is characterized by excessive production and/or amount of IL-4, IL-5, and/or IL-13, e.g., relative to IFN-γ and/or TNF β e.g., in at least some at least one tissue, organ, or structure In some embodiments, a chronic complement-mediated disorder is a Th17-associated disorder. In some aspects, as described in further detail in PCT/US2012/043845, filed Jun. 22, 2012, entitled "Methods of Treating Chronic Disorders with Complement Inhibitors", complement activation and Th17 cells participate in a cycle that involves dendritic cells and antibodies and that contributes to maintenance of a pathologic immunologic microenvironment underlying a range of disorders. Without wishing to be bound by any theory, the pathologic immunologic microenvironment, once established, is self-sustaining and contributes to cell and tissue injury. In some aspects, long-acting compstatin analogs are of use to treat Th17-associated disorders.

As used herein, a Th17-associated disorder is a disorder characterized by an excessive number and/or excessive or inappropriate activity of CD4+ helper T cells of the Th17 subtype ("Th17 cells") in the body or a portion thereof, e.g., in at least one tissue, organ, or structure. For example, there may be a predominance of Th17 cells relative to Th1 and/or Th2 cells, e.g., in at least one tissue, organ, or structure affected by a disorder. In some embodiments a predominance of Th17 cells is a relative predominance, e.g., the ratio of Th17 cells to Th1 cells and/or the ratio of Th17 cells to Th2 cells, is increased relative to normal values. In some embodiments the ratio of Th17 cells to T regulatory cells ($CD4^+CD25^+$ regulatory T cells, also termed "Treg cells"), is increased relative to normal values. Formation of Th17 cells and/or activation of Th 17 cells is promoted by various cytokines, e.g., interleukin 6 (IL-6), interleukin 21 (IL-21), interleukin 23 (IL-23), and/or interleukin 1β (IL-1β). Formation of Th17 cells encompasses differentiation of precursor T cells, e.g., naïve CD4+ T cells, towards a Th17 phenotype and their maturation into functional Th17 cells. In some embodiments, formation of Th17 cells encompasses any aspect of development, proliferation (expansion), survival, and/or maturation of Th17 cells. In some embodiments, a Th17-associated disorder is characterized by excessive production and/or amount of IL-6, IL-21, IL-23, and/or IL-10. Th17 cells typically secrete characteristic cytokines such as interleukin-17A (IL-17A), interleukin-17F (IL-17F), interleukin-21 (IL-21), and interleukin-22 (IL-22). In some embodiments, a Th17-associated disorder is characterized by excessive production and/or amount of a Th17 effector cytokine, e.g., IL-17A, IL-17F, IL-21, and/or IL-22. In some embodiments excessive production or amount of a cytokine is detectable in the blood. In some embodiments excessive production or amount of a cytokine is detectable locally, e.g., in at least one tissue, organ or structure. In some embodiments a Th17-associated disorder is associated with a decreased number of Tregs and/or decreased amount of a Treg-associated cytokine. In some embodiments a Th17 disorder is any chronic inflammatory disease, which term encompasses a range of ailments characterized by self-perpetuating immune insults to a variety of tissues and that seem to be dissociated from the initial insult that caused the ailment (which may be unknown). In some embodiments a Th17-associated disorder is any autoimmune disease. Many if not most "chronic inflammatory diseases" may in fact be auto-immune diseases. Examples of Th17-associated disorders include inflammatory skin diseases such as psoriasis and atopic dermatitis; systemic scleroderma and sclerosis; inflammatory bowel disease (IBD) (such as Crohn's disease and ulcerative colitis); Behcet's Disease; dermatomyositis; polymyositis; multiple sclerosis (MS); dermatitis; meningitis; encephalitis; uveitis; osteoarthritis; lupus nephritis; rheumatoid arthritis (RA), Sjogren's syndrome, multiple sclerosis, vasculitis; central nervous system (CNS) inflammatory disorders, chronic hepatitis; chronic pancreatitis, glomerulonephritis; sarcoidosis; thyroiditis, pathologic immune responses to tissue/organ transplantation (e.g., transplant rejection); COPD, asthma, bronchiolitis, hypersensitivity pneumonitis, idiopathic pulmonary fibrosis (IPF), periodontitis, and gingivitis. In some embodiments a Th17 disease is a classically known auto-immune disease such as Type I diabetes or psoriasis. In some embodiments a Th17-associated disorder is age-related macular degeneration.

In some embodiments, a chronic complement-mediated disorder is an IgE-associated disorder. As used herein, an "IgE-associated disorder" is a disorder characterized by excessive and/or inappropriate production and/or amount of IgE, excessive or inappropriate activity of IgE producing cells (e.g., IgE producing B cells or plasma cells), and/or excessive and/or inappropriate activity of IgE responsive cells such as eosinophils or mast cells. In some embodiments, an IgE-associated disorder is characterized by elevated levels of total IgE and/or in some embodiments, allergen-specific IgE, in the plasma of a subject and/or locally.

In some embodiments, a chronic complement-mediated disorder is characterized by the presence of autoantibodies and/or immune complexes in the body, which may activate complement via, e.g., the classical pathway. Autoantibodies may, for example, bind to self antigens, e.g., on cells or tissues in the body. In some embodiments, autoantibodies bind to antigens in blood vessels, skin, nerves, muscle, connective tissue, heart, kidney, thyroid, etc. In some embodiments, a subject has neuromyelitis optica and produces an autoantibody (e.g., an IgG autoantibody) to aquaporin 4. In some embodiments, a subject has pemphigoid and produces an autoantibody (e.g., an IgG or IgE autoantibody) to a structural component of the hemidesmosome (e.g., transmembrane collagen XVII (BP180 or BPAG2) and/or plakin family protein BP230 (BPAG1). In some embodiments, a chronic complement-mediated disorder is not characterized by autoantibodies and/or immune complexes.

In some embodiments, a chronic complement-mediated disorder is a respiratory disorder. In some embodiments, a chronic respiratory disorder is asthma or chronic obstructive pulmonary disease (COPD). In some embodiments, a chronic respiratory disorder is pulmonary fibrosis (e.g., idiopathic pulmonary fibrosis), radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans. In some embodiments, the disclosure provides a method of treating a subject in need of treatment for a chronic respiratory disorder, e.g., asthma, COPD, pulmonary fibrosis, radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder is allergic rhinitis, rhinosinusitis, or nasal polyposis. In some embodiments, the disclosure provides a method of treating a subject in need of treatment for allergic rhinitis, rhinosinusitis, or nasal polyposis, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder is a disorder that affects the musculoskeletal system. Examples of such disorders include inflammatory joint conditions (e.g., arthritis such as rheumatoid arthritis or psoriatic arthritis, juvenile chronic arthritis, spondyloarthropathies Reiter's syndrome, gout). In some embodiments, a musculoskeletal system disorder results in symptoms such as pain, stiffness and/or limitation of motion of the affected body part(s). Inflammatory myopathies include dermatomyositis, polymyositis, and various others are disorders of chronic muscle inflammation of unknown etiology that result in muscle weakness. In some embodiments, a chronic complement-mediated disorder is myasthenia gravis. In some embodiments, the disclosure provides a method of treating any of the foregoing disorders affecting the musculoskeletal system, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder is a disorder that affects the integumentary system. Examples of such disorders include, e.g., atopic dermatitis, psoriasis, pemphigoid, pemphigus, systemic lupus erythematosus, dermatomyositis, scleroderma, sclerodermatomyositis, Sjögren syndrome, and chronic urticaria. In some aspects, the disclosure provides a method of treating any of the foregoing disorders affecting the integumentary system, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder affects the nervous system, e.g., the central nervous system (CNS) and/or peripheral nervous system (PNS). Examples of such disorders include, e.g., multiple sclerosis, other chronic demyelinating diseases (e.g., neuromyelits optica), amyotrophic lateral sclerosis, chronic pain, stroke, allergic neuritis, Huntington's disease, Alzheimer's disease, and Parkinson's disease. In some embodiments, the disclosure provides a method of treating any of the foregoing disorders affecting the nervous system, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder affects the circulatory system. For example, in some embodiments the disorder is a vasculitis or other disorder associated with vessel inflammation, e.g., blood vessel and/or lymph vessel inflammation. In some embodiments, a vasculitis is polyarteritis nodosa, Wegener's granulomatosis, giant cell arteritis, Churg-Strauss syndrome, microscopic polyangiitis, Henoch-Schonlein purpura, Takayasu's arteritis, Kawasaki disease, or Behcet's disease. In some embodiments, a subject, e.g., a subject in need of treatment for vasculitis, is positive for antineutrophil cytoplasmic antibody (ANCA).

In some embodiments, a chronic complement-mediated disorder affects the gastrointestinal system. For example, the disorder may be inflammatory bowel disease, e.g., Crohn's disease or ulcerative colitis. In some embodiments, the disclosure provides a method of treating a chronic complement-mediated disorder that affects the gastrointestinal system, the method comprising administering an miRNA or siRNA described herein (or a vector comprising a nucleotide sequence encoding an miRNA or siRNA described herein), alone or in combination with one or more additional complement inhibitors described herein, to a subject in need of treatment for the disorder.

In some embodiments, a chronic complement-mediated disorder is a thyroiditis (e.g., Hashimoto's thyroiditis, Graves' disease, post-partum thyroiditis), myocarditis, hepatitis (e.g., hepatitis C), pancreatitis, glomerulonephritis (e.g., membranoproliferative glomerulonephritis or membranous glomerulonephritis), or panniculitis.

In some embodiments, the disclosure provides methods of treating a subject suffering from chronic pain, the methods comprising administering an miRNA or siRNA described herein (or a vector comprising a nucleotide sequence encoding an miRNA or siRNA described herein), alone or in combination with one or more additional complement inhibitors described herein, to a subject in need thereof. In some embodiments, a subject suffers from neuropathic pain. Neuropathic pain has been defined as pain initiated or caused by a primary lesion or dysfunction in the nervous system, in particular, pain arising as a direct consequence of a lesion or disease affecting the somatosensory system. For example, neuropathic pain may arise from lesions that involve the somatosensory pathways with damage to small fibres in peripheral nerves and/or to the spino-thalamocortical system in the CNS. In some embodiments, neuropathic pain arises from autoimmune disease (e.g., multiple sclerosis), metabolic disease (e.g., diabetes), infection (e.g., viral disease such as shingles or HIV), vascular disease (e.g., stroke), trauma (e.g., injury, surgery), or cancer. For example, neuropathic pain can be pain that persists after healing of an injury or after cessation of a stimulus of peripheral nerve endings or pain that arises due to damage to nerves. Exemplary conditions of or associated with neuropathic pain include painful diabetic neuropathy, postherpetic neuralgia (e.g., pain persisting or recurring at the site of acute herpes zoster 3 or more months after the acute episode), trigeminal neuralgia, cancer related neuropathic pain, chemotherapy-associated neuropathic pain, HIV-related neuropathic pain (e.g., from HIV neuropathy), central/post-stroke neuropathic pain, neuropathy associated with back pain, e.g., low back pain (e.g., from radiculopathy such as spinal root compression, e.g., lumbar root compression, which compression may arise due to disc herniation), spinal stenosis, peripheral nerve injury pain, phantom limb pain, polyneuropathy, spinal cord injury related pain, myelopathy, and multiple sclerosis. In certain embodiments of the disclosure, an miRNA or siRNA described herein (or a vector comprising a nucleotide sequence encoding an miRNA or siRNA described herein), alone or in combination with one or more additional complement inhibitors described herein, is administered according to a dosing schedule to treat neuropathic pain in a subject with one or more of the afore-mentioned conditions.

In some embodiments, a chronic complement-mediated disorder is a chronic eye disorder. In some embodiments, the chronic eye disorder is characterized by macular degeneration, choroidal neovascularization (CNV), retinal neovascularization (RNV), ocular inflammation, or any combination of the foregoing. Macular degeneration, CNV, RNV, and/or ocular inflammation may be a defining and/or diagnostic feature of the disorder. Exemplary disorders that are characterized by one or more of these features include, but are not limited to, macular degeneration related conditions, diabetic retinopathy, retinopathy of prematurity, proliferative vitreoretinopathy, uveitis, keratitis, conjunctivitis, and scleritis. Macular degeneration related conditions include, e.g., age-related macular degeneration (AMD). In some embodiments, a subject is in need of treatment for wet AMD. In some embodiments, a subject is in need of treatment for dry AMD. In some embodiments, a subject is in need of treatment for geographic atrophy (GA). In some embodiments, a subject is in need of treatment for ocular inflammation. Ocular inflammation can affect a large number of eye structures such as the conjunctiva (conjunctivitis), cornea (keratitis), episclera, sclera (scleritis), uveal tract, retina, vasculature, and/or optic nerve. Evidence of ocular inflammation can include the presence of inflammation-associated cells such as white blood cells (e.g., neutrophils, macrophages) in the eye, the presence of endogenous inflammatory mediator(s), one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. In some embodiments, the chronic eye disorder is an eye disorder characterized by optic nerve damage (e.g., optic nerve degeneration), such as glaucoma.

As noted above, in some embodiments, the chronic respiratory disease is asthma. Information regarding risk factors, epidemiology, pathogenesis, diagnosis, current management of asthma, etc., may be found, e.g., in "Expert Panel Report 3: Guidelines for the Diagnosis and Management of Asthma". National Heart Lung and Blood Institute. 2007. http://www.nhlbi.nih.gov/guidelines/asthma/asthgdln.pdf. ("NHLBI Guidelines"; www.nhlbi.nih.gov/guidelines/asthma/asthgdln.htm), Global Initiative for Asthma, Global Strategy for Asthma Management and Prevention 2010 "GINA Report") and/or standard textbooks of internal medicine such as Cecil Textbook of Medicine (20th edition), Harrison's Principles of Internal Medicine (17th edition), and/or standard textbooks focusing on pulmonary medicine. Asthma is a chronic inflammatory disorder of the airways in which many cells and cellular elements play a role, such as, mast cells, eosinophils, T lymphocytes, macrophages, neutrophils, and epithelial cells Asthmatic individuals experience recurrent episodes associated with symptoms such as wheezing, breathlessness (also termed dyspnea or shortness of breath), chest tightness, and coughing. These episodes are usually associated with widespread but variable airflow obstruction that is often reversible, either spontaneously or with treatment. The inflammation also causes an associated increase in the existing bronchial hyperresponsiveness to a variety of stimuli. Airway hyperresponsiveness (an exaggerated bronchoconstrictor response to stimuli) is a typical feature of asthma. In general, airflow limitation results from bronchoconstriction and airway edema. Reversibility of airflow limitation may be incomplete in some patients with asthma. For example, airway remodeling can lead to fixed airway narrowing. Structural changes can include thickening of the sub-basement membrane, subepithelial fibrosis, airway smooth muscle hypertrophy and hyperplasia, blood vessel proliferation and dilation, and mucous gland hyperplasia, and hypersecretion.

Individuals with asthma may experience exacerbations, which are identified as events characterized by a change from the individual's previous status. Severe asthma exacerbations can be defined as events that require urgent action on the part of the individual and his/her physician to prevent a serious outcome, such as hospitalization or death from asthma. For example, a severe asthma exacerbation may require use of systemic corticosteroids (e.g., oral corticosteroids) in a subject whose asthma is usually well controlled without OCS or may require an increase in a stable maintenance dose. Moderate asthma exacerbations can be defined as events that are troublesome to the subject, and that prompt a need for a change in treatment, but that are not severe. These events are clinically identified by being outside the subject's usual range of day-to-day asthma variation.

Current medications for asthma are typically categorized into two general classes: long-term control medications ("controller medications") such as inhaled corticosteroids (ICS), oral corticosteroids (OCS), long-acting bronchodilators (LABAs), leukotriene modifiers (e.g., leukotriene receptor antagonists or leukotriene synthesis inhibitors, anti-IgE antibodies (omalizumab (Xolair®)), cromolyn and nedocromil, which are used to achieve and maintain control of persistent asthma and quick-relief medications such as short-acting bronchodilators (SABAs), which are used to treat acute symptoms and exacerbations. For purposes of the present invention, these treatments may be referred to as "conventional therapy". Treatment of exacerbations may also include increasing the dose and/or intensity of controller medication therapy. For example, a course of OCS can be used to regain asthma control. Current guidelines mandate daily administration of controller medication or, in many cases, administration of multiple doses of controller medication each day for subjects with persistent asthma (with the exception of Xolair, which is administered every 2 or 4 weeks).

A subject is generally considered to have persistent asthma if the subject suffers from symptoms on average more than twice a week and/or typically uses a quick relief medication (e.g., SABA) more than twice a week for symptom control. "Asthma severity" can be classified based on the intensity of treatment required to control the subject's asthma once relevant comorbidities have been treated and inhaler technique and adherence have been optimized (see, e.g., GINA Report; Taylor, DR, Eur Respir J 2008; 32:545-554). The description of treatment intensity can be based on the medications and doses recommended in the stepwise treatment algorithm found in guidelines such as NHLBI Guidelines 2007, GINA Report, and their predecessors and/or in standard medical textbooks. For example, asthma can be classified as intermittent, mild, moderate, or severe as indicated in Table 4, where "treatment" refers to treatment sufficient to achieve subject's best level of asthma control. (It will be understood that the categories of mild, moderate, and severe asthma in general imply persistent rather than intermittent asthma). One of ordinary skill in the art will appreciate that Table 4 is exemplary, and that not all of these medications will be available in all healthcare systems, which may affect the assessment of asthma severity in some environments. It will also be appreciated that other emerging or new approaches may affect the classification of mild/ moderate asthma. However, the same principle, of mild asthma being defined by the ability to achieve good control using very low-intensity treatment and severe asthma being defined by the requirement for high-intensity treatment, can still be applied. Asthma severity can also or alternately be classified based on intrinsic intensity of the disease in the absence of treatment (see, e.g., NHBLI Guidelines 2007). Assessment can be made on the basis of current spirometry and the patient's recall of symptoms over the previous 2-4 weeks. Parameters of current impairment and future risk may be assessed and included in a determination of the level of asthma severity. In some embodiments, asthma severity is defined as shown in FIG. 3.4(a), 3.4(b), 3.4(c) of the NHBLI Guidelines, for individuals 0-4, 5-11, or ≥12 years of age, respectively.

TABLE 4

Treatment-based Asthma Classification

| Asthma Classification | Treatment |
|---|---|
| Intermittent | SABA as needed (typically no more than twice a week) |
| Mild | Low-dose ICS or other low-intensity treatment (e.g., LTRA, cromolyn, nedocromil, theophylline) |
| Moderate | Low to moderate dose ICS and LABA or other extra treatment |
| Severe | High-intensity treatment (high-dose ICS and LABA ± oral corticosteroids and/or other extra treatment) |

Figure 4:
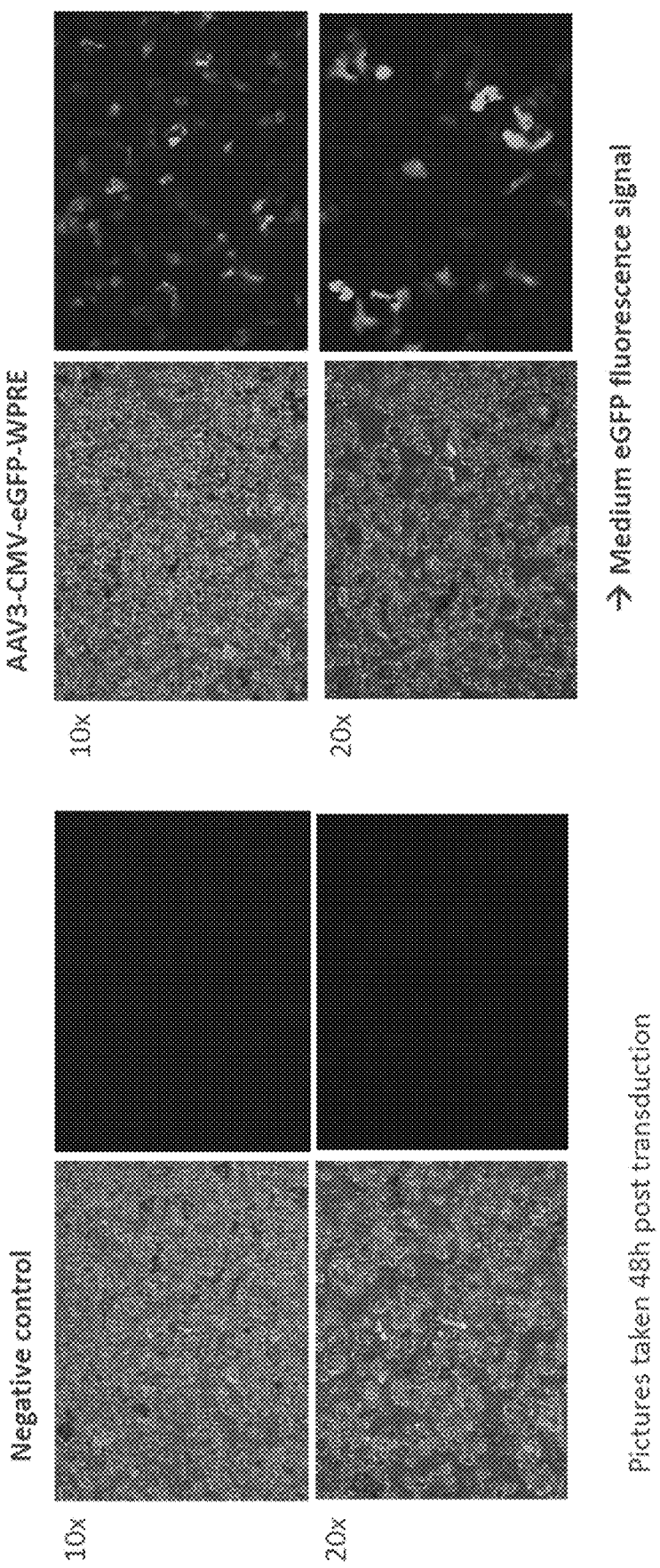
FIG. 4 shows micrographs of rAAV serotype testing in primary cryopreserved hepatocyte cells at MOI 100,000 at 48 hours post transduction.
Figure 4:
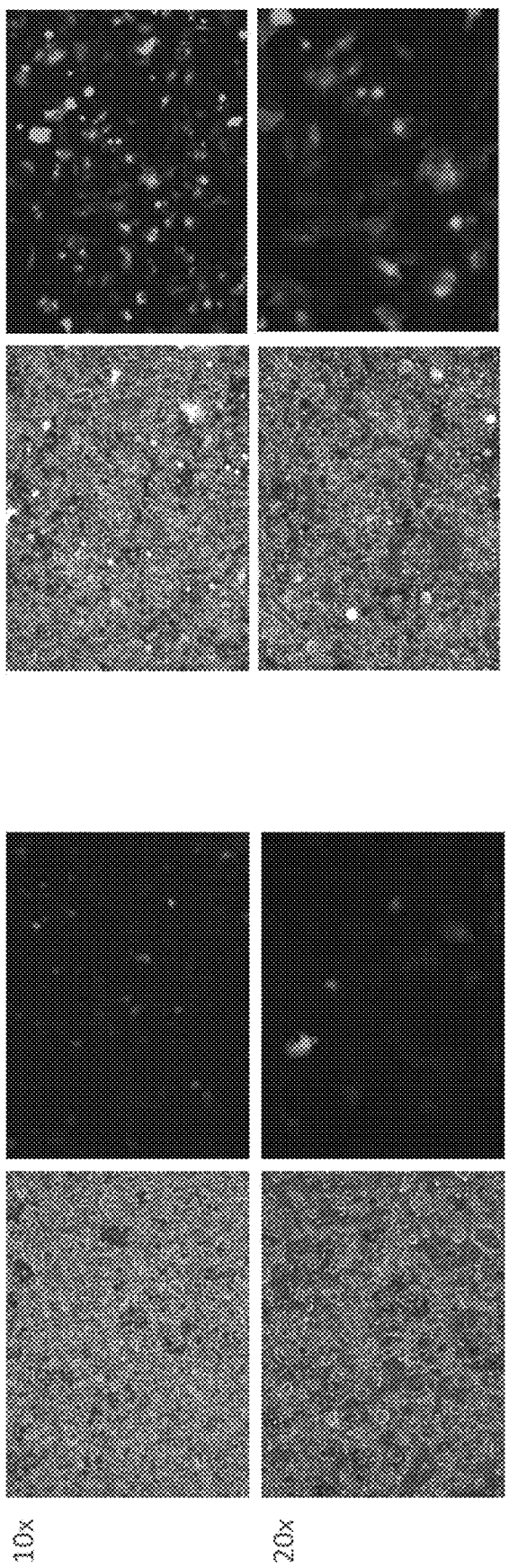

"Asthma control" refers to the extent to which the manifestations of asthma have been reduced or removed by treatment (whether pharmacological or non-pharmacological). Asthma control can be assessed based on factors such as symptom frequency, nighttime symptoms, objective measures of lung function such as spirometry parameters (e.g., % $FEV_1$ of predicted, $FEV_1$ variability, requirement for use of SABA for symptom control. Parameters of current impairment and future risk may be assessed and included in a determination of the level of asthma control. In some embodiments, asthma control is defined as shown in FIG. 4.3(a), 4.3(b), or 4.3(c) of NHBLI Guidelines, for individuals 0-4, 5-11, or ≥12 years of age, respectively.

In general, one of ordinary skill in the art can select an appropriate means of determining asthma severity level and/or degree of control, and any classification scheme considered reasonable by those of ordinary skill in the art can be used.

In some embodiments of the disclosure, a subject suffering from persistent asthma is treated with an miRNA or siRNA described herein (or a vector comprising a nucleotide sequence encoding an miRNA or siRNA described herein), alone or in combination with one or more additional complement inhibitors described herein, using a dosing regimen. In some embodiments, the subject suffers from mild or moderate asthma. In some embodiments, the subject suffers from severe asthma. In some embodiments, a subject has asthma that is not well controlled using conventional therapy. In some embodiments, a subject has asthma that, when treated using conventional therapy, requires use of ICS in order to be well controlled. In some embodiments, a subject has asthma that fails to be well controlled despite use of ICS. In some embodiments, a subject has asthma that, if treated using conventional therapy, would require use of OCS in order to be well controlled. In some embodiments, a subject has asthma that fails to be well controlled despite use of high intensity conventional therapy that includes OCS. In some embodiments, an miRNA or siRNA described herein (or a vector comprising a nucleotide sequence encoding an miRNA or siRNA described herein), alone or in combination with one or more additional complement inhibitors described herein, is administered as a controller medication or allow the subject to avoid using or reduce their dose of a conventional controller medication.

In some embodiments, the subject suffers from allergic asthma, which is the case for most asthmatic individuals. In some embodiments, an asthmatic subject is considered to have allergic asthma if a non-allergic trigger for the asthma (e.g., cold, exercise) is not known and/or is not identified in a standard diagnostic evaluation. In some embodiments, an asthmatic subject is considered to have allergic asthma if the subject (i) reproducibly develops asthma symptoms (or worsening of asthma symptoms) following exposure to an allergen or allergen(s) to which the subject is sensitive; (ii) exhibits IgE specific for an allergen or allergen(s) to which the subject is sensitive; (iii) exhibits a positive skin-prick test to an allergen or allergen(s) to which the subject is sensitive; and/or (iv) exhibits other symptom(s) of characteristic(s) consistent with atopy such as allergic rhinitis, eczema, or elevated total serum IgE. It will be appreciated that a specific allergic trigger may not be identified but may be suspected or inferred if the subject experiences worsening symptoms in particular environments, for example.

Allergen challenge by inhalation is a technique that is widely used in evaluating allergic airway disease. Inhalation of allergen leads to cross-linking of allergen-specific IgE bound to IgE receptors on, e.g., mast cells and basophils. Activation of secretory pathways ensues, resulting in release of mediators of bronchoconstriction and vascular permeability. Individuals with allergic asthma may develop various manifestations following allergen challenge, e.g., early asthmatic response (EAR), late asthmatic response (LAR), airway hyperreactivity (AHR), and airway eosinophilia, each of which can be detected and quantified as known in the art. For example, airway eosiphophilia may be detected as an increase in eosinophils in sputum and/or BAL fluid. The EAR, sometimes referred to as the immediate asthmatic response (IAR), is a response to allergen challenge by inhalation that becomes detectable shortly after the inhalation, typically within 10 minutes (min) of the inhalation, e.g., as a decrease in $FEV_1$. The EAR typically reaches a maximum within 30 min and resolves within 2-3 hours (h) post-challenge. For example, a subject may be considered to exhibit a "positive" EAR if his/her $FEV_1$ decreases by at least 15%, e.g., at least 20%, within this time window relative to baseline $FEV_1$ (where "baseline" in this context refers to conditions before the challenge, e.g., conditions equivalent to the subject's usual condition when not experiencing an asthma exacerbation and not exposed to allergic stimuli to which the subject is sensitive). The late asthmatic response (LAR) typically starts between 3 h and 8 h post-challenge and is characterized by cellular inflammation of the airway, increased bronchiovascular permeability, and mucus secretion. It is typically detected as a decrease in $FEV_1$, which may be greater in magnitude than that associated with the EAR and potentially more clinically important. For example, a subject may be considered to exhibit a "positive" LAR if his/her $FEV_1$ decreases by at least 15%, e.g., at least 20%, relative to baseline $FEV_1$ within the relevant time period as compared with baseline $FEV_1$. A delayed airway response (DAR) may occur beginning between about 26 and 32 h, reaching a maximum between about 32 and 48 h and resolving within about 56 h after the challenge (Pelikan, Z. Ann Allergy Asthma Immunol. 2010, 104(5):394-404).

In some embodiments, the chronic respiratory disorder is chronic obstructive pulmonary disease (COPD). COPD encompasses a spectrum of conditions characterized by airflow limitation that is not fully reversible even with therapy and is usually progressive. Symptoms of COPD include dyspnea (breathlessness), decreased exercise tolerance, cough, sputum production, wheezing, and chest tightness. Persons with COPD can experience episodes of acute (e.g., developing over course of less than a week and often over the course of 24 hours or less) worsening of symptoms (termed COPD exacerbations) that can vary in frequency and duration and are associated with significant morbidity. They may be triggered by events such as respiratory infection, exposure to noxious particles, or may have an unknown etiology. Smoking is the most commonly encountered risk factor for COPD, and other inhalational exposures can also contribute to development and progression of the disease. The role of genetic factors in COPD is an area of active research. A small percentage of COPD patients have a hereditary deficiency of alpha-1 antitrypsin, a major circulating inhibitor of serine proteases, and this deficiency can lead to a rapidly progressive form of the disease.

Characteristic pathophysiologic features of COPD include narrowing of and structural changes in the small airways and destruction of lung parenchyma (in particular around alveoli), most commonly due to chronic inflammation. The chronic airflow limitation observed in COPD typically involves a mixture of these factors, and their relative importance in contributing to airflow limitation and symptoms varies from person to person. The term "emphysema" refers to enlargement of the air spaces (alveoli) distal to the terminal bronchioles, with destruction of their walls. It should be noted that the term "emphysema" is often used clinically to refer to the medical condition associated with such pathological changes. Some individuals with COPD have chronic bronchitis, which is defined in clinical terms as a cough with sputum production on most days for 3 months of a year, for 2 consecutive years. Further information regarding risk factors, epidemiology, pathogenesis, diagnosis, and current management of COPD may be found, e.g., in "Global Strategy for the Diagnosis, Management, and Prevention of Chronic Obstructive Pulmonary Disease" (updated 2009) available on the Global Initiative on Chronic Obstructive Pulmonary Disease, Inc. (GOLD) website (www.goldcopd.org), also referred to herein as the "GOLD Report", the American Thoracic Society/European Respiratory Society Guidelines (2004) available on the ATS website at www.thoracic.org/clinical/copd-guidelines/resources/copddoc.pdf, referred to herein as "ATC/ERS COPD Guidelines" and standard textbooks of internal medicine such as Cecil Textbook of Medicine ($20^{th}$ edition), Harrison's Principles of Internal Medicine ($17^{th}$ edition), and/or standard textbooks focusing on pulmonary medicine.

In some embodiments methods disclosed herein inhibit (interfere with, disrupt) the DC-Th17-B-Ab-C-DC cycle discussed above. For example, administration of an miRNA or siRNA described herein (or a vector comprising a nucleotide sequence encoding an miRNA or siRNA described herein), alone or in combination with one or more additional complement inhibitors described herein, may break the cycle by which complement stimulates DC cells to promote the Th17 phenotype. As a result, the number and/or activity of Th17 cells diminishes, which in turn reduces the amount of Th17-mediated stimulation of B cells and polyclonal antibody production. In some embodiments, these effects result in "resetting" the immunological microenvironment to a more normal, less pathological state. As described in Example 1 of PCT/US2012/043845 (WO/2012/178083) and US Publ. No. 20140371133 evidence supporting the capacity of complement inhibition to have a prolonged inhibitory effect on Th17-associated cytokine production has been obtained in an animal model of asthma.

In some embodiments, inhibiting the DC-Th17-B-Ab-C-DC cycle has a disease-modifying effect. Without wishing to be bound by any theory, rather than merely treating symptoms of a disorder, inhibiting the DC-Th17-B-Ab-C-DC cycle may interfere with fundamental pathologic mechanisms that may contribute to ongoing tissue damage even when symptoms are well controlled and/or that may contribute to exacerbations of the disease. In some embodiments, inhibiting the DC-Th17-B-Ab-C-DC cycle causes a chronic disorder to go into remission. In some embodiments, remission refers to a state of absence or substantial absence of disease activity in a subject with a chronic disorder, with the possibility of return of disease. In some embodiments remission may be sustained for a prolonged period of time (e.g., at least 6 months, e.g., 6-12 months, 12-24 months, or more) in the absence of continued therapy or with a reduced dose or increased dosing interval. In some aspects, inhibition of complement may change the immunological micro-environment of a tissue that is rich in Th17 cells and modify it into a micro-environment that is rich in regulatory T cells (Tregs). Doing so could allow the immune system to "reset" itself and go into a state of remission. In some embodiments, for example, remission may be sustained until occurrence of a triggering event. A triggering event may be, for example, an infection (which may result in production of polyclonal antibodies that react both with an infectious agent and a self protein), exposure to particular environmental conditions (e.g., high levels of air pollutants such as ozone or particulate matter or components of smoke such as cigarette smoke, allergens), etc. Genetic factors may play a role. For example, individuals having particular alleles of genes encoding complement components may have a higher baseline level of complement activity, a more reactive complement system and/or a lower baseline level of endogenous complement regulatory protein activity. In some embodiments an individual has a genotype associated with increased risk of AMD. For example, the subject may have a polymorphism in a gene encoding a complement protein or complement regulatory protein, e.g., CFH, C3, factor B, wherein the polymorphism is associated with an increased risk of AMD.

In some embodiments an immunologic microenvironment may become progressively more polarized towards a pathological state over time, e.g., in a subject who has not yet developed symptoms of a chronic disorder or in a subject who has developed the disorder and has been treated as described herein. Such a transition may occur stochastically (e.g., due at least in part to apparently random fluctuations in antibody levels and/or affinity) and/or as a result of accumulated "sub-threshold" trigger events that are not of sufficient intensity to trigger a symptomatic outbreak of a disorder.

In some embodiments it is contemplated that a relatively short course of an miRNA or siRNA described herein (or a vector comprising a nucleotide sequence encoding an miRNA or siRNA described herein), alone or in combination with one or more additional complement inhibitors described herein, e.g., between 1 week and 6 weeks, e.g., about 2-4 week, may provide a long-lasting benefit. In some embodiments, a remission is achieved for a prolonged period of time, e.g., 1-3 months, 3-6 months, 6-12 months, 12-24 months, or more. In some embodiments a subject may be monitored and/or treated prophylactically before recurrence of symptoms. For example, a subject may be treated prior to or upon exposure to a triggering event. In some embodiments a subject may be monitored, e g., for an increase in a biomarker, e.g., a biomarker comprising an indicator of Th17 cells or Th17 cell activity, or complement activation, and may be treated upon increase in the level of such biomarker. See, e.g., PCT/US2012/043845 for further discussion.

VIII. Combination Therapy

In some aspects, methods of the present disclosure involve administering an miRNA or siRNA described herein (or a vector comprising a nucleotide sequence encoding an miRNA or siRNA described herein), alone or in combination with one or more additional complement inhibitors. In some embodiments, an miRNA or siRNA described herein (or a vector comprising a nucleotide sequence encoding an miRNA or siRNA described herein) is administered to a subject already receiving therapy with another complement inhibitor; in some embodiments, another complement inhibitor is administered to a subject receiving an miRNA or siRNA described herein (or a vector comprising a nucleotide sequence encoding an miRNA or siRNA described herein). In some embodiments, both an miRNA or siRNA described herein (or a vector comprising a nucleotide sequence encoding an miRNA or siRNA described herein) and another complement inhibitor are administered to the subject.

In some embodiments administration of an miRNA or siRNA described herein (or a vector comprising a nucleotide sequence encoding an miRNA or siRNA described herein) may allow for administering a reduced dosing regimen of (e.g., involving a smaller amount in an individual dose, reduced frequency of dosing, reduced number of doses, and/or reduced overall exposure to) a second complement inhibitor, as compared to administration of a second complement inhibitor as single therapy. Without wishing to be bound by any theory, in some embodiments a reduced dosing regimen of a second complement inhibitor may avoid one or more undesired adverse effects that could otherwise result.

In some aspects, administration of an miRNA or siRNA described herein (or a vector comprising a nucleotide sequence encoding an miRNA or siRNA described herein) in combination with a second complement inhibitor can reduce the amount of C3 in the subject's blood sufficiently such that a reduced dosing regimen of an miRNA or siRNA described herein (or a vector comprising a nucleotide sequence encoding an miRNA or siRNA described herein) and/or the second complement inhibitor is required to achieve a desired degree of complement inhibition.

In some embodiments such a reduced dose can be administered in a smaller volume, or using a lower concentration, or using a longer dosing interval, or any combination of the foregoing, as compared to administration of an miRNA or siRNA described herein (or a vector comprising a nucleotide sequence encoding an miRNA or siRNA described herein) or a second complement inhibitor as single therapy.

A. Additional Complement Inhibitors
(i) Compstatin Analogs

Compstatin is a cyclic peptide that binds to C3 and inhibits complement activation. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 5 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32 (Pt 1):28-32, 2004, Mallik, B., et al., *J. Med. Chem.*, 274-286, 2005; Katragadda, M., et al. *J. Med. Chem.*, 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

The $K_d$ of compstatin binding to C3 can be measured using isothermal titration calorimetry (Katragadda, et al., *J. Biol. Chem.*, 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µM and 0.1 µM, between 0.025 µM and 0.05 µM, between 0.015 µM and 0.025 µM, between 0.01 µM and 0.015 µM, or between 0.001 µM and 0.01 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (21g1), dihydrotrpytophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH—W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41: 10262-10269, 2002 (describing, inter alia, singly- and multiply-halogenated Trp analogs); Babitzke & Yanofsky, *J. Biol. Chem.* 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N(α) methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X''aa)$_m$, (SEQ ID NO: 2) wherein each X'aa and each X''aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X''aa (SEQ ID NO: 4), where X'aa and Xaa are each independently selected from Trp and analogs of Trp and X''aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X″aa is Ala or an analog of Ala such as Abu or another unbranched single methyl amino acid. In certain embodiments of the invention the peptide has a core sequence of X'aa-Gln-Asp-Xaa-Gly-X″aa (SEQ ID NO: 4), where X'aa and Xaa are each independently selected from Trp, analogs of Trp, and amino acids or amino acid analogs comprising at least one aromatic side chain, and X″aa is selected from His, Ala, analogs of Ala, Phe, and Trp. In certain embodiments X″aa is selected from analogs of Trp, aromatic amino acids, and aromatic amino acid analogs.

In certain preferred embodiments of the invention the peptide is cyclic. The peptide may be cyclized via a bond between any two amino acids, one of which is $(X'aa)_n$ and the other of which is located within $(X''aa)_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X″aa1-X″aa2-X″aa3-X″aa4-X″aa5 (SEQ ID NO: 5). In certain embodiments X'aa4 and Xaa are selected from Trp and analogs of Trp, and X'aa1, X'aa2, X'aa3, X″aa1, X″aa2, X″aa3, X″aa4, and X″aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X″aa1, X″aa2, X″aa3, X″aa4, and X″aa5 may be identical to the amino acid at the corresponding position in compstatin. In one embodiment, X″aa1 is Ala or a single methyl unbranched amino acid. The peptide may be cyclized via a covalent bond between (i) X'aa1, X'aa2, or X'aa3; and (ii) X″aa2, X″aa3, X″aa4 or X″aa5. In one embodiment the peptide is cyclized via a covalent bond between X'aa2 and X″aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X″aa4 in SEQ ID NO: 5 (or corresponding positions in other sequences) with addition of a $CH_2$, to form a homocysteine at X'aa2 or X″aa4, and introduction of a thioether bond, to form a cystathionine. In one embodiment, the cystathionine is a gamma-cystathionine. In another embodiment, the cystathionine is a delta-cystathionine. Another modification in accordance with the present invention comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:

(SEQ ID NO: 6)
Xaa1-Cys-Val-Xaa2-Gln-Asp-Xaa2*-Gly-Xaa3-His-Arg-Cys-Xaa4;

wherein:
Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.
In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—$NH_2$ or —$NHR^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

(SEQ ID NO: 7)
Xaa1-Cys-Val-Xaa2-Gln-Asp-Xaa2*-Gly-Xaa3-His-Arg-Cys-Xaa4;

wherein:
Xaa1 is Ile, Val, Leu, Ac-Ile, Ac-Val, Ac-Leu or a dipeptide comprising Gly-Ile or Ac-Gly-Ile;
Xaa2 and Xaa2* are independently selected from Trp and analogs of Trp;
Xaa3 is His, Ala or an analog of Ala, Phe, Trp, or an analog of Trp;
Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —$NH_2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 5 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 5 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 5 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 5 contains at least one N-methyl glycine, e.g., at the position corresponding to position 8 of compstatin and/or at the position corresponding to position 13 of compstatin. In some embodiments, one or more of the compstatin analogs in Table 5 contains at least one N-methyl isoleucine, e.g., at the position corresponding to position 13 of compstatin. For example, a Thr at or near the C-terminal end of a peptide whose sequence is listed in Table 5 or any other compstatin analog sequence may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4. In some embodiments the N-methylated amino acids comprise N-methyl Gly in a core sequence such as SEQ ID NO: 5, SEQ ID NO: 6, or SEQ ID NO: 7. In some embodiments, a compstatin analog (e.g., any one of the compstatin analogs listed in Table 5) comprises an isoleucine at position corresponding to position 3 of SEQ ID NO:8, either instead of or in addition to one or more substitutions described herein. For example, in some embodiments, a compstatin analog comprises or consists of the sequence of any one of SEQ ID NOs: 8-36, where position 3 is an isoleucine. In some embodiments, a compstatin analog comprises or consists of the sequence of any one of SEQ ID NOs: 25, 33, or 36, where position 4 is an isoleucine. Additional compstatin analogs are described in, e.g., WO 2012/155107, WO 2014/078731, and WO2019/166411.

TABLE 5

| Peptide | Sequence | SEQ ID NO: | Activity over corn statin |
|---|---|---|---|
| Compstatin | $_H$-ICVVQDWGHHRCT-$_{CONH2}$ | 8 | * |
| Ac-compstatin | $_{Ac}$-ICVWQDWGHHRCT-$_{CONH2}$ | 9 | 3xmore |
| Ac-V4Y/H9A | $_{Ac}$-ICVYQDWGAHRCT-$_{CONH2}$ | 10 | 14xmore |
| Ac-V4W/H9A -OH | $_{Ac}$-ICVWQDWGAHRCT-$_{COOH}$ | 11 | 27xmore |
| Ac-V4W/H9A | $_{Ac}$-ICVWQDWGAHRCT-$_{CONH2}$ | 12 | 45xmore |
| Ac-V4W/H9A/T13dT -OH | $_{Ac}$-ICVWQDWGAHRCdT-$_{COOH}$ | 13 | 55xmore |
| Ac-V4(2-Nal)/H9A | $_{Ac}$-ICV**(2-Nal)QDWGA**HRCT-$_{CONH2}$ | 14 | 99xmore |
| Ac V4(2-Nal)/H9A -OH | $_{Ac}$-ICV**(2-Nal)QDWGA**HRCT-$_{COOH}$ | 15 | 38xmore |
| Ac V4(1-Nal)/H9A -OH | $_{Ac}$-ICV**(1-Nal)QDWGA**HRCT-$_{COOH}$ | 16 | 30xmore |
| Ac-V42IgI/H9A | $_{Ac}$-ICV**(2-IgI)QDWGA**HRCT-$_{CONH2}$ | 17 | 39xmore |
| Ac-V42IgI/H9A -OH | $_{Ac}$-ICV**(2-IgI)QDWGA**HRCT-$_{COOH}$ | 18 | 37xmore |
| Ac-V4Dht/H9A -OH | $_{Ac}$-ICVDhtQDWGAHRCT-$_{COOH}$ | 19 | 5xmore |
| Ac-V4(Bpa)/H9A -OH | $_{Ac}$-ICV**(Bpa)QDWGA**HRCT-$_{COOH}$ | 20 | 49xmore |
| Ac-V4(Bpa)/H9A | $_{Ac}$-ICV**(Bpa)QDWGA**HRCT-$_{CONH2}$ | 21 | 86xmore |
| Ac-V4(Bta)/H9A -OH | $_{Ac}$-ICV**(Bta)QDWGA**HRCT-$_{COOH}$ | 22 | 65xmore |
| Ac-V4(Bta)/H9A | $_{Ac}$-ICV**(Bta)QDWGA**HRCT-$_{CONH2}$ | 23 | 64xmore |
| Ac-V4W/H9(2-Abu) | $_{Ac}$-ICVWQDWG**(2-Abu)**HRCT-$_{CONH2}$ | 24 | 64xmore |
| +G/V4W/H9A +AN -OH | $_H$-GICVWQDWGAHRCTAN-$_{COOH}$ | 25 | 38xmore |

TABLE 5-continued

| Peptide | Sequence | SEQ ID NO: | Activity over corn statin |
|---|---|---|---|
| Ac-V4(5fW)/H9A | $_{Ac}$-ICV(5fW)QDWGAHRCT-$_{CONH_2}$ | 26 | 31xmore |
| Ac-V4(5-MeW)/H9A | $_{Ac}$-ICV(5-methyl-W)QDWGAHRCT-$_{CONH_2}$ | 27 | 67xmore |
| Ac-V4(1-MeW)/H9A | $_{Ac}$-ICV(1-methyl-W)QDWGAHRCT-$_{CONH_2}$ | 28 | 264xmore |
| Ac-V4W/W7(5fW)/H9A | $_{Ac}$-ICVWQD(5fW)GAHRCT-$_{CONH_2}$ | 29 | 121xmore |
| Ac-V4(5fW)/W7(5fW)/H9A | $_{Ac}$-ICV(5fW)QD(5fW)GAHRCT-$_{CONH_2}$ | 30 | NA |
| Ac-V4(5-MeW)/W7(5fW)H9A | $_{Ac}$-ICV(5-methyl-W)QD(5fW)GAHRCT-$_{CONH_2}$ | 31 | NA |
| Ac-V4(1MeW)/W7(5fW)/H9A | $_{Ac}$-ICV(1-methyl-W)QD(5fW)GAHRCT-$_{CONH_2}$ | 32 | 264xmore |
| +G/V4(6fW)/W7(6fW)H9A+FN-OH | $_H$-GICV(6fW)QD(6fW)GAHRCTN-$_{COOH}$ | 33 | 126xmore |
| Ac-V4(1-formyl-W)/H9A | $_{Ac}$-ICV(1-formyl-W)QDWGAHRCT-$_{CONH_2}$ | 34 | 264xmore |
| Ac-V4(5-methoxy-W)/H9A | $_{Ac}$-ICV(1-methyoxy-W)QDWGAHRCT-$_{CONH_2}$ | 35 | 76xmore |
| G/V4(5f-W)/W7(5fW)/H9A+FN-OH | $_H$-GICV(5fW)QD(5fW)GAHRCTN-$_{COOH}$ | 36 | 112xmore |

NA = not available

In certain embodiments of the compositions and methods of the invention the compstatin analog has a sequence selected from sequences 9-36. In one embodiment, the compstatin analog has a sequence of SEQ ID NO: 28. As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety Bia is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$ For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., NH$_2$). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments Xaa0 and/or XaaN in $B^{1a}$-Xaa0 and/or XaaN-$B^{2a}$ may function mainly to increase affinity or activity of the compound, while $B^{1a}$ and/or $B^{2a}$ may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^{2a}$, where SEQUENCE represents any of SEQ ID NOs: 5-36, wherein $B^{1a}$ and $B^{2a}$ may independently be present or absent. For example, in some embodiments a compstatin analog comprises $B^{1a}$—Xaa0-X'aa1-X'aa2-X'aa3-X'aa4-Gln-Asp-Xaa-Gly-X"aa1-X"aa2-X"aa3-X"aa4-X"aa5-XaaN-$B^{2a}$ (SEQ ID NO: 69), where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises Ba-Xaa0-Xaa1-Cys-Val-Xaa2-Gln-Asp-Xaa2*-Gly-Xaa3-His-Arg-Cys-Xaa4-XaaN-$B^{2a}$ (SEQ ID NO: 70), where Xaa1, Xaa2, Xaa2*, Xaa3, and Xaa4 are as set forth above for SEQ ID NO: 6 or wherein Xaa1, Xaa2, Xaa2*, Xaa3, and Xaa4 are as set forth for SEQ ID NO: 6 or SEQ ID NO: 7.

In some embodiments a compstatin analog comprises $B^{1a}$-Xaa0-Xaa1-Xaa2-Xaa3-Xaa4-Xaa5-Xaa6-Xaa7-Xaa8-Xaa9-Xaa10-Xaa11-Xaa12-Xaa13-XaaN-$B^{2a}$ (SEQ ID NO: 71) wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, mVal, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence $B^1$-Ile-[Cys-Val-Trp(Me)-Gln-Asp-Trp-mGly-Ala-His-Arg-Cys]-mIle-$B^2$ (SEQ ID NO: 72). The two Cys residues are joined by a disulfide bond in the active compounds. In some embodiments the peptide is acetylated at the N-terminus and/or amidated at the C-terminus. In some embodiments $B^1$ comprises $B^{1a}$-Xaa0 and/or $B^2$ comprises XaaN-$B^{2a}$, as described above. For example, in some embodiments $B^1$ comprises or consists of Gly, mGly, Tyr, Phe, Arg, Trp, Thr, Tyr(Me), mPhe, mVal, mIle, mAla, DTyr, DPhe, DTrp, DCha, DAla and $B^2$ comprises $NH_2$, e.g., a carboxy terminal —OH of mIle is replaced by $NH_2$. In some embodiments $B^1$ comprises or consists of mGly, Tyr, DTyr, or Tyr(Me) and $B^2$ comprises $NH_2$, e.g., a carboxy terminal —OH of mIle is replaced by $NH_2$. In some embodiments an Ile at position Xaa1 is replaced by Gly. Complement inhibition potency and/or C3b binding parameters of selected compstatin analogs are described in WO/2010/127336 (PCT/US2010/033345) and/or in Qu, et al., Immunobiology (2012), doi:10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 5, but where the Ac-group is replaced by an alternate blocking moiety $B^1$, as described herein. In some embodiments the —$NH_2$ group is replaced by an alternate blocking moiety $B^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., Mol. Immunol., 35:160, 1998; Soulika, A. M., et al., Mol. Immunol. 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 5, e.g., SEQ ID NO: 14, 21, 28, 29, 32, 33, 34, 36, 37, 69, 70, 71, or 72, or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, 36, 37, 69, 70, 71, or 72, or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 5, e.g., SEQ ID NO: 14, 21, 28, 29, 32, 33, 34, or 36, or in some embodiments SEQ ID NO: 30, 31, 37, 69, 70, 71, 72, or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

In certain embodiments, a compstatin analog may be or comprise a cell-reactive compstatin analog. Cell-reactive compstatin analogs are compounds that comprise a compstatin analog moiety and a cell-reactive functional group that is capable of reacting with a functional group exposed at the surface of a cell, e.g., under physiological conditions, to form a covalent bond. The cell-reactive compstatin analog thus becomes covalently attached to the cell. Without wishing to be bound by any particular theory, a cell-tethered compstatin analog protects the cell from complement-mediated damage by, for example, binding to C3 (which may be in the form of $C3(H_2O)$) at the cell surface and/or in the vicinity of the cell and inhibiting C3 cleavage and activation, and/or by binding to C3b and inhibiting its deposition on the cell or participation in the complement activation cascade. In some aspects of the invention, isolated cells are contacted with a cell-reactive compstatin analog ex vivo (outside the body). In some aspects of the invention, the cells are present in an isolated tissue or organ, e.g., a tissue or organ to be transplanted into a subject. In some aspects of the invention, cells are contacted with a cell-reactive compstatin analog in vivo, by administering the cell-reactive compstatin analog to a subject. The cell-reactive compstatin analog becomes covalently attached to cells in vivo. In some aspects, the inventive approach protects cells, tissues, and/or organs from the deleterious effects of complement activation for at least two weeks, without need for retreatment during that time.

In some embodiments, the invention provides and/or utilizes compstatin analogs comprising a targeting moiety that binds non-covalently to a target molecule present at the surface of cells or tissues or to an extracellular substance not attached to cells or tissues. Such compstatin analogs are referred to herein as "targeted compstatin analogs"). Often the target molecule is a protein or carbohydrate attached to the cell membrane and exposed at the cell surface. The targeting moiety targets the compstatin analog to a cell, tissue, or location susceptible to complement activation. In some aspects of the invention, isolated cells are contacted with a targeted compstatin analog ex vivo (outside the body). In some aspects of the invention, the cells are present in an isolated tissue or organ, e.g., a tissue or organ to be transplanted into a subject. In some aspects of the invention, a targeted compstatin analog is administered to a subject and becomes non-covalently attached to a cell, tissue, or extracellular substance in vivo. In some aspects, the inventive approach protects cells, tissues, and/or organs from the deleterious effects of complement activation for at least two weeks, without need for retreatment during that time. In some embodiments, a targeted compstatin analog comprises both a targeting moiety and a cell-reactive moiety. The targeting moiety targets the compstatin analog, e.g., to a particular cell type, by binding non-covalently to a molecule on such cells. The cell-reactive moiety then binds covalently to the cell or extracellular substance. In other embodiments, a targeted compstatin analog does not comprise a cell-reactive moiety.

In some aspects, a compstatin analog may be or comprise a long-acting compstatin analog, wherein the long-acting compstatin analogs comprise a moiety such as polyethylene glycol (PEG) that prolongs the lifetime of the compound in the body (e.g., by reducing its clearance from the blood). In some embodiments, a long-acting compstatin analog does not comprise a targeting moiety or a cell-reactive moiety. In some embodiments, a long-acting compstatin analog comprises a targeting moiety and/or a cell-reactive moiety.

A compstatin analog, optionally linked to a cell-reactive moiety or targeting moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. Adv. Drug Deliv. Rev. 54, 505-530 (2002; Roberts, M. J., Bentley, M. D. & Harris, J. M. Adv. Drug Deliv. Rev. 54, 459-476; 2002); Wang, Y. S. et al. Adv. Drug Deliv. Rev. 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, CA, which also provides details of appropriate conjugation procedures. In another embodiment a compstatin analog is fused to the Fc domain of an immunoglobulin or a portion thereof. In some other embodiments a compstatin analog is conjugated to an albumin moiety or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, the compstatin analog comprises an amino acid having a side chain comprising a primary or secondary amine, e.g., a Lys residue. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. The spacer may, for example, comprise a substituted or unsubstituted, saturated or unsaturated alkyl chain, oligo (ethylene glycol) chain, and/or other moieties, e.g., as described in Section VI with regard to linkers. The length of the chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

(ii) Compstatin Mimetics

The structure of compstatin is known in the art, and NMR structures for a number of compstatin analogs having higher activity than compstatin are also known (Malik, supra). Structural information may be used to design compstatin mimetics.

In one embodiment, the compstatin mimetic is any compound that competes with compstatin or any compstatin analog (e.g., a compstatin analog whose sequence is set forth in Table 5) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 5, e.g., SEQ ID NO: 14, 21, 28, 29, 32, 33, 34, or 36 or in certain embodiments SEQ ID NO: 30 or 31 or other compstatin analog sequence, in a peptide-C3 structure. In certain embodiments the compstatin mimetic is a compound that could substitute for a peptide having a sequence set forth in Table 5, e.g., SEQ ID NO: 14, 21, 28, 29, 32, 33, 34, or 36 or in certain embodiments SEQ ID NO: 30 or 31 or other compstatin analog sequence, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far. It will be appreciated that compstatin mimetics could be used in the cell-reactive compounds of the invention, and the invention provides such cell-reactive compstatin mimetics.

(iii) Cell-reactive or Long-Acting Compstatin Analogs

As noted above, in certain embodiments, the invention provides and/or utilizes a variety of cell-reactive compstatin analogs. In some aspects, a cell-reactive compstatin analog comprises a compound of formula A-L-M, wherein A is a moiety that comprises a cell-reactive functional group J, L is an optionally present linking portion, and M comprises a compstatin analog moiety. The compstatin analog moiety can comprise any compstatin analog, e.g., any compstatin analog described above, in various embodiments. Formula A-L-M encompasses embodiments in which A-L is present at the N-terminus of the compstatin analog moiety, embodiments in which A-L is present at the C-terminus of the compstatin analog moiety, embodiments in which A-L is attached to a side chain of an amino acid of the compstatin analog moiety, and embodiments where the same or different A-Ls are present at both ends of M. It will be appreciated that when certain compstatin analog(s) are present as a compstatin analog moiety in a compound of formula A-L-M, a functional group of the compstatin analog will have reacted with a functional group of L to form a covalent bond to A or L. For example, a cell-reactive compstatin analog in which the compstatin analog moiety comprises a compstatin analog that contains an amino acid with a side chain containing a primary amine ($NH_2$) group (which compstatin analog can be represented by formula R'—($NH_2$)), can have a formula R'—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compound described above. In some embodiments, a blocking moiety at the N-terminus or C-terminus of a compstatin analog, e.g., a compstatin analog described in Section IV above, is replaced by A-L in the structure of a cell-reactive compstatin analog. In some embodiments, A or L comprises a blocking moiety. In some embodiments, a cell-reactive compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a cell-reactive moiety. In some embodiments in which a cell-reactive compstatin analog comprises multiple compstatin analog moieties, the molar activity of the cell-reactive compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

Cell-reactive moiety A can comprise any of a variety of different cell-reactive functional groups J, in various embodiments. In general, a cell-reactive functional group may be selected based at least in part on factors such as (a) the particular functional group to be targeted; (b) the ability of the reactive functional group to react with the target functional group under physiologically acceptable ex vivo conditions (e.g., physiologically acceptable pH and osmolarity) and/or in vivo conditions (e.g., in blood); (c) the specificity of the reaction between the reactive functional group and the target functional group under physiologically acceptable ex vivo conditions and/or in vivo; (d) the stability (e.g., under in vivo conditions) of the covalent bond that would result from reaction of the reactive functional group with its target functional group; (e) the ease of synthesizing a cell-reactive compstatin analog comprising the reactive functional group, etc. In some embodiments, a reactive functional group that reacts with its target chemical group without releasing a leaving group is selected. In some embodiments, a reactive functional group that results in release of a leaving group upon reaction with a target is selected. Compounds containing such groups may be useful, e.g., to monitor progress and/or extent of a reaction. In some embodiments, a leaving group is physiologically acceptable to cells, tissues, or organs in the amount generated (e.g., based on concentration and/or absolute amount generated) and/or is medically acceptable to a subject in the amount generated in vivo (e.g., based on concentration in a relevant body fluid such as blood and/or based on the absolute amount generated). In some embodiments, a leaving group generated ex vivo is at least in part removed, e.g., by washing cells or by washing or perfusing a tissue or organ, e.g., with saline.

In many embodiments, a cell-reactive functional group of use in the invention reacts with a side chain of an amino acid residue and/or with an N-terminal amino group or C-terminal carboxyl group of a protein. In some embodiments, the cell-reactive functional group is reactive with sulfhydryl (—SH) groups, which are found in the side chains of cysteine residues. In some embodiments, a maleimide group is used. Maleimide groups react with sulfhydryl groups of cysteine residues of proteins at physiologic pH and form a stable thioether linkage. In some embodiments, a haloacetyl group, such as an iodoacetyl or a bromoacetyl group, is used. Haloacetyls react with sulfhydryl groups at physiologic pH. The reaction of the iodoacetyl group proceeds by nucleophilic substitution of iodine with a sulfur atom from a sulfhydryl group resulting in a stable thioether linkage. In other embodiments, an iodoacetamide group is used. In some embodiments, the cell-reactive functional group reacts with amino (—NH$_2$) groups, which are present at the N-termini of proteins and in the side chain of lysine residues (ε-amino group). In some embodiments an activated ester, e.g., a succinimidyl ester (i.e., NHS ester) is used. For example, N-hydroxysuccinimide (NHS) or its water-soluble analog (sulfo-NHS) can be used in the synthesis, whereby the resulting cell-reactive compstatin analog comprises an NHS ester. In some embodiments, the cell-reactive functional group reacts with carboxyl (—COOH) groups, which are present at the C-termini of proteins and in the side chains of various amino acid residues. In some embodiments, the cell-reactive compstatin analog is reactive with hydroxyl (—OH) groups, which are present in the side chains of various amino acids and in carbohydrate moieties of glycosylated proteins.

In general, linking portion L can comprise any one or more aliphatic and/or aromatic moieties consistent with the formation of a stable compound joining the linked moieties. The term "stable", as used herein, preferably refers to compounds which possess stability sufficient to allow manufacture and which maintain the integrity of the compound for a sufficient period of time, e.g., to be useful for one or more purposes described herein. In some embodiments, L comprises a saturated or unsaturated, substituted or unsubstituted, branched or unbranched, aliphatic chain having a length of between 1 and 30, between 1 and 20, between 1 and 10, between 1 and 6, or 5 or less carbon atoms, where length refers to the number of C atoms in the main (longest) chain. In some embodiments, the aliphatic chain comprises one or more heteroatoms (O, N, S), which may be independently selected. In some embodiments, at least 50% of the atoms in the main chain of L are carbon atoms. In some embodiments, L comprises a saturated alkyl moiety (CH$_2$)$_n$, wherein n is between 1 and 30.

In some embodiments, L comprises one or more heteroatoms and has a length of between 1 and 1000, between 1 and 800, between 1 and 600, between 1 and 400, between 1 and 300, between 1 and 200, between 1 and 100, between 1 and 50, between 1 and 30, or between 1 and 10 total carbon atoms in a chain. In some embodiments, L comprises an oligo(ethylene glycol) moiety (—(O—CH$_2$—CH$_2$—)$_n$) wherein n is between 1 and 500, between 1 and 400, between 1 and 300, between 1 and 200, between 1 and 100, between 10 and 200, between 200 and 300, between 100 and 200, between 40 and 500, between 30 and 500, between 20 and 500, between 10 and 500, between 1 and 40, between 1 and 30, between 1 and 20, or between 1 and 10.

In some embodiments, L comprises an unsaturated moiety such as —CH=CH— or —CH$_2$—CH=CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(=O)—N—); an ester moiety (—CO—O—); a carbonyl moiety (—C(=O)—); an imine moiety (—C=N—); a thioether moiety (—C—S—C—); an amino acid residue; and/or any moiety that can be formed by the reaction of two compatible reactive functional groups. In certain embodiments, one or more moieties of a linking portion or cell-reactive moiety is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; Cl; Br; I; —NO$_2$; —CN; —CF3; —CH2CF3; —CHC12; —CH2OH; —CH2CH2OH; —CH2NH2; —CH2SO2CH3; — or -GRG1 wherein G is —O—, —S—, —NRG2-, —C(=O)—, —S(=O)—, —SO2-, —C(=O)O—, —C(=O)NRG2-, —OC(=O)—, —NRG2C(=O)—, —OC(=O)O—, —OC(=O)NRG2-, —NRG2C(=O)O—, —NRG2C(=O)NRG2-, —C(=S)—, —C(=S)S—, —SC(=S)—, —SC(=S)S—, —C(=NRG2)-, —C(=NRG2)O—, —C(=NRG2)NRG3-, —OC(=NRG2)-, —NRG2C(=NRG3)-, —NRG2SO2-, —NRG2SO2NRG3-, or —SO2NRG2-, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the methods described herein, e.g., useful for the treatment of one or more disorders and/or for contacting a cell, tissue, or organ, as described herein, and/or useful as intermediates in the manufacture of one or more such compounds.

L can comprise one or more of any of the moieties described in the preceding paragraph, in various embodiments. In some embodiments, L comprises two or more different moieties linked to one another to form a structure typically having a length of between 1 to about 60 atoms, between 1 to about 50 atoms, e.g., between 1 and 40, between 1 and 30, between 1 and 20, between 1 and 10, or between 1 and 6 atoms, where length refers to the number of atoms in the main (longest) chain. In some embodiments, L comprises two or more different moieties linked to one another to form a structure typically having between 1 to about 40, e.g., between 1 and 30, e.g., between 1 and 20, between 1 and 10, or between 1 and 6 carbon atoms in the main (longest) chain. In general, the structure of such a cell-reactive compstatin analog can be represented by formula A-(L$^{Pj}$)j-M, wherein j is typically between 1 and 10, and each L$^{Pj}$ is independently selected from among the moieties described in the preceding paragraph. In many embodiments, L comprises one or more carbon-containing chains such as —(CH$_2$)n- and/or —(O—CH$_2$—CH$_2$—)n, which are joined covalently to each other and/or to a cell-reactive functional group or compstatin analog, e.g., by moieties (e.g., amide, ester, or ether moieties) that result from the reaction of two compatible reactive functional groups. In some embodiments, L comprises an oligo(ethylene glycol) moiety and/or a saturated alkyl chain. In some embodiments, L comprises —(CH$_2$)$_m$—C(=O)—NH—(CH$_2$CH$_2$O)$_n$(CH$_2$)$_p$C(=O)— or —(CH$_2$)$_m$—C(=O)—NH—(CH$_2$)$_p$(OCH$_2$CH$_2$)$_n$C(=O)—. In some embodiments, m, n, and p are selected so that the number of carbons in the chain is between 1 and 500, e.g., between 2 and 400, between 2 and 300, between 2 and 200, between 2 and 100, between 2 and 50, between 4 and 40, between 6 and 30, or between 8 and 20. In some embodiments, m is between 2 and 10, n is between 1 and 500, and/or p is between 2 and 10. In some embodiments, m is between 2 and 10, n is between 1 and 400, and/or p is between 2 and 10. In some embodiments, m is between 2 and 10, n is between 1 and 300, and/or p is between 2 and 10. In some embodiments, m is between 2 and 10, n is between 1 and 200, and/or p is between 2 and 10. In some embodiments, m is between 2 and 10, n is between 1 and 100, and/or p is between 2 and 10. In some embodiments, m is between 2 and 10, n is between 1 and 50, and/or p is between 2 and 10. In some embodiments, m is between 2 and 10, n is between 1 and 25, and/or p is between 2 and 10. In some embodiments, m is between 2 and 10, n is between 1 and 8, and/or p is between 2 and 10. Optionally, at least one —$CH_2$— is replaced by CH—R, wherein R can be any substituent. Optionally, at least one —$CH_2$— is replaced by a heteroatom, cyclic ring system, amide, ester, or ether moiety. In some embodiments, L does not comprise an alkyl group having more than 3 carbon atoms in the longest chain. In some embodiments, L does not comprise an alkyl group having more than 4, 5, 6, 7, 8, 9, 10, or 11 carbon atoms in the longest chain.

In some embodiments of the invention, A comprises a cell-reactive functional group J and a linker $L^1$ comprising a linking portion $L^{P1}$ and a reactive functional group that reacts with the compstatin analog to generate A-M In some embodiments, a bifunctional linker $L^2$ comprising two reactive functional groups and a linking portion $L^{P2}$ is used. The reactive functional groups of L react with appropriate reactive functional groups of A and M to produce a cell-reactive compstatin analog A-L-M. In some embodiments, the compstatin analog comprises a linker $L^3$ comprising a linking portion $L^{P3}$. For example, as discussed below, a linker comprising a reactive functional group may be present at the N- or C-terminus or a moiety comprising a reactive functional group may be attached to the N- or C-terminus via a linker. Thus L may contain multiple linking portions $L^P$ contributed, e.g., by A, by linker(s) used to join A and M, and/or by the compstatin analog. It will be understood that, when present in the structure A-L-M, certain reactive functional group(s) present prior to reaction in $L^1$, $L^2$, $L^3$, etc., will have undergone reaction, so that only a portion of said reactive functional group(s) will be present in the final structure A-L-M, and the compound will contain moieties formed by reaction of said functional groups. In general, if a compound contains two or more linking portions, the linking portions can be the same or different, and can be independently selected in various embodiments. Multiple linking portions $L^P$ can be attached to one another to form a larger linking portion L, and at least some of such linking portions can have one or more compstatin analog(s) and/or cell-reactive functional group(s) attached thereto. In molecules comprising multiple compstatin analogs, the compstatin analogs can be the same or different and, if different, can be independently selected. The same applies to the linking portions and reactive functional groups. The invention encompasses the use of multivalent compstatin analogs comprising one or more cell-reactive functional group(s) and use of concatamers of compstatin analogs comprising one or more cell-reactive functional group(s). In some embodiments, at least one linkage is a stable non-covalent linkage such as a biotin/(strept)avidin linkage or other noncovalent linkage of approximately equivalent strength.

In some embodiments a cell-reactive compstatin analog comprises a compstatin analog in which any of SEQ ID NOs: 3-36, 69, 70, 71, or 72 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring. In some embodiments, the amino acid(s) is/are L-amino acids. In some embodiments, any one or more of the amino acid(s) is a D-amino acid. If multiple amino acids are added, the amino acids can be independently selected. In some embodiments, the reactive functional group (e.g., a primary or secondary amine) is used as a target for addition of a moiety comprising a cell-reactive functional group. Amino acids having a side chain that comprises a primary or secondary amine include lysine (Lys) and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry*, Volumes 1-4, Wiley-VCH (2009-2011); Blaskovich, M., Handbook on Syntheses of Amino Acids General Routes to Amino Acids, Oxford University Press, 2010. The invention encompasses embodiments in which one or more non-standard amino acid(s) is/are used to provide a target for addition of a moiety comprising a cell-reactive functional group. Any one or more of the amino acid(s) may be protected as appropriate during synthesis of the compound. For example, one or more amino acid(s) may be protected during reaction(s) involving the target amino acid side chain. In some embodiments, wherein a sulfhydryl-containing amino acid is used as a target for addition of a moiety comprising a cell-reactive functional group, the sulfhydryl is protected while the compound is being cyclized by formation of an intramolecular disulfide bond between other amino acids such as cysteines.

In the discussion in this paragraph, an amino acid having a side chain containing an amine group is used as an example. The invention encompasses analogous embodiments in which an amino acid having a side chain containing a different reactive functional group is used. In some embodiments, an amino acid having a side chain comprising a primary or secondary amine is attached directly to the N-terminus or C-terminus of any of SEQ ID NOs: 3-36, 37, 69, 70, 71, or 72 or via a peptide bond. In some embodiments, an amino acid having a side chain comprising a primary or secondary amine is attached to the N- or C-terminus of any of SEQ ID NOs: 3-36, 37, 69, 70, 71, or 72, or via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein. Thus in some embodiments, a cell-reactive compstatin analog comprises a compstatin analog moiety M of formula B1-R1-$M_1$-R2-B2, wherein $M_1$ represents any of SEQ ID NOs: 3-36, 37, 69, 70, 71, or 72, either R1 or R2 may be absent, at least one of R1 and R2 comprises an amino acid having a side chain that contains a primary or secondary amine, and B1 and B2 are optionally present blocking moieties. R1 and/or R2 may be joined to $M_1$ by a peptide bond or a non-peptide bond. R1 and/or R2 may comprise a linking portion $L^{P3}$. For example, R1 can have formula $M_2$-$L^{P3}$ and/or R2 can have formula $L^{P3}$-$M_2$ wherein $L^{P3}$ is a linking portion, and $M_2$ comprises at least one amino acid having a side chain comprising a primary or secondary amine. For example, $M_2$ can be Lys or an amino acid chain comprising Lys. In some embodiments, $L^{P3}$ comprises of consists of one or more amino acids. For example, $L^{P3}$ can be between 1 and about 20 amino acids in length, e.g., between 4 and 20 amino acids in length. In some embodiments, $L^{P3}$ comprises or consist of multiple Gly, Ser, and/or Ala residues. In some embodiments, $L^{P3}$ does not comprise an amino acid that comprises a reactive SH group, such as Cys. In some embodiments, $L^{P3}$ comprises an oligo(ethylene glycol) moiety and/or a saturated alkyl chain. In some embodiments, $L^{P3}$ is attached to the N-terminal amino acid of $M_1$ via an amide bond. In some embodiments, $L^{P3}$ is attached to the C-terminal amino acid of $M_1$ via an amide bond. The compound may be further extended at either or both termini by addition of further linking portion(s) and/or amino acid(s). The amino acids can be the same or different and, if different, can be independently selected. In some embodiments, two or more amino acids having side chains comprising reactive functional groups are used, wherein the reactive functional groups can be the same or different. The two or more reactive functional groups can be used as targets for addition of two or more moieties. In some embodiments, two or more cell-reactive moieties are added. In some embodiments, a cell-reactive moiety and a targeting moiety are added. In some embodiments, a linker and/or cell-reactive moiety is attached to an amino acid side chain after incorporation of the amino acid into a peptide chain. In some embodiments, a linker and/or cell-reactive moiety is already attached to the amino acid side chain prior to use of the amino acid in the synthesis of a cell-reactive compstatin analog. For example, a Lys derivative having a linker attached to its side chain can be used. The linker may comprise a cell-reactive functional group or may subsequently be modified to comprise a cell-reactive functional group.

Certain cell-reactive compstatin analogs are described in further detail below. In the following discussion, a peptide having the amino acid sequence Ile-Cys*-Val-(1Me)Trp-Gln-Asp-Trp-Gly-Ala-His-Arg-Cys*-Thr (SEQ ID NO: 37) (corresponding to the compstatin analog of SEQ ID NO: 28, wherein asterisks in SEQ ID NO: 37 represent cysteines joined by a disulfide bond in the active compound, and (1Me)Trp represents 1-methyl-tryptophan)), is used as an exemplary compstatin analog moiety; maleimide (abbreviated Mal) is used as an example of a cell-reactive functional group; $(CH_2)_n$ and $(O-CH_2-CH_2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and are represented in italics, i.e., as Ac and $NH_2$ respectively. It will be appreciated that the compounds can be prepared using a variety of synthetic approaches and using a variety of precursors. The discussion of various synthetic approaches and precursors below is not intended to limit the invention. In general, any of the features of any of the compounds described below or herein can be freely combined with feature(s) of other compounds described below or elsewhere herein, and the invention encompasses such embodiments.

In some embodiments, the cell-reactive moiety is provided by a cell-reactive compound comprising a maleimide group (as a cell-reactive functional group) and an alkanoic acid (RCOOH), where R is an alkyl group. For example, 6-malemeidocaproic acid (Mal-$(CH_2)_5$—COOH), depicted below, can be used.

Compound I

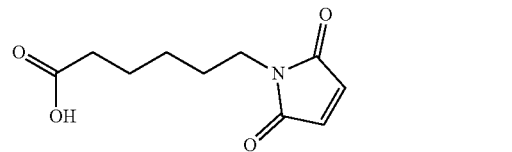

In some embodiments, the cell-reactive moiety is provided by a derivative of an alkanoic acid in which the carboxylic acid moiety has been activated, e.g., the OH moiety has been converted to a better leaving group. For example, the carboxyl group of compound I may be reacted with EDC, followed by reaction with NHS (which can optionally be provided as water-soluble sulfo-NHS), resulting in an N-hydroxysuccinimide ester derivative of 6-malemeidocaproic acid, i.e., 6-maleimidohexanoic acid N-hydroxysuccinimide (NHS) ester (depicted below).

Compound II

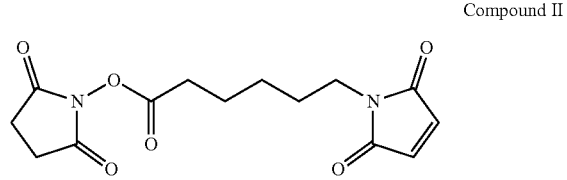 [SMILES: O=C(CCCCCN1C(=O)C=CC1=O)ON1C(=O)CCC1=O]

The compound of SEQ ID NO: 37 can be modified at the N- and/or C-terminus to generate a cell-reactive compstatin analog. For example, compound II can be used to generate the following cell-reactive compstatin analog by reaction with the N-terminal amino group of Ile.

Maleimide-$(CH_2)_5$—C(=O)-Ile-Cys*-Val-(1Me)Trp-Gln-Asp-Trp-Gly-Ala-His-Arg-Cys*-Thr-$NH_2$ (SEQ ID NO: 38). It will be appreciated that in SEQ ID NO: 38 the —C(=O) moiety is attached to the immediately C-terminal amino acid (Ile), via a C—N bond, wherein the N is part of the amino acid and is not shown.

In other embodiments, a maleimide group is linked to Thr at the C-terminus, resulting in the following cell-reactive compstatin analog:

(SEQ ID NO: 39)
Ac-Ile-Cys*-Val-(1Me)Trp-Gln-Asp-Trp-Gly-Ala-His-

Arg-Cys*-Thr-(C=O)-$(CH_2)_5$-maleimide.

In some embodiments, a cell-reactive compstatin analog can be synthesized using bifunctional linker (e.g., a heterobifunctional linker). An exemplary heterobifunctional linker comprising $(CH_2-CH_2-O)_n$ and $(CH_2)_m$ (where m=2) moieties is shown below:

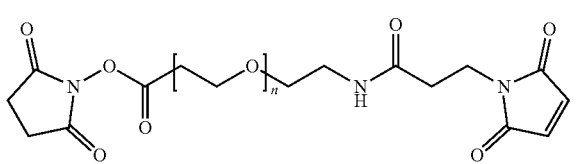

Compound III

Compound III comprises a maleimide group as a cell-reactive functional group and an NHS ester moiety that reacts readily with an amino group (e.g., an N-terminal amino group or an amino group of an amino acid side chain).

An embodiment of compound III in which n=2 can be used to generate the following cell-reactive compstatin analog using the compstatin analog of SEQ ID NO: 37:

```
                                             (SEQ ID NO: 40)
Maleimide-(CH₂)₂-C(=O)-NH-CH₂CH₂OCH₂CH₂OCH₂CH₂C(=O)-

Ile-Cys*-Val-(1Me)Trp-Gln-Asp-Trp-Gly-Ala-His-Arg-

Cys*-Thr-NH₂
```

It will be appreciated that in the compound of SEQ ID NO: 40 a —C(=O) moiety is attached to the N-terminal amino acid (Ile residue via a C—N bond, wherein the N is part of the amino acid and is not shown. In some embodiments a linker has the formula of Compound III wherein n≥1. Exemplary values for n in a $(CH_2-CH_2-O)_n$ moiety are provided herein.

In some embodiments, the alkyl chain that links the maleimide moiety to the rest of the molecule contains more or fewer methylene units, the oligo(ethylene glycol) moiety contains more or fewer ethylene glycol units, and/or there are more or fewer methylene units flanking either or both sides of the oligo(ethylene glycol) moiety, as compared with the compound of SEQ ID NO: 39 or SEQ ID NO: 40. Exemplary cell-reactive compstatin analogs illustrative of a few such variations are presented below (SEQ ID NOs: 41-46):

```
                                             (SEQ ID NO: 41)
Maleimide-(CH₂)₂-C(=O)-NH-CH₂CH₂OCH₂CH₂C(=O)-Ile- Cys*-Val-(1Me)Trp-Gln-Asp-Trp-Gly-Ala-His-Arg- Cys*-Thr-NH₂

(SEQ ID NO: 42)
Maleimide-(CH₂)₃-C(=O)-NH-CH₂CH₂OCH₂CH₂OCH₂C(=O)-

Ile-Cys*-Val-(1Me)Trp-Gln-Asp-Trp-Gly-Ala-His-Arg-

Cys*-Thr-NH₂

(SEQ ID NO: 43)
Maleimide-(CH₂)₅—C(=O)-NH-CH₂CH₂OCH₂CH₂OCH₂C(=O)-

Ile-Cys*-Val-(1Me)Trp-Gln-Asp-Trp-Gly-Ala-His-

Arg-Cys*-Thr-NH₂

(SEQ ID NO: 44)
Maleimide-(CH₂)₄-C(=O)-NH-CH₂CH₂OCH₂CH₂OCH₂CH₂C (=O)-Ile-Cys*-Val-(1Me)Trp-Gln-Asp-Trp-Gly-Ala- His-Arg-Cys*-Thr-NH₂

(SEQ ID NO: 45)
Maleimide-(CH₂)₂-C(=O)-NH-CH₂CH₂OCH₂CH₂OCH₂CH₂C (=O)-Ile-Cys*-Val-(1Me)Trp-Gln-Asp-Trp-Gly-Ala- His-Arg-Cys*-Thr-NH₂

(SEQ ID NO: 46)
Maleimide-(CH₂)₅-C(=O)-NH-CH₂CH₂OCH₂CH₂OCH₂C(=O)-

Ile-Cys*-Val-(1Me)Trp-Gln-Asp-Trp-Gly-Ala-His-

Arg-Cys*-Thr-NH₂
```

In some embodiments, SEQ ID NO: 37 is extended to comprise a Lys residue at the N- or C-terminus of the peptide, e.g., as exemplified below for a C-terminal linkage:

```
                                             (SEQ ID NO: 47)
Ac-Ile-Cys*-Val-(1Me)Trp-Gln-Asp-Trp-Gly-Ala-His-

Arg-Cys*-Thr-Lys-NH₂.
```

In some embodiments, a Lys residue is attached to the N- or C-terminus of SEQ ID NO: 37 via a peptide linker, e.g., as exemplified below for a C-terminal linkage:

```
                                             (SEQ ID NO: 48)
Ac-Ile-Cys*-Val-(1Me)Trp-Gln-Asp-Trp-Gly-Ala-His-

Arg-Cys*-Thr-(Gly)₅-Lys-NH₂.
```

In some embodiments, a linker comprising a primary or secondary amine is added to the N- or C-terminus of a compstatin analog. In some embodiments, the linker comprises an alkyl chain and/or an oligo(ethylene glycol) moiety. For example, $NH_2(CH_2CH_2O)nCH_2C(=O)OH$ (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 1l-amino-3,6,9-trioxaundecanoic acid), can be used. In some embodiments, the resulting compound is as follows (wherein the portion contributed by the linker is shown in bold):

```
                                             (SEQ ID NO: 49)
NH₂(CH₂)₅C(=O)-Ile-Cys-Val-(1Me)Trp-Gln-Asp-Trp-

Gly-Ala-His-Arg-Cys-Thr-NH₂

(SEQ ID NO: 50)
NH₂(CH₂CH₂O)CH₂C(=O)-Ile-Cys-Val-(1Me)Trp-Gln-Asp-

Trp-Gly-Ala-His-Arg-Cys-Thr-NH₂
```

In some embodiments, a Lys residue is attached to the N- or C-terminus of SEQ ID NO: 37 via a linker comprising a non-peptide portion. For example, the linker can comprise an alkyl chain, oligo(ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

```
                                              (SEQ ID NO: 51)
Ac-Ile-Cys*-Val-(1Me)Trp-Gln-Asp-Trp-Gly-Ala-His-

Arg-Cys*-Thr-NH-CH₂CH₂OCH₂CH₂OCH₂-C(=O)-Lys-NH₂
```

It will be appreciated that in SEQ ID NOs: 49 and 50, a —C(=O) moiety is attached to the adjacent Ile residue via a C—N bond, wherein the N is part of the amino acid and is not shown. Similarly, in SEQ ID NO: 51, a —C(=O) moiety is attached to the adjacent Lys residue via a C—N bond, wherein the N is part of the amino acid and is not shown. It will also be appreciated that that in SEQ ID NO: 51 the NH moiety is attached to the immediately N-terminal amino acid (Thr), via a C—N bond, wherein the C is the carbonyl carbon of the amino acid and is not shown.

The compounds of SEQ ID NOs: 47-51 can readily be modified at the primary amine group to produce a cell-reactive compstatin analog. For example, the compounds of SEQ ID NOs: 47-51 (or other compounds comprising a primary or secondary amine and a compstatin analog moiety) can be reacted with 6-maleimidocaproic acid N-succinimidyl ester to produce the following cell-reactive compstatin analogs:

```
                                              (SEQ ID NO: 52)
Ac-Ile-Cys*-Val-(1Me)Trp-Gln-Asp-Trp-Gly-Ala-His-

Arg-Cys*-Thr-Lys-(C(=O)-(CH₂)₅-Mal)-NH₂.

(SEQ ID NO: 53)
Ac-Ile-Cys*-Val-(1Me)Trp-Gln-Asp-Trp-Gly-Ala-His-

Arg-Cys*-Thr-(Gly)₅-Lys-(C(=O)-(CH₂)₅-Mal)-NH₂.

(SEQ ID NO: 54)
Mal-(CH₂)₅-(C(=O)-NH(CH2)₅C(=O)-(Ile-Cys-Val-(1Me)

Trp-Gln-Asp-Trp-Gly-Ala-His-Arg-Cys-Thr-NH₂

(SEQ ID NO: 55)
Mal-(CH₂)₅-(C(=O)NH(CH₂CH₂O)₂CH₂C(=O)-Ile-Cys-Val- (1Me)Trp-Gln-Asp-Trp-Gly-Ala-His-Arg-Cys-Thr-NH₂

(SEQ ID NO: 56)
Ac-Ile-Cys*-Val-(1Me)Trp-Gln-Asp-Trp-Gly-Ala-His-

Arg-Cys*-Thr-NH-CH₂CH₂OCH₂CH₂OCH₂C(=O)-Lys- (C(=O)-(CH₂)₅-Mal)-NH₂
```

In another embodiment, a cell-reactive compstatin analog is represented as:

```
                                              (SEQ ID NO: 57)
Ac-Ile-Cys*-Val-(1Me)Trp-Gln-Asp-Trp-Gly-Ala-

His-Arg-Cys*-Thr-Lys-

C(=O)-CH₂(OCH₂CH₂)₂NH(C(=O)-(CH₂)₅-Mal)-NH₂.
```

The invention provides variants of SEQ ID NOs: 38-57 in which -Ile-Cys*-Val-(1Me)Trp-Gln-Asp-Trp-Gly-Ala-His-Arg-Cys*-Thr- is replaced by an amino acid sequence comprising the amino acid sequence of any other compstatin analog, e.g., of any of SEQ ID NOs 3-27, 29-36, 37, 69, 70, 71, or 72 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Other bifunctional cross-linkers comprising a maleimide as a cell-reactive moiety and an NHS ester as an amine-reactive moiety of use in various embodiments of the invention include, e.g., succinimidyl 4-(p-maleimidophenyl) butyrate (SMPB); succinimidyl 4-(N-maleimidomethyl)-cyclohexane-1-carboxylate (SMCC); N-γ-maleimidobutyryl-oxysuccinimide ester (GMBS). Addition of a sulfonate to the NHS ring results in water-soluble analogs such as sulfo-succinimidyl(4-iodoacetyl)-aminobenzoate (sulfo-SIAB), sulfo-succinimidyl 4-(N-maleimidomethyl)-cyclohexane-1-carboxylate (sulfo-SMCC), sulfo-succinimidyl 4-(p-maleimidophenyl)butyrate (sulfo-SMPB), sulfo-N-γ-maleimidobutyryl-oxysuccinimide ester (sulfo-GMBS) etc., which can avoid the need for an organic solvent. In some embodiments, a long chain version of any of the foregoing, comprising a spacer arm between the NHS ester moiety and the remainder of the molecule, is used. The spacer can comprise, e.g., an alkyl chain. An example is succinimidyl-4-[N-Maleimidomethyl]cyclohexane-1-carboxy-[6-amido-caproate].

In some embodiments, a bifunctional linker comprising an NHS ester (as an amine-reactive moiety) and an iodoacetyl group (reactive with sulfhydryl groups) is used. Such linkers include, e.g., N-succinimidyl(4-iodoacetyl)-amino benzoate (SIAB); succinimidyl 6-[(iodoacetyl)-amino] hexanoate (SIAX); succinimidyl 6-[6-(((iodoacetyl)amino)-hexanoyl) amino]hexanoate (SIAXX); succinimidyl 4-((iodoacetyl)amino)methyl)-cyclohexane-1-carboxylate (SIAC); succinimidyl 6-((((4-(iodoacetyl)amino)methyl-cyclohexane-1-carbonyl)amino)hexanoate (SIACX);

In some embodiments, a bifunctional linker comprising an NHS ester (as an amine-reactive moiety) and a pyridy disulfide group (as a cell-reactive moiety reactive with sulfhydryl groups) is used. Examples include N-succinimidyl 3-(2-pyridyldithio)propionate (SPDP); succinimidyloxycarbonyl-α-methyl-α-(2-pyridyldithio)toluene (SMPT) and versions comprising a sulfonate on the NHS ring and/or a spacer comprising an alkyl chain between the NHS ester moiety and the rest of the molecule (e.g., succinimidyl 6-(3-[2-pyridyldithio]-propionamido)hexanoate) (LC-SPDP). Variations of such linkers that include additional or different moieties could be used. For example, a longer or shorter alkyl chain could be used in a spacer, or an oligo (ethylene glycol) moiety instead of an alkyl chain.

In general, a cell-reactive compstatin analog can be synthesized using a variety of approaches. Cell-reactive compounds that comprise a cell-reactive functional group and a linker can often be purchased as preformed building blocks. For example, 6-malemeidocaproic acid and 6-maleimido-caproic acid N-hydroxysuccinimide ester can be purchased from various suppliers. Alternately, such compounds can be synthesized using methods known in the art. See, e.g., Keller O, Rudinger J. Helv Chim Acta. 58(2):531-41, 1975 and Hashida S, et al., J Appl Biochem., 6(1-2):56-63, 1984. See also, Hermanson, G. supra, and references therein, for discussion of methods and reagents of use for synthesizing conjugates. In general, the invention encompasses any method of producing a compound comprising a compstatin analog moiety and a cell-reactive functional group, and the resulting compounds.

In some embodiments, an amino acid having a linker attached to a side chain is used in the synthesis of a linear peptide. The linear peptide can be synthesized using standard methods for peptide synthesis known in the art, e.g., standard solid-phase peptide synthesis. The linear peptide is then cyclized (e.g., by oxidation of the Cys residues to form an intramolecular disulfide). The cyclic compound may then be reacted with a linker comprising a cell-reactive functional group. In other embodiments, a moiety comprising a cell-reactive functional group is reacted with a linear compound prior to cyclization thereof. In general, reactive functional groups can be appropriately protected to avoid undesired reaction with each other during synthesis of a cell-reactive compstatin analog. The cell-reactive functional group, any of the amino acid side chains, and/or either or both termini of the peptide may be protected during the reaction and subsequently deprotected. For example, SH groups of Cys residues and/or SH-reactive moieties such as maleimides can be protected until after cyclization to avoid reaction between them. The reaction conditions are selected based at least in part on the requirements of the particular reactive functional group(s) to achieve reasonable yield in a reasonable time period. Temperature, pH, and the concentration of the reagents can be adjusted to achieve the desired extent or rate of reaction. See, e.g., Hermanson, supra. The desired product can be purified, e.g., to remove unreacted compound comprising the cell-reactive functional group, unreacted compstatin analog, linker(s), products other than the desired cell-reactive compstatin analog that may have been generated in the reaction, other substances present in the reaction mixture, etc. Compositions and methods for making the cell-reactive compstatin analogs, and intermediates in the synthesis, are aspects of the invention.

In some aspects of the invention, linker(s) described above are used in the production of compstatin analogs comprising a moiety such as a polyethylene glycol (PEG) chain or other polymer(s) that, e.g., stabilize the compound, increase its lifetime in the body, increase its solubility, decrease its immunogenicity, and/or increase its resistance to degradation. Without limiting the invention in any way, such a moiety may be referred to herein as a "clearance reducing moiety" (CRM), and a compstatin analog comprising such a moiety may be referred to as a "long-acting compstatin analog" (LACA). In some embodiments, a long-acting compstatin analog has an average plasma half-life of at least 1 day, e.g., 1-3 days, 3-7 days, 7-14 days, or 14-28 days, when administered IV at a dose of 10 mg/kg to humans or to non-human primates, or a dose of about 1-3 mg/kg, 3-5 mg/kg, 5-10 mg/kg, e.g., 7 mg/kg. In some embodiments, a long-acting compstatin analog has an average plasma half-life of at least 1 day, e.g., 1-3 days, 3-7 days, 7-14 days, or 14-28 days, when administered subcutaneously at, e.g., a dose of about 1-3 mg/kg, 3-5 mg/kg, 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5, 5.5, 6, 6.5, 7, 7.5, 8, 8.5, 9, 9.5 or 10 days when administered intravenously at, e.g., a dose of about 1-3 mg/kg, 3-5 mg/kg, or 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5, 5.5, 6, 6.5, 7, 7.5, 8, 8.5, 9, 9.5 or 10 days, when administered subcutaneously at, e.g., a dose of about 1-3 mg/kg, 3-5 mg/kg, 5-10 mg/kg, e.g., 7 mg/kg to humans or to non-human primates. In certain embodiments a long-acting compstatin analog is characterized in that it is extensively absorbed from the site of administration during the time period following subcutaneous injection and provides, e.g., at or after about 1-2 days following administration, a blood level comparable to that which would be achieved had the same amount of compound been administered intravenously instead. In some embodiments, the blood level at or after about 2, 3, 4, 5, 6, 7, 8, or more days following administration of a subcutaneous dose is within about 5%, 10%, 15%, 20%, or 25% of the blood level which would be achieved had the same amount of compound been administered intravenously instead. In some embodiments, average plasma half-life of a long-acting compstatin analog following administration IV at a dose of 10 mg/kg to humans or to non-human primates is increased by at least a factor of 2, e.g., by a factor of 2-5, 5-10, 10-50, or 50-100-fold or 100-150-fold or 150-200 fold as compared with that of a corresponding compstatin analog having the same amino acid sequence (and, if applicable, one or more blocking moiet(ies)) but not comprising the CRM. It will be understood that in various embodiments such an increase in half-life may be observed following administration via other routes such as subcutaneous administration and/or using other doses, e.g., other doses described herein, e.g., 20 mg/kg.

As noted above, in some embodiments a compstatin analog of any of SEQ ID NOs: 3-36, 37, 69, 70, 71, or 72 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring, which facilitate conjugation with a reactive functional group to attach a CRM to the compstatin analog. It will be understood that a corresponding compstatin analog not comprising the CRM may also lack one or more such amino acids which are present in the long-acting compstatin analog to which it corresponds. Thus, a corresponding compstatin analog comprising any of SEQ ID NOs: 3-36, 37, 69, 70, 71, or 72 and lacking a CRM will be understood to "have the same amino acid sequence" as SEQ ID NO: 3-36, 37, 69, 70, 71, or 72, respectively. For example, a corresponding compstatin analog comprising the amino acid sequence of SEQ ID NO: 14, 21, 28, 29, 32, 33, 34, or 36 and lacking a CRM will be understood to "have the same amino acid sequence" as SEQ ID NO: 14, 21, 28, 29, 32, 33, 34, or 36, respectively.

In some embodiments, a plasma half-life is a terminal half-life after administration of a single IV dose. In some embodiments, a plasma half-life is a terminal half-life after steady state has been reached following administration of multiple IV doses. In some embodiments, a long-acting compstatin analog achieves a Cmax in plasma at least 5-fold as great as that of a corresponding compstatin analog not comprising the CRM, e.g., between 5- and 50-fold as great, following administration of a single IV dose to a primate, or following administration of multiple IV doses. In some embodiments, a long-acting compstatin analog achieves a Cmax in plasma between 10- and 20-fold as great as that of a corresponding compstatin analog not comprising the CRM following administration of a single IV dose to a primate, or following administration of multiple IV doses.

In some embodiments a primate is human. In some embodiments a primate is a non-human primate, e.g., a monkey, such as a Cynomolgus monkey or Rhesus monkey.

In some embodiments, renal clearance of a long-acting compstatin analog during the first 24 hours following administration IV at a dose of 10 mg/kg or 20 mg/kg to humans or to non-human primates is reduced by at least a factor of 2, e.g., by a factor of 2-5, 5-10, 10-50, or 50-100-fold or 100-150-fold or 150-200 fold as compared with renal clearance of a corresponding compstatin analog. It will be understood that in various embodiments such a reduction in renal clearance may be observed following administration via other routes such as subcutaneous administration and/or using other doses, e.g., other doses described herein, e.g., 20 mg/kg.

The concentration of compstatin analog can be measured in blood and/or urine samples using, e.g., UV, HPLC, mass spectrometry (MS) or antibody to the CRM, or combinations of such methods, such as LC/MS or LC/MS/MS. Pharmacokinetic parameters such as half-life and clearance can be determined using methods known to those of ordinary skill in the art. Pharmacokinetic analysis can be performed, e.g., with WinNonlin software v 5.2 (Pharsight Corporation, St. Louis, MO) or other suitable programs.

In certain embodiments a CRM is stable in physiological conditions for at least 24 hours or more. In certain embodiments a CRM is stable in mammalian, e.g., primate, e.g., human or non-human primate (e.g., monkey) blood, plasma, or serum for at least 24 hours. In various embodiments at least 50%, 60%, 70%, 80%, 90%, 95%, 96%, 97%, 98%, 99%, or more, of the CRM molecules remains intact upon incubation in physiological conditions for 24 hours, 48 hours, 72 hours, 96 hours, 120 hours, 144 hours, 168 hours, or more. In various embodiments at least 50%, 60%, 70%, 80%, 90%, 95%, 96%, 97%, 98%, 99%, or more, of the CRM molecules remains intact upon incubation in blood, plasma, or serum at 37 degrees C. for 48 hours, 72 hours, 96 hours, 120 hours, 144 hours, 168 hours, or more. Incubation may be performed using a CRM at a concentration of between 1 microgram/ml to about 100 mg/ml in various embodiments. Samples may be analyzed at various time points. Size or intactness may be assessed using, e.g., chromatography (e.g., HPLC), mass spectrometry, Western blot, or any other suitable method. Such stability characteristics may be conferred on a moiety conjugated to the CRM. In various embodiments, a long-acting compstatin analog comprising a CRM may have any of the afore-mentioned stability characteristics. In some aspects intact with regard to a long-acting compstatin analog means that the compstatin analog moiety remains conjugated to the CRM and the CRM size remains about the same as at the start of incubation or administration.

In some embodiments, a long-acting compstatin analog has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CRM. In some embodiments wherein a long-acting compstatin analog comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

In some embodiments, a polyethylene glycol (PEG) comprises a $(CH_2CH_2O)_n$ moiety having a molecular weight of at least 500 daltons.

In some embodiments, a linker described above comprises an $(CH_2CH_2O)_n$ moiety having an average molecular weight of between about 500; 1,000; 1,500; 2,000; 5,000; 10,000; 20,000; 30,000; 40,000; 50,000; 60,000; 70,000; 80,000; 90,000; and 100,000 daltons.

In some embodiments the average molecular weight of a PEG is at least 20,000 daltons, up to about 100,000; 120,000; 140,000; 160,000; 180,000; or 200,000 daltons. "Average molecular weight" refers to the number average molecular weight. In some embodiments, the polydispersity D of a $(CH_2CH_2O)_n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)_n$ moiety is monodisperse and the polydispersity of a $(CH_2CH_2O)_n$ moiety is 1.0. Such monodisperse $(CH_2CH_2O)_n$ moieties are known in the art and are commercially available from Quanta BioDesign (Powell, OH), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)_n$ moieties is between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)_n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments n is between about 30 and about 3000.

In some embodiments a compstatin analog moiety is attached at each end of a linear PEG. A bifunctional PEG having a reactive functional group at each end of the chain may be used, e.g., as described above. In some embodiments the reactive functional groups are identical while in some embodiments different reactive functional groups are present at each end.

In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)_n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a long-acting compstatin analog thus may comprise, e.g., 3-10 compstatin analog moieties, e.g., 4-8 compstatin analog moieties, each attached to a $(CH_2CH_2O)_n$ chain via a functional group at the end of the chain. In some embodiments a long-acting compstatin analog may comprise, e.g., 10-100 compstatin analog moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a compstatin analog moiety attached thereto. In some embodiments at least about 30%, 40%, 50%, 60%, 70%, 80%, 90%, 95%, or 100% of the chains has a compstatin analog moiety attached thereto.

In general and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group ($OCH_3$) but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A

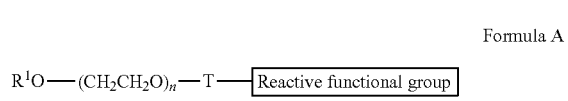

wherein "Reactive functional group" and n are as defined above and described in classes and subclasses herein;

R' is hydrogen, aliphatic, or any suitable end group; and

T is a covalent bond or a $C_{1-12}$ straight or branched, hydrocarbon chain wherein one or more carbon units of T are optionally and independently replaced by —O—, —S—, —N($R^x$)—, —C(O)—, —C(O)O—, —OC(O)—, —N($R^x$)C(O)—, —C(O)N($R^x$)—, —S(O)—, —S(O)$_2$—, —N(R)SO$_2$—, or —SO$_2$N($R^x$)—; and each $R^x$ is independently hydrogen or $C_{1-6}$ aliphatic.

Exemplary monofunctional PEGs of formula A include:

Formula I

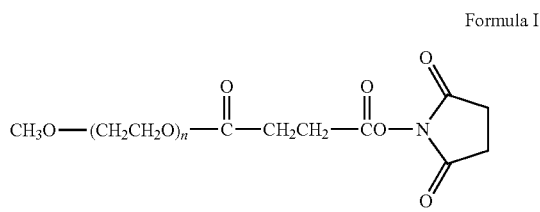

In Formula I, the moiety comprising the reactive functional group has the general structure —CO—$(CH_2)_m$—COO—NHS, where m=2. In some embodiments, a monofunctional PEGs has the structure of Formula I, where m is between 1 and 10, e.g., between 1 and 5. For example, in some embodiments m is 3, as shown below:

Formula Ia

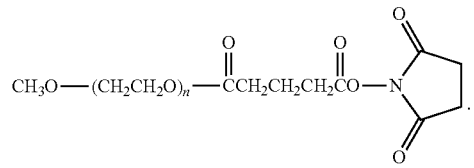

Formula II

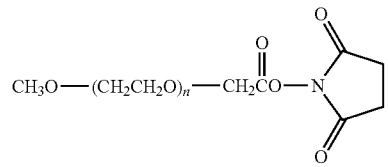

In Formula II, the moiety comprising the reactive functional group has the general structure —$(CH_2)_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

Formula III

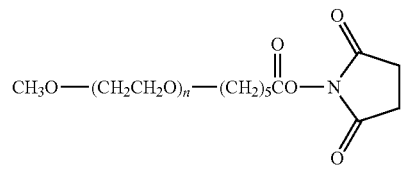

Formula IIIa

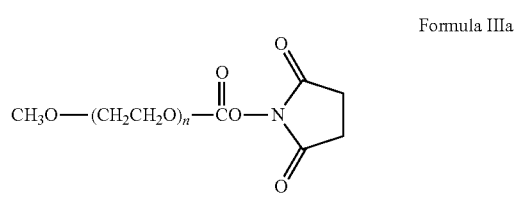

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —$(CH_2CH_2O)_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

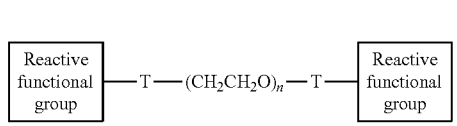

Formula B wherein each T and "Reactive functional group" is independently as defined above and described in classes and subclasses herein, and n is as defined above and described in classes and subclasses herein.

Exemplary bifunctional PEGs of formula B include:

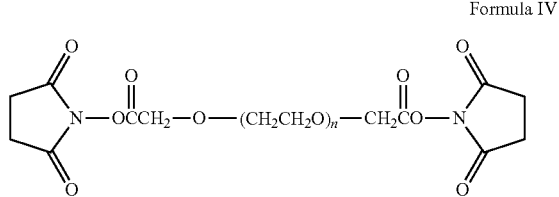

Formula IV

In Formula IV, the moiety comprising the reactive functional group has the general structure $-(CH_2)_m-COO-NHS$, where $m=1$. In some embodiments, a bifunctional PEG has the structure of Formula IV, where m is between 1 and 10, e.g., between 1 and 5. In certain embodiments m is 0, e.g., embodiments the moiety comprising the reactive functional group has the general structure $-COO-NHS$. For example, in some embodiments a bifunctional PEG has the structure of Formula IVa, as shown below:

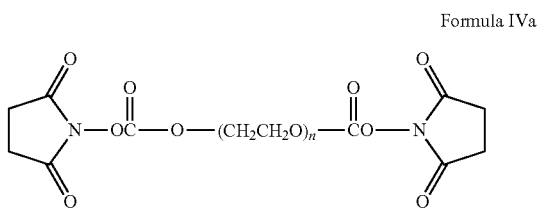

Formula IVa

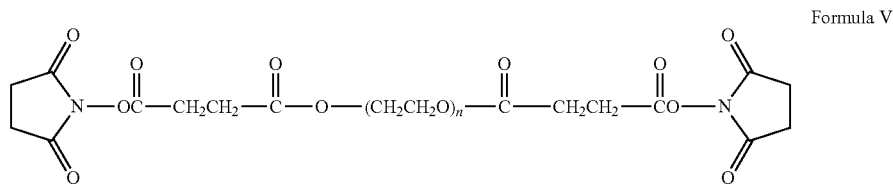

Formula V

In Formula V, the moiety comprising the reactive functional group has the general structure $-CO-(CH_2)_m-COO-NHS$, where $m=2$. In some embodiments, a bifunctional PEGs has the structure of Formula V, where m is between 1 and 10, e.g., between 1 and 5. In certain embodiments, for example, m is 2, as shown below:

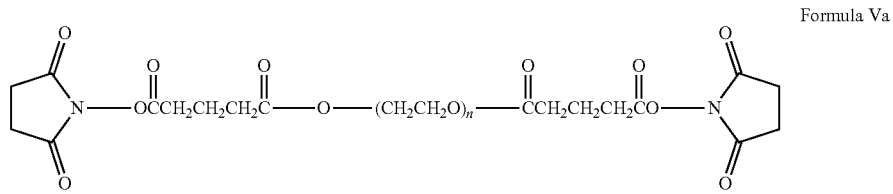

Formula Va

In some embodiments, the present invention provides a compstatin analog conjugated to a polymer. In certain embodiments, the present invention provides compstatin analog conjugates of PEG-containing compounds and genera depicted herein. In some embodiments, a functional group (for example, an amine, hydroxyl, or thiol group) on a compstatin analog is reacted with a PEG-containing compound having a "reactive functional group" as described herein, to generate such conjugates. By way of example, Formulae III and IV, respectively, can form compstatin analog conjugates having the structure:

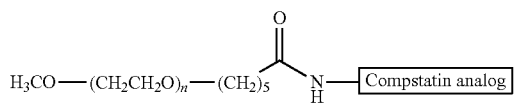

or

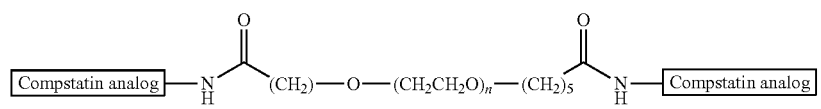

wherein

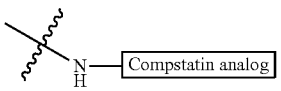 [SMILES: *NC]

represents the attachment point of an amine group on a compstatin analog. In certain embodiments, an amine group is a lysine side chain group.

It will be appreciated that corresponding conjugates can be formed with any of the PEG-containing compounds and genera depicted herein, depending on the choice of reactive functional group and/or compstatin functional group. For example, Formulae IVa and Va, respectively, can form compstatin analog conjugates having the following structures

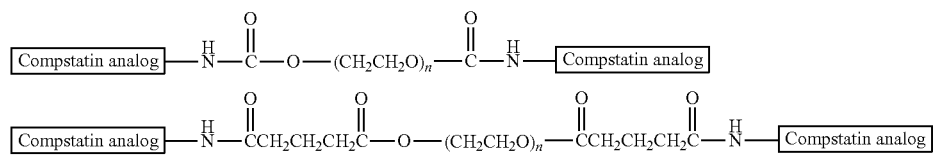

In certain embodiments, the PEG component of such conjugates has an average molecular weight of between about 20 kD-100 kD, about 20 kD-90 kD, about 20 kD-80 kD, about 20 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In certain embodiments, the PEG component of such conjugates has an average molecular weight of about 40 kD.

The term "bifunctional" or "bifunctionalized" is sometimes used herein to refer to a compound comprising two compstatin analog moieties linked to a CRM. Such compounds may be designated with the letter "BF". In some embodiments a bifunctionalized compound is symmetrical. In some embodiments the linkages between the CRM and each of the compstatin analog moieties of a bifunctionalized compound are the same. In some embodiments, each linkage between a CRM and a compstatin analog of a bifunctionalized compound comprises a carbamate. In some embodiments, each linkage between a CRM and a compstatin analog of a bifunctionalized compound comprises a carbamate and does not comprise an ester. In some embodiments, each compstatin analog of a bifunctionalized compound is directly linked to a CRM via a carbamate. In some embodiments, each compstatin analog of a bifunctionalized compound is directly linked to a CRM via a carbamate, and the bifunctionalized compound has the structure:

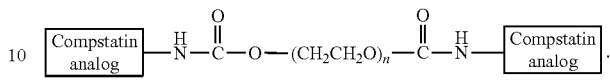

In some embodiments of formulae and embodiments described herein,

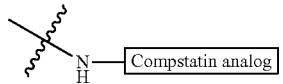 [SMILES: *NC]

represents point of attachment of a lysine side chain group in a compstatin analog having the structure:

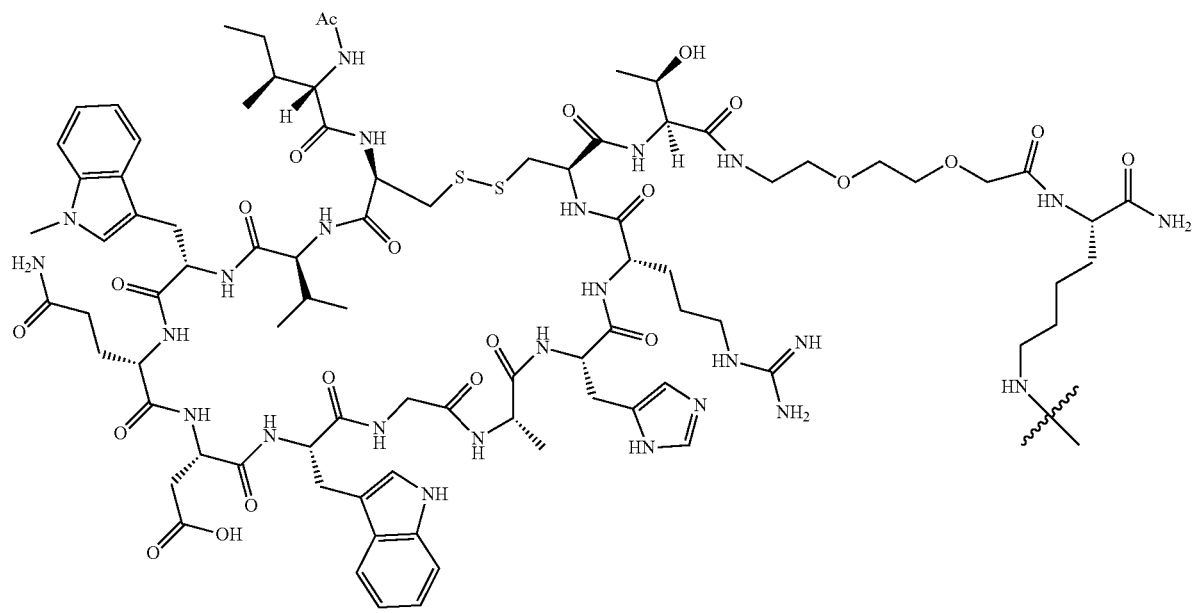 [SMILES: *NCCCC[C@H](NC(=O)COCCOCCNC(=O)[C@@H](NC(=O)[C@@H]1CSSC[C@H](NC(=O)[C@@H](NC(C)=O)[C@@H](C)CC)C(=O)N[C@@H](C(C)C)C(=O)N[C@@H](Cc2cn(C)c3ccccc23)C(=O)N[C@@H](CCC(N)=O)C(=O)N[C@@H](CC(=O)O)C(=O)N[C@@H](Cc2c[nH]c3ccccc23)C(=O)NCC(=O)N[C@@H](C)C(=O)N[C@@H](Cc2cnc[nH]2)C(=O)N[C@@H](CCCNC(=N)N)C(=O)N1)[C@@H](C)O)C(N)=O]

wherein the symbol "∿" denotes the point of attachment of a chemical moiety to the remainder of a molecule or chemical formula.

In some embodiments, a branched, comb, or star-shaped PEG comprises a moiety comprising a reactive functional group at the end of each of multiple —(CH$_2$CH$_2$O)$_n$ chains. The reactive functional groups may be the same or there may be at least two different groups. In some embodiments, a branched, comb, or star-shaped PEG is of the following formulae:

Formula C

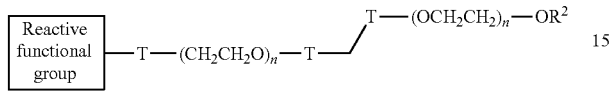

Formula D

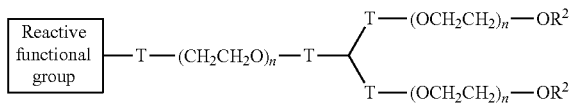

Formula E

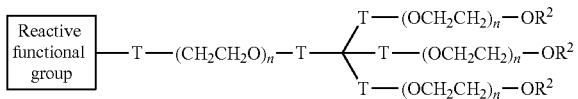

Formula F

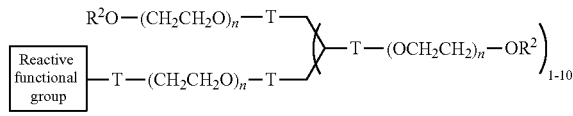

Formula G

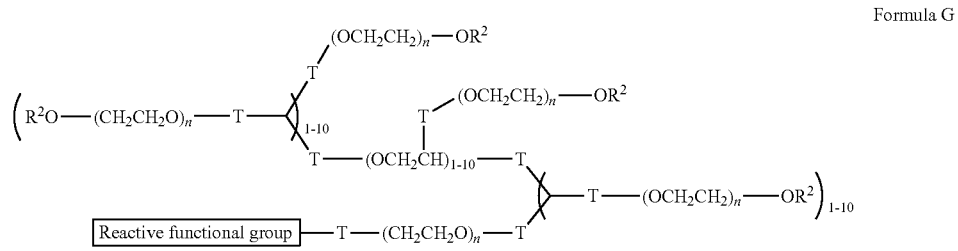

Formula H

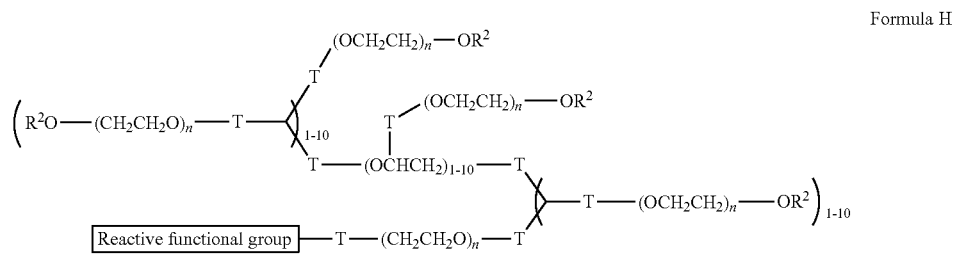

wherein each $R^2$ is independently a "Reactive functional group" or $R^1$, and each T, n, and "Reactive functional group" is independently as defined above and described in classes and subclasses herein. The structure of exemplary branched PEGs (having 8 arms, or branches) comprising NHS moieties as reactive functional groups is depicted below:

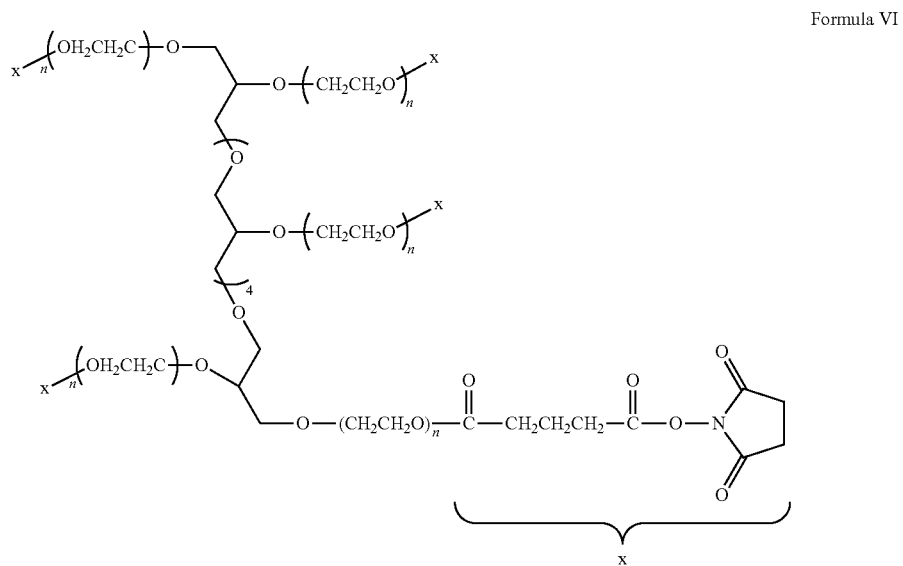

Formula VI

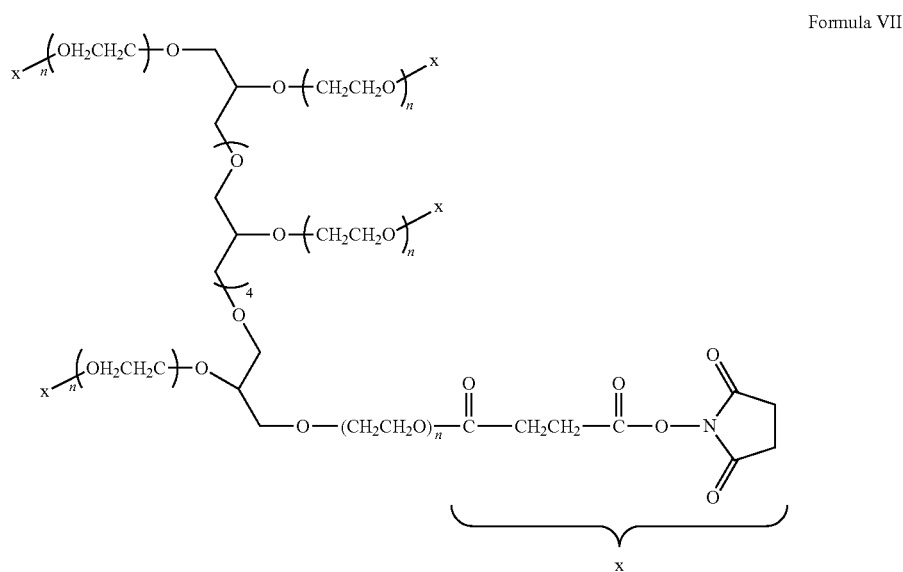

Formula VII

The structure of exemplary branched PEGs (having 4 arms, or branches) comprising NHS moieties as reactive functional groups is depicted below:

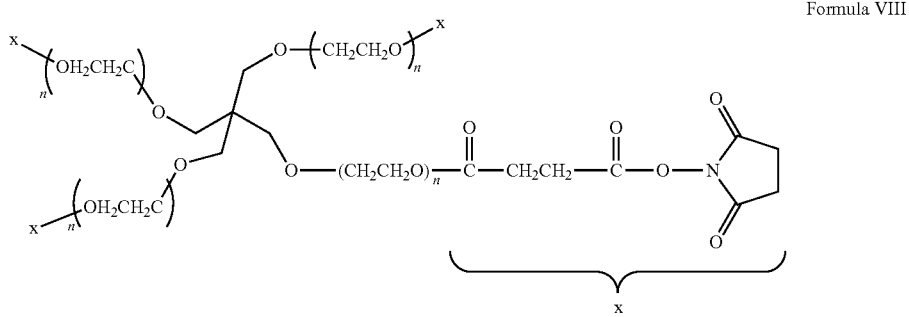

Formula VIII

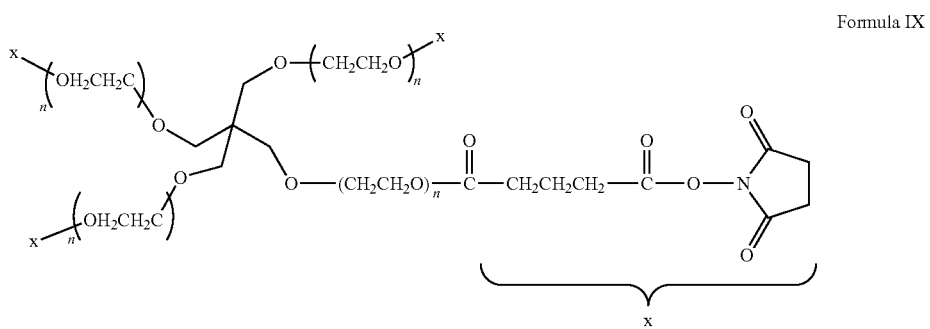

Formula IX

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a —CH$_2$CH$_2$OH or —CH$_2$CH$_2$OR group, as described above.

In some embodiments a branched PEG has the structure of Formula VII, VIII, or IX (or variants thereof having different numbers of branches) with the proviso that x is

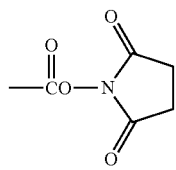

In some embodiments a branched PEG has the structure of Formula VII, VIII, or IX (or variants thereof having different numbers of branches) with the proviso that x is

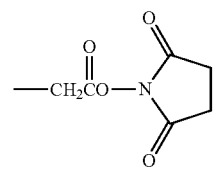

Of course the methylene (CH$_2$) group in the above x moiety may instead comprise a longer alkyl chain (CH$_2$)$_m$, where m is up to 2, 3, 4, 5, 6, 8, 10, 20, or 30, or may comprise one or more other moieties described herein.

In some embodiments, exemplary branched PEGs having NHS or maleimide reactive groups are depicted below:

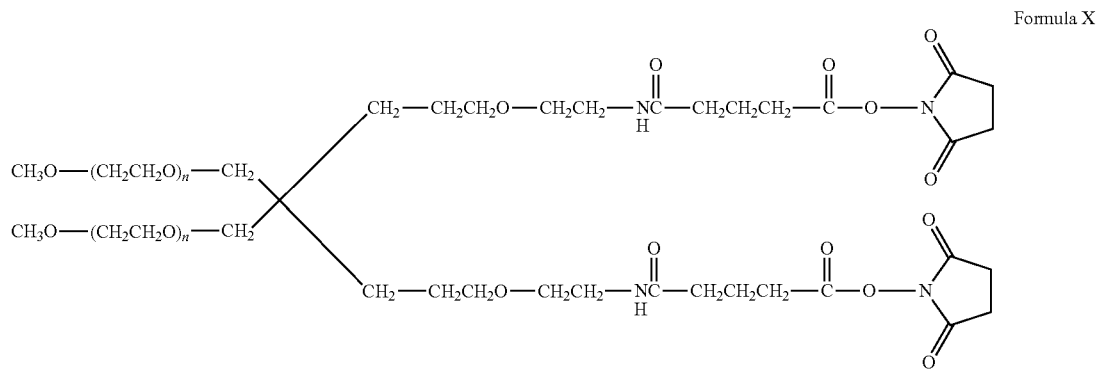
Formula X
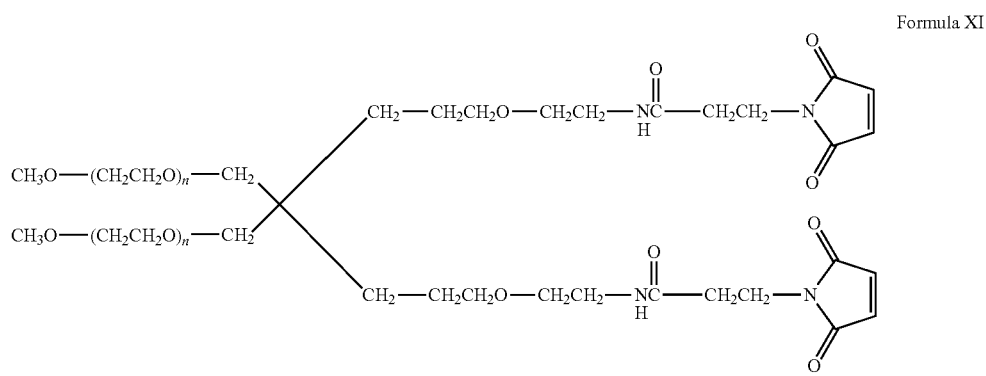
Formula XI
In some embodiments, a variant of Formula X or XI are used, wherein 3 or each of the 4 branches comprise a reactive functional group.
Still other examples of PEGs may be represented as follows:
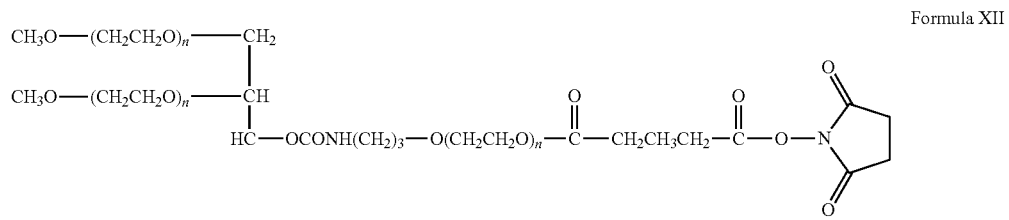
Formula XII
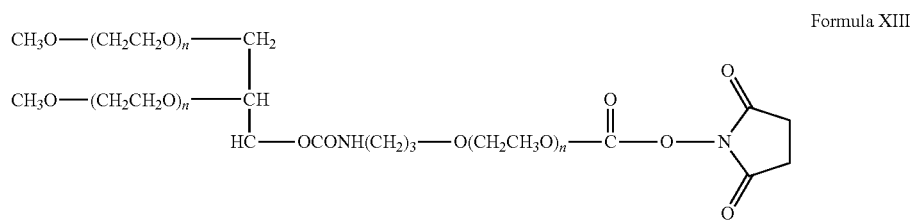
Formula XIII As noted above, it will be appreciated that, as described herein, in various embodiments any of a variety of moieties may be incorporated between the peptide component and $(CH_2CH_2O)_n$-R moiety of a long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the compound from the CRM. In some embodiments, such release may enhance the in vivo tissue penetration and/or activity of the compound. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a reactive functional group are as follows:

Formula XIV

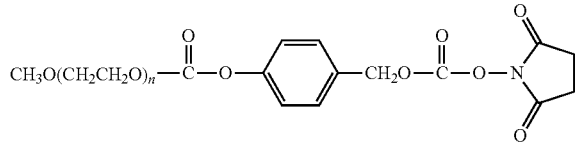

Formula XV

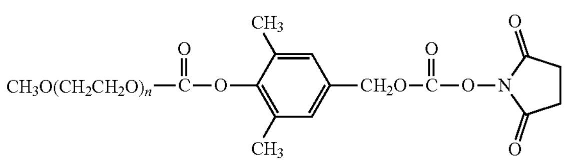

Formula XVI

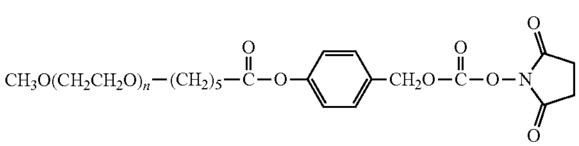

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Monofunctional, bifunctional, branched, and other PEGs comprising one or more reactive functional groups may, in some embodiments, be obtained from, e.g., NOF America Corp. White Plains, NY or BOC Sciences 45-16 Ramsey Road Shirley, NY 11967, USA, among others, or may be prepared using methods known in the art.

In some embodiments, a linkage between a CRM and a compstatin analog comprises a carbamate. In some embodiments, a compstatin analog is directly linked to a CRM via a carbamate. In some embodiments, a linkage between a CRM and a compstatin analog does not comprise an ester. In some embodiments, a linkage between a CRM and a compstatin analog comprises a carbamate and does not comprise an ester. In some embodiments, a linkage between a CRM and a compstatin analog comprises a carbamate and does not comprise a bond that is more susceptible to hydrolysis in aqueous medium than a carbamate. In some embodiments the CRM comprises or consists of a PEG moiety.

In some embodiments, a linkage between a CRM and a compstatin analog comprises an amide. In some embodiments, a compstatin analog is directly linked to a CRM via an amide. In some embodiments, a linkage between a CRM and a compstatin analog comprises an amide and does not comprise an ester. In some embodiments, a linkage between a CRM and a compstatin analog comprises an amide and does not comprise a bond that is more susceptible to hydrolysis in aqueous medium than an amide. In some embodiments the CRM comprises or consists of a PEG moiety.

In some embodiments, one or more compstatin analogs of a multifunctionalized compound (e.g., a bifunctionalized, trifunctionalized, or more extensively functionalized compound) is linked to a CRM by a linkage comprising a carbamate. In some embodiments, one or more compstatin analogs of a multifunctionalized compound (e.g., a bifunctionalized, trifunctionalized, or more extensively functionalized compound) is linked to a CRM by a linkage that does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise a bond that is more susceptible to hydrolysis in aqueous medium than a carbamate. In some embodiments, each compstatin analog of a multifunctionalized compound (e.g., a bifunctionalized, trifunctionalized, or more extensively functionalized compound) is directly linked to a CRM via a carbamate.

In some embodiments the CRM comprises or consists of a PEG moiety. In some embodiments, one or more compstatin analogs of a multifunctionalized compound (e.g., a bifunctionalized, trifunctionalized, or more extensively functionalized compound) is linked to a CRM by a linkage comprising an amide. In some embodiments, one or more compstatin analogs of a multifunctionalized compound (e.g., a bifunctionalized, trifunctionalized, or more extensively functionalized compound) is linked to a CRM by a linkage that comprises an amide and does not comprise an ester. In some embodiments, one or more compstatin analogs of a multifunctionalized compound (e.g., a bifunctionalized, trifunctionalized, or more extensively functionalized compound) is linked to a CRM by a linkage that comprises an amide and does not comprise a bond that is more susceptible to hydrolysis in aqueous medium than an amide. In some embodiments, each compstatin analog of a multifunctionalized compound (e.g., a bifunctionalized, trifunctionalized, or more extensively functionalized compound) is directly linked to a CRM via an amide. In some embodiments the CRM comprises or consists of a PEG moiety.

In some embodiments, the present invention provides a compstatin analog conjugated with a polymer, wherein the polymer is other than PEG. In some embodiments, a polymer is a polyoxazoline (POZ). Exemplary mono- and polyfunctionalized polyoxazoline derivatives for direct conjugation, or for conjugation via a linker, are depicted below:

Z-T-[N(COR$^x$)CH$_2$CH$_2$]$_n$-T-R$^1$;

R$^1$—{[N(CO-T-Z)CH$_2$CH$_2$]$_m$—[N(COR$^x$)CH$_2$CH$_2$]$_n$}$^a$-T-R$^1$;

R$^1$—{[N(CO-T-Z$^1$)CH$_2$CH$_2$]$_p$—[N(COR$^x$)CH$_2$CH$_2$]$_n$—[N(CO-T-Z$^2$)CH$_2$CH$_2$]$_m$}$^a$-T-R$^1$;

R$^1$—{[N(CO-T-Z$^1$)CH$_2$CH$_2$]$_p$—[N(COR$^x$)CH$_2$CH$_2$]$_n$—[N(CO-T-Z$^2$)CH$_2$CH$_2$]$_m$}$^a$-T-Z;

R—[N(COR$^x$)CH$_2$CH$_2$]$_n$-T-B(—R$^1$)(-T-Z)-T-[N(COR$^x$)CH$_2$CH$_2$]$_m$—R$^1$;

wherein:

each of Z, Z$^1$ and Z$^2$ is independently a reactive functional group as defined above and described in classes and subclasses herein;

each of T, R$^x$, and R$^1$ is independently as defined above and described in classes and subclasses herein;

each of m, n, and p is independently an integer 0-1000, with the limitation that the sum of m, n, and p for each formula is not 0;

a is "ran," which indicates a random copolymer, or "block," which indicates a block copolymer;

B is a branching moiety that is linked with or without a linker to the other parts of the polymer. Other examples of functionalized polyoxazoline derivatives for conjugation are extensively described in the art, including but not limited to those described in PCT Patent Application Publication Nos. WO/2010/006282, WO/2009/089542, WO/2009/043027 and WO/2008/106186, the entirety of each of which is hereby incorporated by reference.

Exemplary compstatin analog conjugates with polyoxazoline polymers are depicted below:

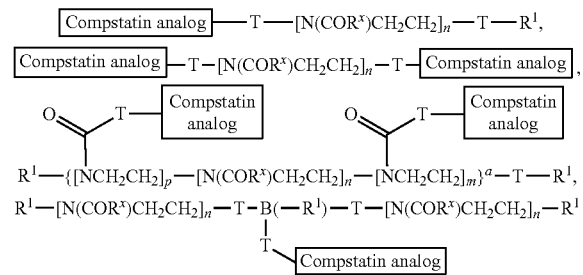

wherein each variable is independently as defined above and described in classes and subclasses herein.

In some embodiments, the present invention provides a compstatin analog conjugated with a polymer, wherein the compstatin analog is connected to the polymer via one or more linkers. In some embodiments, a polymer is selected from PEG-containing compounds and genera described above and in classes and subclasses herein. In some embodiments, the present invention provides compstatin analog conjugates of PEG-containing compounds and genera depicted herein, wherein the compstatin analog is connected to the PEG-containing moieties via one or more linkers. Mono- and poly-functional PEGs that comprise one or more reactive functional groups for conjugation are defined above and described in classes and subclasses herein, including but not limited to those of formula A, I, Ia, II, III, IIIa, B, IV, IVa, V, Va, C, D, E, F, G, H, VI, VII, VIII, IX, X, XI, XII, XIII, XIV, XV, or XVI.

Suitable linkers for connecting a compstatin analog and a polymer moiety such as PEG or polyoxazoline are extensively described above and in classes and subclasses herein. In some embodiments, a linker has multiple functional groups, wherein one functional group is connected to a compstatin analog and another is connected to a polymer moiety. In some embodiments, a linker is a bifunctional compound. In some embodiments, a linker has the structure of NH$_2$(CH$_2$CH$_2$O)nCH$_2$C(=O)OH, wherein n is 1 to 1000. In some embodiments, a linker is 8-amino-3,6-dioxaoctanoic acid (AEEAc). In some embodiments, a linker is activated for conjugation with a polymer moiety or a functional group of a compstatin analog. For example, in some embodiments, the carboxyl group of AEEAc is activated before conjugation with the amine group of the side chain of a lysine group.

In some embodiments, a suitable functional group (for example, an amine, hydroxyl, thiol, or carboxylic acid group) on a compstatin analog is used for conjugation with a polymer moiety, either directly or via a linker. In some embodiments, a compstatin analog is conjugated through an amine group to a PEG moiety via a linker. In some embodiments, an amine group is the α-amino group of an amino acid residue. In some embodiments, an amine group is the amine group of the lysine side chain. In some embodiments, a compstatin analog is conjugated to a PEG moiety through the amino group of a lysine side chain (r-amino group) via a linker having the structure of NH$_2$(CH$_2$CH$_2$O)nCH$_2$C(=O)OH, wherein n is 1 to 1000. In some embodiments, a compstatin analog is conjugated to the PEG moiety through the amino group of a lysine side chain via an AEEAc linker. In some embodiments, the NH$_2$(CH$_2$CH$_2$O)nCH$_2$C(=O)OH linker introduces a —NH(CH$_2$CH$_2$O)nCH$_2$C(=O)— moiety on a compstatin lysine side chain after conjugation. In some embodiments, the AEEAc linker introduces a —NH(CH$_2$CH$_2$O)$_2$CH$_2$C(=O)— moiety on a compstatin lysine side chain after conjugation.

In some embodiments, a compstatin analog is conjugated to a polymer moiety via a linker, wherein the linker comprises an AEEAc moiety and an amino acid residue. In some embodiments, a compstatin analog is conjugated to a polymer moiety via a linker, wherein the linker comprises an AEEAc moiety and a lysine residue. In some embodiments, a polymer is PEG. In some embodiments, the C-terminus of a compstatin analog is connected to the amino group of AEEAc, and the C-terminus of AEEAc is connected to a lysine residue. In some embodiments, the C-terminus of a compstatin analog is connected to the amino group of AEEAc, and the C-terminus of AEEAc is connected to the α-amino group of a lysine residue. In some embodiments, the C-terminus of a compstatin analog is connected to the amino group of AEEAc, the C-terminus of AEEAc is connected to the α-amino group of the lysine residue, and a polymer moiety, such as a PEG moiety, is conjugated through the ε-amino group of said lysine residue. In some embodiments, the C-terminus of the lysine residue is modified. In some embodiments, the C-terminus of the lysine residue is modified by amidation. In some embodiments, the N-terminus of a compstatin analog is modified. In some embodiments, the N-terminus of a compstatin analog is acetylated.

Exemplary conjugates comprising an AEEAc linker and a polymer are depicted below, wherein

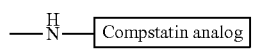

represents the attachment point of an amine group on a compstatin analog,

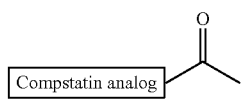

represents a compstatin analog attaching through its C-terminus, and wherein each of the other variables is independently as defined above and described in classes and subclasses herewith. In some embodiments, an amine group is the amino group of a lysine side chain.

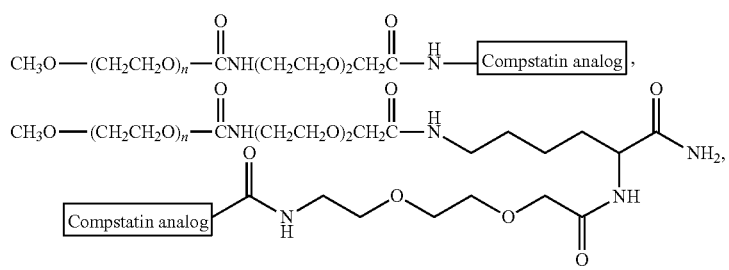

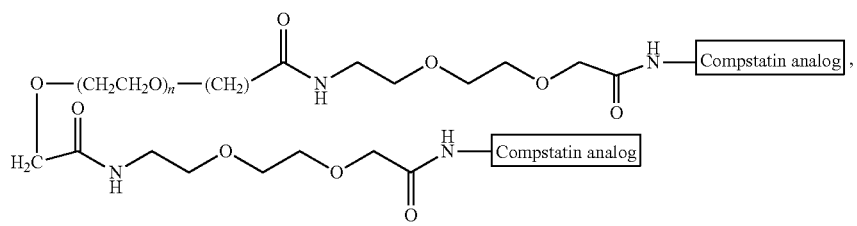

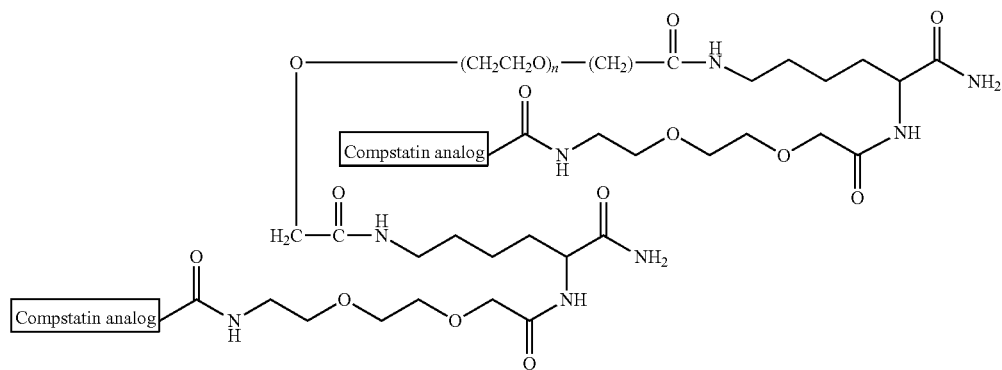

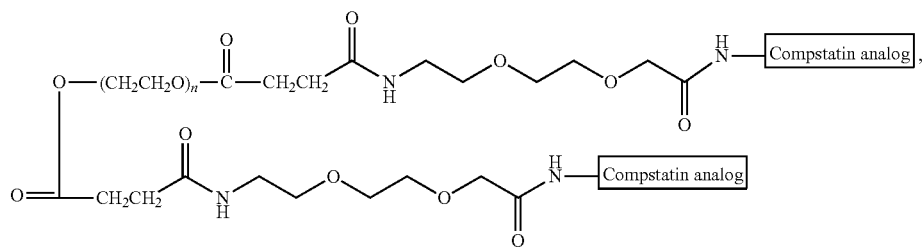

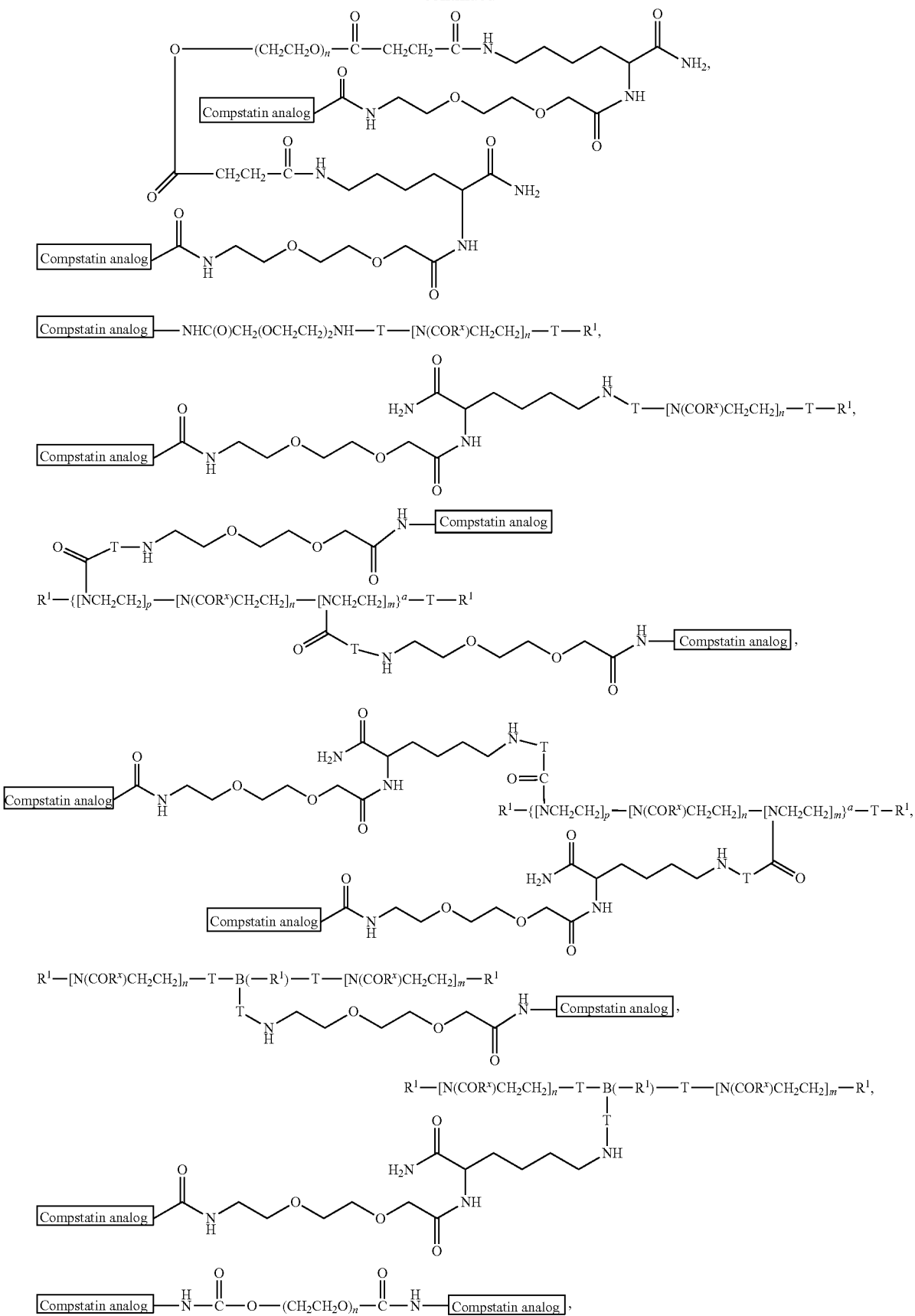

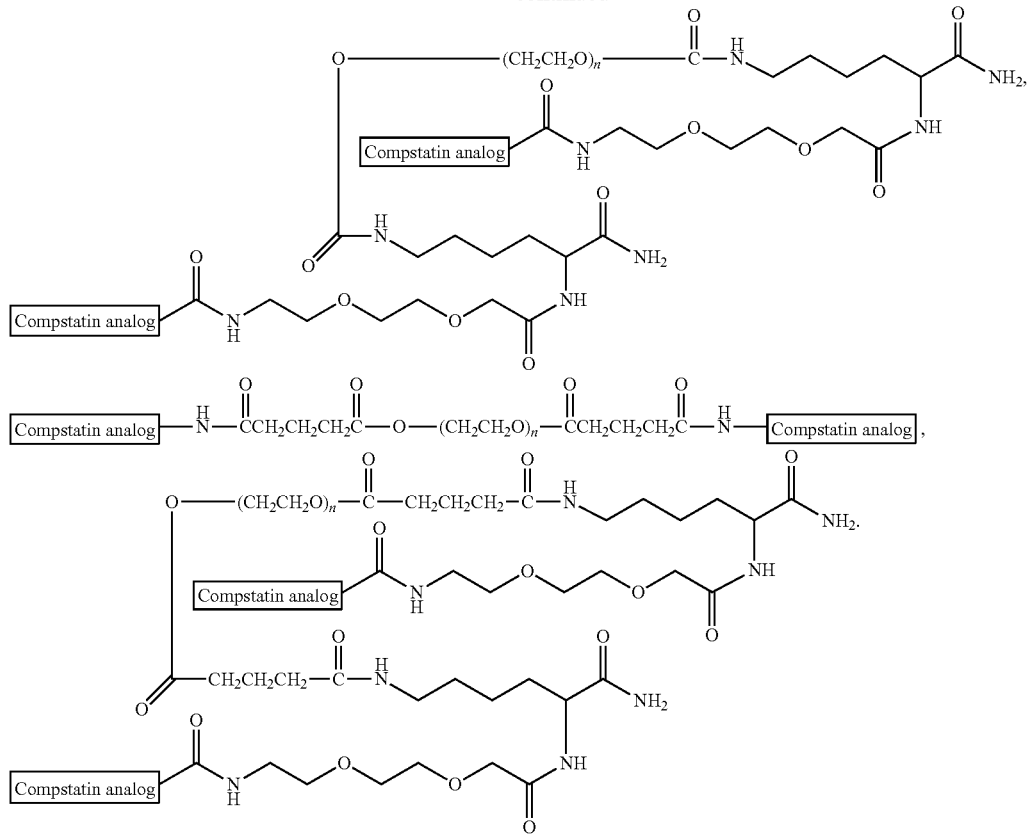

In certain embodiments a compstatin analog may be represented as M-AEEAc-Lys-B$_2$, wherein B$_2$ is a blocking moiety, e.g., NH$_2$, M represents any of SEQ ID NOs: 3-36, 37, 69, 70, 71, or 72, with the proviso that the C-terminal amino acid of any of SEQ ID NOs: 3-36, 37, 69, 70, 71, or 72 is linked via a peptide bond to AEEAc-Lys-B$_2$. The NHS moiety of a monofunctional or multifunctional (e.g., bifunctional) PEG reacts with the free amine of the lysine side chain to generate a monofunctionalized (one compstatin analog moiety) or multifunctionalized (multiple compstatin analog moieties) long-acting compstatin analog. In various embodiments any amino acid comprising a side chain that comprises a reactive functional group may be used instead of Lys (or in addition to Lys). A monofunctional or multifunctional PEG comprising a suitable reactive functional group may be reacted with such side chain in a manner analogous to the reaction of NHS-ester activated PEGs with Lys.

With regard to any of the above formulae and structures, it is to be understood that embodiments in which the compstatin analog component comprises any compstatin analog described herein, e.g., any compstatin analog of SEQ ID NOs; 3-36, 37, 69, 70, 71, or 72, are expressly disclosed. For example, and without limitation, a compstatin analog may comprise the amino acid sequence of SEQ ID NO: 28. An exemplary long-acting compstatin analog in which the compstatin analog component comprises the amino acid sequence of SEQ ID NO: 28 is depicted in FIG. 1. It will be understood that the PEG moiety may have a variety of different molecular weights or average molecular weights in various embodiments, as described herein. For example, individual PEG chains within a preparation may vary in molecular weight and/or different preparations may have different average molecular weights and/or polydispersity, as described herein. In certain embodiments, the PEG moiety in the compound of FIG. 1 has an average molecular weight of between about 20 kD-100 kD, about 20 kD-90 kD, about 20 kD-80 kD, about 20 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In some embodiments the PEG moiety in the compound of FIG. 1 has an average molecular weight between about 30 kD and about 50 kD, e.g., between about 35 kD and about 45 kD, between about 37.5 kD and about 42.5 kD. In certain embodiments in which the PEG moiety has an average molecular weight of about 40 kD, e.g., 37.5 kD-42.5 kD, 38 kD, 39 kD, 40 kD, 41 kD, 42 kD, the compound is sometimes referred to herein as CA28-2TS-BF. In certain embodiments a compound comprising a CRM, e.g., a PEG moiety, that has an average molecular weight of about 40 kD, e.g., 37.5 kD-42.5 kD, 38 kD, 39 kD, 40 kD, 41 kD, 42 kD, the compound has a terminal half-life of at least about 5 days, e.g., about 5-10 days, e.g., about 5, 6, 7, 8, 9 days, when administered IV or subcutaneously to non-human primates or humans, e.g., at a dose of about 1-3 mg/kg, 3-5 mg/kg, or 5-10 mg/kg.

In some aspects, the present invention relates to use of click chemistry in connection with compstatin analogs. "Click chemistry" is well known in the art and is useful in some aspects of the present invention. Click chemistry embodies, in certain embodiments, versatile cycloaddition reactions between azides and alkynes that enable a number of useful applications. Methods of carrying out click chemistry are known in the art, and are described by Kolb, H. C.; Sharpless, K. B., Drug Disc. Today, 2003, 1128-1137; Moses, J. E.; Moorhouse, A. D.; Chem. Soc. Rev., 2007, 1249-1262; the entire contents of each are hereby incorporated by reference. Click chemistry is a popular method of bioconjugation due to its high reactivity and selectivity, even in biological media. See Kolb, H. C.; Finn, M. G.; Sharpless, K. B. Angew. Chem. Int. Ed. 2001, 40, 2004-2021; and Wang, Q.; Chan, T. R.; Hilgraf, R.; Fokin, V. V.; Sharpless, K. B.; Finn, M. G. J Am. Chem. Soc. 2003, 125, 3192-3193. In addition, currently available recombinant techniques and synthetic methods permit the introduction of azides and alkyne-bearing non-canonical amino acids into peptides, proteins, cells, viruses, bacteria, and other biological entities that consist of or display proteins. See Link, A. J.; Vink, M. K. S.; Tirrell, D. A. J. Am. Chem. Soc. 2004, 126, 10598-10602; Deiters, A.; Cropp, T. A.; Mukherji, M.; Chin, J. W.; Anderson, C.; Schultz, P. G. J. Am. Chem. Soc. 2003, 125, 11782-11783.

As used herein, the term "click chemistry group" is sometimes used to refer to a reactive functional group capable of participating in a click chemistry reaction with an appropriate second reactive functional group, which second reactive functional group is also a click chemistry group. The first and second click chemistry groups, or entities (e.g., molecules) comprising such groups, may be referred to as complementary. First and second entities, e.g., molecules, that comprise complementary click chemistry groups may be referred to as click chemistry partners. An entity or molecule comprising a click chemistry group may be referred to as "click-functionalized". A bond formed by reaction of complementary click chemistry partners may be referred to as a "click chemistry bond".

In some embodiments, the present invention provides click-functionalized compstatin analogs for, e.g., conjugation to a complementary moiety on a partner molecule or biomolecule. In some embodiments, a complementary partner molecule or biomolecule is a polymer, peptide, protein, or a molecule that functions as a clearance-reducing moiety. In some embodiments, the "click-functionalized" moiety is an alkyne or an alkyne derivative which is capable of undergoing [3+2]cycloaddition reactions with complementary azide-bearing molecules and biomolecules. In another embodiment, the "click-functionalized" functionality is an azide or an azide derivative which is capable of undergoing [3+2]cycloaddition reactions with complementary alkyne-bearing molecules and biomolecules (i.e. click chemistry).

In some embodiments, a click-functionalized compstatin analog bears an azide group on any side chain group of the compstatin analog. In some embodiments, a click-functionalized compstatin analog bears an azide group on a lysine side chain group.

In some embodiments, a click-functionalized compstatin analog bears an alkyne group on any side chain group of the compstatin compstatin analog. In some embodiments, a click-functionalized compstatin analog bears an alkyne group on a lysine side chain group.

In some embodiments, the present invention provides compstatin conjugates comprising a compstatin analog, a molecule that functions as a clearance-reducing moiety, and a triazole linker. In some embodiments, a triazole linker is the result of click conjugation chemistry between a compstatin conjugate and a molecule that functions as a clearance-reducing moiety. In some embodiments the CRM may be any CRM disclosed herein. For example, the CRM may be a PEG, a polypeptide, or a POZ.

In some embodiments, the present invention provides compstatin conjugates comprising a compstatin analog, a PEG moiety, and a triazole linker. In some embodiments, a triazole linker is the result of click conjugation chemistry between a compstatin conjugate and a PEG moiety.

In some embodiments, the present invention provides compstatin conjugates comprising a compstatin analog, a polyoxazoline moiety, and a triazole linker. In some embodiments, a triazole linker is the result of click conjugation chemistry between a compstatin conjugate and a polyoxazoline moiety.

In some embodiments, click chemistry between a compstatin analog and another moiety is transition metal catalyzed. Copper-containing molecules which catalyze the "click" reaction include, but are not limited to, copper wire, copper bromide (CuBr), copper chloride (CuCl), copper sulfate (CuSO$_4$), copper sulfate pentahydrate (CuSO$_4$·5H2O), copper acetate (Cu$_2$(AcO$_4$), copper iodide (CuI), [Cu(MeCN)$_4$](OTf), [Cu(MeCN)$_4$](PF$_6$), colloidal copper sources, and immobilized copper sources. In some embodiments other metals, such as ruthenium. Reducing agents as well as organic and inorganic metal-binding ligands can be used in conjunction with metal catalysts and include, but are not limited to, sodium ascorbate, tris(triazolyl)amine ligands, tris(carboxyethyl)phosphine (TCEP), sulfonated bathophenanthroline ligands, and benzimidazole-based ligands.

In some embodiments, compstatin analogs are conjugated to other moieties using metal free click chemistry (also known as copper free click chemistry) to give a metal free composition or conjugates. In contrast to standard click chemistry, also known as copper assisted click chemistry (CuACC), metal free click chemistry occurs between either a strained, cyclic alkyne or an alkyne precursor such as an oxanorbornadiene, and an azide group. As the name implies, no metal catalyst is necessary for the reaction to occur. Examples of such chemistries include reactions involving cyclooctyne derivatives (Codelli, et. al. J. Am. Chem. Soc., 2008, 130, 11486-11493; Jewett, et. al. J. Am. Chem. Soc., 2010, 132, 3688-3690; Ning, et. al. Angew. Chem. Int. Ed., 2008, 47, 2253-2255), difluoro-oxanorbornene derivatives (van Berkel, et. al. Chem Bio Chem, 2007, 8, 1504-1508), or nitrile oxide derivatives (Lutz, et. al. Macromolecules, 2009, 42, 5411-5413). In certain embodiments a metal-free click chemistry reaction is a metal-free [3+2]cycloaddition reaction, Diels-Alder reaction, or thiol-alkene radical addition reaction. Exemplary click chemistry reactions and click chemistry groups are described in, e.g., Joerg Lahann, Click Chemistry for Biotechnology and Materials Science, 2009, John Wiley & Sons Ltd, ISBN 978-0-470-69970-6; Becer, Hoogenboom, and Schubert, Click Chemistry beyond Metal-Catalyzed Cycloaddition, Angewandte Chemie International Edition (2009) 48: 4900-4908. In certain embodiments a click chemistry group comprises a diarylcyclooctyne.

Certain examples of metal free click chemistry are shown in the scheme below.

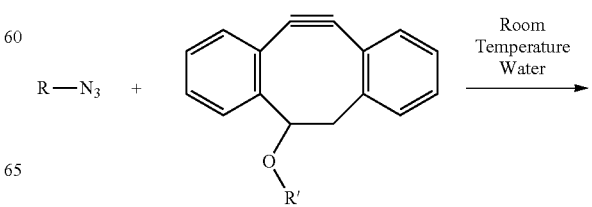

147
-continued

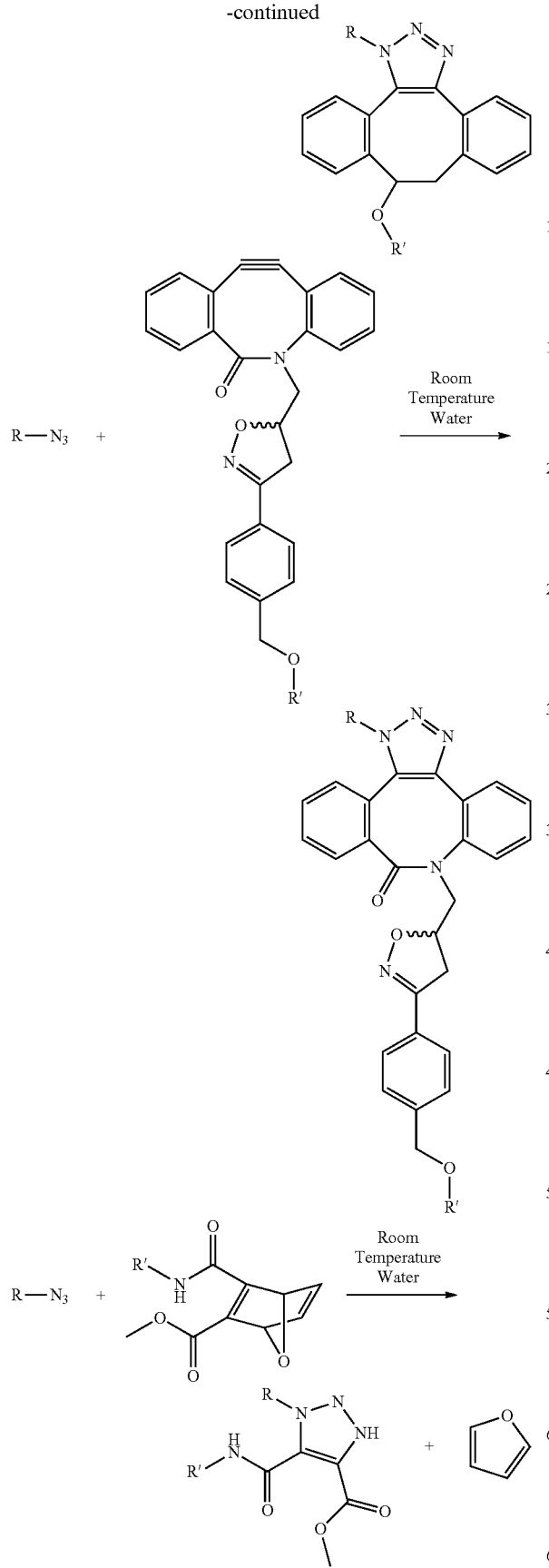

148

Certain metal-free click moieties are known in the literature. Examples include 4-dibenzocyclooctynol (DIBO)

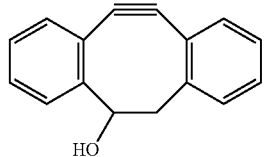 [SMILES: OC1Cc2ccccc2C#Cc2ccccc21]

(from Ning et. al; Angew Chem Int Ed, 2008, 47, 2253); difluorinated cyclooctynes (DIFO or DFO)

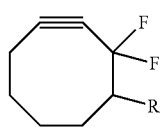

(from Codelli, et. al.; J. Am. Chem. Soc. 2008, 130, 11486-11493.); biarylazacyclooctynone (BARAC)

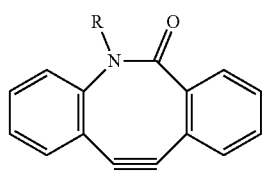

(from Jewett et. al.; J. Am. Chem. Soc. 2010, 132, 3688); or bicyclononyne (BCN)

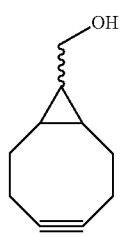 [SMILES: OCC1C2CCC#CCCC12]

(From Dommerholt, et. al.; Angew Chem Int Ed, 2010, 49, 9422-9425) or dibenzylcyclooctyne (DBCO)

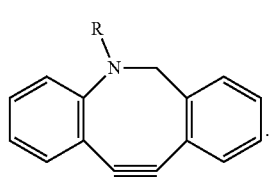

A reaction scheme involving reaction of DBCO and an azide is shown below:

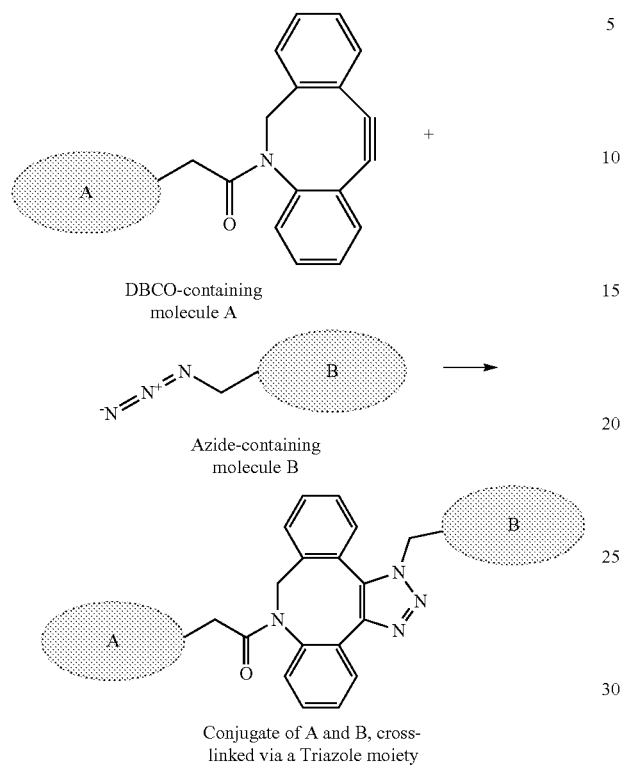

DBCO-containing molecule A

Azide-containing molecule B

Conjugate of A and B, cross-linked via a Triazole moiety

In the above scheme, in various embodiments, A may comprise or consist of a compstatin analog moiety and B may comprise or consist of a CRM, e.g., a polymer, such as a PEG or a POZ or a polypeptide, or B may comprise or consist of a compstatin analog moiety and A may comprise or consist of a CRM, e.g., a polymer, such as a PEG or a POZ or a polypeptide.

In some embodiments, the "metal free click-functionalized" moiety is an acetylene or an acetylene derivative which is capable of undergoing [3+2]cycloaddition reactions with complementary azide-bearing molecules and biomolecules without the use of a metal catalyst.

In some embodiments, the R and R' groups of the metal-free click chemistry reagents are a compstatin analog or any molecule described herein to which a compstatin analog may be conjugated. In some embodiments, such compstatin analogs bear a click-functionalized moiety on a lysine side chain. In some embodiments, such compstatin analogs are connected to a click-functionalized moiety via a linker. In some embodiments, such compstatin analogs are connected to a click-functionalized moiety via AEEAc.

In some embodiments, a click chemistry reagent comprises DBCO. Exemplary reagents and exemplary uses thereof are set forth below:

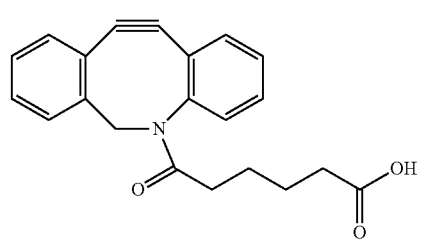 [SMILES: O=C(O)CCCCC(=O)N1Cc2ccccc2C#Cc2ccccc21]

DBCO-Acid. In some embodiments a DBCO-Acid may be used to react with an amine-containing moiety.

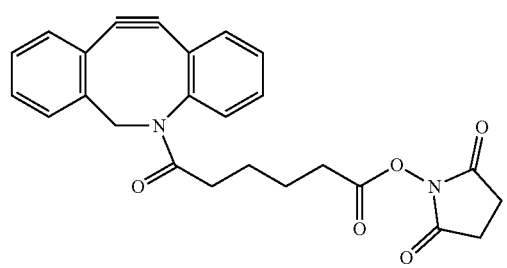 [SMILES: O=C(CCCCC(=O)N1Cc2ccccc2C#Cc2ccccc21)ON1C(=O)CCC1=O]

DBCO-NHS ester (above) or DBCO-sulfo-NHS ester (below) may be used to incorporate a DBCO functionality into an amine-containing molecule, such as a compstatin analog or a polypeptide comprising a lysine residue.

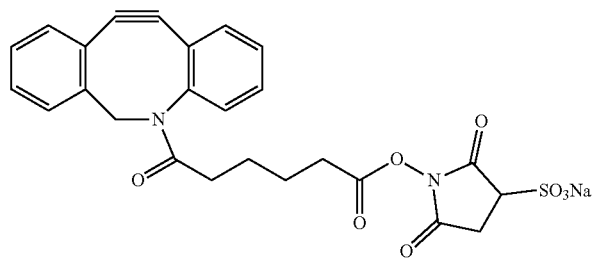

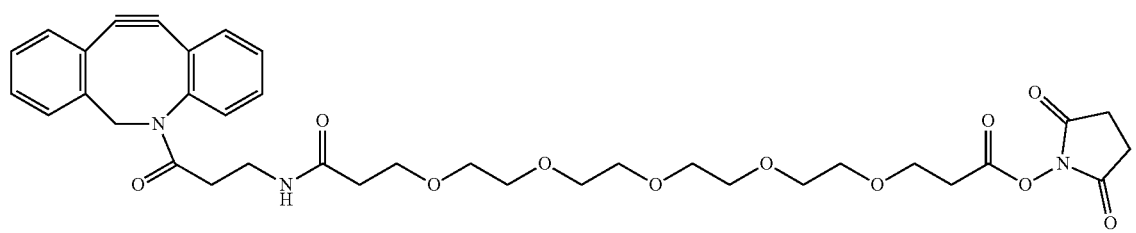

DBCO-PEG4-NHS ester. In some embodiments such reagent is useful for introducing a DBCO moiety by reaction with an available amine functionality. In some aspects, the presence of a PEG chain as a hydrophilic spacer may be useful to, e.g., increase solubility or provide flexibility.

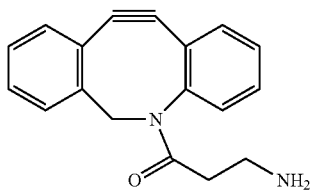 [SMILES: NCCC(=O)N1Cc2ccccc2C#Cc2ccccc21]

DBCO-Amine. In some embodiments a click chemistry reagent comprises a carbonyl/carboxyl reactive dibenzylcyclooctyne, which may react with acids, active esters and/or aldehydes.

In certain embodiments a click chemistry reaction involves a cyclooctyne depicted below:

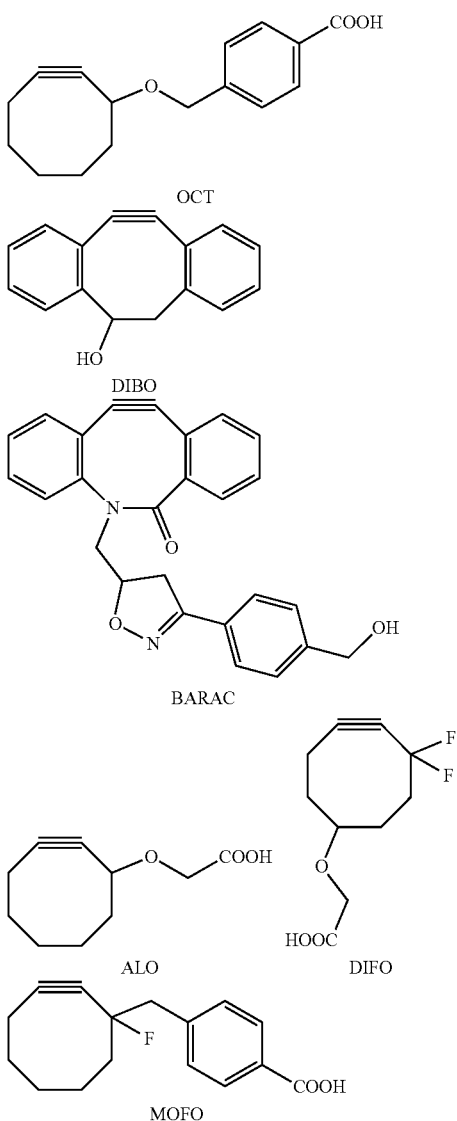

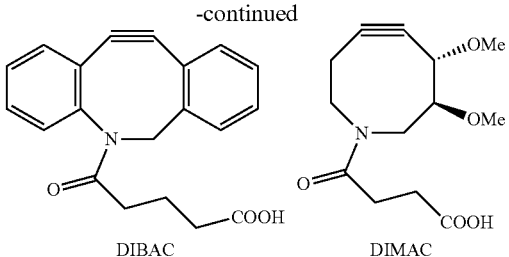

In certain embodiments click chemistry reactions comprise reactions between nitrones and cyclooctynes (see, e.g., Ning, Xinghai; Temming, Rinske P.; Dommerholt, Jan; Guo, Jun; Ania, Daniel B.; Debets, Marjoke F.; Wolfert, Margreet A.; Boons, Geert-Jan et al. (2010). "Protein Modification by Strain-Promoted Alkyne-Nitrone Cycloaddition". Angewandte Chemie International Edition 49 (17): 3065), oxime/hydrazone formation from aldehydes and ketones, tetrazine ligations (see, e.g., Blackman, Melissa L.; Royzen, Maksim; Fox, Joseph M. (2008). "The Tetrazine Ligation: Fast Bioconjugation based on Inverse-electron-demand Diels-Alder Reactivity". Journal of the American Chemical Society 130 (41): 13518-9), tetrazole ligations, the isonitrile-based click reaction (see, e.g., Stackmann, Henning; Neves, André A.; Stairs, Shaun; Brindle, Kevin M.; Leeper, Finian J. (2011). "Exploring isonitrile-based click chemistry for ligation with biomolecules". Organic & Biomolecular Chemistry 9 (21): 7303), and the quadricyclane ligation (see, e.g., Sletten, Ellen M.; Bertozzi, Carolyn R. (2011). "A Bioorthogonal Quadricyclane Ligation". Journal of the American Chemical Society 133 (44): 17570-3). In certain embodiments a click chemistry reaction is a Staudinger ligation (phosphine-azide).

Any compstatin analog may be modified to incorporate a click chemistry group in various embodiments. For example, a compstatin analog comprising the sequence of any of SEQ ID NOs: 3-36, 37, 69, 70, 71, or 72 may be so modified. In some embodiments any such sequence further comprises a lysine residue or an AEEAc-Lys moiety, e.g., at the C-terminus. In some embodiments a click chemistry group is incorporated after peptide synthesis. For example, a Lys side chain may be reacted with azido acetic acid in order to introduce an azide moiety as a click chemistry group. In some embodiments a click chemistry group is incorporated after cyclization and, in some embodiments, after addition of a blocking moiety at the N- and/or C-terminus. In some embodiments a click chemistry group is incorporated during peptide synthesis. For example, an amino acid comprising a side chain that comprises a click chemistry group may be used in the synthesis of a compstatin analog. A variety of such amino acids are commercially available from a number of sources, e.g., AAPPTec (Louisville, KY), Jena Bioscience GmBH (Jena, Germany). In some aspects, methods of making a click chemistry functionalized compstatin analog are provided herein.

In some embodiments compositions comprising a compstatin analog and a click chemistry reagent are provided. The click chemistry reagent may be any molecule capable of reacting with an amino acid side chain or terminus of a compound comprising a compstatin analog so as to install a click chemistry group, e.g., any click chemistry group known in the art. In some aspects, the composition may be incubated under suitable conditions (which may include providing a suitable catalyst, light (e.g., UV)) to functionalize the compstatin analog with a click chemistry functionality. In some embodiments, the invention provides compstatin analogs that comprise any click chemistry group including, but not limited to, those described herein. In some embodiments methods of making a long-acting compstatin analog are provided. In some embodiments the methods comprise mixing a compstatin analog comprising a first click chemistry group with a CRM comprising a complementary click chemistry group under conditions suitable for a click chemistry reaction to occur. Additional steps may comprise purifying the resulting conjugate. In some embodiments purifying comprises removing at least some unreacted components, e.g., with an appropriate scavenger.

In some embodiments a click chemistry reaction is used to join two or more CRMs, at least two of which have a compstatin analog moiety attached thereto. The compstatin analog moieties may be the same or different in various embodiments. The compstatin analog moieties may or may not be attached to the CRM via a click chemistry reaction. For example, in some embodiments a first heterobifunctional PEG comprising a first click chemistry group at a first terminus and an NHS ester at a second terminus is coupled to a compstatin analog moiety via the NHS ester. In a separate reaction, a second heterobifunctional PEG comprising a second click chemistry group at a first terminus and an NHS ester at a second terminus is coupled to a compstatin analog moiety via the NHS ester. The resulting two compounds are then reacted via a click chemistry reaction to form a larger molecule comprising two compstatin analog moieties. PEG is mentioned as an example of a CRM but it should be understood that this approach may be used with any CRM. For example, in some embodiments it may be used with a CRM comprising a polypeptide, e.g., HSA or a portion thereof, or an albumin or albumin-binding peptide, or an antibody or portion thereof. In some embodiments this approach may be used with a POZ.

Compstatin analogs comprising a click chemistry group have a variety of uses. In some embodiments a compstatin analog comprising a first click chemistry group is reacted with any entity that comprises a complementary click chemistry group. The entity comprising the complementary click chemistry group may comprise, for example, a label (e.g., a flurophore, fluorescent protein, radioisotope, etc.), an affinity reagent, an antibody, a targeting moiety, a metal, a particle, etc. In some embodiments a click chemistry group is used to attach a compstatin analog moiety to a surface, wherein the surface comprises or is functionalized to comprise a complementary click chemistry group. In some embodiments a surface is for a sensor, e.g., a surface or sensor for capture/detection of C3. In some embodiments a surface forms part of a medical device, tubing, membrane, reservoir, implant, or other material that may come in contact with blood (e.g., extracorporeally) or be temporarily or indefinitely implanted into the body of a subject (e.g., a prosthetic device or drug delivery device). In some embodiments a surface is functionalized with compstatin analog to reduce complement activation thereon. In some embodiments a device or tubing is used for circulating blood, e.g., for dialysis, during surgery, etc. In some embodiments a device is a hemodialyzer or an extracorporeal circulatory support unit. Such compstatin analog functionalized devices and methods of making thereof are provided herein.

In some embodiments of the invention, a compstatin analog comprises both a cell-reactive functional group and a CRM. In some aspects, the invention provides variants of the molecules of any of the afore-mentioned cell-reactive compstatin analogs wherein a cell-reactive functional group or moiety is replaced by a $(CH_2CH_2O)_n$ moiety (e.g., any of the PEGs described herein) or other polymer (e.g., a POZ, a polypeptide) having a molecular weight of at least 500 daltons, e.g., at least 1,500 daltons up to about 100,000 daltons (e.g., an average molecular weight of about 20,000; 30,000; 40,000; 50,000; 60,000; 70,000; 80,000; 90,000; or 100,000 daltons). In some embodiments the average molecular weight of the compound or $(CH_2CH_2O)_n$ moieties (or other polymer, e.g., a POZ or polypeptide) is at least 20,000 daltons, up to about 100,000; 120,000; 140,000; 160,000; 180,000; or 200,000 daltons. It will thus be understood that the teachings herein regarding cell-reactive compstatin analogs, e.g., the compstatin analog moieties used and the linkages by which a compstatin analog moiety is attached to a cell-reactive moiety, can apply to long-acting compstatin analogs, and long-acting compstatin analog can have any of the structures denoted by A-L-M, as described above, wherein A comprises a clearance reducing moiety (e.g., any of the clearance reducing moieties described herein), and furthermore wherein there may be one, two, or more (e.g., 3, 4, 5, 6, 7, 8) compstatin analog moieties M attached to A via linking portions denoted as L (or $L^{P1}$, $L^{P2}$, or $L^{P3}$) herein). Compstatin analog moieties may comprise a peptide whose sequence comprises any of SEQ ID NOs: 3-36, 37, 69, 70, 71, or 72, or variants thereof (e.g., any variant described herein), optionally extended by one or more amino acids at the N-terminus, C-terminus, or both wherein at least one of the amino acids has a side chain that comprises a reactive functional group such as a primary or secondary amine (e.g., a Lys), a sulfhydryl group, a carboxyl group (which may be present as a carboxylate group), a guanidino group, a phenol group, an indole ring, a thioether, or an imidazole ring, which facilitates conjugation of a moiety comprising a CRM to the compstatin analog (it being understood that after conjugation, such reactive functional group will have reacted to form a bond). It will further be understood that where a compstatin analog moiety comprising any of SEQ ID NOs: 3-36, 37, 69, 70, 71, or 72, or variants thereof, is extended by one or more amino acids at the N-terminus, C-terminus, or both wherein at least one of the amino acids has a side chain that comprises a reactive functional group, such one or more amino acid extension may be separated from the cyclic portion of the compstatin analog moiety by a rigid or flexible spacer moiety comprising, for example, a substituted or unsubstituted, saturated or unsaturated alkyl chain, oligo(ethylene glycol) chain, and/or any of the other moieties denoted by L (or $L^{P1}$, $L^{P2}$, or $L^{P3}$) herein.

Exemplary long-acting compstatin analogs are set forth below, wherein n is sufficient to provide an average molecular weight of between about 500; 1,000; 1,500; 2,000; 5,000; 10,000; 20,000; 30,000; 40,000; 50,000; 60,000; 70,000; 80,000; 90,000; and 100,000 daltons. In some embodiments n is sufficient to provide an average molecular weight of between about 20,000 daltons, up to about 100,000; 120,000; 140,000; 160,000; 180,000; or 200,000 daltons.

(SEQ ID NO: 58)
$(CH_2CH_2O)_n C(=O)$-Ile-Cys-Val-(1Me)Trp-Gln-Asp-Trp-Gly-Ala-His-Arg-Cys-Thr-*NH₂)*

(SEQ ID NO: 59)
Ac-Ile-Cys*-Val-(1Me)Trp-Gln-Asp-Trp-Gly-Ala-His-Arg-Cys*-Thr-NH—$CH_2CH_2OCH_2CH_2OCH_2$—$C(=O)$-Lys-$C(=O)$—$(CH_2CH_2O)n$-*NH₂*

-continued (SEQ ID NO: 60)
Ac-Ile-Cys*-Val-(1Me)Trp-Gln-Asp-Trp-Gly-Ala-His-

Arg-Cys*-Thr-Lys-C(=O)-(CH$_2$CH$_2$O)n-NH$_2$.

(SEQ ID NO: 61)
Ac-Ile-Cys*-Val-(1Me)Trp-Gln-Asp-Trp-Gly-Ala-His-

Arg-Cys*-Thr-(Gly)$_5$-Lys-C(=O)-(CH$_2$CH$_2$O)n-NH$_2$ (SEQ ID NO: 62)
Ac-(CH$_2$CH$_2$O)nC(=O)Lys-(Gly)5-Ile-Cys*-Val-(1Me)

Trp-Gln-Asp-Trp-Gly-Ala-His-Arg-Cys*-Thr-NH$_2$)

(SEQ ID NO: 63)
Ac-(CH$_2$CH$_2$O)nC(=O)Lys-Ile-Cys*-Val-(1Me)Trp-Gln-

Asp-Trp-Gly-Ala-His-Arg-Cys*-Thr-NH$_2$)

In SEQ ID NO: 58, the (CH$_2$CH$_2$O)$_n$ is coupled via an amide bond to the N-terminal amino acid. In SEQ ID NOs: 59-63, the (CH$_2$CH$_2$O)$_n$ moiety is coupled via an amide bond to a Lys side chain; thus it will be understood that the NH$_2$ at the C-terminus in SEQ ID NOs: 59, 60, and 61, represents amidation of the C-terminus of the peptide, and it will be understood that in SEQ ID NOs: 62 and 63, the Ac at the N-terminus represents acetylation of the N-terminus of the peptide, as described above. It will also be appreciated by those of ordinary skill in the art that a free end of a (CH$_2$CH$_2$O)$_n$ moiety typically terminates with an (OR) where the underlined O represents the O atom in the terminal (CH$_2$CH$_2$O) group. (OR) is often a moiety such as a hydroxyl (OH) or methoxy (—OCH$_3$) group though other groups (e.g., other alkoxy groups) could be used. Thus SEQ ID NO: 59, for example, may be represented as Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-(C(=O)—(CH$_2$CH$_2$O)$_n$—R)—NH$_2$ (SEQ ID NO: 64) wherein R is, e.g., either H or CH$_3$ in the case of a linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 64, in which the moiety comprising the reactive functional group comprises an ester and/or alkyl chain may be represented as follows (SEQ ID NO: 65)
Ac-Ile-Cys*-Val-(1Me)Trp-Gln-Asp-Trp-Gly-Ala-His- Arg-Cys*-Thr-NH-CH$_2$CH$_2$OCH$_2$CH$_2$OCH$_2$—C(=O)-Lys- (C(=O)-(CH$_2$)$_m$-(CH$_2$CH$_2$O)$_n$-R)-NH2;

(SEQ ID NO: 66)
Ac-Ile-Cys*-Val-(1Me)Trp-Gln-Asp-Trp-Gly-Ala-His-

Arg-Cys*-Thr-NH-CH$_2$CH$_2$OCH$_2$CH$_2$OCH$_2$—C(=O)-Lys- (C(=O)-(CH$_2$)$_m$-C(=O)-(CH$_2$CH$_2$O)$_n$-R)-NH2

(SEQ ID NO: 67)
Ac-Ile-Cys*-Val-(1Me)Trp-Gln-Asp-Trp-Gly-Ala-His-

Arg-Cys*-Thr-NH-CH$_2$CH$_2$OCH$_2$CH$_2$OCH$_2$—C(=O)-Lys- (C(=O)-(CH$_2$)$_m$-C(=O)-(CH$_2$)j(CH$_2$CH$_2$O)$_n$-R)-NH2

In SEQ ID NOs: 65-67 m may range from 1 up to about 2, 3, 4, 5, 6, 7, 8, 10, 15, 20, or 30 in various embodiments, In SEQ ID NOs: 67 j may range from 1 up to about 2, 3, 4, 5, 6, 7, 8, 10, 15, 20, or 30 in various embodiments.

It will also be appreciated that, as described herein, in various embodiments other moieties may be incorporated between the Lys-(C(=O)— and (CH$_2$CH$_2$O)$_n$—R, such as an amide, aromatic ring (e.g., a substituted or unsubstituted phenyl), or a substituted or unsubstituted cycloalkyl structure.

The invention provides variants of SEQ ID NOs: 58-67 in which -Ile-Cys*-Val-(1Me)Trp-Gln-Asp-Trp-Gly-Ala-His-Arg-Cys*-Thr- is replaced by an amino acid sequence comprising the amino acid sequence of any other compstatin analog, e.g., of any of SEQ ID NOs 3-27 or 29-36, 37, 69, 70, 71, or 72 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-37, 69, 70, 71, or 72 may, in various embodiments, can be attached via or near its N-terminal or C-terminal end (e.g., via a side chain of an amino acid at or near its N-terminal or C-terminal amino acid) directly or indirectly to any moiety comprising a reactive functional group, e.g., any compound of Formulae I-XVI or Formulae A-H.

In some embodiments the CRM comprises a polypeptide that occurs in human serum, or a fragment thereof or a substantially similar variant of the polypeptide or fragment thereof. In some embodiments the polypeptide, fragment, or variant has a molecular weight of between 5 kD and 150 kD, e.g., at least 5, 10, 20, 30, 40, 50, 60, 70, 80, 90, 100 kd, or more, e.g., between 100 and 120, or 120 and 150 kD. In some embodiments, producing a long-acting compstatin analog comprises reacting a compstatin analog comprising a reactive functional group with one or more amino acid side chains of the polypeptide, wherein the side chain comprises a compatible functional group. In some embodiments, producing a long-acting compstatin analog comprises reacting a compstatin analog comprising a reactive functional group with the N-terminal amine and/or C-terminal carboxyl group of the polypeptide. In some embodiments, producing a long-acting compstatin analog comprises reacting a compstatin analog comprising an amine-reactive functional group with amino acids having a side chain comprising a primary amine (e.g., lysine) and/or with the N-terminal amine of the polypeptide. In some embodiments, producing a long-acting compstatin analog comprises reacting a compstatin analog comprising a carboxyl-reactive functional group with the C-terminal carboxyl group of the polypeptide. In some embodiments a compstatin analog moiety is attached at each terminus of the polypeptide and, optionally, to the side chain of one or more internal amino acids. In some embodiments, producing a long-acting compstatin analog comprises reacting a compstatin analog comprising a sulfhydryl-reactive functional group with one or more sulfhydryl groups of the polypeptide.

In some embodiments, at least one reactive functional group is introduced into the polypeptide. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising one or more thiols may be reacted with a compstatin analog comprising a maleimide group, such as Ac-Ile-Cys*-Val-Trp(1-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 68) to generate a long-acting compstatin analog.

In some embodiments the polypeptide is recombinantly produced. In some embodiments the polypeptide is at least in part recombinantly produced (e.g., in bacteria or in eukaryotic host cells such as fungal, insect, plant, or vertebrate) and/or at least in part produced using chemical synthesis. In some embodiments the polypeptide is purified. For example, in some embodiments the polypeptide is purified from a host cell lysate or from culture medium into which it has been secreted by host cells. In some embodiments the polypeptide is glycosylated. In some embodiments the polypeptide is non-glycosylated. In some embodiments the polypeptide is human serum albumin (HSA). In some embodiments a substantially similar variant of the polypeptide is sufficiently similar to the polypeptide of which it is a variant so as to not be recognized as foreign by a normal immune system of a subject, e.g., a human subject. In some embodiments alterations in the sequence of substantially similar variant as compared with the polypeptide of which it is a variant are selected so as to avoid generating MHC Class I epitopes. Various methods known in the art can be used to predict whether a sequence comprises an MHC Class I epitope.

In some embodiments, one or more amino acids in a polypeptide or linker or composition may be selected to be hydrophobic or hydrophilic or selected to confer increased hydrophilicity or, in some embodiments, increased hydrophobicity, on a compound that contains it. As known in the art, the terms "hydrophilic" and "hydrophobic" are used to refer to the degree of affinity that a substance has with water. In some aspects a hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be classified based on their hydrophobicity as well known in the art. Examples of "hydrophilic amino acids" are arginine, lysine, threonine, alanine, asparagine, glutamine, aspartate, glutamate, serine, and glycine. Examples of "hydrophobic amino acids" are tryptophan, tyrosine, phenylalanine, methionine, leucine, isoleucine, and valine. In certain embodiments an analog of a standard amino acid is used, wherein the analog has increased or decreased hydrophilic or hydrophobic character as compared with the amino acid of which it is an analog.

The invention further provides multimers, e.g., concatamers, comprising two or more (e.g., between 2 and 10) compstatin analogs comprising a CRM, wherein the average molecular weight of the resulting molecule (or the CRM components thereof) is between 20,000; 30,000; 40,000; 50,000; 60,000; 70,000; 80,000; 90,000; and 100,000 daltons. In some embodiments the average molecular weight of the resulting molecule (or the CRM components thereof) is at least 20,000 daltons, up to about 100,000; 120,000; 140,000; 160,000; 180,000; or 200,000 daltons. In some embodiments, the compstatin analogs comprising a CRM can be linked using any of the linking moieties described above. Compositions and methods for making long-acting compstatin analogs, and intermediates in the synthesis, are aspects of the invention.

In some embodiments the total molecular weight of a long-acting compstatin analog, including the compstatin analog moieties, is no greater than 50 kD. For example, in the case of a LACA comprising a 40 kD PEG, in some embodiments the molecular weight contributed by the remainder of the compound, including the compstatin analog moie(ties), may be no greater than 10 kD, e.g., 1.5 kD-5.0 kD or 5.0 kD-10 kD. In some embodiments the total molecular weight of a LACA, including the compstatin analog moieties, is between 45 kD and 50 kD. In some embodiments the total molecular weight of a LACA, including the compstatin analog moieties, is between 40 kD and 45 kD, between 15 kD and 40 kD, e.g., between 15 kD and 25 kD, between 25 kD and 35 kD, between 35 kD and 40 kD. Thus, wherever the present disclosure refers to a compstatin analog comprising a polymer or CRM having a particular molecular weight, or having a molecular weight within a particular range, in some embodiments the total molecular weight of the compstatin analog may be, e.g., between 1.5 kD and 5 kD greater than the molecular weight of the polymer or CRM, or in some embodiments between 5 kD and 10 kD greater than the molecular weight of the polymer. It will be understood that molecular weight of a compound, e.g., a compound comprising a polymer, can refer to the average molecular weight of molecules of such compound in a composition.

A wide variety of methods and assays useful for detection of polymers, e.g., PEGs, POZs, and/or polypeptides and/or useful for measurement of physical and/or structural properties of polymers, e.g., PEGs, POZs, and/or polypeptides are known in the art and may, if desired, be used to detect a compstatin analog, e.g., a cell-reactive, long-acting, targeted compstatin analog or a compstatin analog moiety. For example, methods and assays useful for determining properties such as aggregation, solubility, size, structure, melting properties, purity, presence of degradation products or contaminants, water content, hydrodynamic radius, etc., are available. Such methods include, e.g., analytical centrifugation, various types of chromatography such as liquid chromatography (e.g., HPLC-ion exchange, HPLC-size exclusion, HPLC-reverse phase), light scattering, capillary electrophoresis, circular dichroism, isothermal calorimetry, differential scanning calorimetry, fluorescence, infrared (IR), nuclear magnetic resonance (NMR), Raman spectroscopy, refractometry, UV/Visible spectroscopy, mass spectrometry, immunological methods, etc. It will be understood that methods may be combined. In some aspects, a cell-reactive, long-acting, or targeted compstatin analog (or composition comprising a cell-reactive, long-acting, or targeted compstatin analog) has one or more properties described herein, as assessed using any of the foregoing methods. In some aspects, methods useful to detect and/or quantify a long-acting compstatin analog are described herein.

(iv) Targeted Compstatin Analogs

The invention provides and/or utilizes targeted compstatin analogs that comprise a targeting moiety and a compstatin analog moiety, wherein the targeting moiety binds non-covalently to a target molecule. In some aspects, the invention provides targeted compstatin analogs analogous to the cell-reactive compstatin analogs described in Section VI, wherein the compounds comprise a targeting moiety in addition to, or instead of, a cell-reactive moiety. The targeting moiety can comprise, e.g., an antibody, polypeptide, peptide, nucleic acid (e.g., an aptamer), carbohydrate, small molecule, or supramolecular complex, that specifically binds to the target molecule. In some embodiments, the affinity (as measured by the equilibrium dissociation constant, Kd) of targeting moiety for the target molecule (as measured by the equilibrium dissociation constant, Kd) is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions.

In those embodiments of the invention in which the targeting moiety is an antibody, the antibody may be any immunoglobulin or a derivative thereof, which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., Nature Reviews Cancer, Vol. 2, 750-765, 2002, and references therein. Monovalent, bivalent or multivalent antibodies can be used. The antibody may be a chimeric antibody in which, for example, a variable domain of rodent origin is fused to a constant domain of human origin, thus retaining the specificity of the rodent antibody. In some embodiments, a human antibody or portion thereof is generated, for example, in rodents whose genome incorporates human immunoglobulin genes, using a display technology such as phage display, etc. In some embodiments, a humanized antibody is generated by grafting one or more complementarity determining region(s) from a non-human species (e.g., mouse) into a human antibody sequence. The antibody may be partially or completely humanized. See, e.g., Almagro J C, Fransson J. Humanization of antibodies. Front Biosci. 13:1619-33 (2008) for review of various methods of obtaining humanized antibodies that may be used to obtain a targeting moiety of use in the invention. An antibody may be polyclonal or monoclonal, though for purposes of the present invention monoclonal antibodies are generally preferred. In certain embodiments of the invention a F(ab')2 or F(ab') fragment is use while in other embodiments antibodies comprising an Fc domain are used. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture. Methods of generating antibody fragments, e.g., by digestion, disulfide reduction, or synthesis are known in the art.

In various embodiments of the invention a targeting moiety can be any molecule that specifically binds to a target molecule through a mechanism other than an antigen-antibody interaction. Such a targeting moiety is referred to as a "ligand". For example, in various embodiments of the invention a ligand can be a polypeptide, peptide, nucleic acid (e.g., DNA or RNA), carbohydrate, lipid or phospholipid, or small molecule. In some embodiments a small molecule is an organic compound, whether naturally-occurring or artificially created, that has relatively low molecular weight and is not a protein, polypeptide, nucleic acid, or lipid, typically with a molecular weight of less than about 1500 g/mol and typically having multiple carbon-carbon bonds. In general, an aptamer is an oligonucleotide (e.g., RNA or DNA, optionally comprising one or more modified nucleosides (e.g., bases or sugars other than the 5 standard bases (A, G, C, T, U) or sugars (ribose and deoxyribose) found most commonly in RNA and DNA), or modified internucleoside linkages (e.g., non-phosphodiester bonds) that, e.g., stabilize the molecule, e.g., by rendering it more resistant to degradation by nucleases) that binds to a particular protein. In some embodiments an oligonucleotide is up to about 100 nucleosides long, e.g., between 12 and 100 nucleosides long. Aptamers can be derived using an in vitro evolution process called SELEX, and methods for obtaining aptamers specific for a protein of interest are known in the art. See, e.g., Brody E N, Gold L. J Biotechnol. 2000 March; 74(1):5-13. In some embodiments, a peptide nucleic acid or locked nucleic acid is used.

In certain embodiments of the invention a targeting moiety comprises a peptide. In some embodiments a peptide that binds to a target molecule of interest is identified using a display technology such as phage display, ribosome display, yeast display, etc.

Small molecules can be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., Pharm. & Ther. 86: 201-215, 2000).

In certain embodiments of the invention targeting moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the targeting moiety is not an Fc portion of an immunoglobulin molecule. In some embodiments, a targeting moiety is part of a complex comprising one or more additional moieties to which it is covalently or noncovalently attached.

In various embodiments of the invention a target molecule can be any molecule produced by a cell (including any forms expressed on the cell surface or modified forms thereof resulting at least in part from extracellular modification). In some embodiments a target molecule is an extracellular substance present in or on a tissue. In some embodiments, a target molecule is characteristic of a particular diseased or physiological state or characteristic of one or more cell type(s) or tissue type(s). A target molecule is often a molecule at least partly present at the cell surface (e.g., a transmembrane or otherwise membrane-attached protein) so that at least a portion of the molecule is accessible to binding by an extracellular binding agent such as an antibody. A target molecule may, but need not be, cell type specific. For example, a cell type specific target molecule is often a protein, peptide, mRNA, lipid, or carbohydrate that is present at a higher level on or in a particular cell type or cell type(s) than on or in many other cell types. In some instances a cell type specific target molecule is present at detectable levels only on or in a particular cell type of interest. However, it will be appreciated that a useful cell type specific target molecule need not be absolutely specific for the cell type of interest in order to be considered cell type specific. In some embodiments, a cell type specific target molecule for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. In some embodiments, the cell type specific target molecule is present at levels at least 4-5 fold, between 5-10 fold, or more than 10-fold greater than its average expression in a reference population. In some embodiments, detection or measurement of a cell type specific target molecule allows one of ordinary skill in the art to distinguish a cell type or types of interest from cells of many, most, or all other types. In general, the presence and/or abundance of most target molecules may be determined using one or more standard techniques such as Northern blotting, in situ hybridization, RT-PCR, sequencing, immunological methods such as immunoblotting, immunodetection (e.g., by immunohistochemistry), or fluorescence detection following staining with fluorescently labeled antibodies (e.g., using FACS), oligonucleotide or cDNA microarray or membrane array, protein microarray analysis, mass spectrometry, etc.

In some embodiments, a target molecule is a channel, transporter, receptor, or other molecule at least in part exposed at the cell surface. In some embodiments a target molecule is an anion transporter or water channel (e.g., an aquaporin protein).

In some embodiments, the target molecule is a protein at least in part exposed at the surface of red blood cells, such as a glycophorin (e.g., glycophorin A, B, C, or D) or band 3.

In some embodiments, the target molecule is a protein at least in part exposed at the surface of endothelial cells. In some embodiments, the target molecule is present at the surface of normal, healthy vasculature. In some embodiments, the target molecule is present at the surface of activated endothelial cells. In some embodiments, the target molecule is present at the surface of activated endothelial cells but not at the surface of non-activated endothelial cells. In some embodiments a target molecule is a molecule whose expression or exposure is induced by a stimulus such as injury or inflammation. In some embodiments, a target molecule would be recognized as "non-self" by a recipient receiving a transplant containing cells that express the target molecule. In some embodiments, the target molecule is a carbohydrate xenoantigen to which antibodies are commonly found in human beings. In some embodiments the carbohydrate comprises a blood group antigen. In some embodiments the carbohydrate comprises a xenoantigen, e.g., an alpha-gal epitope (Galalpha1-3Galbeta1-(3) 4GlcNAc-R) (see, e.g., Macher B A and Galili U. The Galalpha1, 3Galbeta1, 4GlcNAc-R (alpha-Gal) epitope: a carbohydrate of unique evolution and clinical relevance. Biochim Biophys Acta. 1780(2):75-88 (2008).

In some embodiments of the invention, a compstatin analog comprises both a targeting moiety and a CRM.

In some embodiments, a targeted compstatin analog comprises multiple targeting moieties, which can be the same or different. Different targeting moieties may bind to the same target molecule or to different target molecules. The invention provides a targeted compstatin analog that is multivalent with respect to the targeting moiety, the compstatin analog, or both.

In general, the invention encompasses any method of producing a compound comprising a compstatin analog moiety and a targeting moiety, and the resulting compounds. In some embodiments, a targeted compstatin analog may be produced using methods generally similar to those described in Section VII(A)(iii), wherein a targeting moiety is used instead of, or in addition to, a cell-reactive moiety. In some embodiments, a targeted compstatin analog comprising a peptide as a targeting moiety is synthesized as a polypeptide chain comprising a compstatin analog moiety and a peptide targeting moiety. Optionally, the polypeptide chain comprises one or more spacer peptides between the compstatin analog moiety and the targeting moiety.

In some embodiments, a targeted compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a targeting moiety. In some embodiments wherein a targeted compstatin analog comprises multiple compstatin analog moieties, the molar activity of the targeted compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. Compositions and methods for making targeted compstatin analogs, and intermediates in the synthesis, are aspects of the invention.

(v) Antibodies

The present disclosure also contemplates using antibodies that inhibit complement activation. Complement activation may be inhibited by inhibiting C3 activation. C3 dependent complement activation may be inhibited by a C3 complement inhibitor. Exemplary agents may comprise an antibody or an antibody fragment. In some embodiments, an antibody may bind to C3. In some embodiments, an antibody fragment may be used to inhibit C3 activation. The fragmented anti-C3 antibody may be Fab', Fab'(2), Fv, or single chain Fv. In some embodiments, the anti-C3 antibody is monoclonal. In some embodiments, the anti-C3 antibody is polyclonal. In some embodiments, the anti-C3 antibody is de-immunized. In some embodiments the anti-C3 antibody is a fully human monoclonal antibody.

In some embodiments, the anti-C3 antibody or anti-C3 antibody fragment may bind to C3 to inhibit complement activation. In some embodiments, the anti-C3 antibody or anti-C3 antibody fragment may bind to C3 fragments to inhibit complement activation. In some embodiments, a C3 fragment is C3b.

(vi) Other Complement Inhibiting Agents

A variety of other complement inhibitors can be used in various embodiments of the disclosure. In some embodiments, the complement inhibitor is a naturally occurring mammalian complement regulatory protein or a fragment or derivative thereof. For example, the complement regulatory protein may be CR1, DAF, MCP, CFH, or CFI. In some embodiments, the complement regulatory polypeptide is one that is normally membrane-bound in its naturally occurring state. In some embodiments, a fragment of such polypeptide that lacks some or all of a transmembrane and/or intracellular domain is used. Soluble forms of complement receptor 1 (sCR1), for example, can also be used. For example the compounds known as TP10 or TP20 (Avant Therapeutics) can be used. C1 inhibitor (C1-INH) can also be used. In some embodiments a soluble complement control protein, e.g., CFH, is used. In some embodiments, the polypeptide is modified to increase its solubility.

Inhibitors of C1s can also be used. For example, U.S. Pat. No. 6,515,002 describes compounds (furanyl and thienyl amidines, heterocyclic amidines, and guanidines) that inhibit C1s. U.S. Pat. Nos. 6,515,002 and 7,138,530 describe heterocyclic amidines that inhibit C1s. U.S. Pat. No. 7,049,282 describes peptides that inhibit classical pathway activation. Certain of the peptides comprise or consist of WESNGQPENN (SEQ ID NO: 73) or KTISKAKGQPREPQVYT (SEQ ID NO: 74) or a peptide having significant sequence identity and/or three-dimensional structural similarity thereto. In some embodiments these peptides are identical or substantially identical to a portion of an IgG or IgM molecule. U.S. Pat. No. 7,041,796 discloses C3b/C4b Complement Receptor-like molecules and uses thereof to inhibit complement activation. U.S. Pat. No. 6,998,468 discloses anti-C2/C2a inhibitors of complement activation. U.S. Pat. No. 6,676,943 discloses human complement C3-degrading protein from *Streptococcus pneumoniae*.

B. Administration

In some embodiments, an miRNA or siRNA described herein (or a vector comprising a nucleotide sequence encoding an miRNA or siRNA described herein) administered in an amount that inhibits plasma complement activity by an average of no more than 95%, optionally between 50% and 95%, as measured using an alternative pathway assay, a classical pathway assay, or both, may be administered in combination with a second complement inhibitor, e.g., a long-acting compstatin analog (LACA). In some embodiments, a LACA administered in an amount that inhibits plasma complement activity by an average of no more than 95%, optionally between 50% and 95%, as measured using an alternative pathway assay, a classical pathway assay, or both, may be administered in combination with an miRNA or siRNA described herein (or a vector comprising a nucleotide sequence encoding an miRNA or siRNA described herein). In some embodiments, the assay is a hemolysis assay. In some embodiments, an miRNA or siRNA described herein (or a vector comprising a nucleotide sequence encoding an miRNA or siRNA described herein) administered in an amount effective to reduce the steady state plasma level of C3 by between 30% and 95% on average, e.g., between 50% and 95%, e.g., between 50% and 60%, between 60% and 70%, between 70% and 80%, or between 80% and 90%, on average, may be administered in combination with a LACA. In some embodiments an miRNA or siRNA described herein (or a vector comprising a nucleotide sequence encoding an miRNA or siRNA described herein) may be administered in amounts that are effective to reduce the steady state plasma level of C3 by more than 95% but still do not achieve a desired efficacy. Combined administration with the LACA allows such efficacy to be achieved. In some embodiments an miRNA or siRNA described herein (or a vector comprising a nucleotide sequence encoding an miRNA or siRNA described herein) may be administered at between 80% and 100% of its maximum tolerated dose. In some embodiments, combined administration with a LACA allows the use of smaller doses of miRNA or siRNA described herein (or a vector comprising a nucleotide sequence encoding an miRNA or siRNA described herein) than those required to achieve a desired level of efficacy. In some embodiments an miRNA or siRNA described herein (or a vector comprising a nucleotide sequence encoding an miRNA or siRNA described herein) may be administered at less than 50%, 60%, 70%, or 80% of its maximum tolerated dose.

In some embodiments an miRNA or siRNA described herein (or a vector comprising a nucleotide sequence encoding an miRNA or siRNA described herein) and a second complement inhibitor may be administered once daily, weekly, every 2, 3, or 4 weeks, or even at longer intervals. In some embodiments, a vector comprising a nucleotide sequence encoding an miRNA or siRNA described herein is administered to a subject once, e.g., as a single injection or as a single infusion over time (e.g., over 5, 10, 15, 20, 30, 40, 50, 60, 90, 120 minutes, or longer), and a second complement inhibitor is administered once a week, twice a week, every three days, thrice a week, every other day, once every 2 weeks, every 3 weeks, once a month, every 6 weeks, once every 2 months, 3 months, 4 months, 5 months, or longer. In some embodiments, a vector comprising a nucleotide sequence encoding an miRNA or siRNA described herein is administered to a subject twice, e.g., as two injections (e.g., 2, 4, 6, 8, 10, or 12 hours apart) or as two infusions (e.g., 2, 4, 6, 8, 10, or 12 hours apart), and a second complement inhibitor is administered once a week, twice a week, every three days, thrice a week, every other day, once every 2 weeks, every 3 weeks, once a month, every 6 weeks, once every 2 months, 3 months, 4 months, 5 months, or longer. In some embodiments, an miRNA or siRNA described herein (or a vector comprising a nucleotide sequence encoding an miRNA or siRNA described herein) and a second complement inhibitor may be administered according to a dosing regimen that includes a second complement inhibitor administered once a week, twice a week, every three days, thrice a week, every other day, once every 2 weeks, every 3 weeks, once a month, every 6 weeks, once every 2 months, 3 months, 4 months, 5 months, or longer; and (i) a single administration or an initial administration of an miRNA or siRNA described herein (or a vector comprising a nucleotide sequence encoding an miRNA or siRNA described herein) that is once daily, weekly, every 2, 3, or 4 weeks, or even at longer intervals; followed by (ii) a period of no administration of an miRNA or siRNA described herein (or a vector comprising a nucleotide sequence encoding an miRNA or siRNA described herein) of, e.g., 1, 2, 3, 4, 5, 6, 8, or 10 months, or 1, 2, 3, 4, 5, 6, 7, 8, 9, or 10 years. In some embodiments, a subject is monitored before and/or following treatment for level of C3 expression and/or activity, e.g., as measured using an alternative pathway assay, a classical pathway assay, or both. Suitable assays are known in the art and include, e.g., a hemolysis assay. In some embodiments, a subject is treated (e.g., with an miRNA or siRNA described herein (or a vector comprising a nucleotide sequence encoding an miRNA or siRNA described herein) and/or with a second complement inhibitor), or is retreated (e.g., with an miRNA or siRNA described herein (or a vector comprising a nucleotide sequence encoding an miRNA or siRNA described herein) and/or with a second complement inhibitor), if a measured level of C3 expression and/or activity is more than 10%, 20%, 30%, 40%, 50%, 100%, 200%, or more, relative to measured level of C3 expression and/or activity in a control subject.

In some embodiments it may be desirable to administer the miRNA or siRNA described herein (or a vector comprising a nucleotide sequence encoding an miRNA or siRNA described herein) and the second complement inhibitor according to the same dosing schedule (e.g., once per day, every other day, or once per week), while in other embodiments different dosing schedules may be used (e.g., daily or weekly for the second complement inhibitor and about every 4 weeks, e.g., monthly for the miRNA or siRNA described herein (or a vector comprising a nucleotide sequence encoding an miRNA or siRNA described herein), or vice versa). In many embodiments both the miRNA or siRNA described herein (or a vector comprising a nucleotide sequence encoding an miRNA or siRNA described herein) and the second complement inhibitor are administered subcutaneously. In some embodiments the miRNA or siRNA described herein (or a vector comprising a nucleotide sequence encoding an miRNA or siRNA described herein) may be administered intravenously.

In some embodiments the miRNA or siRNA described herein (or a vector comprising a nucleotide sequence encoding an miRNA or siRNA described herein) achieves therapeutically useful levels of complement inhibition when administered as sole complement inhibiting therapy once or twice daily, e.g., subcutaneously. In some embodiments the miRNA or siRNA described herein (or a vector comprising a nucleotide sequence encoding an miRNA or siRNA described herein) achieves therapeutically useful levels of C3 inhibition when administered as sole C3 inhibiting therapy once or twice daily, e.g., subcutaneously. In some embodiments such an miRNA or siRNA described herein (or a vector comprising a nucleotide sequence encoding an miRNA or siRNA described herein) may be administered in a lower total amount (as measured over a relevant time period such as a month) when administered in combination with a second complement inhibitor that inhibits C3 expression. In some embodiments the total amount administered may be lower by a factor of at least 1.5, e.g., lower by a factor of between 1.5 and 5, between 5 and 10, or between 10 and 20, over a relevant time period such as a month. In some embodiments, the miRNA or siRNA described herein (or a vector comprising a nucleotide sequence encoding an miRNA or siRNA described herein) may be administered in smaller daily doses as compared with the doses that would be used if the miRNA or siRNA described herein (or a vector comprising a nucleotide sequence encoding an miRNA or siRNA described herein) was administered as sole complement inhibitor therapy or as sole C3 inhibiting therapy. In some embodiments, the miRNA or siRNA described herein (or a vector comprising a nucleotide sequence encoding an miRNA or siRNA described herein) may be administered using a longer dosing interval as compared with the dosing interval that would be used if the miRNA or siRNA described herein (or a vector comprising a nucleotide sequence encoding an miRNA or siRNA described herein) was administered as sole complement inhibitor therapy or as sole C3 inhibiting therapy. For example, in some embodiments an miRNA or siRNA described herein (or a vector comprising a nucleotide sequence encoding an miRNA or siRNA described herein) that would typically be administered daily to achieve a desired effect may instead be administered every other day, every 3 days, or weekly, to achieve substantially the same effect. In some embodiments the miRNA or siRNA described herein (or a vector comprising a nucleotide sequence encoding an miRNA or siRNA described herein) may be administered using both lower individual doses and a longer dosing interval when administered in combination with a LACA than when administered as sole complement inhibitor therapy or as sole C3 inhibiting therapy.

Certain LACAs comprising a PEG of about 40 kD demonstrate pharmacological activity when administered subcutaneously at daily doses of 180 mg and 270 mg, with 270 mg/day being particularly effective. In some embodiments, such a LACA, when administered in combination with a miRNA or siRNA described herein (or a vector comprising a nucleotide sequence encoding an miRNA or siRNA described herein) may be administered at a reduced dose, e.g., a dose that is lower by a factor of at least 1.5, e.g., lower by a factor of between 1.5 and 5, between 5 and 10, or between 10 and 20, relative to administration of LACA alone. In some embodiments, for example, the dose may be between about 9 mg/day and about 150 mg/day, e.g., between about 9 mg/day and about 20 mg/day, between about 20 mg/day and about 50 mg/day, between about 50 mg/day and 100 mg/day, between about 100 mg/day and about 150 mg/day, and in at least some embodiments achieves at least equivalent efficacy to a 180 mg/day dose or in some embodiments a 270 mg/day dose. In some embodiments the dose may be between about 150 mg/day and about 200 mg/day, and in at least some embodiments achieves at least equivalent efficacy to a 270 mg/day dose. In some embodiments the dose is 10 mg/day-20 mg/day, 20 mg/day-30 mg/day, 30 mg/day-40 mg/day, 40 mg/day-50 mg/day, 50 mg/day 60 mg/day, 60 mg/day-70 mg/day, 70 mg/day-80 mg/day, 80 mg/day-90 mg/day, 90 mg/day-100 mg/day, 100 mg/day-110 mg/day, 110 mg/day-120 mg/day, 120 mg/day-130 mg/day, 130 mg/day-140 mg/day, 140 mg/day-150 mg/day, 150 mg/day-160 mg/day, 160 mg/day-170 mg/day, 170 mg/day-180 mg/day, 180 mg/day-190 mg/day, or 190 mg/day-200 mg/day. In some embodiments the dose is 200 mg/day-210 mg/day, 210 mg/day-220 mg/day, 220 mg/day-230 mg/day, 230 mg/day-240 mg/day, or 240 mg/day-250 mg/day. In some embodiments the dose of LACA is administered as a single daily dose, e.g., subcutaneously. In some embodiments a dose of LACA is administered as a single weekly dose, e.g., subcutaneously.

In some aspects, a reduced dose of LACA may be administered in a smaller volume and/or at a reduced concentration, when administered in combination with a miRNA or siRNA described herein (or a vector comprising a nucleotide sequence encoding an miRNA or siRNA described herein), relative to administration of LACA alone. For example, if the dose is reduced by a factor of 10, the volume could also be reduced by a factor of 10 while keeping the concentration the same. Alternately, the concentration could be reduced by a factor of 10 while keeping the volume the same. Alternately both the concentration and volume may be reduced. In certain embodiments the volume of an individual dose is about 0.8 ml or less, e.g., 0.5 ml or less, e.g., between 0.02 ml and 0.5 ml, e.g., 0.1 ml, 0.2 ml, 0.3 ml, 0.4 ml, or 0.5 ml. In certain embodiments the concentration is below about 100 mg/ml. For example, the concentration may be 10 mg/ml-20 mg/ml, 20 mg/ml-30 mg/ml, 30 mg/ml-40 mg/ml, 40 mg/ml-50 mg/ml, 50 mg/ml-60 mg/ml, 60 mg/ml-70 mg/ml, 70 mg/ml-80 mg/ml, 80 mg/ml-90 mg/ml, or 90 mg/ml-100 mg/ml. The volume and concentration can be selected to deliver a desired amount. For example, in an exemplary embodiment a dose of 40 mg is administered in a volume of 0.5 ml at a concentration of 80 mg/ml. In another exemplary embodiment a dose of 60 mg is administered in a volume of 0.6 ml at a concentration of 100 mg/ml. In some embodiments a 28, 29, 30, or 31 gauge needle may be used to administer the LACA, miRNA or siRNA described herein (or a vector comprising a nucleotide sequence encoding an miRNA or siRNA described herein), or both.

In some embodiments, a LACA described herein is administered twice weekly or every 3 days or thrice weekly, at a dosage of about 10 mg to about 10 g, e.g., about 10 mg to about 20 mg, e.g., about 20 mg to about 40 mg, e.g., about 40 mg to about 60 mg, e.g., about 60 mg to about 80 mg, e.g., about 80 mg to about 100 mg, e.g., about 100 mg to about 120 mg, e.g., about 120 mg to about 140 mg, e.g., about 140 mg to about 160 mg, e.g., about 160 mg to about 180 mg, e.g., about 180 mg to about 200 mg, e.g., about 200 mg to about 220 mg, e.g., about 220 mg to about 240 mg, e.g., about 240 mg to about 260 mg, e.g., about 260 mg to about 280 mg, e.g., about 280 mg to about 300 mg, e.g., about 300 mg to about 320 mg, e.g., about 320 mg to about 340 mg, e.g., about 340 mg to about 360 mg, e.g., about 360 mg to about 380 mg, e.g., about 380 mg to about 400 mg, e.g., about 400 mg to about 420 mg, e.g., about 420 mg to about 440 mg, e.g., about 440 mg to about 460 mg, e.g., about 460 mg to about 480 mg, e.g., about 480 mg to about 500 mg, e.g., about 500 mg to about 520 mg, e.g., about 520 mg to about 540 mg, e.g., about 540 mg to about 560 mg, e.g., about 560 mg to about 580 mg, e.g., about 580 mg to about 600 mg, e.g., about 100 mg to about 200 mg, e.g., about 545 mg to about 1690 mg, e.g., about 585 mg to about 2510 mg, e.g., about 630 mg to about 930 mg, e.g., about 795 mg to about 885 mg, e.g., about 900 mg to about 1395 mg, e.g., about 990 mg to about 1215 mg, e.g., about 1215 mg to about 1395 mg, e.g., about 2160 mg to about 2520 mg, e.g., about 2520 mg to about 2880 mg, e.g., about 2880 mg to about 3240 mg, e.g., about 3240 mg to about 3600 mg, e.g., about 800 mg to about 1200 mg, e.g., about 1060 mg to about 1100 mg, e.g., about 1070 mg to about 1090 mg, e.g., about 1075 mg to about 1085 mg, e.g., about 1080 mg, e.g., about 1080 mg to about 5040 mg, about 5000 mg-1.0 g, e.g., about 1.0-2.0 g, or more, e.g., up to about 4.0-5.0 g, or up to about 6.0 g, or up to about 10.0 g, e.g., between about 4.0 g and about 6.0 g, e.g., between about 4.5 g and about 5.5 g, e.g., about 5.0 g, e.g., between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g, for about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 1.2 years, 1.4 years, 1.6 years, 1.8 years, 2 years, 3 years, 4 years, 5 years, or longer.

In some embodiments, a LACA described herein is administered to a subject in need thereof at about 10 mg to about 10 g (e.g., about 10 mg to about 600 mg, about 600 mg to about 1200 mg, about 1250 mg to about 2000 mg, about 2000 mg to about 2500 mg, about 10-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-220 mg, about 220-240 mg, about 240-260 mg, about 260-280 mg, about 280-300 mg, about 300-320 mg, about 320-340 mg, about 340-360 mg, about 360-380 mg, about 380-400 mg, about 400-420 mg, about 420-440 mg, about 440-460 mg, about 460-480 mg, about 480-500 mg, about 500-520 mg, about 520-540 mg, about 540-560 mg, about 560-580 mg, about 580-600 mg, about 600-620 mg, about 620-640 mg, about 640-660 mg, about 660-680 mg, about 680-700 mg, about 700-720 mg, about 720-740 mg, about 740-760 mg, about 760-780 mg, about 780-800 mg, about 800-820 mg, about 820-840 mg, about 840-860 mg, about 860-880 mg, about 880-900 mg, about 900-920 mg, about 920-940 mg, about 940-960 mg, about 960-980 mg, about 980-1000 mg, about 1000-1020 mg, about 1020-1040 mg, about 1040-1060 mg, about 1060-1080 mg, about 1080-1100 mg, about 1100-1120 mg, about 1120-1140 mg, about 1140-1160 mg, about 1160-1180 mg, about 1180-1200 mg, about 1200-1250 mg, about 1250-1300 mg, about 1300-1350 mg, about 1350-1400 mg, about 1400-1450 mg, about 1450-1500 mg, about 1500-1550 mg, about 1550-1600 mg, about 1600-1650 mg, about 1650-1700 mg, about 1700-about 1750 mg, about 1750-1800 mg, about 1800-1850 mg, about 1850-1900 mg, about 1900-1950 mg, about 1950-2000 mg, about 2000-2050 mg, about 2050-2100 mg, about 2100-2150 mg, about 2150-2200 mg, about 2200-2250 mg, about 2250-2300 mg, about 2300-2350 mg, about 2350-2400 mg, about 2400-2450 mg, about 2450-2500 mg, about 2500-5000 mg, about 5000 mg-1.0 g, about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g) or more.

In some embodiments, a LACA described herein is administered as two or more doses. In some embodiments, a first dose (e.g., a loading dose) and a second dose (e.g., a maintenance dose) are administered. In some embodiments, the first dose and the second dose comprise the same amount of the LACA. In some embodiments, the first dose and the second dose comprise different amounts of the LACA.

In some embodiments, the first dose comprises about 10 mg to about 10 g of the LACA (e.g., about 10-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-220 mg, about 220-240 mg, about 240-260 mg, about 260-280 mg, about 280-300 mg, about 300-320 mg, about 320-340 mg, about 340-360 mg, about 360-380 mg, about 380-400 mg, about 400-420 mg, about 420-440 mg, about 440-460 mg, about 460-480 mg, about 480-500 mg, about 500-520 mg, about 520-540 mg, about 540-560 mg, about 560-580 mg, about 580-600 mg, about 600-620 mg, about 620-640 mg, about 640-660 mg, about 660-680 mg, about 680-700 mg, about 700-720 mg, about 720-740 mg, about 740-760 mg, about 760-780 mg, about 780-800 mg, about 800-820 mg, about 820-840 mg, about 840-860 mg, about 860-880 mg, about 880-900 mg, about 900-920 mg, about 920-940 mg, about 940-960 mg, about 960-980 mg, about 980-1000 mg, about 1000-1020 mg, about 1020-1040 mg, about 1040-1060 mg, about 1060-1080 mg, about 1080-1100 mg, about 1100-1120 mg, about 1120-1140 mg, about 1140-1160 mg, about 1160-1180 mg, about 1180-1200 mg, about 1200-1250 mg, about 1250-1300 mg, about 1300-1350 mg, about 1350-1400 mg, about 1400-1450 mg, about 1450-1500 mg, about 1500-1550 mg, about 1550-1600 mg, about 1600-1650 mg, about 1650-1700 mg, about 1700-about 1750 mg, about 1750-1800 mg, about 1800-1850 mg, about 1850-1900 mg, about 1900-1950 mg, about 1950-2000 mg, about 2000-2050 mg, about 2050-2100 mg, about 2100-2150 mg, about 2150-2200 mg, about 2200-2250 mg, about 2250-2300 mg, about 2300-2350 mg, about 2350-2400 mg, about 2400-2450 mg, about 2450-2500 mg, about 2500-5000 mg, about 5000 mg-1.0 g, about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g) and the second dose comprises about 10 mg to about 10 g of the LACA (e.g., about 10-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-220 mg, about 220-240 mg, about 240-260 mg, about 260-280 mg, about 280-300 mg, about 300-320 mg, about 320-340 mg, about 340-360 mg, about 360-380 mg, about 380-400 mg, about 400-420 mg, about 420-440 mg, about 440-460 mg, about 460-480 mg, about 480-500 mg, about 500-520 mg, about 520-540 mg, about 540-560 mg, about 560-580 mg, about 580-600 mg, about 600-620 mg, about 620-640 mg, about 640-660 mg, about 660-680 mg, about 680-700 mg, about 700-720 mg, about 720-740 mg, about 740-760 mg, about 760-780 mg, about 780-800 mg, about 800-820 mg, about 820-840 mg, about 840-860 mg, about 860-880 mg, about 880-900 mg, about 900-920 mg, about 920-940 mg, about 940-960 mg, about 960-980 mg, about 980-1000 mg, about 1000-1020 mg, about 1020-1040 mg, about 1040-1060 mg, about 1060-1080 mg, about 1080-1100 mg, about 1100-1120 mg, about 1120-1140 mg, about 1140-1160 mg, about 1160-1180 mg, about 1180-1200 mg, about 1200-1250 mg, about 1250-1300 mg, about 1300-1350 mg, about 1350-1400 mg, about 1400-1450 mg, about 1450-1500 mg, about 1500-1550 mg, about 1550-1600 mg, about 1600-1650 mg, about 1650-1700 mg, about 1700-about 1750 mg, about 1750-1800 mg, about 1800-1850 mg, about 1850-1900 mg, about 1900-1950 mg, about 1950-2000 mg, about 2000-2050 mg, about 2050-2100 mg, about 2100-2150 mg, about 2150-2200 mg, about 2200-2250 mg, about 2250-2300 mg, about 2300-2350 mg, about 2350-2400 mg, about 2400-2450 mg, about 2450-2500 mg, about 2500-5000 mg, about 5000 mg-1.0 g, about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g).

In some embodiments, a composition comprising one or more miRNA or siRNA described herein (or one or more vectors comprising one or more nucleotide sequences encoding one or more miRNA or siRNA described herein) is administered to a subject in combination with a LACA, such that the LACA and/or the miRNA or siRNA composition is administered less frequently and/or at a lower dosage, relative to administration of a LACA alone or relative to administration of the miRNA or siRNA (or vector comprising one or more nucleotide sequences encoding the miRNA or siRNA) alone.

In some embodiments, a composition comprising one or more miRNA or siRNA described herein (or one or more vectors comprising one or more nucleotide sequences encoding one or more miRNA or siRNA described herein) is administered to a subject in combination with a LACA, e.g., a LACA of FIG. 1 (comprising a PEG of about 40 kD), such that the LACA is administered once a week, twice a week, every three days, thrice a week, every other day, once every 2 weeks, every 3 weeks, once a month, every 6 weeks, once every 2 months, 3 months, 4 months, 5 months, or longer, at a dosage described herein (for e.g., at a dosage of about 10 mg to about 10 g, about 800 mg to about 1200 mg, e.g., about 1060 mg to about 1100 mg, e.g., about 1070 mg to about 1090 mg, e.g., about 1075 mg to about 1085 mg, e.g., about 1080 mg, e.g., about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g). In some embodiments, a composition comprising vector comprising a nucleotide sequence encoding an miRNA or siRNA described herein is administered to a subject once, e.g., as a single injection or as a single infusion over time (e.g., over 5, 10, 15, 20, 30, 40, 50, 60, 90, 120 minutes, or longer), in combination with a LACA, e.g., a LACA of FIG. 1 (comprising a PEG of about 40 kD), such that the LACA is administered once a week, twice a week, every three days, thrice a week, every other day, once every 2 weeks, once every 3 weeks, once a month, once every 6 weeks, once every 2 months, 3 months, 4 months, 5 months, or longer, at a dosage described herein (for e.g., at a dosage of about 10 mg to about 10 g, about 800 mg to about 1200 mg, e.g., about 1060 mg to about 1100 mg, e.g., about 1070 mg to about 1090 mg, e.g., about 1075 mg to about 1085 mg, e.g., about 1080 mg, e.g., about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g).

In some embodiments, a composition comprising a vector comprising a nucleotide sequence encoding an miRNA or siRNA described herein is administered to a subject twice, e.g., as two injections (e.g., 2, 4, 6, 8, 10, or 12 hours apart) or as two infusions (e.g., 2, 4, 6, 8, 10, or 12 hours apart), in combination with a LACA, e.g., a LACA of FIG. 1 (comprising a PEG of about 40 kD), such that the LACA is administered once a week, twice a week, every three days, thrice a week, every other day, once every 2 weeks, every 3 weeks, once a month, once every 6 weeks, once every 2 months, 3 months, 4 months, 5 months, or longer, at a dosage described herein (for e.g., at a dosage of about 10 mg to about 10 g, about 800 mg to about 1200 mg, e.g., about 1060 mg to about 1100 mg, e.g., about 1070 mg to about 1090 mg, e.g., about 1075 mg to about 1085 mg, e.g., about 1080 mg, e.g., about 1.0-2.0 g, or more, e.g., up to about 4.0-5.0 g, or up to about 6.0 g, or up to about 10.0 g, between about 4.0 g and about 6.0 g, e.g., between about 4.5 g and about 5.5 g, e.g., about 5.0 g, between about 5.0 g and about 7.0 g, e.g., about 5.0 g, about 5.5 g, about 6.0 g, about 6.5 g, or about 7.0 g, between about 8.0 g and about 10.0 g, e.g., about 8.0 g, about 8.5 g, about 9.0 g, about 9.5 g, or about 10.0 g, between about 4.0 g and about 10.0 g, e.g., about 5.0 g, about 6.0 g, about 7.0 g, about 8.0 g, about 8.5 g, about 9.0 g, about 9.5 g, or about 10.0 g).

While doses of 250 mg/day or less are of particular interest for administration, e.g., SC administration, of a LACA in combination with an miRNA or siRNA described herein (or a vector comprising a nucleotide sequence encoding an miRNA or siRNA described herein) that inhibits C3 expression, the present disclosure also contemplates administering doses of more than 250 mg/day in combination with an miRNA or siRNA described herein (or a vector comprising a nucleotide sequence encoding an miRNA or siRNA described herein) that inhibits C3 expression, e.g., doses of 250 mg/day-300 mg/day, 300 mg/day-400 mg/day, or 400 mg/day-500 mg/day. In certain embodiments such a dose may be administered weekly, twice a week, or every 3 days. In certain embodiments, LACA doses in combination with an miRNA or siRNA described herein (or a vector comprising a nucleotide sequence encoding an miRNA or siRNA described herein) that inhibits C3 expression may be administered twice weekly or every 3 days, at a dosage of about 10 mg to about 10 g, about 800 mg to about 1200 mg, e.g., about 1060 mg to about 1100 mg, e.g., about 1070 mg to about 1090 mg, e.g., about 1075 mg to about 1085 mg, e.g., about 1080 mg.

While the present disclosure particularly contemplates embodiments in which a LACA having a terminal half-life of at least 2, 3, 4, or more days when administered IV or SC to a primate, e.g., LACAs comprising a clearance reducing moiety as described herein, is administered in combination with an miRNA or siRNA described herein (or a vector comprising a nucleotide sequence encoding an miRNA or siRNA described herein) that inhibits C3 expression, it is contemplated in certain embodiments that combined administration with such an miRNA or siRNA described herein (or a vector comprising a nucleotide sequence encoding an miRNA or siRNA described herein) may also be useful for compstatin analogs that have shorter half-lives and/or that lack a clearance reducing moiety. Such compstatin analogs may be administered in 1 or 2 doses per day.

In some embodiments efficacy of a particular agent or combination of agents may be measured by lactate dehydrogenase (LDH) level in a patient suffering from a complement-mediated hemolytic disorder such as PNH. As will be appreciated by those of ordinary skill in the art, complement-mediated hemolysis results in release of LDH, which can result in an abnormally elevated plasma LDH level. Thus in some aspects, efficacy of a complement inhibitor may be evidenced in a subject suffering from a complement-mediated hemolytic disorder by a decrease in plasma LDH level, e.g., to within nomal limits. Other indicators of efficacy in a subject suffering from a complement-mediated hemolytic disorder may include, e.g., a reduction in reticulocyte count in a subject who has an elevated reticulocyte count (e.g., normalization of reticulocyte count), a reduced need for transfusions, an increased hemoglobin level, stabilization of hemoglobuin level without need for transfusions in a subject who had required multiple transfusions in the previous year. In some embodiments efficacy may be measured by a classical or alternative pathway complement assay, which may be a hemolysis assay.

In some embodiments a composition as described herein, and e.g., a composition comprising a LACA described herein, is administered using a device that delivers a dose of a pharmaceutical composition by injection, in some embodiments in an at least partly automated fashion upon activation. Such a device is referred to in the art as a "pen" or "autoinjector", and these terms are used interchangeably herein. In general, a pen or autoinjector allows for injecting a dose of pharmaceutical composition contained in a cartridge, reservoir, or syringe through an automatically or manually inserted hypodermic needle(s) or through a high velocity jet. It may be designed for administration of a single dose or multiple doses.

In some embodiments, such a pen or autoinjector is utilized for intramuscular and/or subcutaneous injection. In accordance with the present disclosure, a pen or other autoinjector may be particularly useful for embodiments that utilize subcutaneous injection. Pens are typically devices that contain (or can be loaded with) a medication in a self-contained cartridge or reservoir and to which a needle can be attached.

In some embodiments, such injection is achieved by use of a pen (e.g., that may have been pre-loaded with an appropriate dose or volume). Pens can be durable (and reusable) or disposable. A durable pen typically uses a replaceable cartridge, which is disposed of when empty, and a new one is inserted in the pen. A disposable pen typically comes pre-filled with a medication in a cartridge or reservoir. When the cartridge or reservoir is empty, the pen can be discarded. The cartridge or reservoir may contain a single dose or multiple doses. To use a pen, a needle can be attached to the pen and inserted into the skin. Typically, a button can be pushed to administer a dose though in some embodiments other activation methods may be used. In some embodiments, an autoinjector may comprise a spring-loaded syringe, though one of ordinary skill in the art will appreciate that a variety of technologies are available to afford automatic administration. In some embodiments, by pressing a button or otherwise activating the device, the needle can be automatically inserted, and the medication can be delivered. In some embodiments, an autoinjector may be designed to insert the needle automatically and/or accurately to a desired depth in the subcutaneous tissue. A pen or autoinjector may comprise means such as a dial that allows a user to select or adjust a dose or injection depth.

In some embodiments, a composition as described herein, e.g., a LACA described herein, is administered using a device comprising a dual chamber syringe. Dry drug (e.g., lyophilized) is contained in one chamber. The second chamber contains a suitable pharmaceutically acceptable carrier. In order to use the device, the drug is first reconstituted by mixing the contents of the chambers. This can be accomplished in various ways, as is known in the art. In some embodiments, pushing the plunger causes the contents of the chambers to mix, e.g., by transferring the carrier into the chamber containing the lyophilized drug.

Thus a variety of drug delivery devices comprising a composition as described herein (e.g., a LACA described herein) may be provided e.g., prefilled syringes, dual chamber syringes, durable and/or disposable pens, and cartridges suitable for use with a pen. Such devices may contain one or more doses (e.g., one or more of any of the dose amounts described herein).

In certain embodiments a LACA may be administered, e.g., subcutaneously, using a drug delivery device (sometimes referred to simply as a "delivery device") that comprises a pump to introduce a liquid composition comprising the LACA into the subject's body. As will be appreciated, a pump may be any device that moves fluids by mechanical action as opposed to a conventional manually actuated syringe characterized in that the individual administering the medication (e.g., a health care provider or a subject who self-administers the medication) must directly depress a plunger into a barrel containing medication in order to effect the injection. It will be appreciated that a pump may be powered electrically or mechanically, e.g., as described herein. In some aspects, a delivery device comprising a pump may allow for convenient administration of doses according to a dosing regimen described herein.

In certain embodiments, the delivery device is portable. A portable device, also referred to as an "ambulatory" device, can be sufficiently light in weight and have appropriate dimensions so as to permit the subject to move about freely while the device is in use. In certain embodiments, such device does not require attachment to a pole or power outlet. In some embodiments a portable delivery device may be attached to a belt or shoulder strap or worn in a case that may be attached to a belt or shoulder strap, or may be placed in a pocket of a garment.

One of ordinary skill in the art appreciates that a pump may operate in any of a variety of ways and may utilize a variety of energy sources, e.g., disposable or rechargeable batteries, alternating current power supply (e.g., via a wall socket in a building), compressed gas, or energy stored in a compressed spring or in a stretched expandable resilient chamber. A device in which fluid is held in a stretchable balloon reservoir, and pressure from the elastic walls of the balloon reservoir drives fluid delivery may be referred to as an "elastomeric infusion pump".

In some embodiments, a delivery device comprises a pump and a syringe containing a liquid to be administered and removably associated with the device, and a driving unit, which may be electronically controlled by a controller, arranged to make the plunger of the syringe slide so as to cause infusion of the liquid directly or via flexible tubing through a piercing member such as a needle or cannula that is introduced into the subject's body under the skin. For example, in some embodiments a pump may comprise a motor that turns a screw that pushes the plunger on a syringe that contains the liquid. Pushing of the plunger causes liquid to be expelled from the syringe and introduced into the subject's body via an attached piercing member. Exemplary pumps are described in, e.g., U.S. Pat. Nos. 6,447,487; 6,592,551; 6,645,177; 8,187,228; US Patent Application Publication Nos. 20020123740, 20030229311, 20060184123, 20070100281, 20090123309, 20150038906. The Crono PID (NDC No.: 8423.2000.02), Crono S-PID30, and Crono S-PID 50 (NDC No.: 8423.2000.04) (Canè s.r.l. Medical Technology (Rivoli, Italy)), and the T34™ Ambulatory Syringe Pump and the T60™ Ambulatory Syringe Pump (CME Medical, Blackpool, UK) are exemplary portable syringe infusion pumps that may be used in certain embodiments.

In some embodiments the pump may be electronically programmable or controlled. In some embodiments the pump is not electronically programmable or controlled.

In some embodiments a pump uses electricity as a source of power. In some embodiments a pump does not use electricity as a source of power. Such a pump may, for example, use a compressed spring or compressed gas as an energy source.

In some embodiments the pump is a constant-pressure pump that applies a constant pressure to depress the barrel of a syringe containing the liquid to be administered. An example of a constant-pressure pump is the Freedom60® infusion system (RMS Medical Products, Chester, NY). In some embodiments a FreedomEdge ® infusion system (RMS Medical Products) may be used, e.g., with a syringe capable of holding up to 20 ml or a syringe capable of holding up to 30 ml. Another example of a constant pressure device is the SCIg60 syringe pump (EMED Technologies, El Dorado Hills, CA). In some embodiments a valve may control the flow rate of the liquid. In some embodiments tubing connected to the syringe may control the flow rate of the liquid, e.g., as described in US Patent Application Nos. 20150374911 and/or 20160256625. In some embodiments a delivery rate of between 0.5 ml/minute and 1 ml/minute may be used.

In some embodiments the liquid to be administered is contained in a pressurized chamber prior to administration. In some embodiments the liquid is contained in a resilient, expandable container portion such as a bladder or balloon prior to delivery. The expandable container portion may be made of or comprise an inner lining of compatible medical grade butyl, silicone or other material suitable for holding the liquid. The container portion expands upon filling with liquid (e.g., with a unit dose of the compound to be administered), so as to exert pressure on the liquid. One of ordinary skill in the art appreciates that the container portion may be filled in a variety of ways. In some embodiments filling of the expandable container portion may be accomplished manually, e.g., using a manually actuated syringe, or may be performed using a filling apparatus. After the device is attached to the subject's skin, a piercing member such as a needle or cannula, which may be spring loaded, may automatically or following additional activation, such as by pressing a button, emerge from the device's housing and pierce the skin. Subsequently, either automatically or following additional activation, such as by pressing a button, pressure forces the liquid out of the chamber or container and into the subject's body via the needle or cannula. Exemplary devices are described in US Patent Application Pub. Nos. 20130018326, and/or 20150217058.

In some embodiments the delivery device is an "on-body delivery device", which term refers to a delivery device comprising a chamber or other container portion for holding a liquid to be administered to a subject, wherein the device can deliver the liquid while attached directly to the subject's skin without the need for a separate support or external reservoir and, typically, permits the subject to be mobile during delivery. The chamber for holding the liquid may be contained in a housing. Typically, an on-body delivery device is affixed to the subject's skin using an adhesive. The device is affixed sufficiently strongly so that the device is self-supporting. The device may be provided with an adhesive layer, e.g., on the outer surface of the housing, for use to secure the device directly to the skin. The adhesive layer may surround the portion of the device from which a piercing member such as a needle or cannula projects so as to provide a seal around the penetrated skin. In some embodiments an on-body delivery device is available from Sensile Medical AG (Hagendorf, Switzerland). For example, devices known as SenseInfuse, SensePatch, or Senseflex, may be used. In some embodiments an on-body delivery device is available from Enable Injections, Inc. (Cincinnati, OH). In some embodiments the device that comprises a resilient, expandable container portion such as a bladder or balloon to expel the liquid is an on-body delivery device. In some embodiments the device, e.g., an on-body delivery device, is configured such that the piercing member, e.g., needle, is not visible to the user prior to or during use of the device. In some embodiments, the piercing member, e.g., needle, may retract when delivery of the liquid is complete or when the device is removed from the skin. It will be appreciated that a piercing member, e.g., a needle, for use with a delivery device described herein may have any suitable gauge or inner diameter, e.g., such gauge or inner diameters as described elsewhere herein.

In some embodiments, a delivery device comprises a housing into which a vial, cartridge, or syringe containing a liquid (e.g., a liquid comprising a LACA) may be inserted. The liquid is administered upon activation of the device. In some embodiments the liquid is transferred to a chamber of the device prior to administration. In some embodiments a delivery device is reusable, e.g., it can be re-filled or supplied with a new vial, cartridge, or syringe following administration of the contents.

In some embodiments a delivery device is a single use device, i.e., the device is designed to be used to administer a single dose or for use in a single administration session. For example, a device may be designed to be affixed to the skin of a subject, activated to administer a dose, removed, and then recycled or discarded rather than used to administer one or more additional doses.

In some embodiments a delivery device that allows delivery of a liquid into two or more sites may be used. In some embodiments the number of sites is between 1 and 5. In some embodiments the number of sites is greater than 5, e.g., between 6 and 10. Delivery to the two or more sites may be simultaneous or sequential. The device may comprise a pair of syringes, each arranged to be connected to one of the sites and coupled to a body that houses a driving system of the device. Exemplary devices are described in WO2011154928 and US Patent Application Publication No. 20120143133. In some embodiments a multi-needle infusion set may be used. In some embodiments a multi-needle infusion set comprises a flexible tube that communicates at one end with a chamber (which term is used interchangeably with "reservoir") containing the liquid (e.g., a syringe) while the other end bifurcates into multiple tubes each having a needle at the end. The Neria™ multi infusion sets (Unomedical A/S, Osted, Denmark) are exemplary multi-needle infusion sets.

In some embodiments a delivery device may collect data regarding use of the device. Such data may comprise, for example, the date and time at which the device was used, delivery parameters such as the volume administered, the duration of administration, whether any problems occurred during administration, etc. The data may be stored on a computer-readable medium physically associated with the device and/or may be transmitted to a remote location, e.g., a remote server, where it may be stored, analyzed, or further transmitted for storage or analysis. The device may comprise one or more processors, sensors, software programs, and appropriate connectivity that allow data to be exchanged between the device and other products and systems. Data may be transferred via radio-frequency identification (RFID), bar-code/QR-code scanning, cellular, Bluetooth low energy (BTLE), physical wire, or a combination thereof. The data may be transmitted over any suitable network, e.g., the Internet. The data may be analyzed and/or stored in the Cloud. In some embodiments the device comprises an active or passive RFID tag or chip, hereinafter referred to as an "RFID tag". The RFID tag may contain data that identifies the device. The RFID tag may be an active tag or chip that signals usage-related information such as activation of the device and/or completion of an administration of a dose. In some embodiments data acquired from a particular device may be made available to one or more entities or individuals, such as health care providers or caregivers of the subject. Such entities or individuals may additionally or alternately be automatically notified of the occurrence or non-occurrence of specified events. For example, if a dose is not administered on a day on which such administration is to take place according to the dosing schedule, or if the device is deployed on a day when administration is not supposed to take place according to the dosing schedule, one or more health care providers or caregivers of the subject may be notified. Once notified, an entity or individual may take appropriate action, such as contacting the subject. In some embodiments a monitoring system automatically attempts to contact the subject, e.g., by phone or text message, if a dose is not administered as scheduled.

In some embodiments a delivery system may comprise a delivery device and a remote control device. The remote control device may, for example, allow programming of the delivery device and/or may be used to activate the delivery device to start delivery of the fluid or to cause the delivery device to cease delivery of the fluid.

In some embodiments, the present disclosure contemplates providing to a subject (e.g., by mail or arranged pickup or other regular mode of delivery) a set of devices as described herein that together provide a supply of active agent (e.g., LACA) sufficient to last for a predetermined period of time (e.g., one week, two weeks, three weeks, four weeks, etc.). In some embodiments, such a set is sent to the patient's residence on a regular basis (e.g., every week, two weeks, three weeks, four weeks, etc.) with a timing selected such that the patient does not run out. In some embodiments, a composition (e.g., comprising a LACA) may be contained in a container (e.g., a vial) or in any of the herein-mentioned drug delivery devices or packs. In some embodiments the supply is sufficient to last for between 4 and 12 weeks, between 12 and 26 weeks, or more.

Those skilled in the art, reading the present disclosure, will appreciate that, in accordance with standard practice in the field, a container containing a particular volume, as described herein may include an additional volume sufficient to permit the designated particular volume (e.g., unit dose) to be withdrawn from the container for administration.

All publications, patent applications, patents, and other references mentioned herein, including GenBank Accession Numbers, are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

IX. Exemplification

Example 1: Transfection of HEK293 with C3 Plasmid Construct

Human Embryonic Kidney (HEK) cells are transfected with a plasmid construct including a nucleotide sequence encoding C3 protein ("C3-HEK293" cells). Immortalized hepatocellular carcinoma (HCC) or hepatoblastoma (HB) cell line is used for the design and validation of a RT-qPCR assay for C3 transcript detection. Following design of C3 primers, RT-qPCR is performed on: (1) C3-HEK293 cells, (2) untransfected HEK293 cells as a negative control, and (3) HepG2/Hep3B/HepaRG/HUH-7 cells as a positive control (as C3 expression is known to occur in these cells).

The C3 RT-qPCR is followed by a standard immunodetection assay (ELISA/WB) to detect the presence of C3 protein in C3-HEK293 cells and HepG2/Hep3B/HepaRG/HUH-7 cells, and to ensure that there are at least two C3-producing cell lines. Commercially available C3 purified from human serum is used as a positive control for protein detection.

Example 2: C3-RNAi by Multiple miRNAs in C3-HEK293 Cells and HCC/HB Cell Line Expression constructs are produced that include one of SEQ ID NOs: 86-115. Transfection parameters, e.g., quantity of miRNA, electroporation/lipotransfection agent, confluence of cells, age of cells, etc., are optimized to ensure successful miRNA construct transfection of C3-HEK293 cells and HCC/HB cell line. The ability of each of the C3-targeting miRNAs to induce C3 gene silencing is examined.

In this step either the pol III promoter (H1) construct with collagen stuffer or the pol II promoter (CAB/CMV) construct with the GFP tag is used. qPCR and immunodetection are used to validate successful miRNA-mediated RNA interference (RNAi) for the former construct. The latter construct provides information on the proportion of transfected cells. This step is also used to determine the time taken from delivery of miRNA to detectable change in C3 transcript/protein expression. This is used to determine length of cell culture for following experiments involving hepatocytes.

Several cultures are set up concurrently, and transcript levels are monitored over the course of 2-4 weeks. Cell culture supernatant is collected weekly (on same day of transcript quantification qPCR assay) and is assayed immediately for C3 detection.

Example 3A: C3-RNAi Using miRNAs in Hepatocytes

Following validation of miRNA-mediated RNAi of C3 in C3-HEK293 cells, this method and technology is validated in human hepatocytes in vitro. At least one hepatoma (immortalized) and one primary cell line is cultured and transfected with the selected miRNA constructs that include one of SEQ ID NOs: 86-115, and C3 silencing is quantified as described in Examples 1 and 2. Constructs including pol II and pol III are examined.

Immortalized hepatoma-derived cell lines include HepG2 and Hep3B. The cells are cultured using a sandwich culture method or other established protocol that promotes high cell survival and differentiation achievable in a uniform and reproducible manner. A virus-positive cell line is also selected (e.g., Hep3B), along with a clean cell line for comparative purposes (e.g., not HepaRG). An exemplary combination is HepG2 or HUH-7 and HepaRG. An exemplary primary cell line is a primary human hepatocyte (PHH) cell line, such as a multidonor panel-derived PHH.

Prior optimization of cell transfection is performed using the construct containing the GFP tag to allow for easy confirmation of transfection by confocal microscopy or live cell imaging. A comparative analysis is then conducted to determine efficacy of miRNA-mediated C3 silencing. At this stage, the most potent miRNA(s) are selected for packaging into the rAAV3B vector.

Following transduction, cells are cultured and monitored for 2-4 weeks to allow for C3 protein expression detection and monitoring. Cell culture supernatant is collected weekly and assayed immediately for C3 detection. Live cell imaging techniques are used to assess GFP expression and cell health.

Example 3B: C3-RNAi Using miRNAs in Hepatocytes

The purpose of this example was to assess the C3 silencing capability of miRNA plasmid constructs in HuH7.5 cells by Lipofectamine transfection.

HuH7.5 Cell Plating: Plated HuH7.5 cells were trypsinized for 5 minutes ar 37° C. The reaction was stoped using a solution of DMEM (Dulbecco's Modified Eagle Medium) containing 10% FBS and 1% Penicillin or Streptavidin. The cells were then spun at 1500 rpm for 5 minutes, following which they were counted using a hemocytometer. 400,000 of these cells were plated in 1 mL per well in a 12-well plate. These cells were allowed to grow until they were 75-80% confluent.

Lipofectamin Transfection: Plasmid constructs comprising sequences encoding each of the miRNA sequences of SEQ ID NOs: 76-85 or a control GFP sequence were synthesized. The HuH7.5 cells were transfected with the each of the plasmid constructs (Thermo Fisher Lipofectamine 3000 DNA transfection protocol was used), and C3 silencing was quantified. The cells were imaged 72 hours after transfection.

RNA Isolation and Conversion: The media from each of the well s was removed and the cells in each well were washed in 1 mL PBS. Then, 300 µL of Trizol was added to each well and the cells were allowed to sit for 5 minutes at room temperature. Following this, 60 µL of chloroform was added to each well. The chloroform was mixed well and the cells were allowed to sit for 2 minutes at room temperature. The cells were then spun at 12,000×g for 15 minutes at 4° C. The aqueous phase containing the RNA was removed and placed in a new tube with 250 µL of 100% isopropanol. This was precipitated overnight at 20° C., and then spun at 12,000×g for 10 minutes at 4° C. The RNA pellet was washed with 500 µL of 75% ethanol and spun again at 7,500×g for 5 minutes at 4° C. The pellet was air dryed and resuspended in nuclease free water.

To convert RNA to cDNA, 100 ng of isolated RNA was used in a reverse transcription (RT) reaction. The Applied Biosystems High Capacity RNA-cDNA kit protocol was followed and the RT reaction was aliquoted into PCR tubes. The reaction was incubated for 1 hour at 37° C., following which the reaction was stopped by heating to 95° C. for 5 minutes.

Droplet Digital PCR (ddPCR): The reaction mixture for ddPCR were prepared using the recipe listed below.

| # of reactions | 1 |
|---|---|
| 2XddPCR Supermix for probes | 11 µL |
| 20X target primers/probe (FAM) | 1.1 µL |
| 20X reference primers/probe (HEX) | 1.1 µL |
|  | µL |
| H2O | 7.55 µL |

Figure 10:
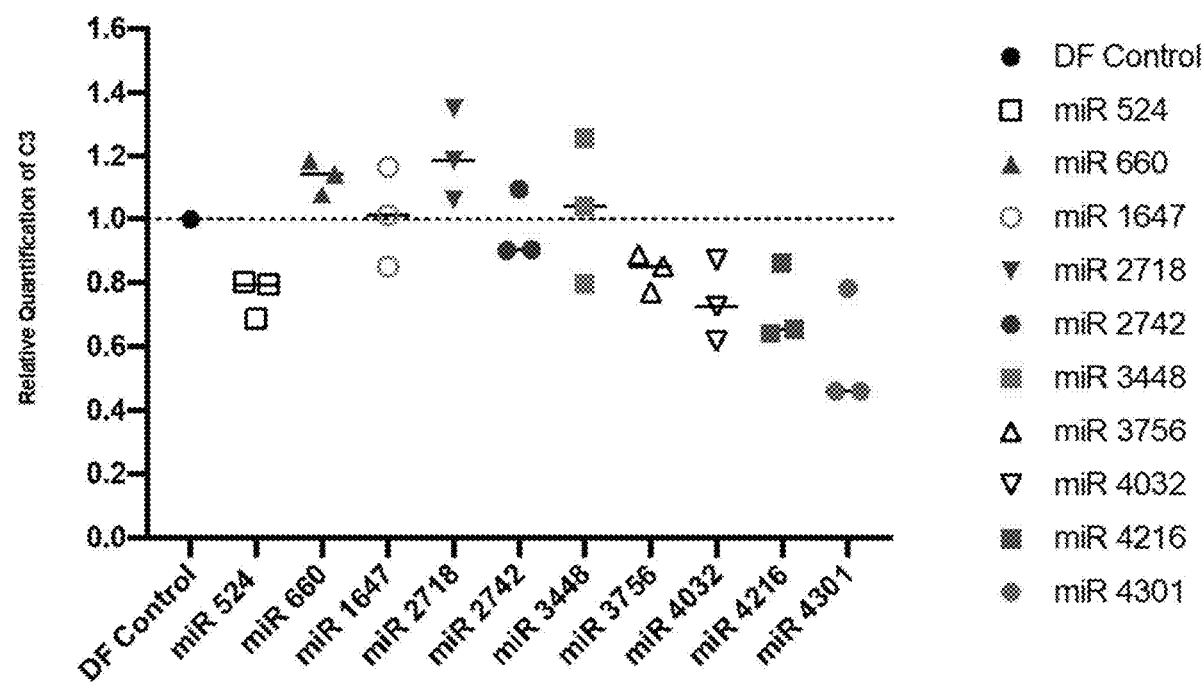
FIG. 10 shows the relative quantification of C3 normalized to a miR Control 72 hours after transfection, where miR 524 corresponds to SEQ ID NO:76, miR 660 corresponds to SEQ ID NO:77, miR 1647 corresponds to SEQ ID NO:78, miR 2718 corresponds to SEQ ID NO:79, miR 2742 corresponds to SEQ ID NO:80, miR 3448 corresponds to SEQ ID NO:81, miR 3756 corresponds to SEQ ID NO:82, miR 4032 corresponds to SEQ ID NO:83, miR 4216 corresponds to SEQ ID NO:84, and miR 4301 corresponds to SEQ ID NO:85.

To each reaction mix, 1.25 µL of 100 ng cDNA was added to bring the total volume per reaction to 22 µL. Droplets were generated using the droplet generator that is part of the Bio-Rad QX100 ddPCR system. These droplets were then run through a standard PCR program and the samples were read using the Bio-Rad QX100 ddPCR system. FIG. 10 shows the results of C3 quantification relative to the GFP control for each of the miRNA sequences.

Example 4: rAAV3B-miRNA Delivery to Hepatocytes rAAV3B-miRNA construct(s) expressing a GFP tag, and including pol II or pol III promoters, are used to verify transduction of primary and immortalized hepatocytes, as described in Examples 1-3.

Following transduction, cells are cultured and monitored for 2-4 weeks to allow for C3 transcript/protein expression silencing to occur. These effects are monitored over 2-4 weeks using traditional monitoring techniques.

Example 5: Transfection of NIH-3T3 Cells with miRNA Plasmid Construct miRNA template oligonucleotide cassettes encoding each of SEQ ID NOs: 76-85 were cloned into a shuttle plasmid under the control of human EF1α promoter. The correctness of the cloned oligonucleotide cassettes was verified by sequencing.

cDNA encoding the N-terminal and C-terminal regions of C3 were PCR-amplified and cloned separately into a validation vector pVal downstream of the EGFP coding region to generate pVal-C3-1 and pVal-C3-2.

Each of the shuttle plasmids encoding SEQ ID NOs: 76-78 were then transferred into pVal-C3-1, while each of the shuttle plasmids encoding SEQ ID NOs 79-85 were transferred into pVal-C3-2 by recombinational cloning to generate validation vectors. A shuttle plasmid encoding for a non-target (NT) miRNA as negative control was also recombinationally cloned into both pVal-C3-1 and pVal-C3-2. These validation vectors contained three transcriptional units, which included a vector-encoded marker transcript as internal reference.

NIH-3T3 cells were transfected at a confluency of about 50% with each of the validation vectors.

Example 6: C3-RNAi by Multiple miRNAs in C3-NIH-3T3 Cells

Figure 2A:
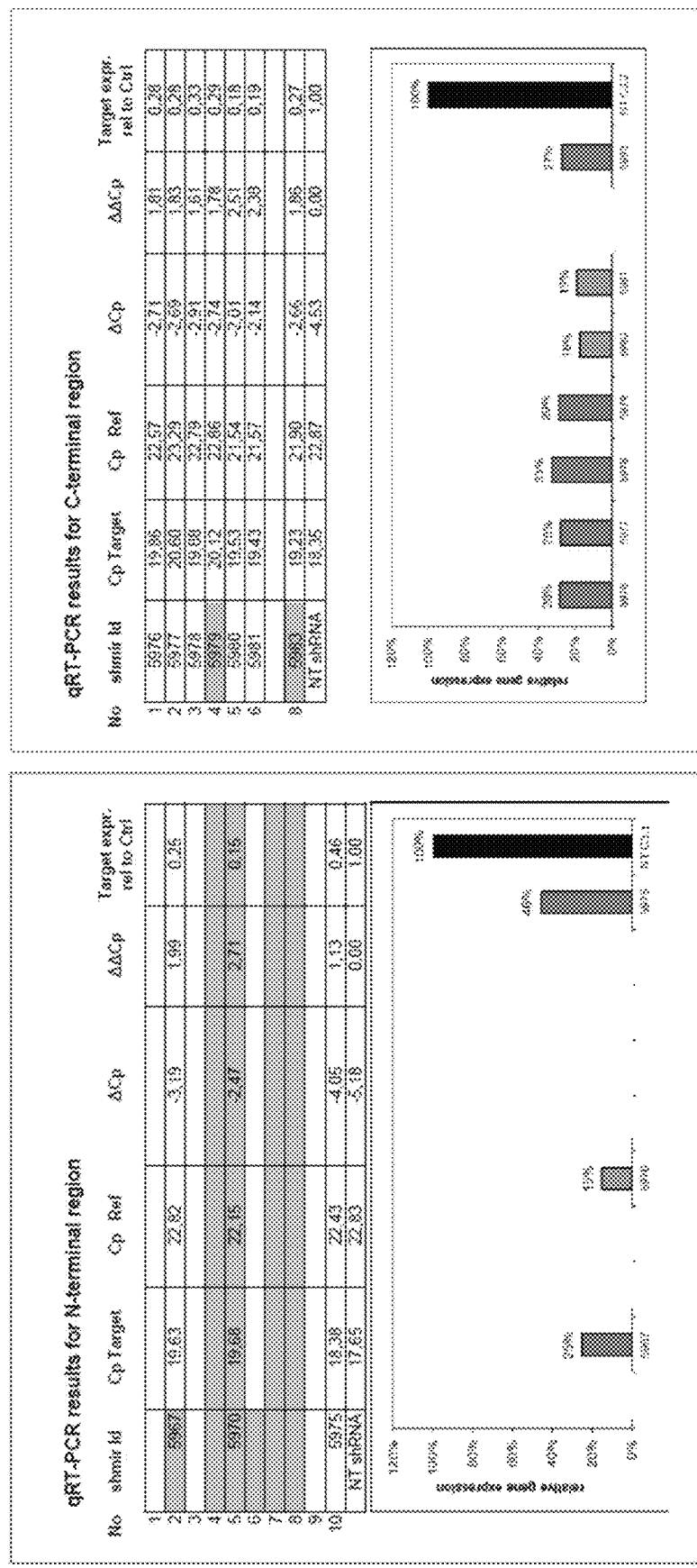
FIGS. 2A and 2B shows results of qRT-PCT sequence validation and relative gene-expression for various C3-targeting miRNA, where shmir Id 5967 corresponds to SEQ ID NO:76, shmir Id 5970 corresponds to SEQ ID NO:77, shmir Id 5975 corresponds to SEQ ID NO:78, shmir Id 5976 corresponds to SEQ ID NO:79, shmir Id 5977 corresponds to SEQ ID NO:80, shmir Id 5978 corresponds to SEQ ID NO:81, shmir Id 5979 corresponds to SEQ ID NO:82, shmir Id 5980 corresponds to SEQ ID NO:83, shmir Id 5981 corresponds to SEQ ID NO:84, and shmir Id 5983 corresponds to SEQ ID NO:85.
Figure 2B:
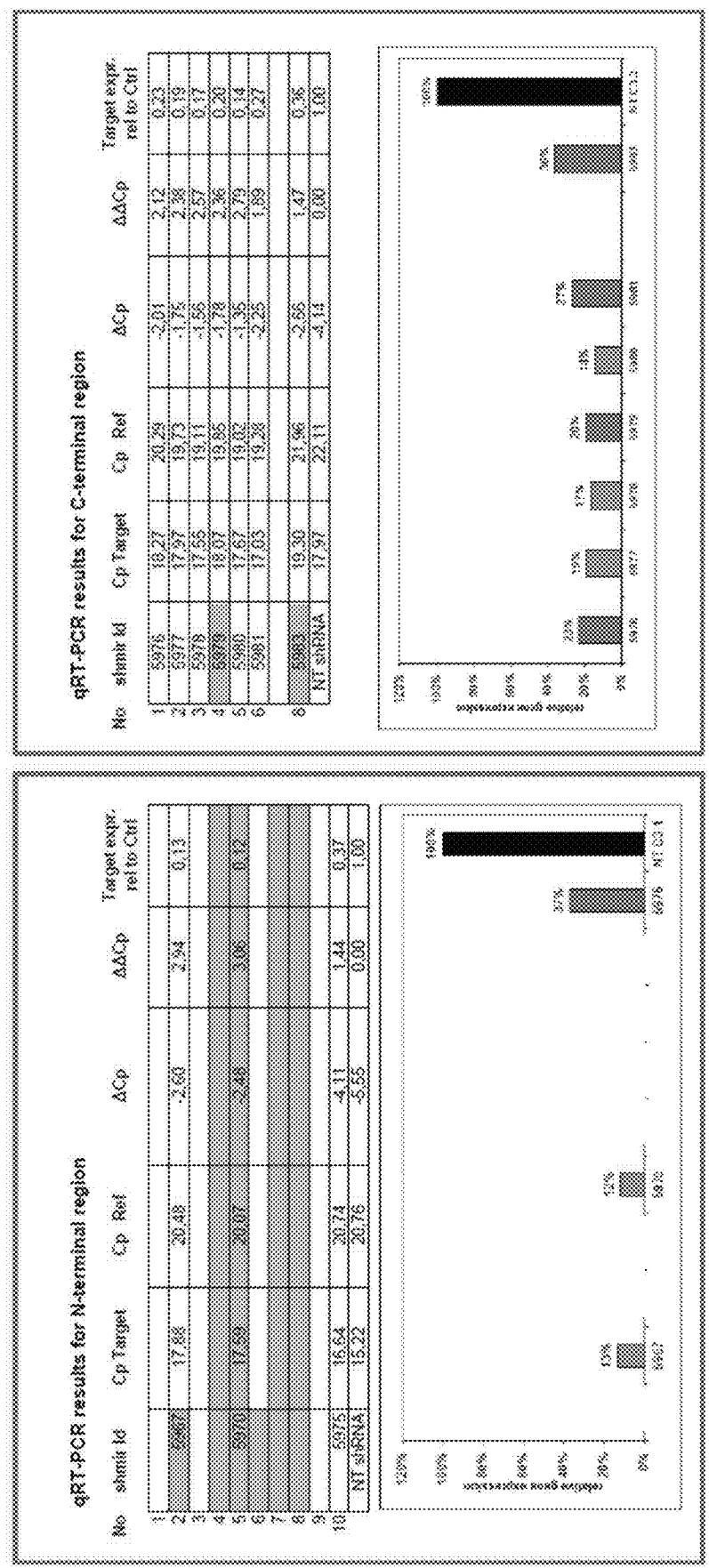

The C3-NIH-3T3 cells of Example 5 were incubated under standard cell culture conditions for 48 hours and the ability of each of the C3-targeting miRNAs to induce C3 gene silencing was examined. Total RNA from the C3-NIH-3T3 cells was isolated and 1 µg was reverse transcribed using a mixture of random hexamer and oligo-dT primer. The silencing efficacy of each miRNA was determined (number of repeats=2) by quantification of the EGFP-target cDNA expression levels relative to that found in cells transfected with the NT-miRNA control vector using the vector-encoded marker transcript as the internal reference gene. Results of the first and second rounds of qRT-PCR sequence validation and relative gene-expression are summarized in FIG. 2A and FIG. 2B, respectively. As shown in FIGS. 2A and 2B, each of the C3-targeting miRNAs of SEQ ID NOs: 76-85 demonstrated significant reduction in expression of C3 relative to the NT miRNA.

Example 7: rAAV Serotype Testing in HepG2 Cells and Hepatocytes

Transduction efficiencies of different AAV serotypes at various MOIs using rAAV construct(s) expressing a GFP were tested in HepG2 and hepatocytes. In this step a pol II promoter (CMV) construct with the GFP transcriptional unit was used, which provided information on the proportion of transfected cells.

Figure 3A:
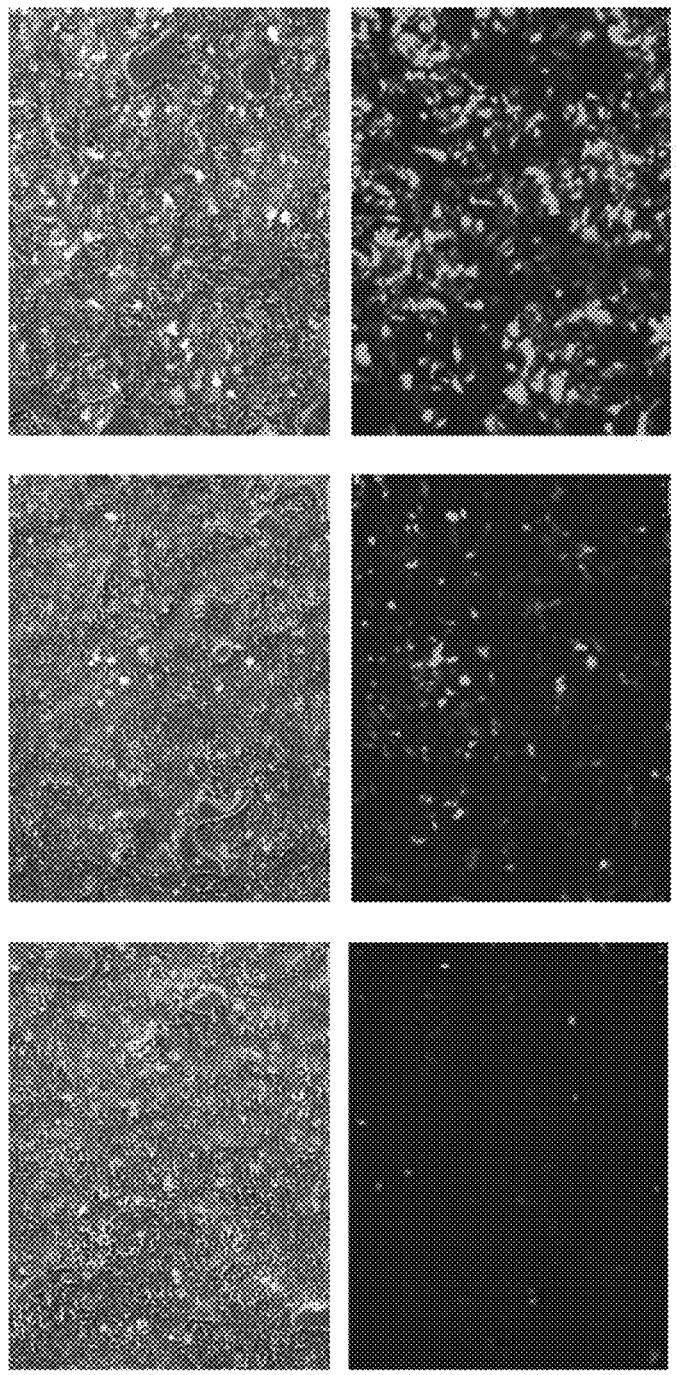
FIG. 3A shows micrographs of rAAV3B serotype testing in HepG2 cells at various MOI at 72 hours post transduction.
Figure 3B:
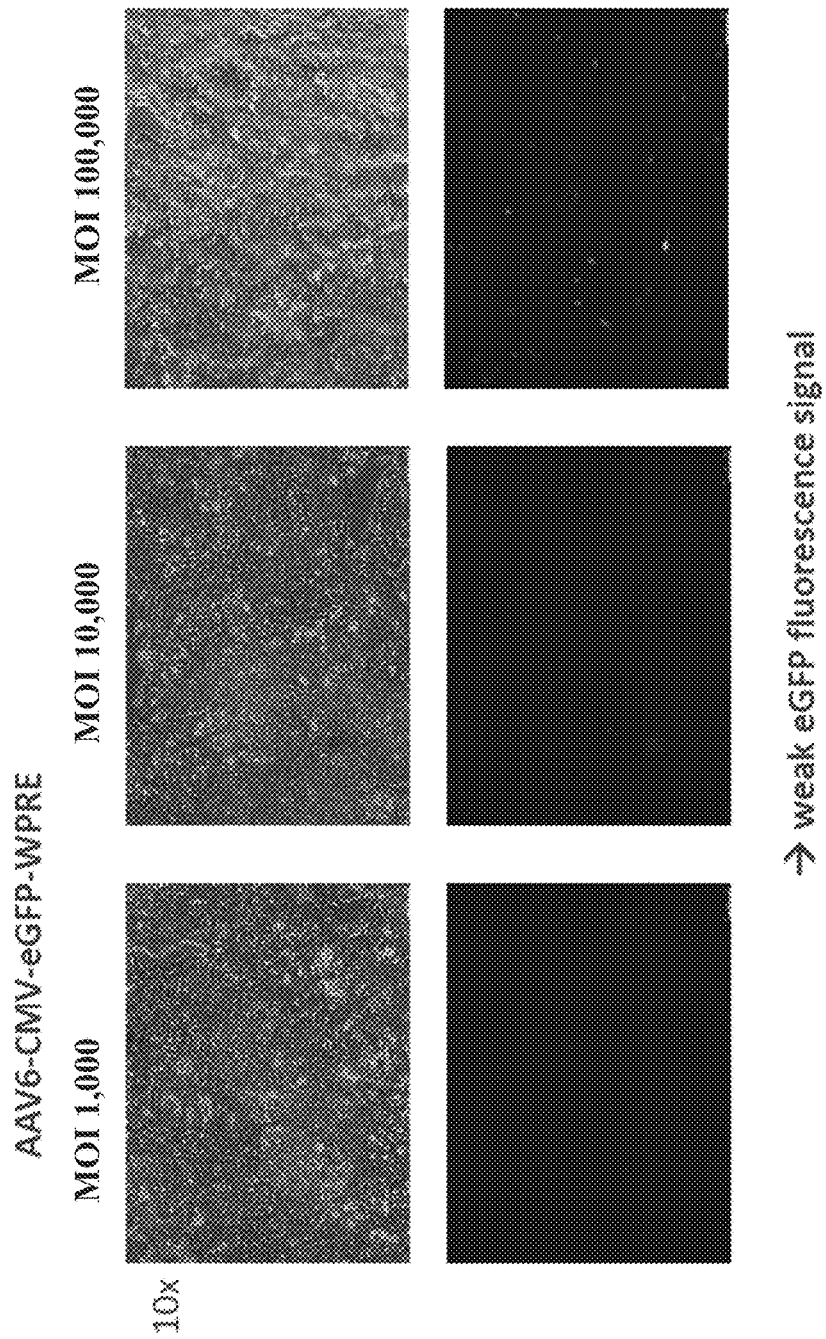
FIG. 3B shows micrographs of rAAV6 serotype testing in HepG2 cells at various MOI at 72 hours post transduction.
Figure 3C:
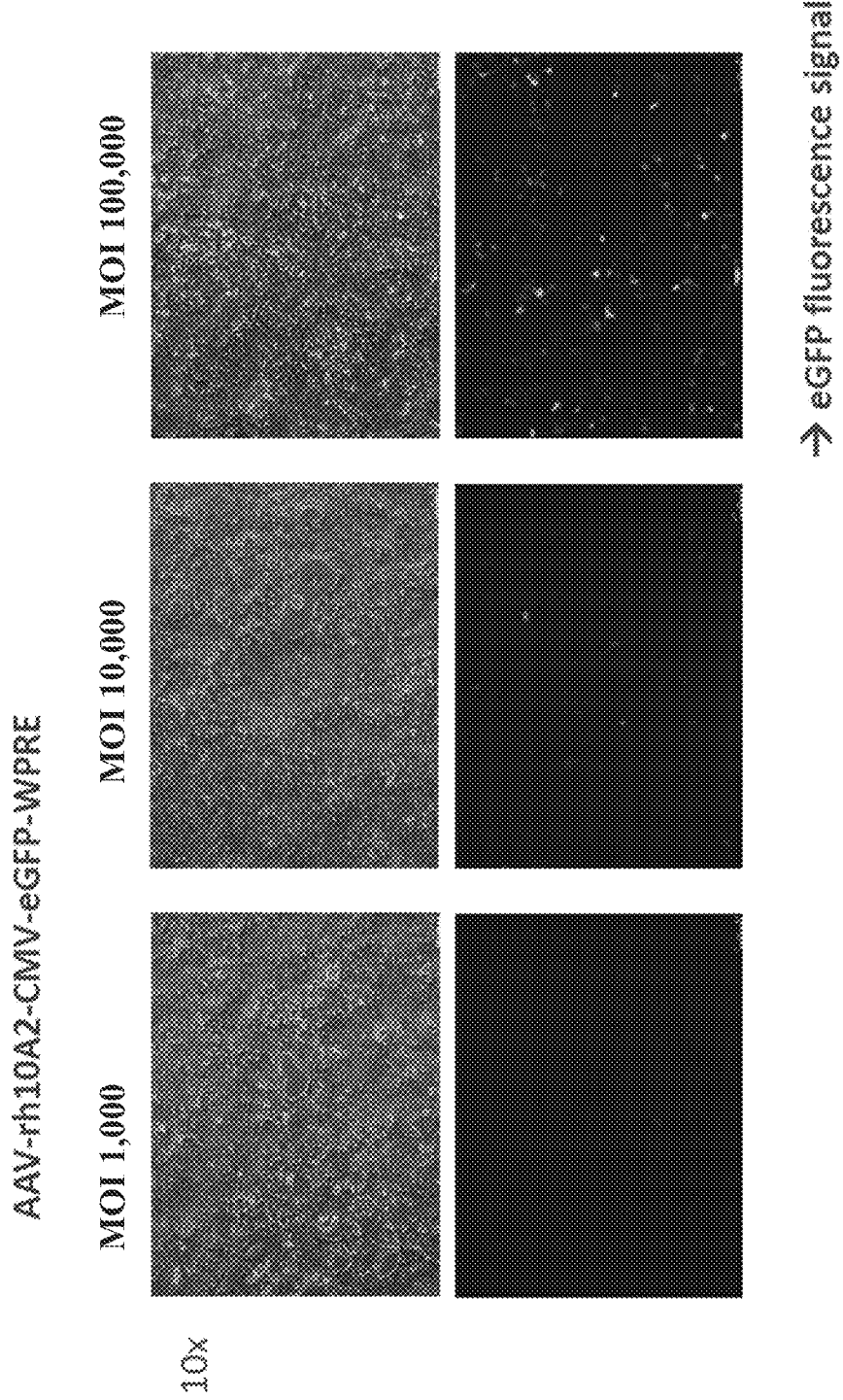
FIG. 3C shows micrographs of rAAV-rh10A2 serotype testing in HepG2 cells at various MOI at 72 hours post transduction.

Following transduction, HepG2 cells were cultured and monitored for 72 hours and the hepatocytes were cultured and monitored for 48 hours, to allow for GFP expression. FIGS. 3A-3C show micrographs of the HepG2 cells, 72 hours post transduction at various MOI with rAAV3B, rAAV6, and rAAV-rh10A2 serotypes respectively. FIG. 4 shows micrographs of the hepatocycte cells, 48 hours post transduction at various MOI with rAAV3B, rAAV8, and rAAV-rh10A2 serotypes respectively. FIG. 5 provides a summary of transduction efficiencies of the different rAAV serotypes in both cell types.

As seen from the micrographs of FIG. 3A and FIG. 4, and summarized in FIG. 5, rAAV3B was found to produce the strongest GFP fluorescence and have the highest transduction efficiency of the tested AAV serotypes in HepG2 cells, while rAAV-rh10A2 was found to have the highest transduction efficiency of the tested AAV serotypes in hepatocytes.

Example 8: In Vitro rAAV3B-miRNA Delivery and Validation in HepG2 Cells

Figure 6:
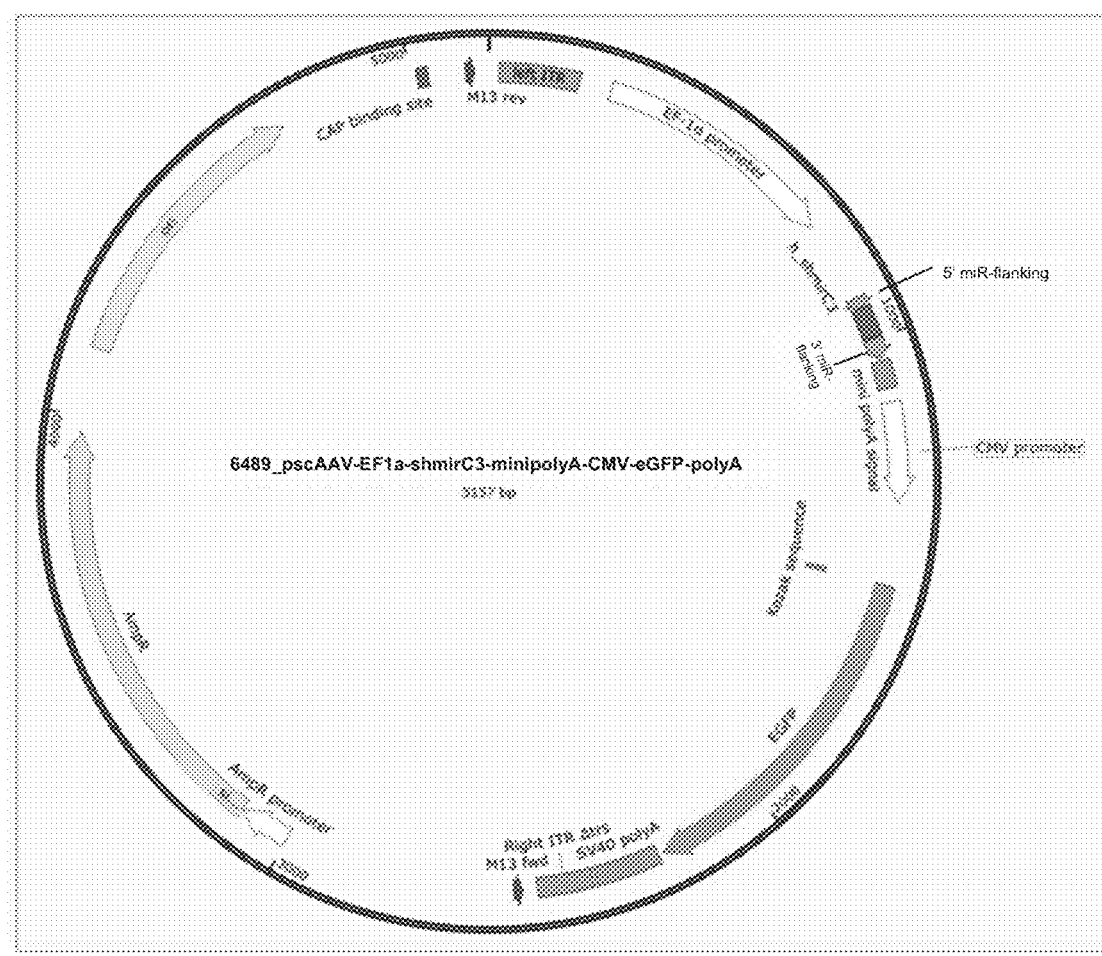
FIG. 6 is a schematic of a rAAV vector design.
Figure 7:
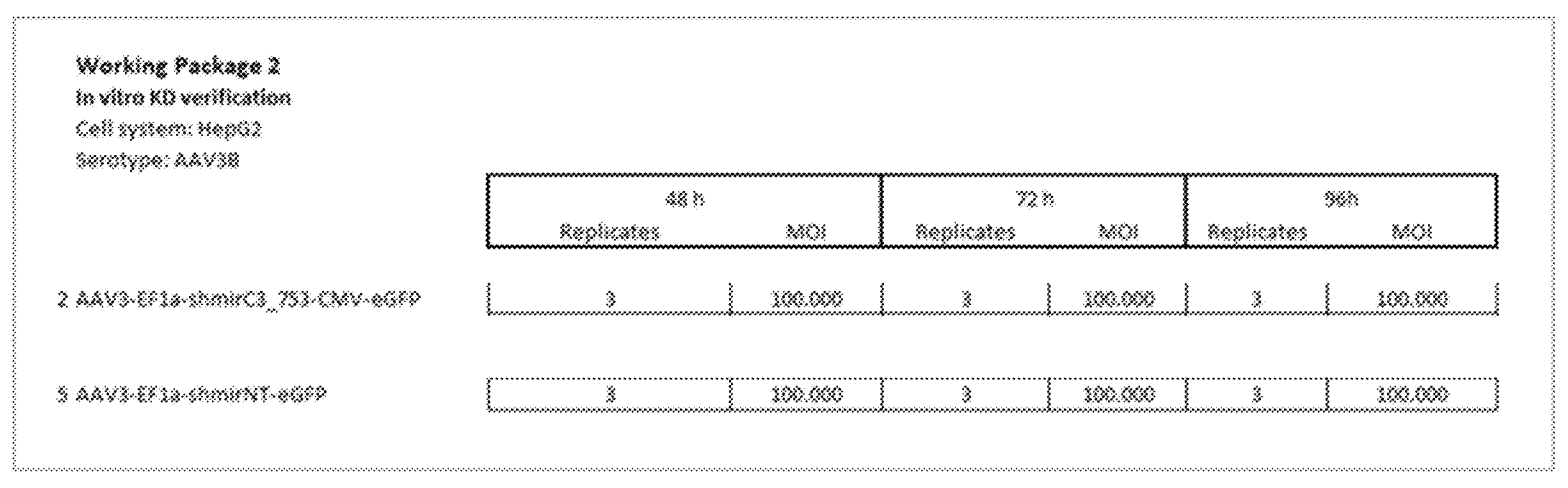

HepG2 cells were seeded at a concentration of 5.0×10$^4$ cells/well in a 12-well plate. rAAV3B-miRNA construct(s) designed as shown in FIG. 6, comprising either a sequence encoding a C3-targeting miRNA of SEQ ID NO: 77 or a NT miRNA under the control of human EF1α promoter, a GFP tag, and including pol II promoters (CMV), were transduced into the seeded HepG2 cells at an MOI of 100.000. Following transduction, cells were cultured and monitored for 48 hours to allow for C3 transcript/protein expression silencing to occur. The cultured cells were then harvested at 48 hours, 72 hours, and 96 hours post transduction and C3 silencing was verified. FIG. 7 summarizes the experimental design.

Figure 8A:
FIG. 8A shows micrographs and qRT-PCR results showing rAAV3B-miRNA based silencing of human C3 (hC3) in HepG2 cells at 48 hours post transduction, where shmirC3_753 corresponds to SEQ ID NO:77.
Figure 8B:
FIG. 8B shows micrographs and qRT-PCR results showing rAAV3B-miRNA based silencing of human C3 (hC3) in HepG2 cells at 72 hours post transduction, where shmirC3_753 corresponds to SEQ ID NO:77.
Figure 8C:
FIG. 8C shows micrographs and qRT-PCR results showing rAAV3B-miRNA based silencing of human C3 (hC3) in HepG2 cells at 96 hours post transduction, where shmirC3_753 corresponds to SEQ ID NO:77.
Figure 9:
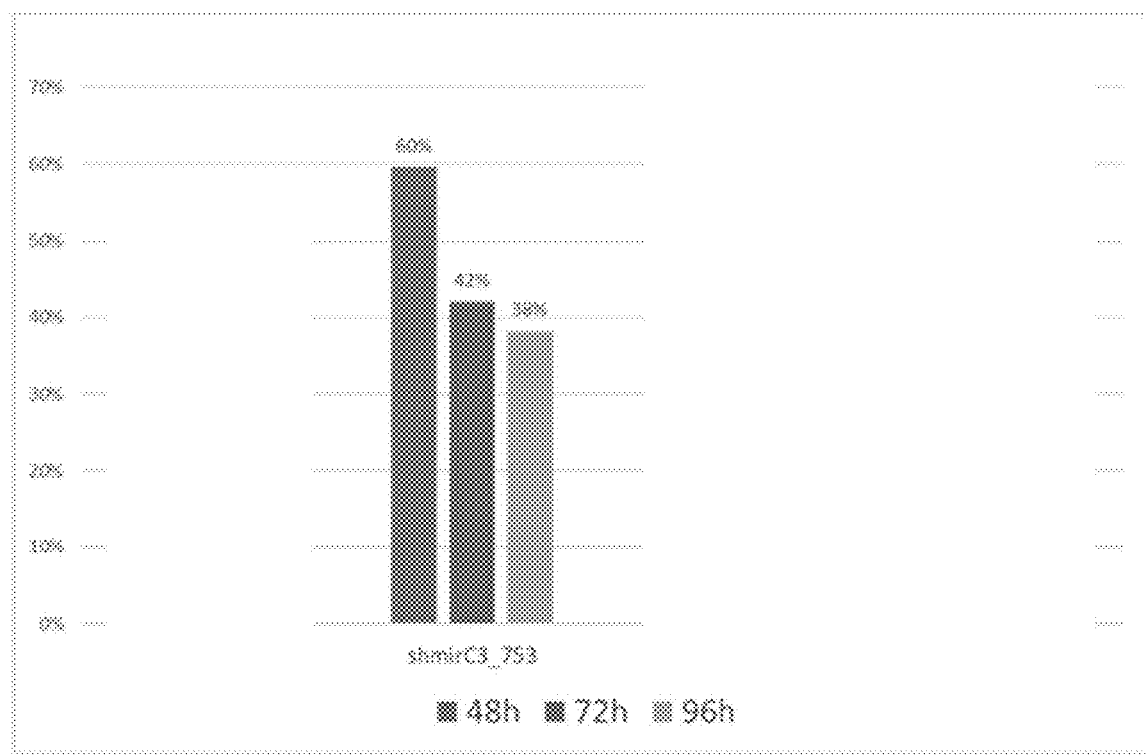
FIG. 9 shows the expression of C3 in HepG2 cells transduced with C3-targeting rAAV3B-miRNA vector relative to those transduced with non-target (NT) rAAV3B-miRNA vector at 48 hours, 72 hours, and 96 hours post transduction, where shmirC3_753 corresponds to SEQ ID NO:77.

FIGS. 8A-8C show micrographs of the transduced cells and the qRT-PCR results at 48, 72, and 96 hours, respectively. FIG. 9 plots the percentage expression of human C3 (hC3) in HepG2 cells transduced with the C3-targeting miRNA expressing AAV vector at various time points relative to those transduced with NT miRNA vector. As seen from both FIGS. 8 and 9, the cells transduced with C3-targeting miRNA vector show reduced C3 expression relative to the control. Furthermore, C3 expression progressively reduces with time. This example demonstrates target (C3) silencing using rAAV3B-miRNA constructs.

Example 9: In Vivo Tolerability, Pharmacodynamic and Biodistribution Assessment of Intravenously Administered scAAV3b-miRs in African Green Monkeys with 6-Week Interim Assessment The purpose of this study is to evaluate the safety and efficacy of intravenously administered scAAV3b-miRNAs test designed to down regulate complement factor 3 (CF3) expression following hepatic targeting and transgene expression. Dosing and subsequent tolerability, pharmacodynamic and biodistribution assessments are performed.

Test System
  Species: African green monkeys (*Chlorocebus sabaeus*)
  Number of Animals: 16 neutralizing antibody (nAb) negative for AAV3b; (32 monkeys are screened).
  Sex & Age: Adult females 4-10 years of age estimated based on size and dentation, ranging in weight from 4-6 kg with maximum mean weight of 5 kg; actual body weight range may vary and is documented following confirmation of seronegative status.

Test and Control Articles
  Test Article(s): scAAV3b-miR1 is provided in vials at a concentration of $5\times10^{12}$ vg/mL and dosed in terms of vg/kg described in Table 6.
  scAAV3b-miR2 is provided in vials at a concentration of $5\times10^{12}$ vg/mL and dosed in terms of vg/kg described in Table 6.

TABLE 6

Treatment Assignment Options

| Group | n/sex | Treatment | Route | Dose Concentration (vg/mL)* | Does (vg/kg, per vector) | Dose Volume (mL/kg) | Sacrifice (day) | Test Article Required |
|---|---|---|---|---|---|---|---|---|
| 1A | 1F | Vehicle | IV | TBD | n/a | 10 | 42 (6 week) | tbd |
| 1B | 1F | Vehicle | IV | TBD | n/a | 10 | 91 (13 week) | tbd |
| 2A | 3F | scAAV3b-NTmiR | IV | TBD | $1\times10^{13}$ | 10 | 42 (6 week) | tbd |
| 2B | 3F | scAAV3b-NTmiR | IV | TBD | $1\times10^{13}$ | 10 | 91 (13 week) | tbd |
| 3A | 4F | scAAV3b-miR1/scAAV3b-miR2 | IV | TBD | $5\times10^{12}$ | 10 | 42 (6 week) | tbd |
| 3B | 4F | scAAV3b-miR1/scAAV3b-miR2 | IV | TBD | $5\times10^{12}$ | 10 | 91 (13 week) | tbd |

F = female; vg = vectore genomes
*Dose concentrations will be based on the actual stock concentration of test articles as supplied by the Sponsor. Actual dose will follow vg/kg.

Control Articles(s): scAAV3b-NTmiR with scrambled sequence is provided in vials at a concentration of $1\times10^{13}$ vg/mL and dosed in terms of vg/kg described in Table 6.
  Vehicle: specify (Manufacturer: TBD Lot #TBD)
  Test & Control Article Handling: Test articles and vehicle are shipped directly to the test facility on dry ice and stored below −80° C. upon receipt.
  Test & Control Article Preparation: AAV3b-miRNA formulations and control articles are dispensed or prepared at least once on the day of dosing. Vials of scAAV3b-miR1 or scAAV3b-miR2 are thawed on wet ice. No dose formulation preparation is required, and formulations are maintained on wet ice until removed for dosing. After dosing, any remaining formulations and partial or unused test article are stored and shipped below −70° C. at study terminus or disposed of.

Dose Analysis
  TBD

Study Design
  Subject Recruitment: The monkeys are AAV3b neutralizing antibody negative animals humanely procured from the wild population. Monkeys are treated with antihelminthics to eliminate possible intestinal parasite burden and are observed in quarantine for a minimum of 4 weeks prior to screening for study enrollment. Age is estimated by size and dentation. All monkeys undergo a minimum of 7 days acclimation to study housing prior to in-life initiation. Prior to study enrollment, a clinical exam is performed on each monkey. Blood samples are collected prior to test article dosing and shipped to designated laboratories, or equivalent clinical pathology lab for comprehensive clinical chemistries, complete blood counts (CBCs) and coagulation profiles. Monkeys with abnormal clinical pathology values, as determined by comparison to the established normal range for monkeys in the colony, are excluded from the study. Baseline serum samples are collected for anti-AAV3b capsid nAb analysis (~1.0 ml serum) and complement analysis (5×150 μl serum), collected as described below. Monkeys that have a<1:5 anti-AAV3b titer are placed in the study and assigned to treatment groups (Table 6). For baseline screening and all subsequent nonsurgical procedures, anesthesia is achieved with intramuscular ketamine (8 mg/kg) and xylazine (1.6 mg/kg) to effect.

Test Article Administration: Dose formulations are removed from wet ice and allowed to equilibrate to approximately room temperature for at least 10 minutes, but no more than 60 minutes prior to dosing. Animals are dosed at the volume of 10 mL/kg. Actual dose volumes are based on the Day 0 body weight. Each monkey receives a single intravenous infusion on Day 0 via a saphenous vein using a calibrated NE-1000 infusion pump (or equivalent) at a target rate of 1 mL/minute (over approximately 30 minutes; the actual start and stop times of dosing are recorded); the leg used is recorded and the injection site is marked and maintained, as appropriate, for collection at necropsy. After dosing, any remaining dose formulations are stored and shipped below −70° C. at study terminus or disposed of.

Clinical Observations: General wellbeing is confirmed twice daily by cage side observations beginning one week prior to dosing. Daily individual food consumption is assessed by visual inspection of the feed pan or cage floor prior to cage washing following routine feeding for overall appetite. Abnormal findings are recorded as they are observed for mortality, abnormalities, and signs of pain or distress.

Injection site observations for all animals is once daily for the first week, and then once weekly. A semiquantitative scoring (on a 0-3 scale) records injection site reactions.

Body weights: Body weights are collected at designated time points (Table 7).

Detailed Observations: Physiology assessments are performed at designated time points (Table 7). Electrocardiography (ECG) is performed using arm, leg and precordial ECG leads (5 leads in total) and recorded at a standard speed of 50 mm/see and standard sensitivity of 10 mm/mV. One representative trace approximately 1 minute in duration is obtained.

Oxygen saturation is determined using a pulse oximeter, Respiratory rate is measured manually over a 15 second interval. Body temperature is determined using a digital rectal thermometer.

Non-invasive blood pressure is measured using a high definition oscillometry (HDO) blood pressure monitor (or equivalent) with the cuff placed around the base of the monkey's tail.

gently inverted 5×. An inversion is defined as one complete turn of the wrist, 180 degrees, and back. The samples are then centrifuged at 2500×g for 7 minutes at 4° C. A clean (non-hemolyzed) ~1 mL plasma sample is carefully transferred to a labeled 1.8 mL cryotube and shipped on ice packs for coagulation profiles. Plasma samples are stored and shipped below −70° C.

Urinalysis: At designed time points (see Table 7) urine (~1.8 mL) samples are collected under sedation by manually expressing the bladder and catching the urine into sterile urine collection jars. Alternatively, a catheter may be introduced to facilitate urine collection. Urine is immediately placed on ice prior to shipment on ice packs for urinalysis. In situations where immediate shipment is not feasible (e.g.

TABLE 7

Study Schedule

| Event* | # | Base-line | −1 | 0 | 1 | 2 | 4 | 5 | 6 | 7 | 14 | 21 | 28 | 42 | 56 | 70 | 84 | 91 |
|---|---|---|---|---|---|---|---|---|---|---|---|---|---|---|---|---|---|---|
| Test article dosing | 16 | — | — | X | — | — | — | — | — | — | — | — | — | — | — | — | — | — |
| Body weights** | 16 | X | — | X | — | — | — | — | — | — | X | X | X | X | X | X | X | X | X |
| Detailed observations | 16 | X | — | — | — | — | — | — | — | — | — | — | X | — | X | — | — | X | — |
| Clinical pathology | 16 | X | — | — | — | — | — | — | — | — | X | X | — | X | X | — | X | — | X |
| Urinalysis*** | 16 | X | — | — | — | — | — | — | — | — | — | — | — | X | — | — | — | — | X |
| Nab analysis**** | 14 | X | — | X | — | — | — | — | — | — | X | X | — | X | X | — | X | — | X |
| Complement analysis (PD) | 16 | X | — | X | X | X | X | X | X | X | X | X | X | X | X | X | — | X | X |
| T-cell (PBMC) antigenicity | 16 | X | — | — | — | — | — | — | — | — | — | — | — | X | — | — | — | — | X |
| AAV vector pharmacokinetics# | 14 | X | — | X | X | X | X | X | X | X | — | — | — | — | — | — | — | — | — |
| Full volume exsanguination+ | 16 | — | — | — | — | — | — | — | — | — | — | — | — | X | — | — | — | X |
| Bone marrow smears+ | 16 | — | — | — | — | — | — | — | — | — | — | — | — | X | — | — | — | X |
| Necropsy+ | 16 | — | — | — | — | — | — | — | — | — | — | — | — | X | — | — | — | X |
| Tissue collection+ | 16 | — | — | — | — | — | — | — | — | — | — | — | — | X | — | — | — | X |

*Test article dosing and all subsequent events will be performed in two cohorts of 8 animals. In the event planned sampling or tests cannot be completed at a specified time point cannot, the reason for the missing sample/value will be recorded. Study days after Day 14 maybe scheduled +/− 1-2 days from original date.
**Body weights obtained weekly: (methylprednisolone 8 mg/kg dosing may be added weekly by veterinarian in case of cytotoxicity or adverse immune response).
***Urine will be collected, as available, when sedated for blood collection
****Plasma for neutralizing antibody analysis and complement analysis (n = 32) will be collected in advance of other baseline activities at approximately 3 weeks in all animals prior to treatment assignment and dosing; Samples for nAb analysis will only be collected for groups 2-3 post-dosing. Phlebotomy collections on Day 91 will occur at time of necropsy.
Groups 2-3 only at pre-dose, 1 h, 2 h, 6 h, 24 h, 48 h, 96 h, 120 h, 144 h, and 168 h post-dose
+Terminal sample collections will be performed for groups 1A, 2A, 3A on Day 42 and 1B, 2B, 3B on Day 91, or as guided by serial complement analyses, or other analytical or clinical findings.

Phlebotomy: Blood collections are performed from a femoral vein phlebotomy at defined time points (Table 7) or for diagnostic purposes if adverse events are detected. An alternate vein may be used if necessary and the site documented. Monkeys are fasted (8-16 hours) prior to all phlebotomy procedures.

Clinical Pathology: A total of 8 mL blood is collected for evaluation of blood chemistry, complete blood counts (CBC), and coagulation profile.

Clinical Chemistry: 3 mL blood is transferred directly to (3 mL) serum separator tubes (red top) and allowed to sit at room temperature for 1 hour prior to centrifugation at 3000 rpm for 10 minutes at 4° C. One serum aliquot (~1 ml) is carefully transferred to a labeled 1.8 mL cryotube and shipped on ice packs for clinical chemistry. All efforts are made to enable collection of a clean plasma sample, but if a hemolyzed sample is obtained, this is noted on the study datasheet. Serum samples are stored and shipped below −70° C.

CBC with Differential: 2 mL blood is transferred directly to $K_2$ lavender top vacutainer tubes containing EDTA and shipped to on ice packs for CBC with differentials analysis.

Coagulation profile: 2.7 mL blood is transferred directly to (2.7 mL) Na-Citrate collection tubes (light-blue top) and on weekends, holidays or natural disasters), urine samples are frozen until an appropriate shipment date is defined.

Neutralizing antibody serum analysis: At defined time points (Table 7), at least 2.5 mL blood is transferred to BD Vacutainer serum collection tubes without clot activators for 30 minutes at room temperature to allow clotting followed by centrifugation at 3000 rpm for 10 minutes at 4° C. 0.5 to 1.0 ml serum is transferred to pre-labeled cryotubes, flash frozen, stored and shipped below −70° C. for serum analysis.

Complement analysis (serum AH50, CH50, C3): At designated timepoints (Table 7), at least 1.5 mL blood is transferred to BD Vacutainer serum collection tubes without clot activators for 30 minutes at room temperature to allow clotting followed by centrifugation at 3000 rpm for 10 minutes at 4° C. Four serum aliquots (~150 μL each) are transferred to pre-labeled cryotubes, flash frozen, stored and shipped below −70° C. for complement biomarker analysis.

PBMC isolation for T-cell activation and antigenicity analysis: At defined time points (Table 7), 7 mL blood is collected by femoral vein phlebotomy (an alternate vein may be used if necessary) and transferred to BD Vacutainer Sodium Heparin CPT tubes (BD REF #362753). The site of blood collection is documented. Tubes are incubated at room temperature (RT) for approximately 60 min then remixed by gently inverting the tube 8 to 10 times immediately prior to centrifugation at 1800×g for 15 minutes at RT. Immediately following centrifuge, half of the supernatant (plasma) is aspirated without disturbing the buffy coat cell layer. The remaining plasma with the cell layer is collected using a Pasteur pipet and transferred to a 15 mL polystyrene conical tube. For washing the cells, PBS is added to bring the volume up to 15 ml. The cells are mixed by inverting the tube 5 times. The mixture is then centrifuged for 15 min at RT at 300×g. The supernatant is aspirated and the remaining pellet is re-suspended in 10 ml PBS. The mixture is inverted 5 times then centrifuged for 10 min at RT at 300×g. The supernatant is discarded without disturbing the pellet layer. Two (2) ml freezing media (Cryostem hPSC freezing medium with 10% DMSO) or equivalent is added and a 1.8 mL aliquot is collected into a sterile labeled cryotube. The sample is then frozen in a Mr. Frosty slow-freeze unit to −80° C. at −1° C./min then stored and shipped below −70° C. for analyses.

Vector pharmacokinetic analysis: Blood (~1.8 ml) is collected into sodium citrate anticoagulated tubes at designated time points (Table 7) and immediately placed on ice prior to centrifugation within 30 minutes at 1300×g for 10 min at 4° C. Plasma (~0.5 ml) is transferred to labeled cryotubes and stored and shipped below −70° C. for analysis. Because of the frequency of blood draws, the site of phlebotomy is alternated to reduce the possibility of vascular injury. Additionally, monkeys are sedated with ketamine alone when possible to speed up recovery time. A mixture of ketamine and xylazine may be introduced if ketamine alone at later sedation time points is not effective.

Unexpected moribundity/mortality: Mortality and morbidity observations are conducted twice each day of the study. Any decision regarding premature sacrifice due to deterioration in animal wellbeing is made based on the recommendations of a Facility Veterinarian. In the event an animal is found dead, a full diagnostic necropsy is performed to determine cause of death. Specified tissues are not collected.

Necropsy and tissue collection: At scheduled sacrifice times (Table 7), or at an earlier time point in the event of detected adverse reaction, monkeys are sedated with ketamine (8-10 mg/kg IM) and euthanized with sodium pentobarbital (25-30 mg/kg IV). Upon loss of corneal reflex, a descending aortic blood collection is performed and as much as 30 mL blood is transferred directly to 7×4.5 ml Na-citrate collection tubes (light-blue top) and gently inverted 5×. An inversion is defined as one complete turn of the wrist, 180 degrees, and back. The samples are then centrifuged at 2500×g for 7 minutes at 4° C. Plasma aliquots of 1 ml (approximately 15 aliquots expected) are carefully transferred to labeled 1.8 mL cryotubes and stored and shipped below −70° C. All efforts are made to enable collection of a clean plasma sample, but if a hemolyzed sample is obtained, this is noted on the study datasheet.

Full post-mortem examination of organs including external features of the carcass, external body orifices, abdominal, thoracic, and cranial cavities, organs, and tissues are performed to document any gross abnormality or pathology, with a full histopathological report obtained.

Bone marrow smears (2 slides) are collected from the sternum of all monkeys and stored and shipped below −70° C.

Defined organs (when present) are weighed or noted as missing. Organ:body weight and organ:brain weight ratios are reported as percentages.

Frozen Tissue Collection for Biodistribution Analysis: With the exception of bone marrow, five approximately 5 mm cubes of each tissue, if possible, (actual size is not documented) are placed into a cryovial (each sample of tissue has its own cryovial), flash frozen in liquid nitrogen, and stored and shipped below −70° C. to the laboratory for biodistribution analysis. Priority is given to histology, as applicable, for each of these tissues.

Frozen Tissue Collection for miRNA/small RNAseq analysis: With the exception of bone marrow, five approximately 5 mm cubes of each tissue, if possible, (actual size is not documented) are placed into a cryovial (each sample of tissue has its own cryovial), flash frozen in liquid nitrogen, and stored and shipped below −70° C. to the laboratory for miRNA/small RNAseq analysis. Priority is given to histology, as applicable, for each of these tissues.

For bone marrow, marrow from the left femur is collected and divided into four samples (actual size is not documented) and each sample placed into a cryovial, flash frozen in liquid nitrogen, and stored and shipped below −70° C.

Tissues Collected in Optimal Cutting Temperature (OCT®): Liver (a sample from each lobe) and spleen are embedded in OCT media, frozen in a mixture of 2-methylbutane and liquid nitrogen, then stored and shipped below −70° C.

Tissues Collected in Fixative: Tissues from each monkey are collected for histopathology in 10% neutral-buffered formalin (unless otherwise indicated) or recorded as missing, if applicable. Tissues are collected, stored in fixative and shipped to HSRL (or equivalent clinical pathology lab) for processing, histopathology evaluation, and generation of full written histopathology report. All efforts are made to have histology reports expedited.

Statistics: Means and standard deviations are calculated for the following parameters: absolute body weight, body weight change, continuous clinical pathology values, terminal body weight, absolute organ weight, organ:body weight percentage, and organ:brain weight percentage.

Study Report: A report detailing methods, in-life exam findings and specimen collection is provided as a draft report, followed by a finalized report.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

SEQUENCE LISTING

```
Sequence total quantity: 115
SEQ ID NO: 1          moltype = AA  length = 13
FEATURE               Location/Qualifiers
source                1..13
```

|                    |                                                                                                                                                                                                                                                                                                                                                                   |
|--------------------|-------------------------------------------------------------------------------------------------------------------------------------------------------------------------------------------------------------------------------------------------------------------------------------------------------------------------------------------------------------------|
|                    | mol_type = protein<br>organism = synthetic construct                                                                                                                                                                                                                                                                                                              |
| DISULFID           | 2..12<br>note = Disulfide bond                                                                                                                                                                                                                                                                                                                                    |
| SEQUENCE: 1        |                                                                                                                                                                                                                                                                                                                                                                   |
| ICVVQDWGHH RCT     | 13                                                                                                                                                                                                                                                                                                                                                                |
| SEQ ID NO: 2       | moltype =    length =                                                                                                                                                                                                                                                                                                                                             |
| SEQUENCE: 2        |                                                                                                                                                                                                                                                                                                                                                                   |
| 000                |                                                                                                                                                                                                                                                                                                                                                                   |
| SEQ ID NO: 3       | moltype =    length =                                                                                                                                                                                                                                                                                                                                             |
| SEQUENCE: 3        |                                                                                                                                                                                                                                                                                                                                                                   |
| 000                |                                                                                                                                                                                                                                                                                                                                                                   |
| SEQ ID NO: 4       | moltype =    length =                                                                                                                                                                                                                                                                                                                                             |
| SEQUENCE: 4        |                                                                                                                                                                                                                                                                                                                                                                   |
| 000                |                                                                                                                                                                                                                                                                                                                                                                   |
| SEQ ID NO: 5       | moltype =    length =                                                                                                                                                                                                                                                                                                                                             |
| SEQUENCE: 5        |                                                                                                                                                                                                                                                                                                                                                                   |
| 000                |                                                                                                                                                                                                                                                                                                                                                                   |
| SEQ ID NO: 6       | moltype = AA   length = 16                                                                                                                                                                                                                                                                                                                                        |
| FEATURE            | Location/Qualifiers                                                                                                                                                                                                                                                                                                                                               |
| source             | 1..16<br>mol_type = protein<br>organism = synthetic construct                                                                                                                                                                                                                                                                                                     |
| VARIANT            | 1..2<br>note = X is Ile, Val, Leu, B1 -Ile, B1 -Val, B1 -Leu or a<br>  dipeptide comprising Gly-Ile or B1 -Gly-Ile,  and B1  repre<br>  sents a first blocking moiety                                                                                                                                                                                             |
| VARIANT            | 5<br>note = X is independently selected from Trp and analogs of<br>  Trp                                                                                                                                                                                                                                                                                          |
| VARIANT            | 8<br>note = X is independently selected from Trp and analogs of<br>  Trp                                                                                                                                                                                                                                                                                          |
| VARIANT            | 10<br>note = X is His, Ala or an analog of Ala, Phe, Trp, or an<br>  analog of Trp                                                                                                                                                                                                                                                                                |
| VARIANT            | 14..16<br>note = X is L-Thr, D-Thr, Ile, Val, Gly, a dipeptide<br>  selected from Thr-Ala or Thr-Asn, or a tripeptide<br>  comprising Thr-Ala-Asn, wherein a carboxy terminal -OH of<br>  any of the L-Thr, D-Thr, Ile, Val, Gly, Ala or Asn is<br>  optionally replaced by a second blocking moiety B2                                                            |
| DISULFID           | 3..13<br>note = Disulfide bond                                                                                                                                                                                                                                                                                                                                    |
| SEQUENCE: 6        |                                                                                                                                                                                                                                                                                                                                                                   |
| XXCVXQDXGX HRCXXX  | 16                                                                                                                                                                                                                                                                                                                                                                |
| SEQ ID NO: 7       | moltype = AA   length = 16                                                                                                                                                                                                                                                                                                                                        |
| FEATURE            | Location/Qualifiers                                                                                                                                                                                                                                                                                                                                               |
| source             | 1..16<br>mol_type = protein<br>organism = synthetic construct                                                                                                                                                                                                                                                                                                     |
| VARIANT            | 1..2<br>note = X is Ile, Val, Leu, Ac-Ile, Ac-Val, Ac-Leu or a<br>  dipeptide comprising Gly-Ile or Ac-Gly-Ile                                                                                                                                                                                                                                                    |
| VARIANT            | 5<br>note = X is independently selected from Trp and analogs of<br>  Trp                                                                                                                                                                                                                                                                                          |
| VARIANT            | 8<br>note = X is independently selected from Trp and analogs of<br>  Trp                                                                                                                                                                                                                                                                                          |
| VARIANT            | 10<br>note = X is His, Ala or an analog of Ala, Phe, Trp, or an<br>  analog of Trp                                                                                                                                                                                                                                                                                |
| VARIANT            | 14..16<br>note = X is L-Thr, D-Thr, Ile, Val, Gly, a dipeptide<br>  selected from Thr-Ala or Thr-Asn, or a tripeptide<br>  comprising Thr-Ala-Asn, wherein a carboxy terminal -OH of<br>  any of L-Thr, D-Thr, Ile, Val, Gly, Ala, or Asn is<br>  optionally replaced by -NH2                                                                                      |
| DISULFID           | 3..13<br>note = Disulfide bond                                                                                                                                                                                                                                                                                                                                    |
| REGION             | 1..16<br>note = See specification as filed for detailed description                                                                                                                                                                                                                                                                                               |

```
                        of substitutions and preferred embodiments
SEQUENCE: 7
XXCVXQDXGX HRCXXX                                                           16

SEQ ID NO: 8           moltype = AA  length = 13
FEATURE                Location/Qualifiers
source                 1..13
                       mol_type = protein
                       organism = synthetic construct
SITE                   1
                       note = N-term H - hydrogenated isoleucine
SITE                   13
                       note = C-term CONH2 - threonine amide
SEQUENCE: 8
ICVVQDWGHH RCT                                                              13

SEQ ID NO: 9           moltype = AA  length = 13
FEATURE                Location/Qualifiers
source                 1..13
                       mol_type = protein
                       organism = synthetic construct
SITE                   1
                       note = N-term Ac - acetyl isoleucine
SITE                   13
                       note = C-term CONH2 - threonine amide
SEQUENCE: 9
ICVVQDWGHH RCT                                                              13

SEQ ID NO: 10          moltype = AA  length = 13
FEATURE                Location/Qualifiers
source                 1..13
                       mol_type = protein
                       organism = synthetic construct
SITE                   1
                       note = N-term Ac - acetyl isoleucine
SITE                   13
                       note = C-term CONH2 - threonine amide
SEQUENCE: 10
ICVYQDWGAH RCT                                                              13

SEQ ID NO: 11          moltype = AA  length = 13
FEATURE                Location/Qualifiers
source                 1..13
                       mol_type = protein
                       organism = synthetic construct
SITE                   1
                       note = N-term Ac - acetyl isoleucine
SITE                   13
                       note = C-term COOH - threonine carboxide
SEQUENCE: 11
ICVWQDWGAH RCT                                                              13

SEQ ID NO: 12          moltype = AA  length = 13
FEATURE                Location/Qualifiers
source                 1..13
                       mol_type = protein
                       organism = synthetic construct
SITE                   1
                       note = N-term Ac - acetyl isoleucine
SITE                   13
                       note = C-term CONH2 - threonine amide
SEQUENCE: 12
ICVWQDWGAH RCT                                                              13

SEQ ID NO: 13          moltype = AA  length = 13
FEATURE                Location/Qualifiers
source                 1..13
                       mol_type = protein
                       organism = synthetic construct
SITE                   13
                       note = D-Threonine
SITE                   1
                       note = N-term Ac - acetyl isoleucine
SITE                   13
                       note = MOD_RES - C-term COOH - D-threonine carboxide
SEQUENCE: 13
ICVWQDWGAH RCT                                                              13

SEQ ID NO: 14          moltype = AA  length = 13
```

```
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 2-Naphthylalanine
SITE                    13
                        note = C-term CONH2 - threonine amide
SEQUENCE: 14
ICVXQDWGAH RCT                                                              13

SEQ ID NO: 15           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 2-Naphthylalanine
SITE                    13
                        note = C-term COOH - threonine carboxide
SEQUENCE: 15
ICVXQDWGAH RCT                                                              13

SEQ ID NO: 16           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 1-Naphthylalanine
SITE                    13
                        note = C-term COOH - threonine carboxide
SEQUENCE: 16
ICVXQDWGAH RCT                                                              13

SEQ ID NO: 17           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 2-Indanylglycine carboxylic acid
SITE                    13
                        note = C-term CONH2 - threonine amide
SEQUENCE: 17
ICVXQDWGAH RCT                                                              13

SEQ ID NO: 18           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 2-Indanylglycine carboxylic acid
SITE                    13
                        note = C-term COOH - threonine carboxide
SEQUENCE: 18
ICVXQDWGAH RCT                                                              13

SEQ ID NO: 19           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = Dihydrotrpytophan
SITE                    13
```

```
                        note = C-term COOH - threonine carboxide
SEQUENCE: 19
ICVXQDWGAH RCT                                                            13

SEQ ID NO: 20           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 4-Benzoyl-L-phenylalanine
SITE                    13
                        note = C-term COOH - threonine carboxide
SEQUENCE: 20
ICVXQDWGAH RCT                                                            13

SEQ ID NO: 21           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = 4-Benzoyl-L-phenylalanine
SITE                    13
                        note = C-term CONH2 - threonine amide
SEQUENCE: 21
ICVXQDWGAH RCT                                                            13

SEQ ID NO: 22           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = Benzothienyl alanine
SITE                    13
                        note = C-term COOH - threonine carboxide
SEQUENCE: 22
ICVXQDWGAH RCT                                                            13

SEQ ID NO: 23           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 4
                        note = Benzothienyl alanine
SITE                    13
                        note = C-term CONH2 - threonine amide
SEQUENCE: 23
ICVXQDWGAH RCT                                                            13

SEQ ID NO: 24           moltype = AA  length = 13
FEATURE                 Location/Qualifiers
source                  1..13
                        mol_type = protein
                        organism = synthetic construct
SITE                    1
                        note = N-term Ac - acetyl isoleucine
MOD_RES                 9
                        note = 2-alpha-aminobutyric acid
SITE                    13
                        note = C-term CONH2 - threonine amide
SEQUENCE: 24
ICVWQDWGXH RCT                                                            13

SEQ ID NO: 25           moltype = AA  length = 16
FEATURE                 Location/Qualifiers
source                  1..16
                        mol_type = protein
                        organism = synthetic construct
```

```
SITE               1
                   note = N-term H - hydrogenated glycine
SITE               16
                   note = C-term COOH - Asparagine carboxide
SEQUENCE: 25
GICVWQDWGA HRCTAN                                                               16

SEQ ID NO: 26      moltype = AA   length = 13
FEATURE            Location/Qualifiers
source             1..13
                   mol_type = protein
                   organism = synthetic construct
SITE               1
                   note = N-term Ac - acetyl isoleucine
MOD_RES            4
                   note = 5-fluoro-L-tryptophan
SITE               13
                   note = C-term CONH2 - threonine amide
SEQUENCE: 26
ICVWQDWGAH RCT                                                                  13

SEQ ID NO: 27      moltype = AA   length = 13
FEATURE            Location/Qualifiers
source             1..13
                   mol_type = protein
                   organism = synthetic construct
SITE               1
                   note = N-term Ac - acetyl isoleucine
MOD_RES            4
                   note = 5-methyl-L-tryptophan
SITE               13
                   note = C-term CONH2 - threonine amide
SEQUENCE: 27
ICVWQDWGAH RCT                                                                  13

SEQ ID NO: 28      moltype = AA   length = 13
FEATURE            Location/Qualifiers
source             1..13
                   mol_type = protein
                   organism = synthetic construct
SITE               1
                   note = N-term Ac - acetyl isoleucine
MOD_RES            4
                   note = 1-methyl-L-tryptophan
SITE               13
                   note = C-term CONH2 - threonine amide
SEQUENCE: 28
ICVWQDWGAH RCT                                                                  13

SEQ ID NO: 29      moltype = AA   length = 13
FEATURE            Location/Qualifiers
source             1..13
                   mol_type = protein
                   organism = synthetic construct
SITE               1
                   note = N-term Ac - acetyl isoleucine
MOD_RES            7
                   note = 5-fluoro-L-tryptophan
SITE               13
                   note = C-term CONH2 - threonine amide
SEQUENCE: 29
ICVWQDWGAH RCT                                                                  13

SEQ ID NO: 30      moltype = AA   length = 13
FEATURE            Location/Qualifiers
source             1..13
                   mol_type = protein
                   organism = synthetic construct
SITE               1
                   note = N-term Ac - acetyl isoleucine
MOD_RES            4
                   note = 5-fluoro-L-tryptophan
MOD_RES            7
                   note = 5-fluoro-L-tryptophan
SITE               13
                   note = C-term CONH2 - threonine amide
SEQUENCE: 30
ICVWQDWGAH RCT                                                                  13
```

```
SEQ ID NO: 31          moltype = AA  length = 13
FEATURE                Location/Qualifiers
source                 1..13
                       mol_type = protein
                       organism = synthetic construct
SITE                   1
                       note = N-term Ac - acetyl isoleucine
MOD_RES                4
                       note = 5-methyl-L-tryptophan
MOD_RES                7
                       note = 5-fluoro-L-tryptophan
SITE                   13
                       note = C-term CONH2 - threonine amide
SEQUENCE: 31
ICVWQDWGAH RCT                                                              13

SEQ ID NO: 32          moltype = AA  length = 13
FEATURE                Location/Qualifiers
source                 1..13
                       mol_type = protein
                       organism = synthetic construct
SITE                   1
                       note = N-term Ac - acetyl isoleucine
MOD_RES                4
                       note = 1-methyl-L-tryptophan
MOD_RES                7
                       note = 5-fluoro-L-tryptophan
SITE                   13
                       note = C-term CONH2 - threonine amide
SEQUENCE: 32
ICVWQDWGAH RCT                                                              13

SEQ ID NO: 33          moltype = AA  length = 15
FEATURE                Location/Qualifiers
source                 1..15
                       mol_type = protein
                       organism = synthetic construct
SITE                   1
                       note = N-term H - hydrogenated glycine
MOD_RES                5
                       note = 6-fluoro-L-tryptophan
MOD_RES                8
                       note = 6-fluoro-L-tryptophan
SITE                   15
                       note = C-term COOH - Asparagine carboxide
SEQUENCE: 33
GICVWQDWGA HRCTN                                                            15

SEQ ID NO: 34          moltype = AA  length = 13
FEATURE                Location/Qualifiers
source                 1..13
                       mol_type = protein
                       organism = synthetic construct
SITE                   1
                       note = N-term Ac - acetyl isoleucine
MOD_RES                4
                       note = 1-formyl-tryptophan
SITE                   13
                       note = C-term CONH2 - threonine amide
SEQUENCE: 34
ICVWQDWGAH RCT                                                              13

SEQ ID NO: 35          moltype = AA  length = 13
FEATURE                Location/Qualifiers
source                 1..13
                       mol_type = protein
                       organism = synthetic construct
SITE                   1
                       note = N-term Ac - acetyl isoleucine
MOD_RES                4
                       note = 1-methyoxy-tryptophan
SITE                   13
                       note = C-term CONH2 - threonine amide
SEQUENCE: 35
ICVWQDWGAH RCT                                                              13

SEQ ID NO: 36          moltype = AA  length = 15
FEATURE                Location/Qualifiers
source                 1..15
```

|  |  |  |
|---|---|---|
|  | mol_type = protein | |
|  | organism = synthetic construct | |
| SITE | 1 | |
|  | note = N-term H - hydrogenated glycine | |
| MOD_RES | 5 | |
|  | note = 5-fluoro-L-tryptophan | |
| MOD_RES | 8 | |
|  | note = 5-fluoro-L-tryptophan | |
| SITE | 15 | |
|  | note = C-term COOH - Asparagine carboxide | |
| SEQUENCE: 36 | | |
| GICVWQDWGA HRCTN | | 15 |
|  | | |
| SEQ ID NO: 37 | moltype = AA   length = 13 | |
| FEATURE | Location/Qualifiers | |
| source | 1..13 | |
|  | mol_type = protein | |
|  | organism = synthetic construct | |
| MOD_RES | 4 | |
|  | note = 1-methyl-tryptophan | |
| DISULFID | 2..12 | |
|  | note = Disulfide bond | |
| SEQUENCE: 37 | | |
| ICVWQDWGAH RCT | | 13 |
|  | | |
| SEQ ID NO: 38 | moltype = AA   length = 13 | |
| FEATURE | Location/Qualifiers | |
| source | 1..13 | |
|  | mol_type = protein | |
|  | organism = synthetic construct | |
| SITE | 1 | |
|  | note = N-term Maleimide-(CH2)5-C(=O) - 6-maleimidohexanoyl isoleucine | |
| MOD_RES | 4 | |
|  | note = 1-methyl-tryptophan | |
| DISULFID | 2..12 | |
|  | note = Disulfide bond | |
| SITE | 13 | |
|  | note = C-term NH2 - threonine amine | |
| SEQUENCE: 38 | | |
| ICVWQDWGAH RCT | | 13 |
|  | | |
| SEQ ID NO: 39 | moltype = AA   length = 13 | |
| FEATURE | Location/Qualifiers | |
| source | 1..13 | |
|  | mol_type = protein | |
|  | organism = synthetic construct | |
| SITE | 13 | |
|  | note = C-term NH2 - threonine amine | |
| MOD_RES | 4 | |
|  | note = 1-methyl-tryptophan | |
| DISULFID | 2..12 | |
|  | note = Disulfide bond | |
| SITE | 13 | |
|  | note = C-term (C=O)-(CH2)5-maleimide - 6-maleimidohexanoyl threonine | |
| SEQUENCE: 39 | | |
| ICVWQDWGAH RCT | | 13 |
|  | | |
| SEQ ID NO: 40 | moltype = AA   length = 13 | |
| FEATURE | Location/Qualifiers | |
| source | 1..13 | |
|  | mol_type = protein | |
|  | organism = synthetic construct | |
| SITE | 1 | |
|  | note = N-term Maleimide-(CH2)2-C(=O)-NH-CH2CH2OCH2CH2OCH2CH2C(=O) - 3-(2-(2-(3-maleimido)propanamidoethoxy)ethoxy)propanoyl isoleucine | |
| MOD_RES | 4 | |
|  | note = 1-methyl-tryptophan | |
| DISULFID | 2..12 | |
|  | note = Disulfide bond | |
| SITE | 13 | |
|  | note = C-term NH2 - threonine amine | |
| SEQUENCE: 40 | | |
| ICVWQDWGAH RCT | | 13 |
|  | | |
| SEQ ID NO: 41 | moltype = AA   length = 13 | |

```
FEATURE                     Location/Qualifiers
source                      1..13
                            mol_type = protein
                            organism = synthetic construct
SITE                        1
                            note = N-term Maleimide-(CH2)2-C(=O)-NH-CH2CH2OCH2CH2C(=O)
                            - 3-(2-(3-maleimido)propanamidoethoxy)propanoyl isoleucine
MOD_RES                     4
                            note = 1-methyl-tryptophan
DISULFID                    2..12
                            note = Disulfide bond
SITE                        13
                            note = C-term NH2 - threonine amine
SEQUENCE: 41
ICVWQDWGAH RCT                                                              13

SEQ ID NO: 42               moltype = AA  length = 13
FEATURE                     Location/Qualifiers
source                      1..13
                            mol_type = protein
                            organism = synthetic construct
SITE                        1
                            note = N-term Maleimide-(CH2)3-C(=O)-NH-CH2CH2OCH2CH2
                            OCH2C(=O) -
                            2-(2-(2-(4-maleimido)butanamidoethoxy)ethoxy)ethanoyl
                            isoleucine
MOD_RES                     4
                            note = 1-methyl-tryptophan
DISULFID                    2..12
                            note = Disulfide bond
SITE                        13
                            note = C-term NH2 - threonine amine
SEQUENCE: 42
ICVWQDWGAH RCT                                                              13

SEQ ID NO: 43               moltype = AA  length = 13
FEATURE                     Location/Qualifiers
source                      1..13
                            mol_type = protein
                            organism = synthetic construct
SITE                        1
                            note = N-term Maleimide-(CH2)5-C(=O)-NH-CH2CH2OCH2CH2
                            OCH2C(=O) -
                            2-(2-(2-(6-maleimido)hexanamidoethoxy)ethoxy)ethanoyl
                            isoleucine
MOD_RES                     4
                            note = 1-methyl-tryptophan
DISULFID                    2..12
                            note = Disulfide bond
SITE                        13
                            note = C-term NH2 - threonine amine
SEQUENCE: 43
ICVWQDWGAH RCT                                                              13

SEQ ID NO: 44               moltype = AA  length = 13
FEATURE                     Location/Qualifiers
source                      1..13
                            mol_type = protein
                            organism = synthetic construct
SITE                        1
                            note = N-term Maleimide-(CH2)4-C(=O)-NH-CH2CH2OCH2CH2
                            OCH2CH2C(=O) -
                            3-(2-(2-(5-maleimido)pentanamidoethoxy)ethoxy)propanoyl
                            isoleucine
MOD_RES                     4
                            note = 1-methyl-tryptophan
DISULFID                    2..12
                            note = Disulfide bond
SITE                        13
                            note = C-term NH2 - threonine amine
SEQUENCE: 44
ICVWQDWGAH RCT                                                              13

SEQ ID NO: 45               moltype = AA  length = 13
FEATURE                     Location/Qualifiers
source                      1..13
                            mol_type = protein
                            organism = synthetic construct
SITE                        1
```

```
                           note = N-term Maleimide-(CH2)2-C(=O)-NH-CH2CH2OCH2CH2
                            OCH2CH2C(=O) -
                            3-(2-(2-(3-maleimido)propanamidoethoxy)ethoxy)propanoyl
                            isoleucine
MOD_RES                    4
                           note = 1-methyl-tryptophan
DISULFID                   2..12
                           note = Disulfide bond
SITE                       13
                           note = C-term NH2 - threonine amine
SEQUENCE: 45
ICVWQDWGAH RCT                                                                    13

SEQ ID NO: 46              moltype = AA  length = 13
FEATURE                    Location/Qualifiers
source                     1..13
                           mol_type = protein
                           organism = synthetic construct
SITE                       1
                           note = N-term Maleimide-(CH2)5-C(=O)-NH-CH2CH2OCH2CH2
                            OCH2C(=O) -
                            2-(2-(2-(6-maleimido)hexanamidoethoxy)ethoxy)ethanoyl
                            isoleucine
MOD_RES                    4
                           note = 1-methyl-tryptophan
DISULFID                   2..12
                           note = Disulfide bond
SITE                       13
                           note = C-term NH2 - threonine amine
SEQUENCE: 46
ICVWQDWGAH RCT                                                                    13

SEQ ID NO: 47              moltype = AA  length = 14
FEATURE                    Location/Qualifiers
source                     1..14
                           mol_type = protein
                           organism = synthetic construct
SITE                       1
                           note = N-term Ac - acetyl isoleucine
MOD_RES                    4
                           note = 1-methyl-tryptophan
DISULFID                   2..12
                           note = Disulfide bond
SITE                       14
                           note = C-term NH2 - Lysine amine
SEQUENCE: 47
ICVWQDWGAH RCTK                                                                   14

SEQ ID NO: 48              moltype = AA  length = 19
FEATURE                    Location/Qualifiers
source                     1..19
                           mol_type = protein
                           organism = synthetic construct
SITE                       1
                           note = N-term Ac - acetyl isoleucine
MOD_RES                    4
                           note = 1-methyl-tryptophan
DISULFID                   2..12
                           note = Disulfide bond
SITE                       19
                           note = C-term NH2 - Lysine amine
SEQUENCE: 48
ICVWQDWGAH RCTGGGGK                                                               19

SEQ ID NO: 49              moltype = AA  length = 13
FEATURE                    Location/Qualifiers
source                     1..13
                           mol_type = protein
                           organism = synthetic construct
SITE                       1
                           note = N-term NH2(CH2)5C(=O) - 6-aminohexanoyl isoleucine
MOD_RES                    4
                           note = 1-methyl-tryptophan
SITE                       13
                           note = C-term NH2 - threonine amine
SEQUENCE: 49
ICVWQDWGAH RCT                                                                    13

SEQ ID NO: 50              moltype = AA  length = 13
```

```
FEATURE                 Location/Qualifiers
source                  1..13
                        mol_type = protein
                        organism = synthetic construct
SITE                    1
                        note = N-term NH2(CH2CH2O)2CH2C(=O) -
                         2-(2-(2-aminoethoxy)ethoxy)ethanoyl isoleucine
MOD_RES                 4
                        note = 1-methyl-tryptophan
SITE                    13
                        note = C-term NH2 - threonine amine
SEQUENCE: 50
ICVWQDWGAH RCT                                                               13

SEQ ID NO: 51           moltype = AA  length = 14
FEATURE                 Location/Qualifiers
source                  1..14
                        mol_type = protein
                        organism = synthetic construct
SITE                    1
                        note = N-term Ac - acetyl isoleucine
MOD_RES                 4
                        note = 1-methyl-tryptophan
DISULFID                2..12
                        note = Disulfide bond
MOD_RES                 14
                        note = NH-CH2CH2OCH2CH2OCH2-C(=O)-Lys
                         8-amino-3,6-dioxaoctanoic acid spacer Lysine) - C-term NH2
                         (amine)
SEQUENCE: 51
ICVWQDWGAH RCTK                                                              14

SEQ ID NO: 52           moltype = AA  length = 14
FEATURE                 Location/Qualifiers
source                  1..14
                        mol_type = protein
                        organism = synthetic construct
SITE                    1
                        note = N-term Ac - acetyl isoleucine
MOD_RES                 4
                        note = 1-methyl-tryptophan
DISULFID                2..12
                        note = Disulfide bond
MOD_RES                 14
                        note = Lys-(C(=O)-(CH2)5-Mal)(Lysine 6-maleimidohexanoyl) -
                         C-term NH2 (amine)
SEQUENCE: 52
ICVWQDWGAH RCTK                                                              14

SEQ ID NO: 53           moltype = AA  length = 19
FEATURE                 Location/Qualifiers
source                  1..19
                        mol_type = protein
                        organism = synthetic construct
SITE                    1
                        note = N-term Ac - acetyl isoleucine
MOD_RES                 4
                        note = 1-methyl-tryptophan
DISULFID                2..12
                        note = Disulfide bond
MOD_RES                 19
                        note = Lys--(C(=O)-(CH2)5-Mal) (Lysine 6-maleimidohexanoyl)
                         - C-term NH2 (amine)
SEQUENCE: 53
ICVWQDWGAH RCTGGGGGK                                                         19

SEQ ID NO: 54           moltype = AA  length = 13
FEATURE                 Location/Qualifiers
source                  1..13
                        mol_type = protein
                        organism = synthetic construct
SITE                    1
                        note = N-term Mal-(CH2)5-(C(=O)-NH(CH2)5C(=O) -
                         (6-(6-maleimidohexanamido)hexanoyl isoleucine
MOD_RES                 4
                        note = 1-methyl-tryptophan
SITE                    13
                        note = C-term NH2 - threonine amine
SEQUENCE: 54
```

```
ICVWQDWGAH RCT                                                                   13

SEQ ID NO: 55            moltype = AA  length = 13
FEATURE                  Location/Qualifiers
source                   1..13
                         mol_type = protein
                         organism = synthetic construct
SITE                     1
                         note = N-term Mal-(CH2)5-(C(=O)NH(CH2CH2O)2CH2C(=O)-
                         2-(2-(2-(6-maleimido)hexanamidoethoxy)ethoxy)ethanoyl
                         isoleucine
MOD_RES                  4
                         note = 1-methyl-tryptophan
SITE                     13
                         note = C-term NH2 - threonine amine
SEQUENCE: 55
ICVWQDWGAH RCT                                                                   13

SEQ ID NO: 56            moltype = AA  length = 14
FEATURE                  Location/Qualifiers
source                   1..14
                         mol_type = protein
                         organism = synthetic construct
SITE                     1
                         note = N-term Ac - acetyl isoleucine
MOD_RES                  4
                         note = 1-methyl-tryptophan
DISULFID                 2..12
                         note = Disulfide bond
MOD_RES                  14
                         note = NH-CH2CH2OCH2CH2OCH2-C(=O)-Lys-(C(=O)-(CH2)5-Mal)
                         (8-amino-3,6-dioxaoctanoic acid spacer Lysine
                         6-maleimidohexanoyl) - C-term NH2 (amine)
SEQUENCE: 56
ICVWQDWGAH RCTK                                                                  14

SEQ ID NO: 57            moltype = AA  length = 14
FEATURE                  Location/Qualifiers
source                   1..14
                         mol_type = protein
                         organism = synthetic construct
SITE                     1
                         note = N-term Ac - acetyl isoleucine
MOD_RES                  4
                         note = 1-methyl-tryptophan
DISULFID                 2..12
                         note = Disulfide bond
MOD_RES                  14
                         note = Lys-C(=O)-CH2(OCH2CH2)2NH(C(=O)-(CH2)5-Mal) (Lysine
                         2-(2-(2-(6-maleimido)hexanamidoethoxy)ethoxy)ethanoyl) -
                         C-term NH2 (amine)
SEQUENCE: 57
ICVWQDWGAH RCTK                                                                  14

SEQ ID NO: 58            moltype = AA  length = 13
FEATURE                  Location/Qualifiers
source                   1..13
                         mol_type = protein
                         organism = synthetic construct
SITE                     1
                         note = N-term (CH2CH2O)nC(=O) - polyethylene glycol ester
                         isoleucine
MOD_RES                  4
                         note = 1-methyl-tryptophan
SITE                     13
                         note = C-term NH2 - threonine amine
REGION                   1..13
                         note = See specification as filed for detailed description
                         of substitutions and preferred embodiments
SEQUENCE: 58
ICVWQDWGAH RCT                                                                   13

SEQ ID NO: 59            moltype = AA  length = 14
FEATURE                  Location/Qualifiers
source                   1..14
                         mol_type = protein
                         organism = synthetic construct
SITE                     1
                         note = N-term Ac - acetyl isoleucine
```

| | |
|---|---|
| MOD_RES | 4 |
| | note = 1-methyl-tryptophan |
| DISULFID | 2..12 |
| | note = Disulphide bond |
| MOD_RES | 14 |
| | note = NH-CH2CH2OCH2CH2OCH2-C(=O)-Lys-C(=O)-(CH2CH2O)n (8-amino-3,6-dioxaoctanoic acid spacer Lysine polyethylene glycol ester) - C-term NH2 (amine) |
| REGION | 1..14 |
| | note = See specification as filed for detailed description of substitutions and preferred embodiments |
| SEQUENCE: 59 | |
| ICVWQDWGAH RCTK | 14 |
| | |
| SEQ ID NO: 60 | moltype = AA   length = 14 |
| FEATURE | Location/Qualifiers |
| source | 1..14 |
| | mol_type = protein |
| | organism = synthetic construct |
| SITE | 1 |
| | note = N-term Ac - acetyl isoleucine |
| MOD_RES | 4 |
| | note = 1-methyl-tryptophan |
| DISULFID | 2..12 |
| | note = Disulphide bond |
| MOD_RES | 14 |
| | note = Lys-C(=O)-(CH2CH2O)n (Lysine polyethylene glycol ester) - C-term NH2 (amine) |
| REGION | 1..14 |
| | note = See specification as filed for detailed description of substitutions and preferred embodiments |
| SEQUENCE: 60 | |
| ICVWQDWGAH RCTK | 14 |
| | |
| SEQ ID NO: 61 | moltype = AA   length = 19 |
| FEATURE | Location/Qualifiers |
| source | 1..19 |
| | mol_type = protein |
| | organism = synthetic construct |
| SITE | 1 |
| | note = N-term Ac - acetyl isoleucine |
| MOD_RES | 4 |
| | note = 1-methyl-tryptophan |
| DISULFID | 2..12 |
| | note = Disulphide bond |
| MOD_RES | 19 |
| | note = Lys-C(=O)-(CH2CH2O)n (Lysine polyethylene glycol ester) - C-term NH2 (amine) |
| REGION | 1..19 |
| | note = See specification as filed for detailed description of substitutions and preferred embodiments |
| SEQUENCE: 61 | |
| ICVWQDWGAH RCTGGGGGK | 19 |
| | |
| SEQ ID NO: 62 | moltype = AA   length = 19 |
| FEATURE | Location/Qualifiers |
| source | 1..19 |
| | mol_type = protein |
| | organism = synthetic construct |
| SITE | 1 |
| | note = MOD_RES - (CH2CH2O)nC(=O)Lys - N-term Ac (Acetylated polyethylene glycol ester lysine) |
| MOD_RES | 10 |
| | note = 1-methyl-tryptophan |
| DISULFID | 8..18 |
| | note = Disulphide bond |
| MOD_RES | 1 |
| | note = (CH2CH2O)nC(=O)Lys |
| REGION | 1..19 |
| | note = See specification as filed for detailed description of substitutions and preferred embodiments |
| SEQUENCE: 62 | |
| KGGGGGICVW QDWGAHRCT | 19 |
| | |
| SEQ ID NO: 63 | moltype = AA   length = 14 |
| FEATURE | Location/Qualifiers |
| source | 1..14 |
| | mol_type = protein |
| | organism = synthetic construct |

|  |  |  |
|---|---|---|
| SITE | 1 | |
| | note = MOD_RES - (CH2CH2O)nC(=O)Lys - N-term Ac (Acetylated polyethylene glycol ester lysine) | |
| MOD_RES | 5 | |
| | note = 1-methyl-tryptophan | |
| DISULFID | 3..13 | |
| | note = Disulphide bond | |
| REGION | 1..14 | |
| | note = See specification as filed for detailed description of substitutions and preferred embodiments | |
| SEQUENCE: 63 | | |
| KICVWQDWGA HRCT | | 14 |
| | | |
| SEQ ID NO: 64 | moltype = AA   length = 14 | |
| FEATURE | Location/Qualifiers | |
| source | 1..14 | |
| | mol_type = protein | |
| | organism = synthetic construct | |
| SITE | 1 | |
| | note = N-term Ac - acetyl isoleucine | |
| MOD_RES | 4 | |
| | note = 1-methyl-tryptophan | |
| DISULFID | 2..12 | |
| | note = Disulphide bond | |
| MOD_RES | 14 | |
| | note = NH-CH2CH2OCH2CH2OCH2-C(=O)-Lys-(C(=O)-(CH2CH2O)n-R) (8-amino-3,6-dioxaoctanoic acid spacer lysine polyethylene glycol ester) - C-term NH2 (amine) | |
| REGION | 1..14 | |
| | note = See specification as filed for detailed description of substitutions and preferred embodiments | |
| SEQUENCE: 64 | | |
| ICVWQDWGAH RCTK | | 14 |
| | | |
| SEQ ID NO: 65 | moltype = AA   length = 14 | |
| FEATURE | Location/Qualifiers | |
| source | 1..14 | |
| | mol_type = protein | |
| | organism = synthetic construct | |
| SITE | 1 | |
| | note = N-term Ac - acetyl isoleucine | |
| MOD_RES | 4 | |
| | note = 1-methyl-tryptophan | |
| DISULFID | 2..12 | |
| | note = Disulphide bond | |
| MOD_RES | 14 | |
| | note = NH-CH2CH2OCH2CH2OCH2-C(=O)-Lys-(C(=O)-(CH2)m-(CH2CH2O)n-R) (8-amino-3,6-dioxaoctanoic acid spacer lysine (polyethylene glycol)alkanoyl) linker - C-term NH2 (amine) | |
| REGION | 1..14 | |
| | note = See specification as filed for detailed description of substitutions and preferred embodiments | |
| SEQUENCE: 65 | | |
| ICVWQDWGAH RCTK | | 14 |
| | | |
| SEQ ID NO: 66 | moltype = AA   length = 14 | |
| FEATURE | Location/Qualifiers | |
| source | 1..14 | |
| | mol_type = protein | |
| | organism = synthetic construct | |
| SITE | 1 | |
| | note = N-term Ac - acetyl isoleucine | |
| MOD_RES | 4 | |
| | note = 1-methyl-tryptophan | |
| DISULFID | 2..12 | |
| | note = Disulphide bond | |
| MOD_RES | 14 | |
| | note = NH-CH2CH2OCH2CH2OCH2-C(=O)-Lys-(C(=O)-(CH2)m-C(=O)-(CH2CH2O)n-R) (8-amino-3,6-dioxaoctanoic acid spacer lysine (polyethylene glycol)-carbonyl-alkanoyl linker - C-term NH2 (amine) | |
| REGION | 1..14 | |
| | note = See specification as filed for detailed description of substitutions and preferred embodiments | |
| SEQUENCE: 66 | | |
| ICVWQDWGAH RCTK | | 14 |

| | |
|---|---|
| SEQ ID NO: 67 | moltype = AA length = 14 |
| FEATURE | Location/Qualifiers |
| source | 1..14 |
| | mol_type = protein |
| | organism = synthetic construct |
| SITE | 1 |
| | note = N-term Ac - acetyl isoleucine |
| MOD_RES | 4 |
| | note = 1-methyl-tryptophan |
| DISULFID | 2..12 |
| | note = Disulphide bond |
| MOD_RES | 14 |
| | note = NH-CH2CH2OCH2CH2OCH2-C(=O)-Lys-(C(=O)-(CH2)m-C(=O)-(CH2)j (CH2CH2O)n-R) (8-amino-3,6-dioxaoctanoic acid spacer lysine (polyethylene glycol)-alkyl-carbonyl-alkanoyl linker - C-term NH2 (amine) |
| SEQUENCE: 67 | |
| ICVWQDWGAH RCTK | 14 |
| | |
| SEQ ID NO: 68 | moltype = AA length = 14 |
| FEATURE | Location/Qualifiers |
| source | 1..14 |
| | mol_type = protein |
| | organism = synthetic construct |
| SITE | 1 |
| | note = N-term Ac - acetyl isoleucine |
| MOD_RES | 4 |
| | note = 1-methyl-tryptophan |
| DISULFID | 2..12 |
| | note = Disulphide bond |
| REGION | 13..14 |
| | note = Threonine is linked to Lysine via spacer 8-amino-3,6-dioxaoctanoic acid |
| MOD_RES | 14 |
| | note = Lys-(C(=O)-(CH2)5-Mal) (lysine-6-maleimidohexanoyl) - C-term NH2 (amine) |
| SEQUENCE: 68 | |
| ICVWQDWGAH RCTK | 14 |
| | |
| SEQ ID NO: 69 | moltype = length = |
| SEQUENCE: 69 | |
| 000 | |
| | |
| SEQ ID NO: 70 | moltype = AA length = 18 |
| FEATURE | Location/Qualifiers |
| source | 1..18 |
| | mol_type = protein |
| | organism = synthetic construct |
| VARIANT | 1 |
| | note = X can be any amino acid |
| VARIANT | 2..3 |
| | note = X is Ile, Val, Leu, B1-Ile, B1-Val, B1-Leu or a dipeptide comprising Gly-Ile or B1-Gly-Ile, wherein B1 represents a first blocking moiety |
| VARIANT | 6 |
| | note = Independently selected from Trp and analogs of Trp |
| VARIANT | 9 |
| | note = Independently selected from Trp and analogs of Trp |
| VARIANT | 11 |
| | note = X is His, Ala or an analog of Ala, Phe, Trp, or an analog of Trp |
| VARIANT | 15..17 |
| | note = X is L-Thr, D-Thr, Ile, Val, Gly, a dipeptide selected from Thr-Ala or Thr-Asn, or a tripeptide comprising Thr-Ala-Asn, wherein a carboxy terminal -OH of any of the L-Thr, D-Thr, Ile, Val, Gly, Ala or Asn is optionally replaced by a second blocking moiety B2 |
| VARIANT | 18 |
| | note = X can be any amino acid |
| DISULFID | 4..14 |
| | note = Disulfide bond |
| REGION | 1..18 |
| | note = See specification as filed for detailed description of substitutions and preferred embodiments |
| SEQUENCE: 70 | |
| XXXCVXQDXG XHRCXXXX | 18 |
| | |
| SEQ ID NO: 71 | moltype = length = |

-continued

```
SEQUENCE: 71
000

SEQ ID NO: 72           moltype = AA  length = 15
FEATURE                 Location/Qualifiers
source                  1..15
                        mol_type = protein
                        organism = synthetic construct
MOD_RES                 5
                        note = Trp(Me)
MOD_RES                 9
                        note = N-methyl glycine
MOD_RES                 14
                        note = N-methyl isoleucine
VARIANT                 1
                        note = X can be any amino acid
VARIANT                 15
                        note = X can be any amino acid
DISULFID                3..13
                        note = Disulfide bond
REGION                  1..15
                        note = See specification as filed for detailed description
                         of substitutions and preferred embodiments
SEQUENCE: 72
XICVWQDWGA HRCIX                                                        15

SEQ ID NO: 73           moltype = AA  length = 10
FEATURE                 Location/Qualifiers
source                  1..10
                        mol_type = protein
                        organism = synthetic construct
SEQUENCE: 73
WESNGQPENN                                                              10

SEQ ID NO: 74           moltype = AA  length = 17
FEATURE                 Location/Qualifiers
source                  1..17
                        mol_type = protein
                        organism = synthetic construct
SEQUENCE: 74
KTISKAKGQP REPQVYT                                                      17

SEQ ID NO: 75           moltype = RNA  length = 5148
FEATURE                 Location/Qualifiers
source                  1..5148
                        mol_type = mRNA
                        organism = Homo sapiens
SEQUENCE: 75
agataaaaag ccagctccag caggcgctgc tcactcctcc ccatcctctc cctctgtccc          60
tctgtccctc tgaccctgca ctgtcccagc accatgggac ccacctcagg tcccagcctg        120
ctgctcctgc tactaaccca cctcccccct gctctgggga gtcccatgta ctctatcatc        180
accccccaaca tcttgcggct ggagagcgag gagaccatgg tgctggaggc ccacgacgcg       240
caaggggatg ttccagtcac tgttactgtc cacgacttcc caggcaaaaa actagtgctg        300
tccagtgaga agactgtgct gacccctgcc accaaccaca tgggcaacgt caccttcacg        360
atcccagcca acagggagtt caagtcagaa aaggggcgca acaagtttga gaccgtgcag        420
gccaccttcg ggacccaagt ggtggagaag gtggtgctgg tcagcctgca gagcgggtac        480
ctcttcatcc agacagacaa gaccatctac cccctggctc cacagttcct ctatcggatc        540
ttcaccgtca accacaagct gctacccgtg gccggacgg tcatggtcaa cattgagaac         600
ccggaaggca tcccggtcaa gcaggactcc ttgtcttctc gaaaccagct tggcgtcttg        660
cccttgtctt gggacattcc ggaactcgtc aacatgggcc agtggaagat ccgagcctac        720
tatgaaaact caccacagca ggtcttctct actgagtttg aggtgaagga gtacgtgctg        780
cccagtttcg aggtcatagt ggagcctaca gagaaattct actacatcta taacgagaag        840
ggcctggagg tcaccatcac cgccaggttc ctctacggga agaaagtgga gggaactgcc        900
tttgtcatct tcgggattca ggatggcgaa cagaggattt ccctgcctga atccctcaag        960
cgcattccga ttgaggatgg ctcgggggag gttgtgctga gccggaaggt actgctggac       1020
ggggtgcaga accccgagc agaagacctg gtggggaagt ctttgtacgt gtctgccacc        1080
gtcatcttgc actcaggcag tgacatggtg caggcagagc gcagcgggat ccccatcgtg       1140
acctctccct accagatcca cttccaccaag acacccaaagt acttcaaacc aggaatgccc    1200
tttgacctca tggtgttcgt gacgaaccct gatggctctc cagcctaccg agtccccatg        1260
gcagtccagg gcgaggacac tgtgcagtct ctaaccccagg gagatggcgt ggccaaactc       1320
agcatcaaca cacacccccag ccagaagccc ttgagcatca cggtgcgcac gaagaagcag      1380
gagctctcgg aggcagagca ggctaccagg accatgcagg ctctgcccta cagcaccgtg       1440
ggcaactcca caattaccct gcatctctca gtgctacgta cagagctcag accgggggag       1500
accctcaacg tcaacttcct cctgcgaatg gaccgcgcc acgaggccga gatccgctac        1560
tacacctacc tgatcatgaa caagggcagg ctgttgaagg cgggacgcca ggtcgcgagg       1620
cccggccagg aactggtggt gctgcccctg tccatcacca ccgacttcat cccttccttc       1680
cgcctggtgg cgtactacac gctgatcggt gccagcggcc agaggaggt ggtggccgac         1740
tccgtgtggg tggacgtcaa ggactcctgc gtgggctcgc tggtggtaaa aagcggccag       1800
tcagaagacc ggcagcctgt acctgggcag cagatgaccc tgaagataga gggtgaccac       1860
```

```
ggggcccggg tggtactggt ggccgtggac aagggcgtgt tcgtgctgaa taagaagaac    1920
aaactgacgc agagtaagat ctgggacgtg gtgagaagg  cagacatcgg ctgcaccccg    1980
ggcagtggga aggattacgc cggtgtcttc tccgacgcag ggctgacctt cacgagcagc    2040
agtggccagc agaccgccca gagggcagaa cttcagtgcc cgcagccagc cgcccgccga    2100
cgccgttccg tgcagctcac ggagaagcga atggacaagg tgccaagta  ccccaaggag    2160
ctgcgcaagt gctgcgagga cggcatgcgg gagaacccca tgaggttctc gtgccagcgc    2220
cggacccgtt tcatctccct gggcgaggcg tgcaagaagg tcttcctgga ctgctgcaac    2280
tacatcacag agctgcggcg gcagcacgcg cgggccagcc acctgggcct ggccaggagt    2340
aacctggatg aggacatcat tgcagaagag aacatcgttt cccgaagtga gttcccagag    2400
agctggctgt ggaacgttga ggacttgaaa gagccaccga aaaatggaat ctctacgaag    2460
ctcatgaata tattttgaa  agactccatc accacgtggg agattctggc tgtgagcatg    2520
tcggacaaga aagggatctg tgtggcagac cccttcgagg tcacagtaat gcaggacttc    2580
ttcatcgacc tgcggctacc ctactctgtt gttcgaaacg agcaggtgga aatccgagcc    2640
gttctctaca attaccggca gaaccaagag ctcaaggtga ggtggaact  actccacaat    2700
ccagccttct gcagcctggc caccaccaag aggcgtcacc agcagaccgt aaccatcccc    2760
cccaagtcct cgttgtccgt tccatatgtc atcgtgccgc taaagaccgg cctgcaggaa    2820
gtggaagtca aggctgctgt ctaccatcat ttcatcagtg acggtgtcag gaagtccctg    2880
aaggtcgtgc cggaaggaat cagaatgaac aaaactgtgg ctgttcgcac cctggatcca    2940
gaacgcctgg gccgtgaagg agtgcagaaa gaggacatcc cacctgcaga cctcagtgac    3000
caagtcccgg acaccgagtc tgagaccaga attctcctgc aagggacccc agtgcccag   3060
atgacagagg atgccgtcga cgcggaacgg ctgaagcacc tcattgtgac cccctcgggc    3120
tgcgggggaac agaacatgat cggcatgacg cccacgtgtc tcgctgtgca ttacctggat    3180
gaaacggagc agtgggagaa gttcggccta gagaagcggc aggggccctt ggagctcatc    3240
aagaaggggt acacccagca gctggccttc agacaaccca gctctgcctt tgcggccttc    3300
gtgaaacggg cacccagcac ctggctgacc gcctacgtgg tcaaggtctt ctctctggct    3360
gtcaacctca tcgccatcga ctcccaagtc tctctgcggg ctgttaaatg gctgatcctg    3420
gagaagcaga agcccgacgg ggtcttccag gaggatgcgc ccgtgataca ccaagaaatg    3480
attggtggat tacggaacaa caacgagaaa gacatggccc tcacgccctt tgttctcatc    3540
tcgctgcagg aggctaaaga tatttgcgag gagcaggtca acagcctgcc aggcagcatc    3600
actaaagcag gagacttcct tgaagccaac tacatgaacc tacagagatc ctacactgtg    3660
gccattgctg gctatgctct ggccagatg  ggcaggctga aggggcctct tcttaacaaa    3720
tttctgacca cagccaaaga taagaaccgc tgggaggacc ctggtaagca gctctacaac    3780
gtggaggcca catcctatgc cctcttggcc ctactgcagc taaaagactt tgactttgtg    3840
cctcccgtcg tgcgttggct caatgaacag agatactacg gtggtggctc tggctctacc    3900
caggcccacct tcatggtgtt ccaagccttg gctcaatacc aaaaggacgc ccctgaccac    3960
caggaactga accttgatgt gtccctccaa ctgcccagcc gcagctccaa gatcacccac    4020
cgtatccact gggaatctgc cagcctcctg cgatcagaag agaccaagga aaatgaggga    4080
ttcacagtca cagctgaagg aaaaggccaa ggcaccttgt cggtggtgac aatgtaccat    4140
gctaaggcca aagatcaact cacctgtaat aaattcgacc tcaaggtcac cataaaacca    4200
gcaccggaaa cagaaaagag gcctcaggat gccaagaaca ctatgatcct tgagatctgt    4260
accaggtacc ggggagacca ggatgccact atgtctatat tggacatatc catgatgact    4320
ggctttgctc cagacacaga tgacctgaag cagctggcca atggtgttga cagatacatc    4380
tccaagtatg actggacaa  agccttctcc gataggaaca ccctcatcat ctacctggac    4440
aaggtctcac actctgagga tgactgtcta gctttcaaag ttcaccaata ctttaatgta    4500
gagcttatcc agcctggagc agtcaaggtc tacgccatt  acaacctgga ggaaagctgt    4560
acccggttct accatccgga aaaggaggat ggaaagctga acaagctctg ccgtgatgaa    4620
ctgtgccgct gtgctgagga gaattgcttc atacaaaagt cggatgacaa ggtcaccctg    4680
gaagaacggc tggacaaggc ctgtgagcca ggagtggact atgtgtacaa gacccgactg    4740
gtcaaggttc agctgtccaa tgactttgac gagtacatca tggccattga gcagaccatc    4800
aagtcaggct cggatgaggt gcaggttgga cagcagcgca cgttcatcag ccccatcaag    4860
tgcagagaag ccctgaagct ggaggagaag aaacactacc tcatgtgggg tctctcctca    4920
gatttctggg gagagaagcc caacctcagc tacatcatcg ggaaggacac ttgggtggaa    4980
cactggcccg aggaggacga atgccaagac aagagaacc  agaaacaatg ccaggacctc    5040
ggcgccttca ccgagagcat ggttgtcttt gggtgcccca actgaccaca cccccattcc    5100
cccactccaa ataaagcttc agttatatct caaaaaaaaa aaaaaaaa                 5148

SEQ ID NO: 76          moltype = RNA   length = 21
FEATURE                Location/Qualifiers
source                 1..21
                       mol_type = other RNA
                       organism = synthetic construct
ncRNA                  1..21
                       ncRNA_class = miRNA
SEQUENCE: 76
aagacaagga gtcctgcttg a                                                21

SEQ ID NO: 77          moltype = RNA   length = 21
FEATURE                Location/Qualifiers
source                 1..21
                       mol_type = other RNA
                       organism = synthetic construct
ncRNA                  1..21
                       ncRNA_class = miRNA
SEQUENCE: 77
tactccttca cctcaaactc a                                                21

SEQ ID NO: 78          moltype = RNA   length = 21
FEATURE                Location/Qualifiers
source                 1..21
```

```
                        mol_type = other RNA
                        organism = synthetic construct
ncRNA                   1..21
                        ncRNA_class = miRNA
SEQUENCE: 78
ttgacgtcca cccacacgga g                                              21

SEQ ID NO: 79           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 79
ttgacttcca cttcctgcag g                                              21

SEQ ID NO: 80           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 80
atgaaatgat ggtagacagc a                                              21

SEQ ID NO: 81           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 81
atctttagcc tcctgcagcg a                                              21

SEQ ID NO: 82           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 82
tgttcattga gccaacgcac g                                              21

SEQ ID NO: 83           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 83
ttagcatggt acattgtcac c                                              21

SEQ ID NO: 84           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 84
agcaaagcca gtcatcatgg a                                              21

SEQ ID NO: 85           moltype = RNA   length = 21
FEATURE                 Location/Qualifiers
source                  1..21
                        mol_type = other RNA
                        organism = synthetic construct
ncRNA                   1..21
                        ncRNA_class = miRNA
SEQUENCE: 85
tatcggagaa ggctttgtcc a                                              21

SEQ ID NO: 86           moltype = DNA   length = 21
FEATURE                 Location/Qualifiers
```

```
source                  1..21
                        mol_type = other DNA
                        organism = synthetic construct
SEQUENCE: 86
aagacaagga gtcctgcttg a                                              21

SEQ ID NO: 87           moltype = DNA   length = 21
FEATURE                 Location/Qualifiers
source                  1..21
                        mol_type = other DNA
                        organism = synthetic construct
SEQUENCE: 87
tactccttca cctcaaactc a                                              21

SEQ ID NO: 88           moltype = DNA   length = 21
FEATURE                 Location/Qualifiers
source                  1..21
                        mol_type = other DNA
                        organism = synthetic construct
SEQUENCE: 88
ttgacgtcca cccacacgga g                                              21

SEQ ID NO: 89           moltype = DNA   length = 21
FEATURE                 Location/Qualifiers
source                  1..21
                        mol_type = other DNA
                        organism = synthetic construct
SEQUENCE: 89
ttgacttcca cttcctgcag g                                              21

SEQ ID NO: 90           moltype = DNA   length = 21
FEATURE                 Location/Qualifiers
source                  1..21
                        mol_type = other DNA
                        organism = synthetic construct
SEQUENCE: 90
atgaaatgat ggtagacagc a                                              21

SEQ ID NO: 91           moltype = DNA   length = 21
FEATURE                 Location/Qualifiers
source                  1..21
                        mol_type = other DNA
                        organism = synthetic construct
SEQUENCE: 91
atctttagcc tcctgcagcg a                                              21

SEQ ID NO: 92           moltype = DNA   length = 21
FEATURE                 Location/Qualifiers
source                  1..21
                        mol_type = other DNA
                        organism = synthetic construct
SEQUENCE: 92
tgttcattga gccaacgcac g                                              21

SEQ ID NO: 93           moltype = DNA   length = 21
FEATURE                 Location/Qualifiers
source                  1..21
                        mol_type = other DNA
                        organism = synthetic construct
SEQUENCE: 93
ttagcatggt acattgtcac c                                              21

SEQ ID NO: 94           moltype = DNA   length = 21
FEATURE                 Location/Qualifiers
source                  1..21
                        mol_type = other DNA
                        organism = synthetic construct
SEQUENCE: 94
agcaaagcca gtcatcatgg a                                              21

SEQ ID NO: 95           moltype = DNA   length = 21
FEATURE                 Location/Qualifiers
source                  1..21
                        mol_type = other DNA
                        organism = synthetic construct
SEQUENCE: 95
tatcggagaa ggctttgtcc a                                              21

SEQ ID NO: 96           moltype = DNA   length = 64
```

```
FEATURE              Location/Qualifiers
source               1..64
                     mol_type = other DNA
                     organism = synthetic construct
misc_feature         order(1..5,27..45)
                     note = DNA
misc_feature         order(6..26,46..64)
                     note = RNA
SEQUENCE: 96
tgctgaagac aaggagtcct gcttgagttt tggccactga ctgactcaag cagctccttg    60
tctt                                                                 64

SEQ ID NO: 97        moltype = DNA  length = 64
FEATURE              Location/Qualifiers
source               1..64
                     mol_type = other DNA
                     organism = synthetic construct
misc_feature         order(5..23,43..63)
                     note = RNA
misc_feature         order(1..4,24..42,64)
                     note = DNA
SEQUENCE: 97
cctgaagaca aggagctgct tgagtcagtc agtggccaaa actcaagcag gactccttgt    60
cttc                                                                 64

SEQ ID NO: 98        moltype = DNA  length = 64
FEATURE              Location/Qualifiers
source               1..64
                     mol_type = other DNA
                     organism = synthetic construct
misc_feature         order(1..5,27..45)
                     note = DNA
misc_feature         order(6..26,46..64)
                     note = RNA
SEQUENCE: 98
tgctgtactc cttcacctca aactcagttt tggccactga ctgactgagt ttggtgaagg    60
agta                                                                 64

SEQ ID NO: 99        moltype = DNA  length = 64
FEATURE              Location/Qualifiers
source               1..64
                     mol_type = other DNA
                     organism = synthetic construct
misc_feature         order(1..4,24..42,64)
                     note = DNA
misc_feature         order(5..23,43..63)
                     note = RNA
SEQUENCE: 99
cctgtactcc ttcaccaaac tcagtcagtc agtggccaaa actgagtttg aggtgaagga    60
gtac                                                                 64

SEQ ID NO: 100       moltype = DNA  length = 64
FEATURE              Location/Qualifiers
source               1..64
                     mol_type = other DNA
                     organism = synthetic construct
misc_feature         order(1..5,27..45)
                     note = DNA
misc_feature         order(6..26,46..64)
                     note = RNA
SEQUENCE: 100
tgctgttgac gtccacccac acggaggttt tggccactga ctgacctccg tgtgtggacg    60
tcaa                                                                 64

SEQ ID NO: 101       moltype = DNA  length = 64
FEATURE              Location/Qualifiers
source               1..64
                     mol_type = other DNA
                     organism = synthetic construct
misc_feature         order(1..4,24..42,64)
                     note = DNA
misc_feature         order(5..23,43..63)
                     note = RNA
SEQUENCE: 101
cctgttgacg tccacacacg gaggtcagtc agtggccaaa acctccgtgt gggtggacgt    60
caac                                                                 64

SEQ ID NO: 102       moltype = DNA  length = 64
FEATURE              Location/Qualifiers
```

```
source                  1..64
                        mol_type = other DNA
                        organism = synthetic construct
misc_feature            order(1..5,27..45)
                        note = DNA
misc_feature            order(6..26,46..64)
                        note = RNA
SEQUENCE: 102
tgctgttgac ttccacttcc tgcagggttt tggccactga ctgaccctgc agggtggaag    60
tcaa                                                                 64

SEQ ID NO: 103          moltype = DNA   length = 64
FEATURE                 Location/Qualifiers
source                  1..64
                        mol_type = other DNA
                        organism = synthetic construct
misc_feature            order(1..4,25..42,64)
                        note = DNA
misc_feature            order(5..24,43..63)
                        note = RNA
SEQUENCE: 103
cctgttgact tccaccctgc agggtcagtc agtggccaaa accctgcagg aagtggaagt    60
caac                                                                 64

SEQ ID NO: 104          moltype = DNA   length = 64
FEATURE                 Location/Qualifiers
source                  1..64
                        mol_type = other DNA
                        organism = synthetic construct
misc_feature            order(1..5,27..45)
                        note = DNA
misc_feature            order(6..26,46..64)
                        note = RNA
SEQUENCE: 104
tgctgatgaa atgatggtag acagcagttt tggccactga ctgactgctg tctcatcatt    60
tcat                                                                 64

SEQ ID NO: 105          moltype = DNA   length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 105
cctgatgaaa tgatgagaca gcagtcagtc agtggccaaa actgctgtct accatcattt    60
catc                                                                 64

SEQ ID NO: 106          moltype = DNA   length = 64
FEATURE                 Location/Qualifiers
source                  1..64
                        mol_type = other DNA
                        organism = synthetic construct
misc_feature            order(1..5,27..45)
                        note = DNA
misc_feature            order(6..26,46..64)
                        note = RNA
SEQUENCE: 106
tgctgatctt tagcctcctg cagcgagttt tggccactga ctgactcgct gcaaggctaa    60
agat                                                                 64

SEQ ID NO: 107          moltype = DNA   length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 107
cctgatcttt agccttgcag cgagtcagtc agtggccaaa actcgctgca ggaggctaaa    60
gatc                                                                 64

SEQ ID NO: 108          moltype = DNA   length = 64
FEATURE                 Location/Qualifiers
source                  1..64
```

```
                        mol_type = other DNA
                        organism = synthetic construct
misc_feature            order(1..5,27..45)
                        note = DNA
misc_feature            order(6..26,46..64)
                        note = RNA
SEQUENCE: 108
tgctgtgttc attgagccaa cgcacggttt tggccactga ctgaccgtgc gttctcaatg   60
aaca                                                                64

SEQ ID NO: 109          moltype = DNA   length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 109
cctgtgttca ttgagaacgc acggtcagtc agtggccaaa accgtgcgtt ggctcaatga   60
acac                                                                64

SEQ ID NO: 110          moltype = DNA   length = 64
FEATURE                 Location/Qualifiers
source                  1..64
                        mol_type = other DNA
                        organism = synthetic construct
misc_feature            order(1..5,27..45)
                        note = DNA
misc_feature            order(6..26,46..64)
                        note = RNA
SEQUENCE: 110
tgctgttagc atggtacatt gtcaccgttt tggccactga ctgacggtga caataccatg   60
ctaa                                                                64

SEQ ID NO: 111          moltype = DNA   length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 111
cctgttagca tggtattgtc accgtcagtc agtggccaaa acggtgacaa tgtaccatgc   60
taac                                                                64

SEQ ID NO: 112          moltype = DNA   length = 64
FEATURE                 Location/Qualifiers
source                  1..64
                        mol_type = other DNA
                        organism = synthetic construct
misc_feature            order(1..5,27..45)
                        note = DNA
misc_feature            order(6..26,46..64)
                        note = RNA
SEQUENCE: 112
tgctgagcaa agccagtcat catggagttt tggccactga ctgactccat gatctggctt   60
tgct                                                                64

SEQ ID NO: 113          moltype = DNA   length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 113
cctgagcaaa gccagatcat ggagtcagtc agtggccaaa actccatgat gactggcttt   60
gctc                                                                64

SEQ ID NO: 114          moltype = DNA   length = 64
FEATURE                 Location/Qualifiers
source                  1..64
                        mol_type = other DNA
```

```
                        organism = synthetic construct
misc_feature            order(1..5,27..45)
                        note = DNA
misc_feature            order(6..26,46..64)
                        note = RNA
SEQUENCE: 114
tgctgtatcg gagaaggctt tgtccagttt tggccactga ctgactggac aaacttctcc    60
gata                                                                 64

SEQ ID NO: 115          moltype = DNA  length = 64
FEATURE                 Location/Qualifiers
source                  1..64
                        mol_type = other DNA
                        organism = synthetic construct
misc_feature            order(1..4,24..42,64)
                        note = DNA
misc_feature            order(5..23,43..63)
                        note = RNA
SEQUENCE: 115
cctgtatcgg agaagtttgt ccagtcagtc agtggccaaa actggacaaa gccttctccg    60
atac                                                                 64
```

We claim:

1. A method of inhibiting expression of C3 in a cell, the method comprising contacting the cell with an miRNA consisting of a nucleotide sequence at least 90% identical to any one of SEQ ID NOs: 76-77 or 79-85, or a portion thereof, wherein the nucleotide sequence is 19-23 nucleotides in length, or an siRNA comprising an antisense strand consisting of the nucleotide sequence.

2. The method of claim 1, wherein the method comprises contacting the cell with a composition comprising a nucleic acid encoding the miRNA or siRNA.

3. The method of claim 2, wherein the nucleic acid comprises any one of SEQ ID NOs: 86-87 or 89-115.

4. The method of claim 2, wherein the composition comprises an expression vector comprising the nucleic acid.

5. The method of claim 4, wherein the expression vector is a viral vector.

6. The method of claim 5, wherein the viral vector is an adeno-associated viral (AAV) vector.

7. The method of claim 1, wherein the cell is a hepatocyte.

* * * * *